US012649778B2

(12) United States Patent

Tombler et al.

(10) Patent No.: US 12,649,778 B2

(45) Date of Patent: Jun. 9, 2026

(54) MONOCLONAL ANTIBODIES AND USES THEREOF

(71) Applicant: NANOPIN TECHNOLOGIES, INC., Gilbert, AZ (US)

(72) Inventors: Thomas Wray Tombler, Gilbert, AZ (US); Christopher John Lyon, River Ridge, LA (US)

(73) Assignee: NANOPIN TECHNOLOGIES, INC., Gilbert, AZ (US)

( * ) Notice: Subject to any disclaimer, the term of this patent is extended or adjusted under 35 U.S.C. 154(b) by 99 days.

(21) Appl. No.: 17/768,818

(22) PCT Filed: Apr. 8, 2021

(86) PCT No.: PCT/US2021/026436

§ 371 (c)(1),
(2) Date: Apr. 13, 2022

(87) PCT Pub. No.: WO2021/207531

PCT Pub. Date: Oct. 14, 2021

(65) Prior Publication Data

US 2024/0124562 A1 Apr. 18, 2024

Related U.S. Application Data

(60) Provisional application No. 63/006,822, filed on Apr. 8, 2020.

(51) Int. Cl.
| | |
|---|---|
| *C07K 16/1289* | (2026.01) |
| *G01N 33/543* | (2006.01) |
| *G01N 33/569* | (2006.01) |

(52) U.S. Cl.
CPC ... *C07K 16/1289* (2013.01); *G01N 33/54313* (2013.01); *G01N 33/5695* (2013.01); *C07K 2317/34* (2013.01); *C07K 2317/55* (2013.01); *C07K 2317/56* (2013.01); *C07K 2317/92* (2013.01); *G01N 2333/35* (2013.01)

(58) Field of Classification Search
CPC ............ C07K 16/1289; C07K 2317/34; G01N 33/54313; G01N 33/5695
See application file for complete search history.

(56) References Cited

U.S. PATENT DOCUMENTS

| | | | |
|---|---|---|---|
| 4,485,045 | A | 11/1984 | Regen |
| 4,544,545 | A | 10/1985 | Ryan et al. |
| 4,676,980 | A | 6/1987 | Segal et al. |
| 4,774,339 | A | 9/1988 | Haugland et al. |
| 4,816,567 | A | 3/1989 | Cabilly et al. |
| 5,013,556 | A | 5/1991 | Woodle et al. |
| 5,030,719 | A | 7/1991 | Umemoto et al. |
| 5,223,409 | A | 6/1993 | Ladner et al. |
| 5,233,409 | A | 8/1993 | Schwab |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,916,771 | A | 6/1999 | Hori et al. |
| 5,939,598 | A | 8/1999 | Kucherlapati et al. |
| 6,365,418 | B1 | 4/2002 | Wagner et al. |
| 2012/0225060 | A1 | 9/2012 | Lee et al. |
| 2017/0008938 | A1* | 1/2017 | Rehm .................. A61K 38/45 |

FOREIGN PATENT DOCUMENTS

| | | |
|---|---|---|
| WO | 94/02602 A1 | 2/1994 |
| WO | 94/11026 A2 | 5/1994 |
| WO | 95/22618 A1 | 8/1995 |
| WO | 96/33735 A1 | 10/1996 |
| WO | 96/34096 A1 | 10/1996 |
| WO | 99/38185 A2 | 7/1999 |
| WO | 99/53049 A1 | 10/1999 |

OTHER PUBLICATIONS

Greenspan et al. 1999 (Defining epitopes: It's not as easy as it seems; Nature Biotechnology, 17:936-937) (Year: 1999).*

Sela-Culang et al. 2013 (The structural basis of antibody-antigen recognition; Frontiers in Immunology 4(302):1-13) (Year: 2013).*

Goel et al. 2004 (Plasticity within the Antigen Combining Site May Manifest as Molecular Mimicry in the Humoral Immune Response; The Journal of Immunology 173(12):7358-7367) (Year: 2004).*

Edwards et al. 2003 (The remarkable flexibility of the human antibody repertoire; isolation of over one thousand different antibodies to a single protein, BlyS. Journal of Molecular Biology 334:103-118) (Year: 2003).*

Lloyd et al. 2009 (Modelling the human immune response: performance of a 1011 human antibody repertoire against a broad panel of therapeutically relevant antigens. Protein Engineering, Design & Selection 22(3):159-168) (Year: 2009).*

Ausubel, F. M. et al. (eds). Current Protocols in Molecular Biology. John Wiley & Sons Inc. (2003).

Bobo, R. H. et al. Convection-enhanced delivery of macromolecules in the brain. Proc. Natl. Acad. Sci. USA 91:2076-2080 (1994).

Brodeur et al., Monoclonal Antibody Production Techniques and Applications. Marcel Dekker, Inc., New York, pp. 51-63 (1987).

Bruchez, M. et al. Semiconductor Nanocrystals as Fluorescent Biological Labels. Science 281: 2013-2016 (1998).

Caron, P. C. et al. Engineered humanized dimeric forms of IgG are more effective antibodies. J. Exp Med., 176: 1191-1195 (1992).

Carrell, T. et al. A Novel Procedure for the Synthesis of Libraries Containing Small Organic Moleculest. Angew. Chem. Int. Ed. Engl. 33: 2059-2061 (1994).

(Continued)

*Primary Examiner* — Mary Maille Lyons

(74) *Attorney, Agent, or Firm* — Baker, Donelson, Bearman, Caldwell & Berkowitz, PC

(57) ABSTRACT

This invention relates generally to isolated monoclonal antibodies that binds to an epitope of the 10 kDa culture filtrate protein (CFP-10) or a peptide fragment thereof, and methods for using the same to detect *Mycobacterium tuberculosis*.

15 Claims, 41 Drawing Sheets

Specification includes a Sequence Listing.

(56) References Cited

OTHER PUBLICATIONS

Chan, W.C.W. and Nie, S. Quantum Dot Bioconjugates for Ultrasensitive Nonisotopic Detection. Science 281: 2016-2018 (1998).

Cho, C.Y. et al. An Unnatural Biopolymer. Science 261: 1303-1305 (1993).

Cole, et al., 1985 In: Monoclonal Antibodies and Cancer Therapy, Alan R. Liss, Inc., pp. 77-96.

Cote, R. J. et al. Generation of human monoclonal antibodies reactive with cellular antigens. Proc Natl Acad Sci USA, 80: 2026-2030 (1983).

Crowther (Ed.). ELISA: Theory and Practice. Methods in Molecular Biology, vol. 42, Human Press, Totowa, NJ (1995).

Cruse, J. M. and Lewis, R. E., Jr. (eds). Conjugate Vaccines. Contributions to Microbiology and Immunology. Carger Press, New York (1989).

Cull, M. G. et al. Screening for receptor ligands using large libraries of peptides linked to the C terminus of the lac repressor. Proc. Natl. Acad. Sci. USA 89: 1865-1869 (1992).

Cwirla, S. E. et al. Peptides on phage: a vast library of peptides for identifying ligands. Proc. Natl. Acad. Sci. U.S.A. 87: 6378-6382 (1990).

Davidson, B. L. et al. A model system for in vivo gene transfer into the central nervous system using an adenoviral vector. Nat. Genet 3:219 (1993).

Davies, D.R. et al. Antibody-antigen complexes. Annual Rev Biochem, 59:439-473 (1990).

Devlin, J. J. et al. Random Peptide Libraries: a Source of Specific Protein Binding Molecules. Science 249: 404-406 (1990).

Dewitt, S.H. et al. "Diversomers": an approach to nonpeptide, nonoligomeric chemical diversity. Proc. Natl. Acad. Sci. U.S.A. 90: 6909 (1993).

Diamandis, E. and Christopoulus, T. Immunoassay. Academic Press, Inc., San Diego, CA (1996).

Diedrich, C. R. et al. HIV-1 and the Mycobacterium tuberculosis granuloma: A systematic review and meta-analysis. Tuberculosis 98 (2016): 62-76.

Dodd, Peter J., et al. "The global burden of tuberculosis mortality in children: a mathematical modelling study." The Lancet Global health 5.9 (2017): e898-e906.

Edwards, D. J., F. Kitetele, and A. Van Rie. "Agreement between clinical scoring systems used for the diagnosis of pediatric tuberculosis in the HIV era." The International Journal of Tuberculosis and Lung Disease 11.3 (2007): 263-269.

Eppstein, D.A. et al. Biological activity of liposome-encapsulated murine interferon gamma is mediated by a cell membrane receptor. Proc. Natl. Acad. Sci. USA, 82: 3688-3692 (1985).

Erb, E. et al. Recursive deconvolution of combinatorial chemical libraries. Proc. Natl. Acad. Sci. U.S.A. 91: 11422 (1994).

Felici, F. et al. Selection of antibody ligands from a large library of oligopeptides expressed on a multivalent exposition vector. J. Mol. Biol. 222: 301-310 (1991).

Feng, T. T. et al. "Novel monoclonal antibodies to ESAT-6 and CFP-10 antigens for ELISA-based diagnosis of pleural tuberculosis." The International journal of tuberculosis and lung disease, 15.6: 804-810 (2011).

Figeys, D. et al. Microfabricated device coupled with an electrospray ionization quadrupole time-of-flight mass spectrometer: protein identifications based on enhanced-resolution mass spectrometry and tandem mass spectrometry data. Rapid Communications in Mass Spec., 12(20), 1435-1444 (1998).

Fischer, R. et al. Production of antibodies in plants and their use for global health. Vaccine, 21(7-8): 820-825 (2003).

Fishwild, D.M. et al. High-avidity human IgGK monoclonal antibodies from a novel strain of minilocus transgenic mice. Nature Biotechnology, 14, 845-51 (1996).

Fodor, S. P. A. et al. Multiplexed biochemical assays with biological chips. Nature 364: 555-556 (1993).

Gallop, M. A. et al. Applications of Combinatorial Technologies to Drug Discovery. 1. Background and Peptide Combinatorial Libraries. J. Med. Chem. 37, 9, 1233-1251 (1994).

Geller, A. I. et al. An HSV-1 Vector Expressing Tyrosine Hydroxylase Causes Production and Release of I-DOPA from Cultured Rat Striatal Cells. J. Neurochem, 64:487-496 (1995).

Geller, A. I et al. Infection of cultured central nervous system neurons with a defective herpes simplex virus 1 vector results in stable expression of Escherichia coli beta-galactosidase. Proc Natl. Acad. Sci USA 87:1149-1153 (1990).

Geller, A. I. et al. Long-term increases in neurotransmitter release from neuronal cells expressing a constitutively active adenylate cyclase from a herpes simplex virus type 1 vector. Proc Natl. Acad. Sci.: U.S.A. 90:7603-7607 (1993).

Goding, W. Monoclonal Antibodies: Principles and Practice, Academic Press, pp. 59-103 (1986).

Harlow, E., and Lane, D. Antibodies: A Laboratory Manual. Cold Spring Harbor Laboratory Press, Cold Spring Harbor, NY (1988).

Hoogenboom, H.R. and Winter, G. By-passing immunisation. Human antibodies from synthetic repertoires of germline VH gene segments rearranged in vitro. J. Mol. Biol., 227:381-8 (1991).

Houghten, R. A. et al. The use of synthetic peptide combinatorial libraries for the identification of bioactive peptides. Biotechniques 13: 412-421 (1992).

Hwang, K.J. et al. Hepatic uptake and degradation of unilamellar sphingomyelin/cholesterol liposomes: a kinetic study. Proc. Natl Acad. Sci. USA, 77: 4030-4 (1980).

Kaplitt, M. G. et al. Long-term gene expression and phenotypic correction using adeno-associated virus vectors in the mammalian brain. Nat. Genet. 8:148-154 (1994).

Kennedy, J. H. et al. Protein-protein coupling reactions and the applications of protein conjugates. Clin. Chim. Acta 70:1-31 (1976).

Killen, J.A. and Lindstrom, J.M. Specific killing of lymphocytes that cause experimental autoimmune myasthenia gravis by ricin toxin-acetylcholine receptor conjugates.J Immunol 1984; 133:2549-2553.

Ko, K. et al. Production of antibodies in plants: approaches and perspectives. Current Topics in Microbiology and Immunology, vol. 332, pp. 55-78 (2009).

Kohler, G. and Milstein, C. Continuous cultures of fused cells secreting antibody of predefined specificity. Nature, 256:495-497 (1975).

Kozbor, D. et al. The production of monoclonal antibodies from human lymphocytes. Immunol Today 4: 72 (1983).

Kozbor, J. A human hybrid myeloma for production of human monoclonal antibodies. Immunol., 133:3001-3005 (1984).

Lalvani, A., and Whitworth, S. H. "Progress in interferon-gamma release assay development and applications: an unfolding story of translational research." Annals of translational medicine, 7. Suppl 3 (2019).

Lam, K. S. et al. A new type of synthetic peptide library for identifying ligand-binding activity. Nature 354: 82-84 (1991).

Lam, K. S. Mini-review. Application of combinatorial library methods in cancer research and drug discovery. Anticancer Drug Design 12: 145-167 (1997).

Li, J. et al. Separation and Identification of Peptides from Gel-Isolated Membrane Proteins Using a Microfabricated Device for Combined Capillary Electrophoresis/Nanoelectrospray Mass Spectrometry. Anal. Chem. 72: 599-609 (2000).

Lim, F., et al., in DNA Cloning: Mammalian Systems, D. Glover, Ed. (Oxford Univ. Press, Oxford England) (1995).

Lonberg, N. and Huszar, D. Human antibodies from transgenic miceIntern. Rev. Immunol. 13 65-93 (1995).

Lonberg, N. et al. Antigen-specific human antibodies from mice comprising four distinct genetic modifications. Nature 368: 856-859 (1994).

Malmqvist, M. Biospecific interaction analysis using biosensor technology. Nature, 361: 186-87 (1993).

Marais, Ben J., et al. "A refined symptom-based approach to diagnose pulmonary tuberculosis in children." Pediatrics 118.5 (2006): e1350-e1359.

(56)                  References Cited

OTHER PUBLICATIONS

Marks, J.D. et al. By-passing immunization. Human antibodies from V-gene libraries displayed on phage. J. Mol. Biol., 222:581 (1991).

Marks, J.D. et al. By-Passing Immunization: Building High Affinity Human Antibodies by Chain Shuffling. Bio/Technology 10, 779-783 (1992).

Martin, F.J. et al. Irreversible coupling of immunoglobulin fragments to preformed vesicles. An improved method for liposome targeting. J. Biol. Chem., 257: 286-288 (1982).

Morrison, P. F. et al. High-flow microinfusion: tissue penetration and pharmacodynamics. Am. J. Physiol. 266:292-305 (1994).

Morrison, S. L. Success in specification. Nature 368, 812-813 (1994).

Munson, P. J. and Rodbard, D. Ligand: a versatile computerized approach for characterization of ligand-binding systems. Anal. Biochem., 107:220-239 (1980).

Nemes, Elisa, et al. "Diagnostic Accuracy of Early Secretory Antigenic Target-6-Free Interferon-gamma Release Assay Compared to QuantiFERON-TB Gold In-tube." Clinical Infectious Diseases 69.10 (2019): 1724-1730.

Neuberger, M. Generating high-avidity human Mabs in mice. Nature Biotechnology, 14, 826, 1 page (1996).

Nicol, Mark P., and Heather J. Zar. "New specimens and laboratory diagnostics for childhood pulmonary TB: progress and prospects." Paediatric respiratory reviews 12.1 (2011): 16-21.

Ramakrishnan, S. et al. Comparison of the Selective Cytotoxic Effects of Immunotoxins Containing Ricin A Chain or Pokeweed Antiviral Protein and Anti-Thy 1.1 Monoclonal Antibodies. Cancer Res. 44:201-208 (1984).

Safdari, Y. et al. Antibody humanization methods—a review and update. Biotechnol Genet Eng Rev., 29: 175-86 (2013).

Scatchard et al., Ann N. Y. Acad. Analysis can be performed using the method of ScL. 51: 660 (1949).

Schuurs, A.H.W.M. et al. Enzyme-immunoassay. Clin. Chim. Acta 81:1-40 (1977).

Scott, J. K. and Smith, G. P. Searching for Peptide Ligands with an Epitope Library. Science 249: 386-390 (1990).

Shevchenko, A. et al. MALDI Quadrupole Time-of-Flight Mass Spectrometry: A Powerful Tool for Proteomic Research. Anal. Chem. 72: 2132-2141 (2000).

Shopes, B. A genetically engineered human IgG with limited flexibility fully initiates cytolysis via complement. J. Immunol., 148: 2918-2922 (1992).

Stevenson, G.T. et al. A chimeric antibody with dual Fc regions (bisFabFc) prepared by manipulations at the IgG hinge. Anti-Cancer Drug Design, 3: 219-230 (1989).

Thomas, T. A. et al. Tuberculosis in children. Pediatric Clinics 64.4 (2017): 893-909.

Tijssen, P. Practice and Theory of Enzyme Immunoassays. Elsevier Science Publishers, Amsterdam (1985).

Vitetta, E.S. et al. Redesigning Nature's Poisons to Create Anti-Tumor Reagents. Science 238: 1098-1104 (1987).

Wilkinson. D. The Scientist, published by The Scientist, Inc., Philadelphia PA, vol. 14, No. 8, pp. 25-28 (2000).

Wu, X. et al. "Preparation of immunochromatographic strips for rapid detection of early secreted protein ESAT-6 and culture filtrate protein CFP-10 from Mycobacterium tuberculosis." Medicine, 96.51 (2017).

Yang, Y. et al. Cellular and humoral immune responses to viral antigens create barriers to lung-directed gene therapy with recombinant adenoviruses. J. Virol. 69:2004-12 (1995).

Zuckermann, R.N. et al. Discovery of nanomolar ligands for 7-transmembrane G-protein-coupled receptors from a diverse N-(substituted)glycine peptoid library. J. Med. Chem. 37: 2678-85 (1994).

International Search Report for PCT/US2021/026436 mailed Sep. 30, 2021, 6 pages.

Written Opinion for PCT/US2021/026436 mailed Sep. 30, 2021, 8 pages.

* cited by examiner

Figure 12 - IMGT Analysis of V(D)J Junctions of 17E4-1

| Sequence | V-GENE and allele | Functionality | V-REGION identity % (nt) | J-GENE and allele | D-GENE and allele | AA Junction | Junction frame |
|---|---|---|---|---|---|---|---|
| VH | Orycun IGHV1S69*01 F | productive | 89.86% (248/276 nt) | Orycun IGHJ4*01 F | | CVREEF DFW | in-frame |
| VL | Orycun IGKV1S46*01 [F] | productive | 89.47% (255/285 nt) | Orycun IGKJ1-2*01 F | - | CLGGYA SIIDMWT F | in-frame |

Figure 13 - IMGT Analysis of V(D)J Junctions of 21H3-1

| Sequence | V-GENE and allele | Functionality | V-REGION identity % (nt) | J-GENE and allele | D-GENE and allele | AA Junction | Junction frame |
|---|---|---|---|---|---|---|---|
| VH | Orycun IGHV1S69*01 F | productive | 92.03% (254/276 nt) | Orycun IGHJ4*01 F | | CAREEF NLW | in-frame |
| VL | Orycun IGKV1S1*01 F | productive | 88.77% (253/285 nt) | Orycun IGKJ1-2*01 F | ~ | CAGYKS SSDGPA F | in-frame |

Figure 14 - IMGT Analysis of V(D)J Junctions of 119C10-1

| Sequence | V-GENE and allele | Functionality | V-REGION identity % (nt) | J-GENE and allele | D-GENE and allele | AA Junction | Junction frame |
|---|---|---|---|---|---|---|---|
| V H | Orycun IGHV1S69*01 F | productive | 93.12% (257/276 nt) | Orycun IGHJ4*01 F | Orycun IGHD3-1*01 ORF | CAGGAP GYTPFN LW | in-frame |
| V L | Orycun IGKV1S56*01 [F] | productive | 87.23% (246/282 nt) | Orycun IGKJ1-2*01 F | - | CAGGYS SSLDIYA F | in-frame |

Figure 15 - IMGT Analysis of V(D)J Junctions of 65D3-1

| Sequence | V-GENE and allele | Functionality | V-REGION identity % (nt) | J-GENE and allele | D-GENE and allele | AA Junction | Junction frame |
|---|---|---|---|---|---|---|---|
| V H | Orycun IGHV1S69*01 F | productive | 90.22% (249/276 nt) | Orycun IGHJ4*01 F | | CAREEF DFW | in-frame |
| V L | Orycun IGKV1S12*01 F, or Orycun IGKV1S40*01 [F] or Orycun IGKV1S52*01 [F] | productive | 91.58% (261/285 nt) | Orycun IGKJ1-2*01 F | - | CLGGYA STIDMW AF | in-frame |

CFP-10 protein sequence alignment for *Mycobacterium tuberculosis* complex species

| Species | Sequence ID | CFP10 Protein sequence | Database |
|---|---|---|---|
| M. tuberculosis | P9WNK5 | MAEMKTDAATLAQEAGNFERISGDLKTQIDQVESTAGSLQGQWRGAAGTAAQAAVVRFQEAANKQKQELDEISTNIRQAGVQYSRADEEQQQALSSQMGF | UniProtKB |
| M. bovis | P0A567 | MAEMKTDAATLAQEAGNFERISGDLKTQIDQVESTAGSLQGQWRGAAGTAAQAAVVRFQEAANKQKQELDEISTNIRQAGVQYSRADEEQQQALSSQMGF | UniProtKB |
| M. canetti | G0TLS4 | MAEMKTDAATLAQEAGNFERISGDLKTQIDQVESTAGSLQGQWRGAAGTAAQAAVVRFQEAANKQKQELDEISTNIRQAGVQYSRADEEQQQALSSQMGF | UniProtKB |
| M. caprae | APU27648.1 | MAEMKTDAATLAQEAGNFERISGDLKTQIDQVESTAGSLQGQWRGAAGTAAQAAVVRFQEAANKQKQELDEISTNIRQAGVQYSRADEEQQQALSSQMGF | GenBank |
| M. orygis | A0A501P5V6 | MAEMKTDAATLAQEAGNFERISGDLKTQIDQVESTAGSLQGQWRGAAGTAAQAAVVRFQEAANKQKQELDEISTNIRQAGVQYSRADEEQQQALSSQMGF | UniProtKB |
| M. pinnipedii | ACF4117L1.1 | MAEMKTDAATLAQEAGNFERISGDLKTQIDQVESTAGSLQGQWRGAAGTAAQAAVVRFQEAANKQKQELDEISTNIRQAGVQYSRADEEQQQALSSQMGF | GenBank |
| M. microti | -- | Not Available | -- |
| M. mungi | -- | Not Available | -- |
| M. suricattae | -- | Not Available | -- |

The sequence of peptide 1593 (TDAATLAQEAGNFER) and peptide 2004 (TQIDQVESTAGSLQGQWR) are indicated by bold and shaded text in the *Mycobacterium tuberculosis* CFP-10 sequences. Both peptides, and the entire CFP-10 sequence, are 100% conserved among all *Mycobacterium tuberculosis* complex members with published CFP-10 sequence.

FIGURE 16

| NO. | well ID | sequence ID | Mutation position | WT | WT OD450nm | Mutant | Mutant OD450nm | Mutant/WT ratio | Mutant site |
|-----|---------|-------------|-------------------|----|------------|--------|----------------|-----------------|-------------|
| 1 | L20-H4 | AHF05110 | L57 | S | 0.477 | T | 0.977 | 2.048 | L S57T |
| 2 | H17-C4 | AHF05120 | H55 | S | 0.623 | W | 1.282 | 2.058 | H S55W |
| 3 | H26-F4 | AHF05123 | H64 | G | 0.837 | K | 1.091 | 1.303 | H G64K |

FIGURE 17 mAb 1593 data

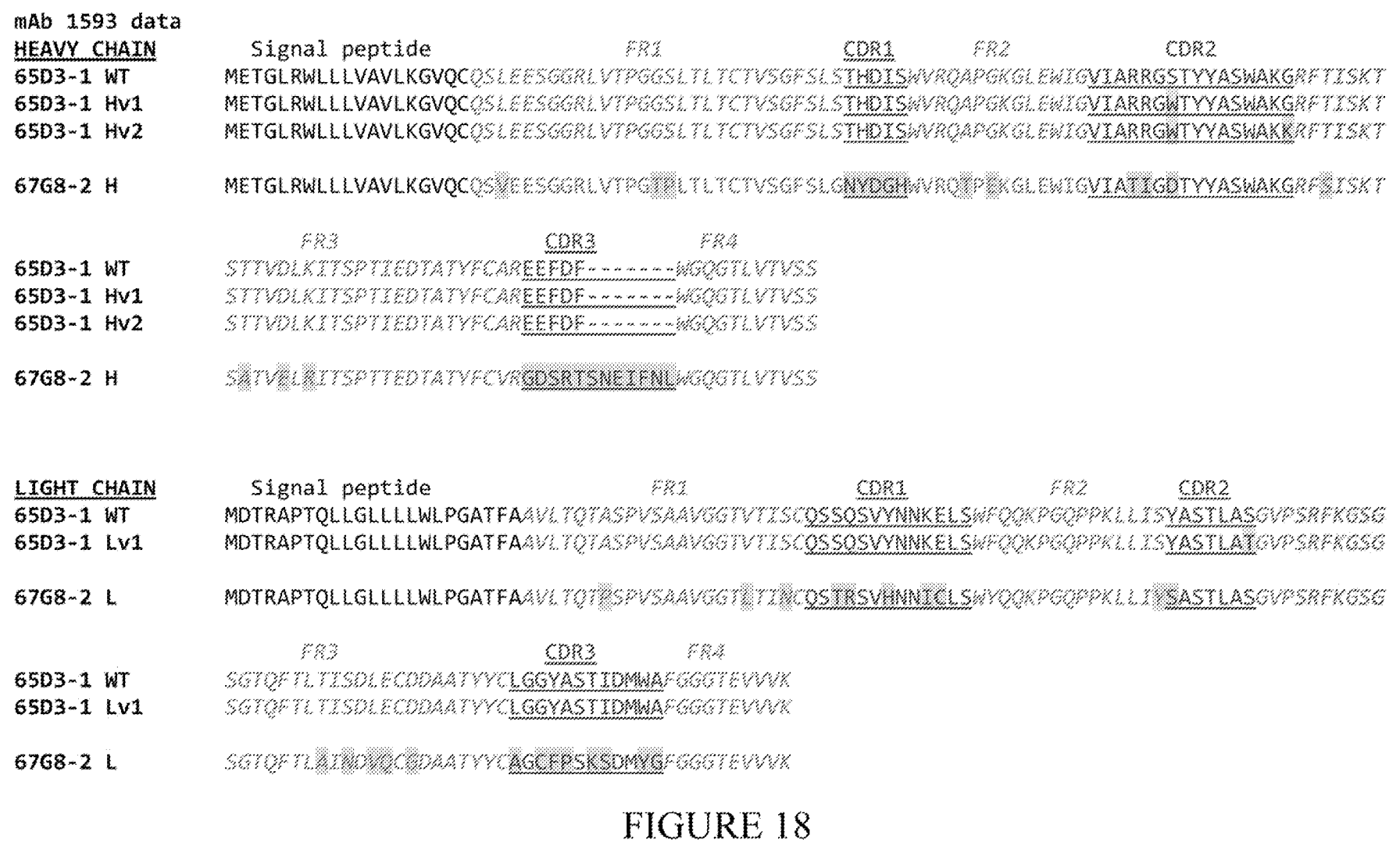

HEAVY CHAIN

| | Signal peptide | FR1 | CDR1 | FR2 | CDR2 |
|---|---|---|---|---|---|
| 65D3-1 WT | METGLRWLLLVAVLKGVQC | QSLEESGGRLVTPGGSLTLTCTVSGFSL | STHDIS | WVRQAPGKGLEWIG | VIARRGSTYYASWAKGRFTISKT |
| 65D3-1 Hv1 | METGLRWLLLVAVLKGVQC | QSLEESGGRLVTPGGSLTLTCTVSGFSL | STHDIS | WVRQAPGKGLEWIG | VIARRGNTYYASWAKGRFTISKT |
| 65D3-1 Hv2 | METGLRWLLLVAVLKGVQC | QSLEESGGRLVTPGGSLTLTCTVSGFSL | STHDIS | WVRQAPGKGLEWIG | VIARRGNTYYASWAKKRFTISKT |
| 67G8-2 H | METGLRWLLLVAVLKGVQC | QSLEESGGRLVTPGGSLTLTCTVSGFSL | GNYDIS | WVRQPEKGLEWIG | VIATIGDTYYASWAKGRFTISKT |

| | FR3 | CDR3 | FR4 |
|---|---|---|---|
| 65D3-1 WT | STTVDLKITSPTTEDTATYFCAR | EEFDF------ | WGQGTLVTVSS |
| 65D3-1 Hv1 | STTVDLKITSPTTEDTATYFCAR | EEFDF------ | WGQGTLVTVSS |
| 65D3-1 Hv2 | STTVDLKITSPTTEDTATYFCAR | EEFDF------ | WGQGTLVTVSS |
| 67G8-2 H | SATVELKITSPTTEDTATYFCVR | DSRTSNEIFNL | WGQGTLVTVSS |

LIGHT CHAIN

| | Signal peptide | FR1 | CDR1 | FR2 | CDR2 |
|---|---|---|---|---|---|
| 65D3-1 WT | MDTRAPTQLLGLLLLWLPGATFA | AVLTQTASPVSAAVGGTVTISC | QSSQSVYNNKELS | WFQQKPGQPPKLLIY | SASTLAS GVPSRFKGSG |
| 65D3-1 Lv1 | MDTRAPTQLLGLLLLWLPGATFA | AVLTQTASPVSAAVGGTVTISC | QSSQSVYNNKELS | WFQQKPGQPPKLLIY | SASTLAI GVPSRFKGSG |
| 67G8-2 L | MDTRAPTQLLGLLLLWLPGATFA | AVLTQTPSPVSAAVGGTVTINC | QSTRSVNNTELS | WYQQKPGQPPKLLIY | BASTLAS GVPSRFKGSG |

| | FR3 | CDR3 | FR4 |
|---|---|---|---|
| 65D3-1 WT | SGTQFTLTISDLECDDAATYYC | LGGYASTIDMNA | FGGGTEVVVK |
| 65D3-1 Lv1 | SGTQFTLTISDLECDDAATYYC | LGGYASTIDMNA | FGGGTEVVVK |
| 67G8-2 L | SGTQFTLTIWNMCDDAATYYC | AGCFPSKSDMNG | FGGGTEVVVK |

FIGURE 18

Biacore 8K data:

| | Chi$^2$ | Ka (1/Ms) | Kd (1/s) | KD (M) | Rmax (RU) |
|---|---|---|---|---|---|
| 65D3-1 Hv0 Lv0 (WT) | $5.32 \times 10^{-1}$ | $2.25 \times 10^{5}$ | $1.70 \times 10^{-4}$ | $7.55 \times 10^{-10}$ | 69.3 |
| 65D3-1 Hv1 Lv0 | $1.07 \times 10^{-1}$ | $1.28 \times 10^{5}$ | $2.60 \times 10^{-4}$ | $2.03 \times 10^{-9}$ | 41.2 |
| 65D3-1 Hv1 Lv1 | $2.57 \times 10^{-1}$ | $1.20 \times 10^{5}$ | $3.93 \times 10^{-4}$ | $3.27 \times 10^{-9}$ | 42.6 |
| 65D3-1 Hv2 Lv1 | $1.49 \times 10^{-1}$ | $1.04 \times 10^{5}$ | $2.70 \times 10^{-4}$ | $2.70 \times 10^{-9}$ | 61.9 |
| 67G8-2L | $1.08 \times 10^{-1}$ | $2.99 \times 10^{5}$ | $3.02 \times 10^{-5}$ | $1.01 \times 10^{-10}$ | 97.2 |

FIGURE 19

| Ligand: | 65D3-1 IgGs | 67G8-2 IgG |
|---|---|---|
| Immobilization level (Ru) | ~6000 | 7206 |
| Association contact time(s) | 180 | 180 |
| Dissociation contact time(s) | 600 | 600 |
| Flow rate(μl/min) | 30 | 30 |
| Sample concentrations(nM) | 1.56 - 100 | 3.12 - 200 |

FIGURE 20

<u>1593 Peptide</u>

<u>Sequence and LC-MS Data</u>

<u>First round had 65D3-1 and Second round had the additional, including 67G8-2</u>

<u>HEAVY CHAIN</u>  Signal peptide                          *FR1*              <u>CDR1</u>       *FR2*          <u>CDR2</u>
  65D3-1H    METGLRWLLLVAVLKGVQCQS*EESGGRLVTPG*SLTLTCTVSGFSLS<u>THDIS</u>*WVRQAPGKGLEWIG*<u>VIARRGSI</u>

67G8-2H    METGLRWLLLVAVLKGVQCQS*VEESGGRLVTPGTPLTLTCTVSGFSL*S<u>NYDGH</u>*WVRQPEKGLEWIG*<u>VIAIIGDT</u>
  135A6-1H   METGLRWLLLVAVLKGVQCQS*VEESGGRLVTPGTPLTLTCTVSGFSL*S<u>NYDIS</u>*WVRQAPGKGLEWIG*<u>VIATVGDT</u>
  101G10-2H  MEAGLRWLLLVAVLKGVQCQS*VEESGGRLVTPGTPLTLTCTVSGFSL*S<u>SYDMT</u>*WVRQAPGKGLEIG*<u>VISVGGA</u>
  125D9-1H   MEAGLRWLLLVAVLKGVQC*VEESGGRLVTPGTPLTLTCTVSGFSL*S<u>SYDMT</u>*WVRQAPGKGLEIG*<u>VVAYGGAI</u>
  91B4-1H    METGLRWLLLVAVLKGVQCQS*EESGGRLVSPG*SLTLTCTVSG*DLSR<u>FGVS</u>*WVRQAPGKGLEWTG*<u>YIHTDGNV</u>

<u>CDR2</u>      *FR3*              <u>CDR3</u>        *FR4*
  65D3-1H   <u>YYASWAKG</u>*RFTISKTSTTVDLKITSPT*EDTATYFCAR<u>EEDE</u>------*WGQGTLVTVSS*

67G8-2H   <u>YYASWAKG</u>*RFSISKTS*TVL*K*ITSPTTEDTATYFC*<u>RGDSRTSNEIFNL</u>*WGQGTLVTVSS*
  135A6-1H  <u>YYASWAKG</u>*RFTISKTS*TVDLKITSPTTEDTATYFC*<u>RGDSPSTNEIFGL</u>*WGQGTLVTVSS*
  101G10-2H <u>YYASWAKG</u>*RFTISKTSTTVDLKITSPTTEDTATYFCAR*<u>GDSDGSSELFNL</u>*WGQGTLVTVSS*
  125D9-1H  <u>YYASWAKG</u>*RFTISKTSTTVDLKITSPTTEDTATYFCAR*<u>GDSDGSSELFNL</u>*WGQGTLVTVSS*
  91B4-1H   <u>YYASWAKG</u>*RFTISKTSTTVDLK*TS*TTEDTATYFCAR*<u>GGYAADL</u>-----*WGQGLVTVSS*

<u>LIGHT CHAIN</u>  Signal peptide                          *FR1*              <u>CDR1</u>         *FR2*         <u>CDR2</u>
  65D3-1L    MDTRAPTQLLGLLLLWLPGATFA*AVLTQT*SPVSAAVGGTVTISC<u>QSSQSVYNNKELS</u>*WQQKPGQPPKLLI*<u>YVA</u>

67G8-2L    MDTRAPTQLLGLLLLWLPGATFA*AVLTQTPSPVSAAVGGT*TINC<u>QSTRSVHNNICLS</u>*WYQQKPGQPPKLLIY*<u>SA</u>
  135A6-1L   MDTRAPTQLLGLLLLWLPGATFA*AVLTQTPSPVSAAVGGT*TINC<u>QSSRTVYNNICLS</u>*WYQQKGQPPKLLIY*<u>QA</u>
  101G10-2L  MDTRAPTQLLGLLLLWLPGAAFA*AVLTQTPSPVSAVGGTV*INC<u>QSSKSVYNNICLS</u>*WYQQKPGQPPNLLIY*GA
  125D9-1L   MDTRAPTQLLGLLLLWLPGATFA*AVLTQTPSPVSAAVGGTVTINC*<u>QSSKSVYNNICLS</u>*WYQQKGQPPKLLIY*<u>QA</u>
  91B4-1L    MDTRAPTQLLGLLLLWLPGAKC*NL*TQTPS*VSAAVGGTVTISC<u>QSSESVYKNY</u>-LA*WYQQKLGQPPKLLI*<u>AI</u>

<u>CDR2</u>     *FR3*               <u>CDR3</u>          *FR4*
  65D3-1L   <u>STLAS</u>*GVPSRFKGSGSGTQFTLTISDI*ECDDAATYYC<u>LGGYASTIDMVA</u>*FGGGTEVVVK*

67G8-2L   <u>STLAS</u>*GVPSRFKGSGSGTQFTL*INDVQC*DDAATYYC<u>AGCFPSKSDMYG</u>*FGGGTEVVVK*
  135A6-1L  <u>STLTS</u>*GVPSRFKGSGSGTQFTLTINDVQC*DDAATYYC<u>AGCFPSTSDMYG</u>*FGGGTEVVVK*
  101G10-2L <u>STLAS</u>*GVPSRFKGSGSGTQFTLTINDVQCDDAATYYC*<u>AGCFASTNDMYG</u>*FGGGTEVVVK*
  125D9-1L  <u>STPAS</u>*GVPSRFKGSGSGTQFTLTINDVQCDDAATYYC*<u>AGCFASTSDMYG</u>*FGGGTEVVVK*
  91B4-1L   <u>STLVS</u>*GVPSRFKGSGS*TQF*LTISDI*CDDAATYYC<u>VGGYIGKNV</u>---*FGGGTEVVVK*

FIGURE 21

HEAVY CHAIN

|          | ----V allele---- | --------D allele-------- | --J allele-- |
|----------|------------------|--------------------------|--------------|
| 65D3-1H  | V1S69*01         | [unknown]                | J4*01        |
| 67G8-2H  | V1S69*01         | D8-1*01                  | J4*01        |
| 135A6-1H | V1S69*01         | D4-2*01                  | J4*01        |
| 101G10-2H| V1S69*01         | D8-1*01                  | J4*01        |
| 125D9-1H | V1S69*01         | D8-1*01                  | J4*01        |
| 91B4-1H  | V1S44*01         | D7-1*01                  | J2*01        |

LIGHT CHAIN

|          | ------------V region alleles------------ | | | | J allele |
|----------|------|------|------|------|----------|
| 65D3-1L  | V1S12*01 V1S40*01 V1S52*01 | | | | J1-2*01 |
| 67G8-2L  | V1S68*01 | | | | J1-2*01 |
| 135A6-1L | V1S52*01 | V1S63*01 | | | J1-2*01 |
| 101G10-2L| V1S52*01 | V1S63*01 | | | J1-2*01 |
| 125D9-1L | V1S52*01 | V1S63*01 | | | J1-2*01 |
| 91B4-1L  | V1S52*01 | | | | J1-2*01 |

FIGURE 23

Figure 24:
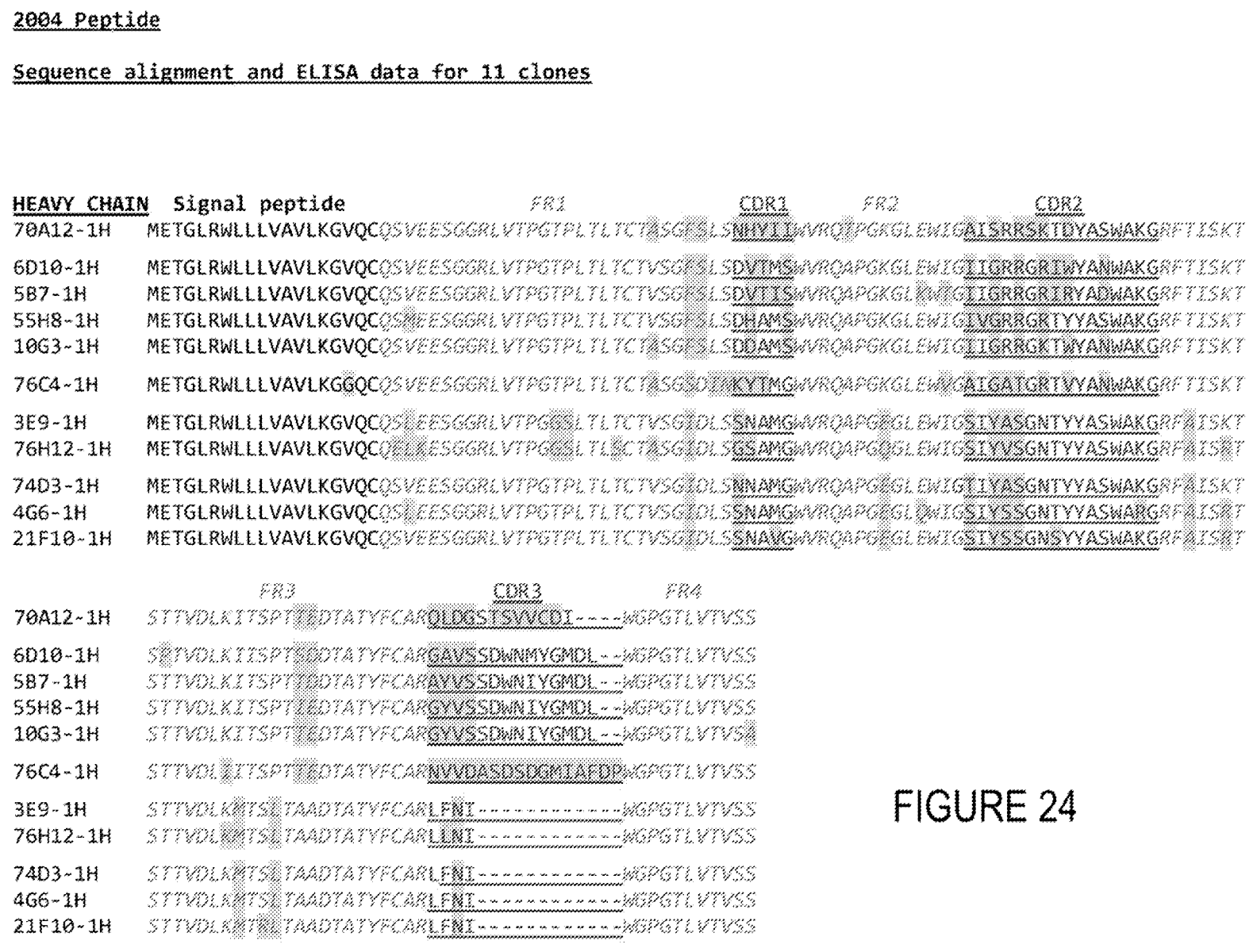

2004 Peptide

Sequence alignment and ELISA data for 11 clones

HEAVY CHAIN   Signal peptide

70A12-1H   METGLRWLLLVAVLKGVQC...

LIGHT CHAIN     Signal peptide                    FR1                          CDR1                   FR2              CDR2

70A12-1L     MDTRAPTQLLGLLLLWLPGATFA-QVLTQTPSPVSAAVGGTVTIMCQASQNVYNDRNLAWYQQKPGQPPKLLIYGPSTLASGVSRFKGS

6D10-1L      MDTRAPTQLLGLLLLWLPGATFA-QVLTQTPSPVSAPVGGTVTIMCQSSQSVYNMENLAWYQQKPGQPPKLLIYGASTLASGVSRFKGS
5B7-1L       MDTRAPTQLLGLLLLWLPGATFA-QVLTQTPSPVSAPVGGTVTIMCQASQSVYNKNLAWYQQKPGQPPKLLIYEASKLASGVSRFKGS
55H8-1L      MDTRAPTQLLGLLLLWLPGATFA-QVLTQTPSPVSAAVGGTVTIMCQASQSVYNKNLAWYQQKPGQPPKLLIYEASTLASGVSRFKGS
10G3-1L      MDTRAPTQLLGLLLLWLPGATFA-QVLTQTPSPVSAAVGGTVTIMCQASQSVYNKNLAWYQQKPGQPPKLLIYEASKLASGVSRFKGS

76C4-1L      MDTRAPTQLLGLLLLWLPGATFA-QVLTQTPSPVSAAVGGTVTIMCQASQSVYNKNLAWYQQKPGQPPKLLIYKASTLASGVSRFKGS

3E9-1L       MDTRAPTQLLGLLLLWLPGARCAD-VLTQTPSSVSVSPVGGTVTIMCQASQSVFDNKNLSWYQQKPGQPPKQLIYGASTLDSGVPSRFKGS
76H12-1L     MDTRAPTQLLGLLLLWLPGARCAD-VLTQTPSAVSAAVGGTVTIMCQASQSVYDNKNLAWYQQKPGQPPKQLIYGASTLASGVPSRFKGS

74D3-1L      MDTRAPTQLLGLLLLWLPGARCAD-VLTQTPSASVSAAVGGTVTIMCQASQSVYDNKNLSWYQQKPGQPPKQLIYKASTLASGVPSRFKGS
4G6-1L       MDTRAPTQLLGLLLLWLPGARCAD-VLTQTPSASVSAAVGGTVTIMCQASQSVYDNKNLAWYQQKPGQPPKQLIYGASTVASGVPSRFKGS
21F10-1L     MDTRAPTQLLGLLLLWLPGARCAD-VLTQTPSASVSAAVGGTVTIMCQASQSVYDNKNLSWYQQKPGQPPKQLIYGASTLASGVPSRFKGS

FR3                            CDR3                    FR4

70A12-1L     GSGTQFTLTISGVQCEDAATYYCQGEFICSSADCRAFGGGTEVVK

6D10-1L      GSGTQFALTISGVQCEDAATYYCQGEFDCSSADCFVFGGGTEVVK
5B7-1L       GSGTQFALTISGVQCEDAATYYCQGEFDCSSADCFVFGGGTEVVK
55H8-1L      GSGTQFTLTISGVQCEDAATYYCQGEFDCSSADCFAFGGGTEVVK
10G3-1L      GSGTQFTLTISGVQCEDAATYYCQGEFSCSSADCFTFGGGTEVVK

76C4-1L      GSGTQFTLTISGVQCEDAATYYCQGEFSCSSGDCVAFGGGTEVVK

3E9-1L       GSGTQFTLTISGVQCEDAATYYCGGRDSGNIYD---FGGGTEVVK
76H12-1L     GSGTQFTLTISGVQCEDAATYYCGGRDSDNIYD---FGGGTEVVK

74D3-1L      GSGTQFTLTISGVQCEDAATYYCGGRDSGNIYD---FGGGTEVVK
4G6-1L       GSGTQFTLTISGVQCEDAATYYCGGRDNNIYD---FGGGTEVVK
21F10-1L     GSGTQFTLTISGVQCEDAATYYCGGRDDNIYD---FGGGTEVVK

FIGURE 24 CONT

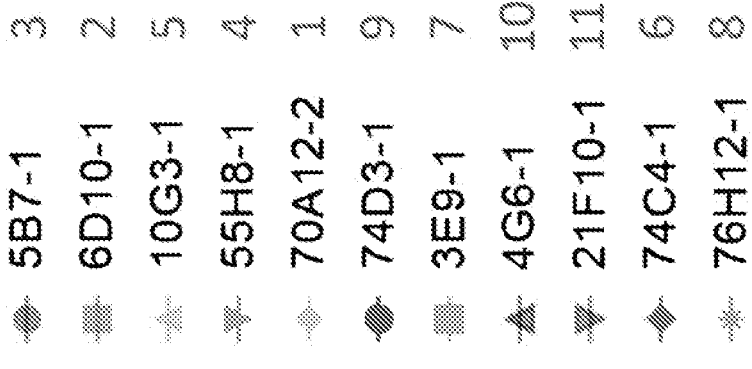
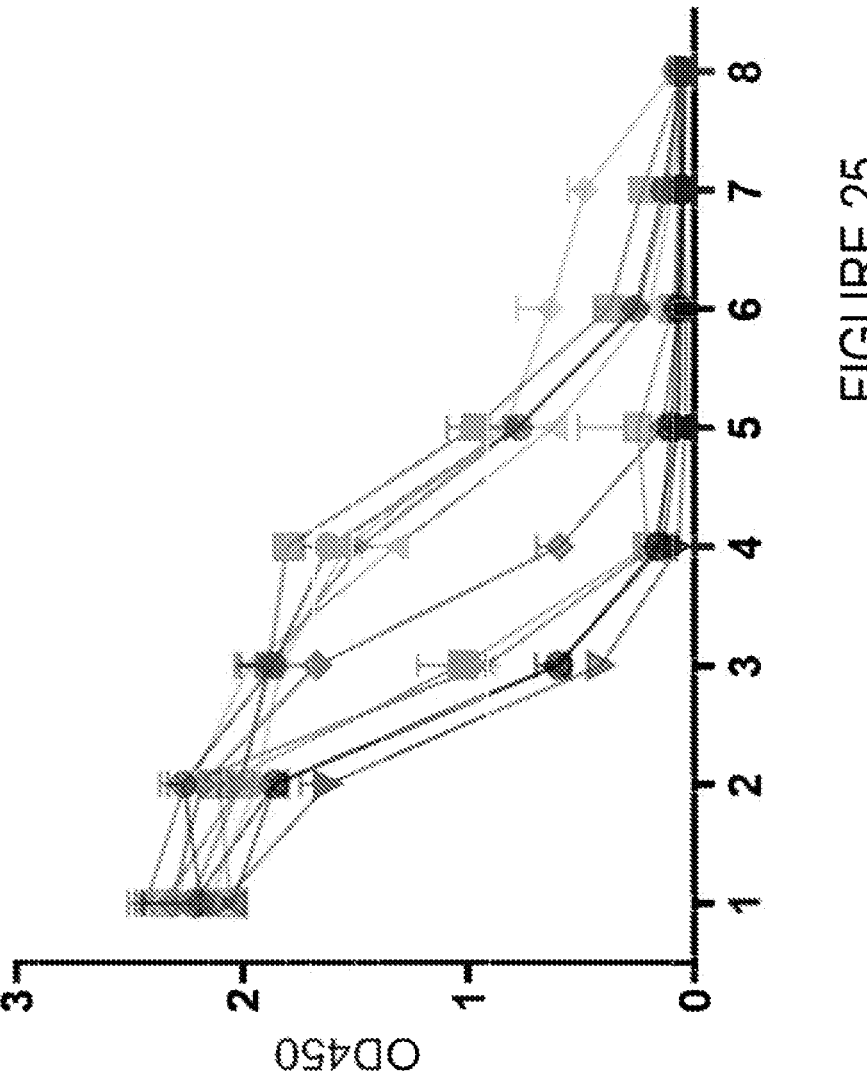
FIGURE 25

HEAVY CHAIN

| | ----V allele---- | ---------------D allele------------------- | ------J allele------ | |
|---|---|---|---|---|
| 3E9-1H | V1S44*01 | D2-1*01 | J4*02 | |
| 4G6-1H | V1S69*01 | | J4*02 | |
| 5B7-1H | V1S69*01 | D4-1*01 | J6*01 | |
| 6D10-1H | V1S69*01 | D4-1*01 | J6*01 | |
| 10G3-1H | V1S69*01 | D4-1*01 | J6*01 | |
| 21F10-1H | V1S69*01 | | J4*02 | |
| 55H8-1H | V1S69*01 | D4-1*01 | J6*01 | |
| 70A12-1H | V1S69*01 | D5-1*01 | J4*02 | |
| 74D3-1H | V1S69*01 | | J4*02 | |
| 76C4-1H | V1S69*01 | D6-1*01 | J2*01 | |
| 76H12-1 | V1S69*01 | D1-1*01 D8-1*01 | J4*02 | |

LIGHT CHAIN

| | -----------V region alleles----------- | J allele |
|---|---|---|
| 3E9-1L | V1S31*01 | J1-2*02 |
| 4G6-1L | V1S31*01 | J1-2*02 |
| 5B7-1L | V1S46*01 | J1-2*02 |
| 6D10-1L | V1S59*01 | J1-2*02 |
| 10G3-1L | V1S62*01 | J1-2*02 |
| 21F10-1L | V1S31*01 | J1-2*02 |
| 55H8-1L | V1S16*01 | J1-2*02 |
| 70A12-1L | V1S59*01 | J1-2*02 |
| 74D3-1L | V1S31*01 | J1-2*02 |
| 76C4-1L | V1S16*01 | J1-2*01 |
| 76H12-1 | V1S31*01 | J1-2*02 |

FIGURE 26

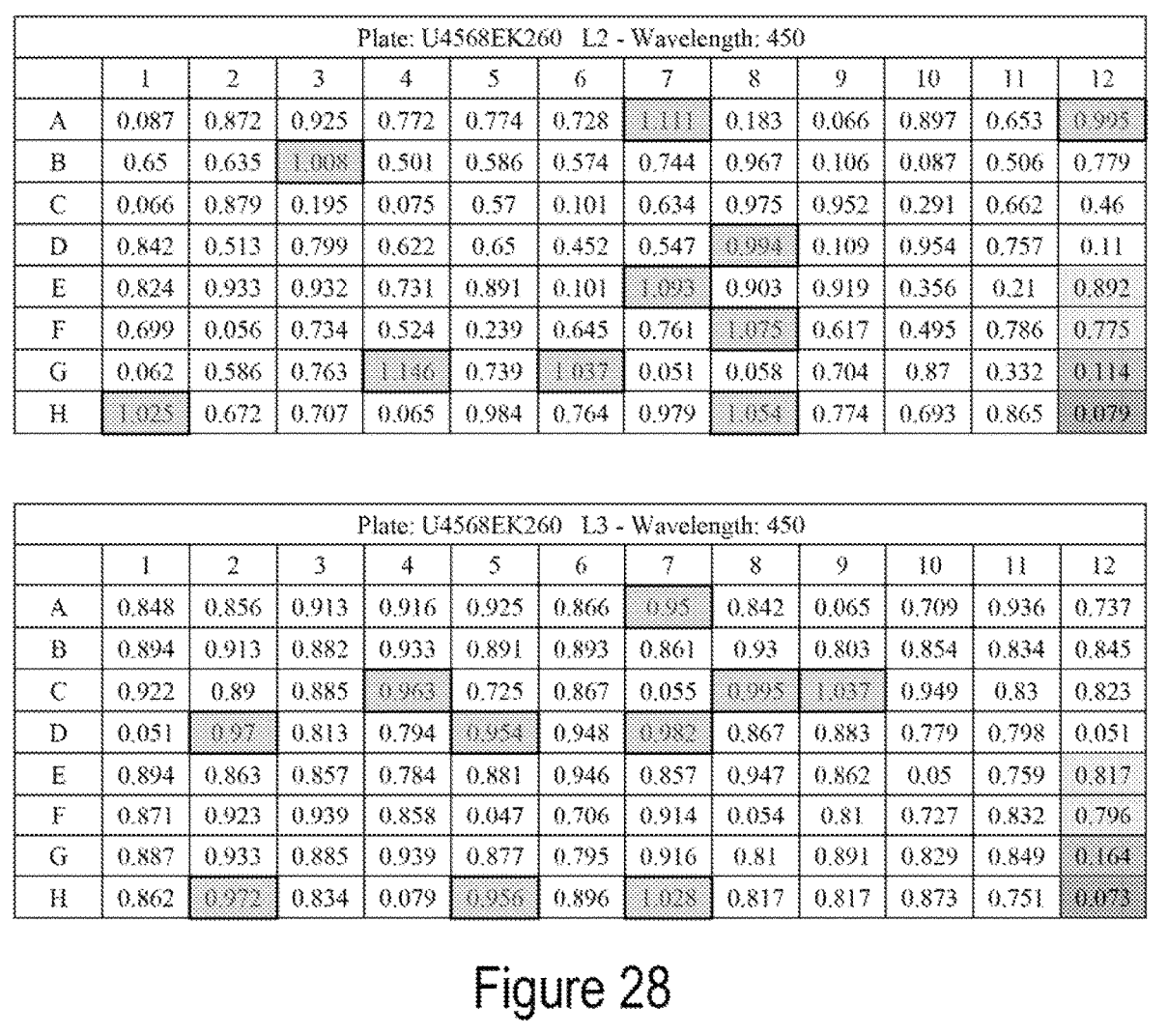

| Plate: U4568EK260  L2 - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 0.087 | 0.872 | 0.925 | 0.772 | 0.774 | 0.728 | 1.111 | 0.183 | 0.066 | 0.897 | 0.653 | 0.995 |
| B | 0.65 | 0.635 | 1.008 | 0.501 | 0.586 | 0.574 | 0.744 | 0.967 | 0.106 | 0.087 | 0.506 | 0.779 |
| C | 0.066 | 0.879 | 0.195 | 0.075 | 0.57 | 0.101 | 0.634 | 0.975 | 0.952 | 0.291 | 0.662 | 0.46 |
| D | 0.842 | 0.513 | 0.799 | 0.622 | 0.65 | 0.452 | 0.547 | 0.994 | 0.109 | 0.954 | 0.757 | 0.11 |
| E | 0.824 | 0.933 | 0.932 | 0.731 | 0.891 | 0.101 | 1.093 | 0.903 | 0.919 | 0.356 | 0.21 | 0.892 |
| F | 0.699 | 0.056 | 0.734 | 0.524 | 0.239 | 0.645 | 0.761 | 1.075 | 0.617 | 0.495 | 0.786 | 0.775 |
| G | 0.062 | 0.586 | 0.763 | 1.146 | 0.739 | 1.037 | 0.051 | 0.058 | 0.704 | 0.87 | 0.332 | 0.114 |
| H | 1.025 | 0.672 | 0.707 | 0.065 | 0.984 | 0.764 | 0.979 | 1.054 | 0.774 | 0.693 | 0.865 | 0.079 |

| Plate: U4568EK260  L3 - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 0.848 | 0.856 | 0.913 | 0.916 | 0.925 | 0.866 | 0.95 | 0.842 | 0.065 | 0.709 | 0.936 | 0.737 |
| B | 0.894 | 0.913 | 0.882 | 0.933 | 0.891 | 0.893 | 0.861 | 0.93 | 0.803 | 0.854 | 0.834 | 0.845 |
| C | 0.922 | 0.89 | 0.885 | 0.963 | 0.725 | 0.867 | 0.055 | 0.995 | 1.037 | 0.949 | 0.83 | 0.823 |
| D | 0.051 | 0.97 | 0.813 | 0.794 | 0.954 | 0.948 | 0.982 | 0.867 | 0.883 | 0.779 | 0.798 | 0.051 |
| E | 0.894 | 0.863 | 0.857 | 0.784 | 0.881 | 0.946 | 0.857 | 0.947 | 0.862 | 0.05 | 0.759 | 0.817 |
| F | 0.871 | 0.923 | 0.939 | 0.858 | 0.047 | 0.706 | 0.914 | 0.054 | 0.81 | 0.727 | 0.832 | 0.796 |
| G | 0.887 | 0.933 | 0.885 | 0.939 | 0.877 | 0.795 | 0.916 | 0.81 | 0.891 | 0.829 | 0.849 | 0.164 |
| H | 0.862 | 0.972 | 0.834 | 0.079 | 0.956 | 0.896 | 1.028 | 0.817 | 0.817 | 0.873 | 0.751 | 0.073 |

Figure 28

| Plate: U4568EK260   L5 - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 0.997 | 0.944 | 0.949 | 0.955 | 0.992 | 1.111 | 0.078 | 0.933 | 0.894 | 0.134 | 0.845 | 0.975 |
| B | 0.9 | 1.04 | 1.039 | 0.853 | 1.05 | 0.933 | 0.886 | 0.964 | 1.007 | 0.578 | 0.913 | 1.012 |
| C | 0.852 | 1.159 | 0.1 | 1.098 | 0.955 | 1.051 | 0.945 | 1.112 | 1.076 | 1.059 | 1.007 | 1.003 |
| D | 0.057 | 0.925 | 0.913 | 0.964 | 0.975 | 0.923 | 1.058 | 0.123 | 0.961 | 1 | 0.956 | 0.867 |
| E | 0.916 | 1.024 | 0.643 | 1.033 | 0.987 | 0.972 | 1.013 | 1.008 | 0.974 | 0.911 | 0.872 | 0.7 |
| F | 0.942 | 1.158 | 0.099 | 1.117 | 1.14 | 1.057 | 1.041 | 1.092 | 1.074 | 0.057 | 0.88 | 0.854 |
| G | 0.231 | 1.015 | 0.928 | 1.049 | 0.821 | 1.039 | 0.997 | 0.972 | 0.63 | 1.117 | 0.089 | 0.222 |
| H | 0.918 | 0.995 | 0.086 | 1.047 | 1.066 | 0.871 | 0.117 | 1.047 | 0.899 | 0.799 | 0.934 | 0.088 |

| Plate: U4568EK260   L8 - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 0.492 | 0.779 | 0.769 | 0.056 | 0.819 | 0.974 | 0.778 | 0.058 | 0.857 | 0.73 | 0.474 | 0.668 |
| B | 0.668 | 0.867 | 0.767 | 0.742 | 1.019 | 0.303 | 0.792 | 0.811 | 0.783 | 1.043 | 0.058 | 0.623 |
| C | 0.831 | 0.957 | 0.593 | 1.026 | 0.899 | 0.877 | 0.799 | 0.104 | 0.792 | 1.024 | 0.664 | 0.698 |
| D | 0.683 | 0.763 | 0.601 | 0.062 | 0.055 | 0.595 | 0.744 | 0.521 | 0.779 | 0.717 | 0.651 | 0.651 |
| E | 0.127 | 0.642 | 0.099 | 0.055 | 0.84 | 0.818 | 0.795 | 0.945 | 0.489 | 0.626 | 0.85 | 0.743 |
| F | 0.743 | 0.686 | 0.913 | 1.006 | 0.749 | 0.825 | 1.161 | 0.536 | 0.818 | 0.217 | 1.009 | 0.782 |
| G | 0.678 | 0.096 | 0.921 | 0.607 | 0.793 | 0.056 | 0.682 | 0.861 | 0.672 | 0.754 | 0.069 | 0.139 |
| H | 0.065 | 0.903 | 0.776 | 0.797 | 0.609 | 0.958 | 0.698 | 0.774 | 0.584 | 0.914 | 0.419 | 0.055 |

| Plate: U4568EK050   L18 - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 0.803 | 0.845 | 0.795 | 0.885 | 0.067 | 0.811 | 0.852 | 0.851 | 0.884 | 0.796 | 0.72 | 0.751 |
| B | 0.796 | 0.755 | 0.053 | 0.869 | 0.812 | 0.856 | 0.858 | 0.875 | 0.801 | 0.833 | 0.813 | 0.794 |
| C | 0.78 | 0.817 | 0.86 | 0.867 | 0.878 | 0.782 | 0.858 | 0.782 | 0.679 | 0.802 | 0.773 | 0.779 |
| D | 0.848 | 0.876 | 0.051 | 0.872 | 0.878 | 0.186 | 0.902 | 0.872 | 0.895 | 0.84 | 0.859 | 0.761 |
| E | 0.817 | 0.858 | 0.797 | 0.846 | 0.968 | 0.807 | 0.882 | 0.803 | 0.815 | 0.902 | 0.729 | 0.658 |
| F | 0.783 | 0.934 | 0.056 | 0.891 | 0.868 | 0.937 | 0.047 | 0.898 | 0.83 | 0.808 | 0.046 | 0.834 |
| G | 0.056 | 0.884 | 0.774 | 0.845 | 0.842 | 0.82 | 0.825 | 0.87 | 0.831 | 0.791 | 0.755 | 0.061 |
| H | 0.807 | 0.056 | 0.76 | 0.773 | 0.873 | 0.847 | 0.808 | 0.853 | 0.775 | 0.058 | 0.742 | 0.049 |

Figure 28 CON'T

Plate: U4568EK050  L20 - Wavelength: 450

|   | 1 | 2 | 3 | 4 | 5 | 6 | 7 | 8 | 9 | 10 | 11 | 12 |
|---|---|---|---|---|---|---|---|---|---|----|----|----|
| A | 0.44 | 0.495 | 0.486 | 0.05 | 0.472 | 0.052 | 0.836 | 0.053 | 0.505 | 0.46 | 0.485 | 0.055 |
| B | 0.477 | 0.56 | 0.487 | 0.509 | 0.504 | 0.499 | 0.508 | 0.047 | 0.473 | 0.488 | 0.464 | 0.489 |
| C | 0.455 | 0.47 | 0.523 | 0.526 | 0.49 | 0.434 | 0.505 | 0.442 | 0.046 | 0.501 | 0.492 | 0.453 |
| D | 0.509 | 0.556 | 0.047 | 0.502 | 0.529 | 0.458 | 0.523 | 0.509 | 0.52 | 0.509 | 0.437 | 0.518 |
| E | 0.47 | 0.501 | 0.072 | 0.049 | 0.514 | 0.422 | 0.533 | 0.473 | 0.492 | 0.455 | 0.4 | 0.478 |
| F | 0.479 | 0.473 | 0.047 | 0.049 | 0.491 | 0.848 | 0.513 | 0.505 | 0.436 | 0.46 | 0.448 | 0.475 |
| G | 0.398 | 0.42 | 0.548 | 0.445 | 0.507 | 0.874 | 0.527 | 0.475 | 0.474 | 0.045 | 0.045 | 0.048 |
| H | 0.44 | 0.447 | 0.054 | 0.977 | 0.052 | 0.596 | 0.052 | 0.387 | 0.46 | 0.496 | 0.408 | 0.05 |

Plate: U4568EK260  H17 - Wavelength: 450

|   | 1 | 2 | 3 | 4 | 5 | 6 | 7 | 8 | 9 | 10 | 11 | 12 |
|---|---|---|---|---|---|---|---|---|---|----|----|----|
| A | 0.499 | 0.07 | 0.54 | 0.481 | 0.586 | 0.695 | 0.661 | 0.578 | 0.533 | 0.525 | 0.514 | 0.62 |
| B | 0.487 | 0.56 | 0.629 | 0.567 | 0.552 | 0.632 | 0.544 | 0.623 | 0.611 | 0.549 | 0.615 | 0.511 |
| C | 0.063 | 0.533 | 0.574 | 1.282 | 0.593 | 0.617 | 0.66 | 0.603 | 0.59 | 0.633 | 0.575 | 0.055 |
| D | 0.55 | 0.369 | 0.052 | 0.62 | 0.677 | 0.61 | 0.724 | 0.592 | 0.584 | 0.336 | 0.568 | 0.562 |
| E | 0.522 | 0.505 | 0.582 | 0.546 | 0.595 | 0.585 | 0.567 | 0.061 | 0.655 | 0.391 | 0.545 | 0.616 |
| F | 0.563 | 0.594 | 0.598 | 0.64 | 0.691 | 0.681 | 0.587 | 0.606 | 0.058 | 0.572 | 0.761 | 0.629 |
| G | 0.51 | 0.631 | 0.566 | 0.516 | 0.607 | 0.527 | 0.61 | 0.728 | 0.593 | 0.664 | 0.607 | 0.053 |
| H | 0.556 | 0.545 | 0.604 | 0.633 | 0.649 | 0.637 | 0.72 | 0.624 | 0.583 | 0.588 | 0.561 | 0.049 |

Plate: U4568EK260  H25 - Wavelength: 450

|   | 1 | 2 | 3 | 4 | 5 | 6 | 7 | 8 | 9 | 10 | 11 | 12 |
|---|---|---|---|---|---|---|---|---|---|----|----|----|
| A | 0.553 | 0.624 | 0.589 | 0.23 | 0.663 | 0.199 | 0.643 | 0.603 | 0.532 | 0.498 | 0.566 | 0.051 |
| B | 0.056 | 0.613 | 0.62 | 0.658 | 0.549 | 0.054 | 0.769 | 0.673 | 0.813 | 0.722 | 0.558 | 0.057 |
| C | 0.592 | 0.588 | 0.054 | 0.666 | 0.053 | 0.504 | 0.053 | 0.053 | 0.642 | 0.099 | 0.622 | 0.376 |
| D | 0.643 | 0.723 | 0.698 | 0.739 | 0.69 | 0.046 | 0.45 | 0.049 | 0.757 | 0.704 | 0.773 | 0.738 |
| E | 0.057 | 0.872 | 0.689 | 0.599 | 0.643 | 0.639 | 0.054 | 0.627 | 0.055 | 0.055 | 0.581 | 0.675 |
| F | 0.642 | 0.052 | 0.584 | 0.686 | 0.051 | 0.714 | 0.45 | 0.693 | 0.638 | 0.052 | 0.05 | 0.568 |
| G | 0.616 | 0.601 | 0.694 | 0.637 | 0.665 | 0.658 | 0.723 | 0.059 | 0.751 | 0.685 | 0.051 | 0.052 |
| H | 0.707 | 0.5 | 0.656 | 0.639 | 0.68 | 0.056 | 0.061 | 0.05 | 0.052 | 0.625 | 0.63 | 0.048 |

Figure 28 CON'T

| | 1 | 2 | 3 | 4 | 5 | 6 | 7 | 8 | 9 | 10 | 11 | 12 |
|---|---|---|---|---|---|---|---|---|---|---|---|---|
| | | | | Plate: U4568EK260   H26 - Wavelength: 450 | | | | | | | | |
| A | 0.711 | 0.68 | 0.36 | 0.722 | 0.763 | 0.75 | 0.859 | 0.809 | 0.801 | 0.781 | 0.055 | 0.605 |
| B | 0.732 | 0.759 | 0.738 | 0.789 | 0.817 | 0.782 | 0.782 | 0.719 | 0.755 | 0.73 | 0.705 | 0.756 |
| C | 0.812 | 0.791 | 0.724 | 0.597 | 0.726 | 0.763 | 0.846 | 0.849 | 0.724 | 0.738 | 0.783 | 0.784 |
| D | 0.286 | 0.734 | 0.779 | 0.318 | 0.824 | 0.715 | 0.731 | 0.709 | 0.779 | 0.752 | 0.66 | 0.652 |
| E | 0.764 | 0.745 | 0.787 | 0.662 | 0.856 | 0.721 | 0.879 | 0.565 | 0.775 | 0.781 | 0.801 | 0.879 |
| F | 0.776 | 0.722 | 0.727 | 1.091 | 0.849 | 0.87 | 0.75 | 0.84 | 0.385 | 0.685 | 0.678 | 0.794 |
| G | 0.704 | 0.748 | 0.698 | 0.411 | 0.727 | 0.75 | 0.808 | 0.796 | 0.73 | 0.473 | 0.623 | 0.058 |
| H | 0.587 | 0.779 | 0.107 | 0.673 | 0.707 | 0.77 | 0.774 | 0.785 | 0.691 | 0.694 | 0.734 | 0.094 |

Chimeric was marked yellow, negative control was marked green, blank was marked blue.

Figure 28 CON'T

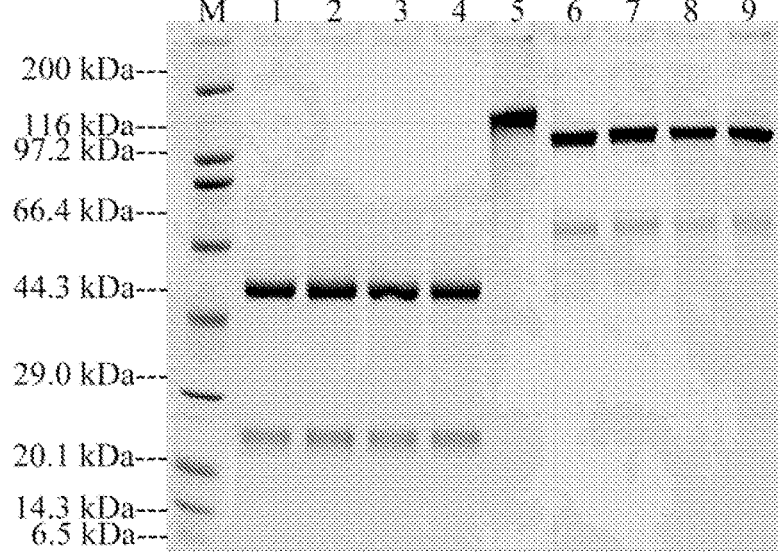

Lane M: Marker: TaKaRa, Cat. No. 3452.
Lane 1: U4568EK260 S55W&G64K-VH+S57T-VL under reducing condition          Purity: 99%
Lane 2: U4568EK260 S55W-VH+S57T-VL under reducing condition               Purity: 99%
Lane 3: U4568EK260 S55W-VH+VL under reducing condition                    Purity: 99%
Lane 4: U4568EK260 VH+VL under reducing condition                         Purity: 99%
Lane 5: Human IgG under non-reducing condition
Lane 6: U4568EK260 S55W&G64K-VH+S57T-VL under non-reducing condition   Purity: 90%
Lane 7: U4568EK260 S55W-VH+S57T-VL under non-reducing condition            Purity: 90%
Lane 8: U4568EK260 S55W-VH+VL under non-reducing condition                 Purity: 91%
Lane 9: U4568EK260 VH+VL under non-reducing condition                      Purity: 90%

Figure 29

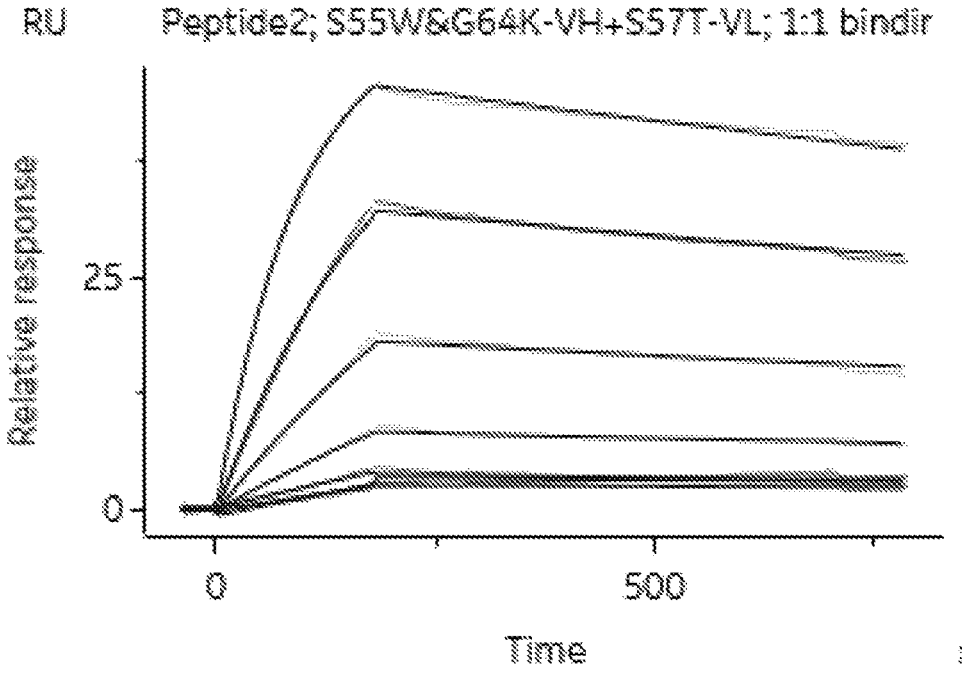
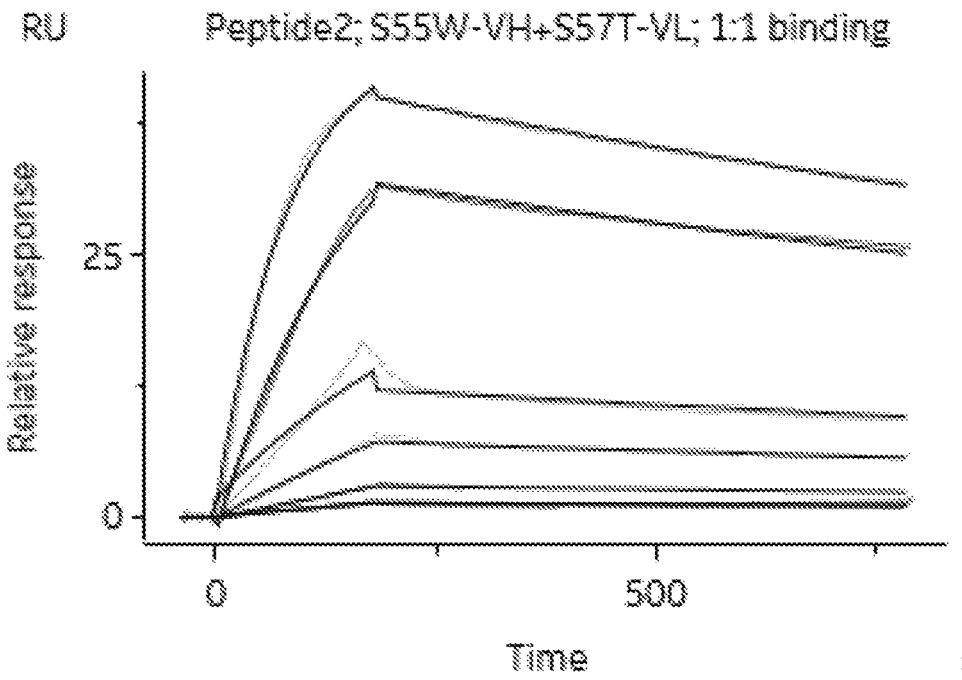
FIGURE 30

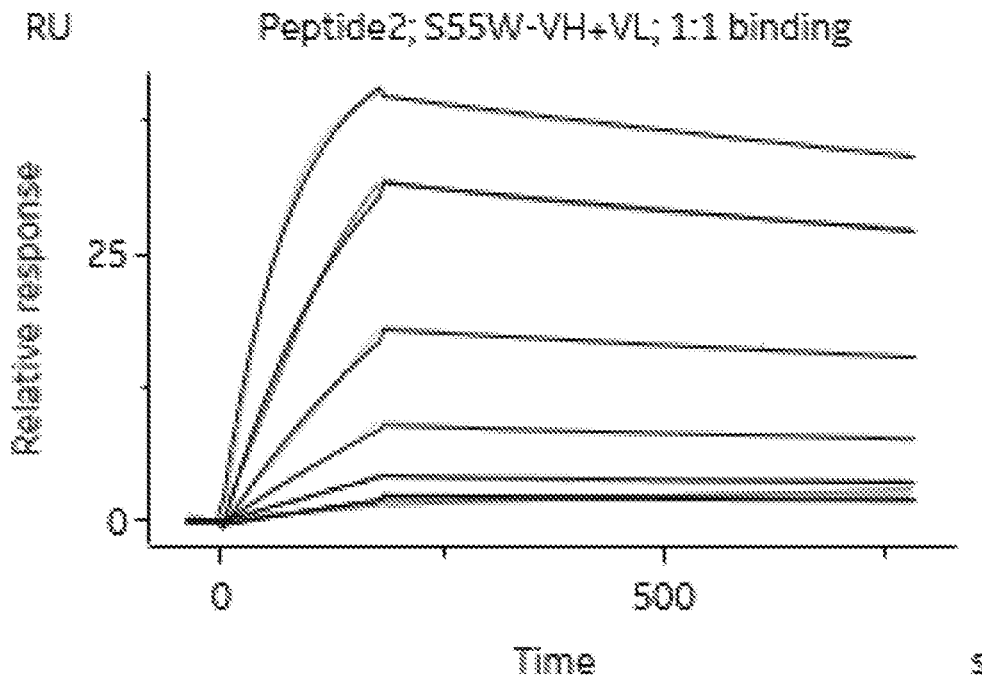
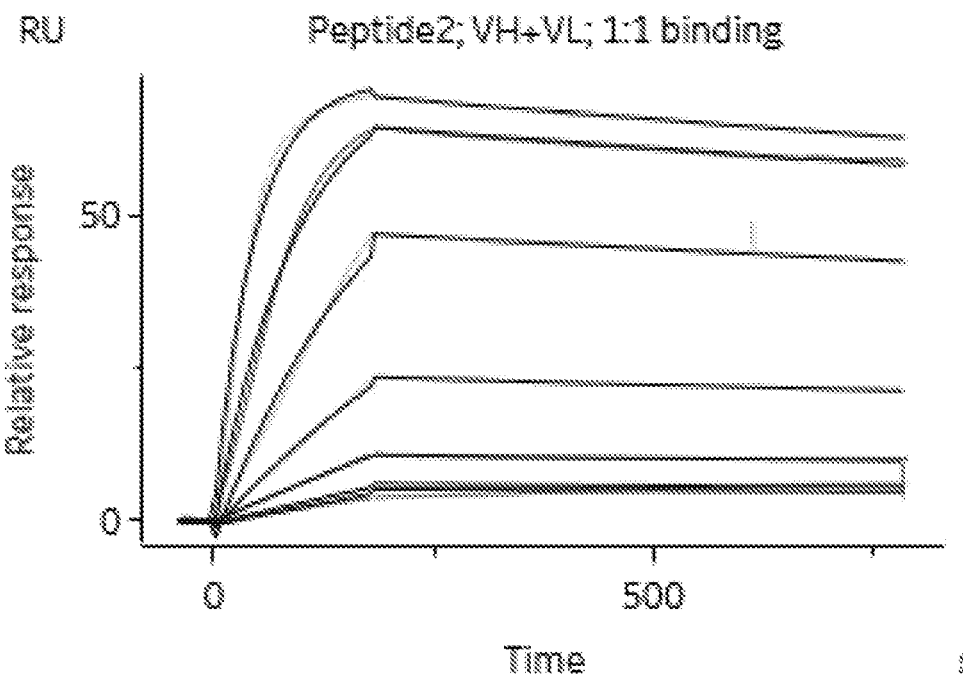
FIGURE 30 CON'T

| Plate: U4568EK260 R1 - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 0.156 | 0.184 | 0.082 | 0.078 | 0.284 | 0.081 | 0.082 | 0.136 | 0.235 | 0.078 | 0.139 | 0.119 |
| B | 0.267 | 0.19 | 0.289 | 0.1 | 0.105 | 0.287 | 0.104 | 0.086 | 0.284 | 0.202 | 0.287 | 0.246 |
| C | 0.394 | 0.265 | 0.11 | 0.158 | 0.233 | 0.313 | 0.09 | 0.082 | 0.187 | 0.319 | 0.097 | 0.165 |
| D | 0.168 | 0.395 | 0.277 | 0.11 | 0.275 | 0.207 | 0.08 | 0.076 | 0.108 | 0.113 | 0.49 | 0.202 |
| E | 0.084 | 0.335 | 0.184 | 0.227 | 0.089 | 0.081 | 0.112 | 0.3 | 0.289 | 0.104 | 0.318 | 0.094 |
| F | 0.079 | 0.078 | 0.074 | 0.213 | 0.254 | 0.075 | 0.083 | 0.093 | 0.393 | 0.214 | 0.158 | 0.118 |
| G | 0.101 | 0.208 | 0.174 | 0.361 | 0.08 | 0.076 | 0.281 | 0.311 | 0.082 | 0.443 | 0.088 | 0.175 |
| H | 0.18 | 0.082 | 0.228 | 0.331 | 0.331 | 0.257 | 0.084 | 0.137 | 0.458 | 0.106 | 0.438 | 0.078 |

| Plate: U4568EK260 R2 - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 0.136 | 0.129 | 0.136 | 0.152 | 0.163 | 0.162 | 0.17 | 0.191 | 0.163 | 0.178 | 0.172 | 0.184 |
| B | 0.395 | 0.073 | 0.078 | 0.133 | 0.09 | 0.097 | 0.123 | 0.108 | 0.107 | 0.11 | 0.113 | 0.126 |
| C | 0.076 | 0.066 | 0.062 | 0.067 | 0.063 | 0.065 | 0.074 | 0.074 | 0.073 | 0.074 | 0.072 | 0.093 |
| D | 0.11 | 0.079 | 0.069 | 0.062 | 0.06 | 0.057 | 0.065 | 0.057 | 0.055 | 0.054 | 0.067 | 0.096 |
| E | 0.077 | 0.069 | 0.067 | 0.061 | 0.055 | 0.053 | 0.058 | 0.051 | 0.053 | 0.058 | 0.073 | 0.104 |
| F | 0.072 | 0.065 | 0.067 | 0.067 | 0.068 | 0.065 | 0.06 | 0.062 | 0.063 | 0.054 | 0.066 | 0.098 |
| G | 0.081 | 0.069 | 0.066 | 0.075 | 0.072 | 0.065 | 0.066 | 0.062 | 0.066 | 0.063 | 0.071 | 0.167 |
| H | 0.148 | 0.103 | 0.107 | 0.483 | 0.118 | 0.095 | 0.092 | 0.1 | 0.094 | 0.088 | 0.109 | 0.118 |

FIGURE 32

| Plate: U4568EK260 R3 - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 0.118 | 0.12 | 1.375 | 1.116 | 0.157 | 0.144 | 1.52 | 0.149 | 0.152 | 0.133 | 0.145 | 0.128 |
| B | 0.08 | 0.086 | 0.081 | 1.434 | 0.095 | 0.085 | 0.092 | 0.087 | 0.67 | 0.089 | 0.091 | 0.102 |
| C | 0.074 | 0.063 | 0.073 | 0.062 | 0.058 | 0.062 | 0.07 | 0.064 | 0.059 | 0.066 | 0.074 | 0.089 |
| D | 0.079 | 0.067 | 0.065 | 0.059 | 1.826 | 0.054 | 0.057 | 0.063 | 0.067 | 0.066 | 0.06 | 0.074 |
| E | 0.076 | 0.061 | 0.071 | 0.061 | 0.072 | 0.052 | 0.053 | 0.054 | 0.057 | 1.154 | 0.07 | 0.087 |
| F | 1.164 | 0.062 | 0.06 | 0.057 | 0.064 | 0.059 | 0.055 | 0.064 | 0.074 | 0.06 | 0.059 | 0.078 |
| G | 0.08 | 0.069 | 0.061 | 0.059 | 0.058 | 0.063 | 0.057 | 0.06 | 0.06 | 0.062 | 0.069 | 0.107 |
| H | 0.11 | 1.68 | 0.081 | 0.09 | 0.09 | 0.099 | 0.105 | 0.097 | 0.097 | 0.093 | 0.09 | 0.114 |

| Plate: U4568EK260 R4 - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 1.815 | 1.752 | 2.001 | 2.121 | 0.056 | 0.099 | 0.084 | 0.058 | 0.056 | 2.055 | 0.474 | 2.058 |
| B | 1.919 | 0.103 | 2.231 | 2.346 | 2.359 | 0.059 | 2.111 | 1.955 | 0.061 | 2.040 | 1.827 | 2.047 |
| C | 2.231 | 2.053 | 0.105 | 2.084 | 0.057 | 2.540 | 2.310 | 2.478 | 1.870 | 0.049 | 1.633 | 0.058 |
| D | 0.075 | 0.050 | 1.788 | 2.308 | 2.373 | 0.070 | 0.086 | 0.050 | 0.085 | 2.029 | 0.361 | 0.050 |
| E | 2.013 | 0.049 | 0.426 | 0.050 | 2.169 | 2.230 | 0.051 | 0.075 | 0.085 | 1.919 | 0.086 | 1.882 |
| F | 1.981 | 2.060 | 2.160 | 0.051 | 0.070 | 0.050 | 2.160 | 1.802 | 1.305 | 1.870 | 1.702 | 0.064 |
| G | 0.056 | 0.083 | 2.280 | 2.133 | 0.053 | 1.901 | 2.117 | 1.836 | 2.036 | 1.993 | 1.822 | 0.107 |
| H | 1.941 | 0.056 | 2.427 | 0.089 | 2.252 | 2.115 | 0.067 | 0.057 | 0.807 | 0.077 | 0.077 | 0.054 |

Negative control was marked green, blank was marked blue. And clones with OD >0.5 were marked red.

FIGURE 32 CON'T

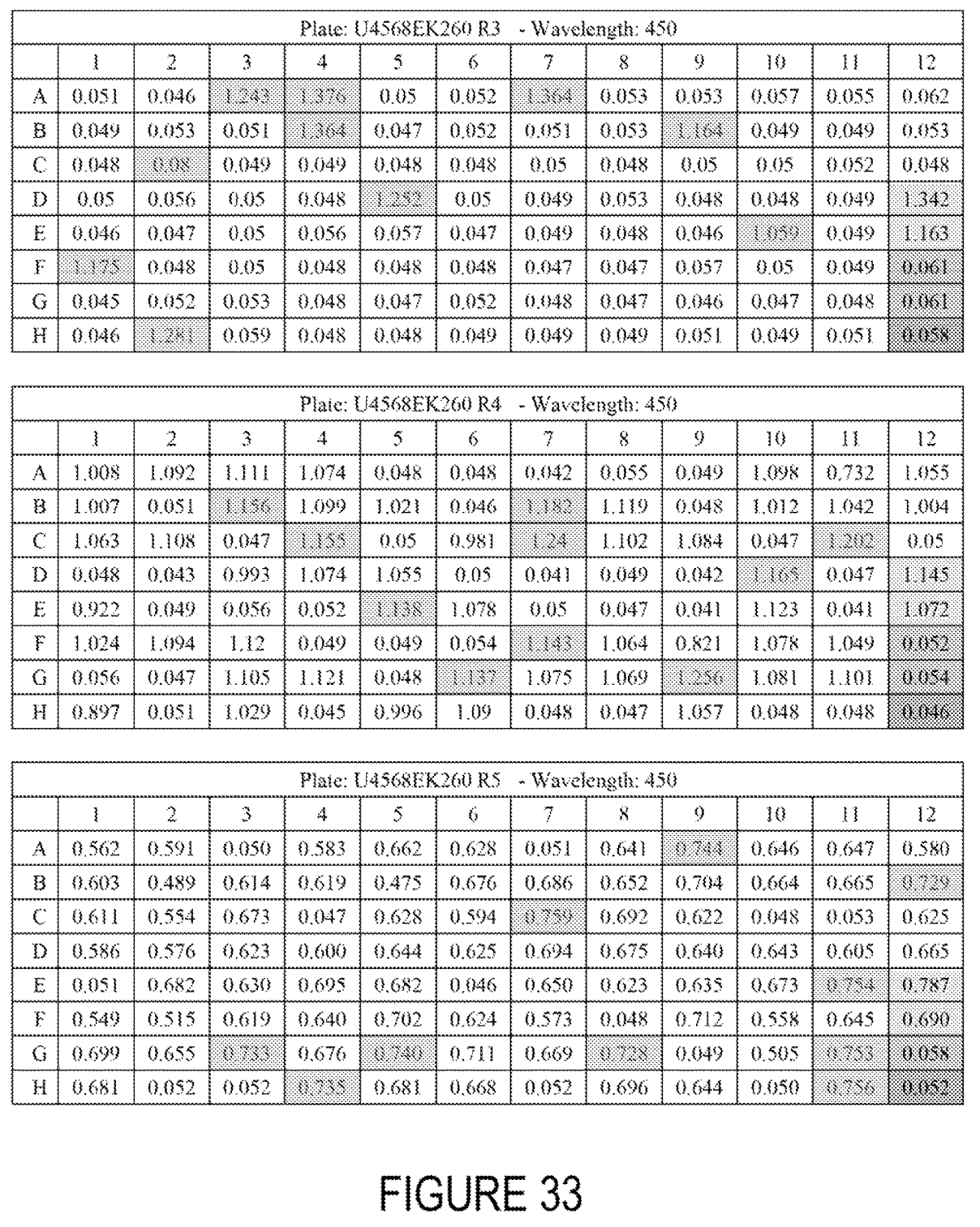

| Plate: U4568EK260 R3  - Wavelength: 450 | | | | | | | | | | | |
|---|---|---|---|---|---|---|---|---|---|---|---|
|  | 1 | 2 | 3 | 4 | 5 | 6 | 7 | 8 | 9 | 10 | 11 | 12 |
| A | 0.051 | 0.046 | 1.343 | 1.376 | 0.05 | 0.052 | 1.364 | 0.053 | 0.053 | 0.057 | 0.055 | 0.062 |
| B | 0.049 | 0.053 | 0.051 | 1.364 | 0.047 | 0.052 | 0.051 | 0.053 | 1.164 | 0.049 | 0.049 | 0.053 |
| C | 0.048 | 0.08 | 0.049 | 0.049 | 0.048 | 0.048 | 0.05 | 0.048 | 0.05 | 0.05 | 0.052 | 0.048 |
| D | 0.05 | 0.056 | 0.05 | 0.048 | 1.282 | 0.05 | 0.049 | 0.053 | 0.048 | 0.048 | 0.049 | 1.342 |
| E | 0.046 | 0.047 | 0.05 | 0.056 | 0.057 | 0.047 | 0.049 | 0.048 | 0.046 | 1.059 | 0.049 | 1.163 |
| F | 1.175 | 0.048 | 0.05 | 0.048 | 0.048 | 0.048 | 0.047 | 0.047 | 0.057 | 0.05 | 0.049 | 0.061 |
| G | 0.045 | 0.052 | 0.053 | 0.048 | 0.047 | 0.052 | 0.048 | 0.047 | 0.046 | 0.047 | 0.048 | 0.061 |
| H | 0.046 | 1.281 | 0.059 | 0.048 | 0.048 | 0.049 | 0.049 | 0.049 | 0.051 | 0.049 | 0.051 | 0.058 |

| Plate: U4568EK260 R4  - Wavelength: 450 | | | | | | | | | | | |
|---|---|---|---|---|---|---|---|---|---|---|---|
|  | 1 | 2 | 3 | 4 | 5 | 6 | 7 | 8 | 9 | 10 | 11 | 12 |
| A | 1.008 | 1.092 | 1.111 | 1.074 | 0.048 | 0.048 | 0.042 | 0.055 | 0.049 | 1.098 | 0.732 | 1.055 |
| B | 1.007 | 0.051 | 1.156 | 1.099 | 1.021 | 0.046 | 1.182 | 1.119 | 0.048 | 1.012 | 1.042 | 1.004 |
| C | 1.063 | 1.108 | 0.047 | 1.155 | 0.05 | 0.981 | 1.24 | 1.102 | 1.084 | 0.047 | 1.202 | 0.05 |
| D | 0.048 | 0.043 | 0.993 | 1.074 | 1.055 | 0.05 | 0.041 | 0.049 | 0.042 | 1.165 | 0.047 | 1.145 |
| E | 0.922 | 0.049 | 0.056 | 0.052 | 1.138 | 1.078 | 0.05 | 0.047 | 0.041 | 1.123 | 0.041 | 1.072 |
| F | 1.024 | 1.094 | 1.12 | 0.049 | 0.049 | 0.054 | 1.143 | 1.064 | 0.821 | 1.078 | 1.049 | 0.052 |
| G | 0.056 | 0.047 | 1.105 | 1.121 | 0.048 | 1.137 | 1.075 | 1.069 | 1.256 | 1.081 | 1.101 | 0.054 |
| H | 0.897 | 0.051 | 1.029 | 0.045 | 0.996 | 1.09 | 0.048 | 0.047 | 1.057 | 0.048 | 0.048 | 0.046 |

| Plate: U4568EK260 R5  - Wavelength: 450 | | | | | | | | | | | |
|---|---|---|---|---|---|---|---|---|---|---|---|
|  | 1 | 2 | 3 | 4 | 5 | 6 | 7 | 8 | 9 | 10 | 11 | 12 |
| A | 0.562 | 0.591 | 0.050 | 0.583 | 0.662 | 0.628 | 0.051 | 0.641 | 0.744 | 0.646 | 0.647 | 0.580 |
| B | 0.603 | 0.489 | 0.614 | 0.619 | 0.475 | 0.676 | 0.686 | 0.652 | 0.704 | 0.664 | 0.665 | 0.729 |
| C | 0.611 | 0.554 | 0.673 | 0.047 | 0.628 | 0.594 | 0.759 | 0.692 | 0.622 | 0.048 | 0.053 | 0.625 |
| D | 0.586 | 0.576 | 0.623 | 0.600 | 0.644 | 0.625 | 0.694 | 0.675 | 0.640 | 0.643 | 0.605 | 0.665 |
| E | 0.051 | 0.682 | 0.630 | 0.695 | 0.682 | 0.046 | 0.650 | 0.623 | 0.635 | 0.673 | 0.784 | 0.787 |
| F | 0.549 | 0.515 | 0.619 | 0.640 | 0.702 | 0.624 | 0.573 | 0.048 | 0.712 | 0.558 | 0.645 | 0.690 |
| G | 0.699 | 0.655 | 0.733 | 0.676 | 0.740 | 0.711 | 0.669 | 0.728 | 0.049 | 0.505 | 0.753 | 0.058 |
| H | 0.681 | 0.052 | 0.052 | 0.735 | 0.681 | 0.668 | 0.052 | 0.696 | 0.644 | 0.050 | 0.756 | 0.052 |

FIGURE 33

| Plate: U4568EK260 R6   0.01ug/ml   - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 1.08 | 1.061 | 0.055 | 1.042 | 1.073 | 1.131 | 1.069 | 1.184 | 1.022 | 1.059 | 1.129 | 1.115 |
| B | 1.054 | 0.972 | 1.197 | 1.05 | 1.097 | 1.115 | 1.142 | 1.065 | 1.1 | 0.047 | 1.073 | 1.043 |
| C | 1.059 | 1.035 | 1.06 | 1.092 | 1.114 | 1.203 | 1.086 | 1.136 | 1.075 | 1.206 | 1.074 | 1.121 |
| D | 0.908 | 1.055 | 1.175 | 1.096 | 1.056 | 1.105 | 0.046 | 1.117 | 0.047 | 1.021 | 1.085 | 1.088 |
| E | 0.981 | 1.084 | 1.118 | 1.093 | 1.118 | 1.066 | 1.184 | 1.102 | 1.096 | 0.978 | 0.046 | 1.039 |
| F | 0.953 | 1.013 | 1.109 | 1.148 | 1.091 | 1.073 | 1.126 | 1.066 | 1.099 | 0.046 | 1.049 | 1.111 |
| G | 0.046 | 1.084 | 1.142 | 1.097 | 1.073 | 1.101 | 1.195 | 1.017 | 1.112 | 0.046 | 1.12 | 0.056 |
| H | 1.027 | 0.049 | 1.163 | 1.091 | 1.09 | 1.114 | 1.131 | 1.022 | 0.053 | 1.123 | 1.054 | 0.049 |

| Plate: U4568EK260 R6   0.001ug/ml   - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 0.807 | 0.841 | 0.895 | 1.012 | 0.923 | 0.05 | 0.048 | 0.937 | 0.903 | 0.965 | 0.048 | 0.918 |
| B | 0.046 | 0.047 | 0.048 | 1.028 | 0.896 | 1.06 | 0.954 | 0.046 | 0.047 | 0.047 | 1.053 | 1.022 |
| C | 0.894 | 0.046 | 1.029 | 0.998 | 0.941 | 1.036 | 0.046 | 0.947 | 1.011 | 0.988 | 1.015 | 0.962 |
| D | 0.939 | 1.031 | 0.969 | 1.118 | 0.997 | 1.006 | 0.978 | 0.048 | 0.989 | 0.96 | 1.012 | 0.979 |
| E | 0.047 | 0.046 | 0.971 | 1.024 | 0.968 | 1.089 | 0.991 | 0.046 | 0.896 | 0.047 | 0.982 | 1.006 |
| F | 0.047 | 0.947 | 1.031 | 1.034 | 0.861 | 1.089 | 0.048 | 0.046 | 0.924 | 0.994 | 0.971 | 0.91 |
| G | 0.047 | 0.047 | 1.028 | 0.047 | 1.036 | 0.052 | 0.995 | 0.046 | 0.963 | 0.954 | 0.046 | 0.054 |
| H | 0.05 | 0.969 | 0.967 | 0.988 | 0.053 | 0.048 | 0.987 | 0.984 | 0.974 | 0.965 | 0.951 | 0.047 |

| Plate: U4568EK260 R6   0.001ug/ml competition   - Wavelength: 450 | | | | | | | | | | | |
|---|---|---|---|---|---|---|---|---|---|---|---|
| | 1 | 2 | 3 | 4 | 5 | 6 | 7 | 8 | 9 | 10 | 11 | 12 |
| A | 0.059 | 1.127 | 1.174 | 1.163 | 0.051 | 1.047 | 1.123 | 1.135 | 1.224 | 1.139 | 1.031 | 1.089 |
| B | 0.048 | 1.115 | 0.046 | 1.161 | 1.148 | 1.212 | 1.158 | 1.193 | 1.069 | 1.119 | 1.093 | 1.137 |
| C | 1.082 | 0.047 | 1.087 | 1.101 | 1.082 | 0.044 | 1.092 | 1.218 | 1.147 | 1.106 | 1.121 | 1.121 |
| D | 1.144 | 1.118 | 1.138 | 1.099 | 0.045 | 1.147 | 0.045 | 1.183 | 1.097 | 1.148 | 1.045 | 1.195 |
| E | 0.995 | 1.128 | 1.176 | 0.046 | 1.211 | 0.046 | 1.202 | 1.16 | 1.191 | 1.088 | 1.013 | 1.051 |
| F | 0.047 | 1.076 | 1.107 | 1.151 | 1.2 | 1.17 | 1.203 | 1.075 | 1.131 | 1.078 | 0.045 | 1.076 |
| G | 0.048 | 0.045 | 0.046 | 1.169 | 1.163 | 1.165 | 1.139 | 1.167 | 1.006 | 0.044 | 1.014 | 0.056 |
| H | 1.182 | 1.132 | 1.222 | 1.2 | 0.056 | 1.163 | 1.13 | 1.08 | 0.047 | 1.126 | 1.084 | 0.049 |

FIGURE 33 CON'T

FIGURE 34

MONOCLONAL ANTIBODIES AND USES THEREOF

This application is a National Stage Application under 35 U.S.C. 371 of PCT Application No. PCT/US2021/026436, filed on Apr. 8, 2021, which is an International Application which claims priority from U.S. provisional patent application No. 63/006,822 filed on Apr. 8, 2020, the contents of each of the above applications are incorporated herein by reference in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted electronically in ASCII format and is hereby incorporated by reference in its entirety. Said ASCII copy, created on Dec. 12, 2024, is named 2949515-002US2 and is 199,337 bytes in size.

FIELD OF THE INVENTION

Aspects of this invention are drawn to isolated monoclonal antibodies that binds to an epitope of the culture filtrate antigen-10 (CFP-10) protein or peptide fragment thereof, and methods for using the same to detect *Mycobacterium tuberculosis*.

BACKGROUND OF THE INVENTION

Tuberculosis (TB) is a disease caused by the bacterium *Mycobacterium tuberculosis*, which can produce infections in lung tissue but can also establish infections in multiple other tissues and organs, including liver, kidney, spine, and brain. TB is the leading cause of death from infectious disease in humans, but not everyone infected with *Mycobacterium tuberculosis* develops TB, since the immune system can contain the pathogen to produce a latent TB infection (LTBI) that does not exhibit TB pathology but which can progress to active TB disease at any point, even decades later, this containment fails.

SUMMARY OF THE INVENTION

The invention is based upon the discovery of monoclonal antibodies which binding to an epitope of the culture filtrate antigen-10 (CFP-10) protein or peptide fragment thereof.

In some embodiments, the epitope comprises TDAAT-LAQEAGNFER (SEQ ID NO: 17) or TQIDQVE-STAGSLQGQWR (SEQ ID NO: 18) or a portion thereof. For example, the epitope can comprise a linear amino acid sequence that is about 5 or 6 amino acids in length of peptide 1593 and peptide 2004.

In some embodiments the epitope comprises the amino acid position amino acids 6-20 and 27-44 of the protein.

Exemplary monoclonal antibodies include monoclonal antibody 65D3-1, 17E4-1, 21H3-1, 119C10-1, 65D3-1, 67G8-1, 135A6-1, 101G10-2, 125D9-1, 91B4-1, 70A12-1, 6D10-1, 5B7-1, 55H8-1, 10G3-1, 76C4-1, 3E9-1, 76H12-1, 74D3-1, 4G6-1, 21F10-1, 65D3-1 Hv1, 65D3-1 Hv2, 65D3-1 Lv1, or an antibody that binds to the same epitope, a similar epitope, or an epitope adjacent to that of 65D3-1, 17E4-1, 21H3-1, 119C10-1, 65D3-1, 67G8-1, 135A6-1, 101G10-2, 125D9-1, 91B4-1, 70A12-1, 6D10-1, 5B7-1, 55H8-1, 10G3-1, 76C4-1, 3E9-1, 76H12-1, 74D3-1, 4G6-1, 21F10-1, 65D3-1 Hv1, 65D3-1 Hv2, or 65D3-1 Lv1. For example, the antibody that binds to the same epitope, a similar epitope, or an epitope adjacent to that of 65D3-1, 17E4-1, 21H3-1, 119C10-1, 65D3-1, 67G8-1, 135A6-1, 101G10-2, 125D9-1, 91B4-1, 70A12-1, 6D10-1, 5B7-1, 55H8-1, 10G3-1, 76C4-1, 3E9-1, 76H12-1, 74D3-1, 4G6-1, 21F10-1, 65D3-1 Hv1, 65D3-1 Hv2, or 65D3-1 Lv1 competes with the binding of monoclonal antibodies 65D3-1, 17E4-1, 21H3-1, 119C10-1, 65D3-1, 67G8-1, 135A6-1, 101G10-2, 125D9-1, 91B4-1, 70A12-1, 6D10-1, 5B7-1, 55H8-1, 10G3-1, 76C4-1, 3E9-1, 76H12-1, 74D3-1, 4G6-1, 21F10-1, 65D3-1 Hv1, 65D3-1 Hv2, or 65D3-1 Lv1.

The monoclonal antibodies of the invention can have the binding affinity of monoclonal antibody 65D3-1, 17E4-1, 21H3-1, 119C10-1, 65D3-1, 67G8-1, 135A6-1, 101G10-2, 125D9-1, 91B4-1, 70A12-1, 6D10-1, 5B7-1, 55H8-1, 10G3-1, 76C4-1, 3E9- 1, 76H12-1, 74D3-1, 4G6-1, 21F10-1, 65D3-1 Hv1, 65D3-1 Hv2, or 65D3-1 Lv1.

Also provided by the invention is an monoclonal antibody or fragment thereof, where the antibody has a heavy chain with three CDRs comprising the amino acid sequences SCDVN (SEQ ID NO: 19), VIARAGSTYYASWAKG (SEQ ID NO: 20), and EEFDF (SEQ ID NO: 21), respectively, and/or a light chain with three CDRs comprising the amino acid sequences QSSQSVYNNNELS (SEQ ID NO: 22), YSSTLAS (SEQ ID NO: 23), and LGGYASIIDMWT (SEQ ID NO: 24), respectively; a heavy chain with three CDRs comprising the amino acid sequences SYDVS (SEQ ID NO: 25), VISRGGTTYSTNWAKG (SEQ ID NO: 26), and EEFNL (SEQ ID NO: 27), respectively and/or a light chain with three CDRs comprising the amino acid sequences QASESVYWNNRLA (SEQ ID NO: 28), EASKLAS (SEQ ID NO: 29), and AGYKSSSDGPA (SEQ ID NO: 30), respectively; a heavy chain with three CDRs comprising the amino acid sequences SYNMG (SEQ ID NO: 31), FIGTT-GRAFYASWAKG (SEQ ID NO: 32), and GAPGYTPFNL (SEQ ID NO: 33), respectively and/or a light chain with three CDRs comprising the amino acid sequences QSSQSVISNDLS (SEQ ID NO: 34), QTSKLAS (SEQ ID NO: 35), and AGGYSSSLDIYA (SEQ ID NO: 36), respectively; a heavy chain with three CDRs comprising the amino acid sequences THDIS (SEQ ID NO: 37), VIARRG-STYYASWAKG (SEQ ID NO: 38), and EEFDF (SEQ ID NO: 21), respectively and/or a light chain with three CDRs comprising the amino acid sequences QSSQSVYNNKELS (SEQ ID NO: 39), YASTLAS (SEQ ID NO: 40), and LGGYASTIDMWA (SEQ ID NO: 41), respectively; a heavy chain with three CDRs comprising the amino acid sequences NYDGH (SEQ ID NO: 42), VIATIGDTYYASWAKG (SEQ ID NO: 43), and GDSRTSNEIFNL (SEQ ID NO: 44), respectively and/or a light chain with three CDRs comprising the amino acid sequences QSTRSVHNNICLS (SEQ ID NO: 45), SASTLAS (SEQ ID NO: 46), and AGCFPSKSDMYG (SEQ ID NO: 47), respectively; a heavy chain with three CDRs comprising the amino acid sequences NYDIS (SEQ ID NO: 48), VIATVGDTYYAS-WAKG (SEQ ID NO: 49), and GDSPSTNEIFGL (SEQ ID NO: 50), respectively and/or a light chain with three CDRs comprising the amino acid sequences QSSRTVYNNICLS (SEQ ID NO: 51), GASTLTS (SEQ ID NO: 52), and AGCFPSTSDMYG (SEQ ID NO: 53), respectively; a heavy chain with three CDRs comprising the amino acid sequences SYDMT (SEQ ID NO: 54), VISYGGSAYYASWAKG (SEQ ID NO: 55), and GDSDGSSELFNL (SEQ ID NO: 56), respectively and/or a light chain with three CDRs comprising the amino acid sequences QSSKSVYNNNCLS (SEQ ID NO: 57), GASTLAS (SEQ ID NO: 58), and AGCFASTNDMYG (SEQ ID NO: 59), respectively; a heavy chain with three CDRs comprising the amino acid sequences SYDMT (SEQ ID NO: 54), VVAYGGATYYAS-WAKG (SEQ ID NO: 60), and GDSDGSSELFNL (SEQ ID NO: 56), respectively and/or a light chain with three CDRs comprising the amino acid sequences QSSKSVYNNCLS (SEQ ID NO: 57), QASTPAS (SEQ ID NO: 61), and AGCFASTSDMYG (SEQ ID NO: 62), respectively; a heavy chain with three CDRs comprising the amino acid sequences RFGVS (SEQ ID NO: 63), YIHTDGNVYYAS-WAKG (SEQ ID NO: 64), and GGYAADL (SEQ ID NO: 65), respectively and/or a light chain with three CDRs comprising the amino acid sequences QSSESVYKNYLA (SEQ ID NO: 66), ATSTLVS (SEQ ID NO: 67), and VGGYTGKNV (SEQ ID NO: 68), respectively; a heavy chain with three CDRs comprising the amino acid sequences NHYII (SEQ ID NO: 69), AISRRSKTDYASWAKG (SEQ ID NO: 70), and QLDGSTSVVCDI (SEQ ID NO: 71), respectively and/or a light chain with three CDRs comprising the amino acid sequences QASQNVYNDRNLG (SEQ ID NO: 72), GPSTLAS (SEQ ID NO: 73), and QGEFICS-SADCCA (SEQ ID NO: 74), respectively; a heavy chain with three CDRs comprising the amino acid sequences DVTMS (SEQ ID NO: 75), IIGRRGRIWYANWAKG (SEQ ID NO: 76), and GAVSSDWNMYGMDL (SEQ ID NO: 77), respectively and/or a light chain with three CDRs comprising the amino acid sequences QSSQSVYNNENLA (SEQ ID NO: 78), GASTLAS (SEQ ID NO: 58), and QGEFDCSSADCFA (SEQ ID NO: 79), respectively; a heavy chain with three CDRs comprising the amino acid sequences DVTIS (SEQ ID NO: 80), IIGRRGRIRYAD-WAKG (SEQ ID NO: 81), and AYVSSDWNIYGMDL (SEQ ID NO: 82), respectively and/or a light chain with three CDRs comprising the amino acid sequences QASQSVYNNKNLA (SEQ ID NO: 83), EASKLAS (SEQ ID NO: 29), and QGEFDCSSADCFV (SEQ ID NO: 84), respectively; a heavy chain with three CDRs comprising the amino acid sequences DHAMS (SEQ ID NO: 85), IVGRR-GRTYYASWAKG (SEQ ID NO: 86), and GYVSSDWNIYGMDL (SEQ ID NO: 87), respectively and/or a light chain with three CDRs comprising the amino acid sequences QASQSVYNNKNLA (SEQ ID NO: 83), EASTLAS (SEQ ID NO: 88), and QGEFDCSSADCFA (SEQ ID NO: 79), respectively; a heavy chain with three CDRs comprising the amino acid sequences DDAMS (SEQ ID NO: 89), IIGRRGKTWYANWAKG (SEQ ID NO: 90), and GYVSSDWNIYGMDL (SEQ ID NO: 87), respectively and/or a light chain with three CDRs comprising the amino acid sequences QASQSVYNNKNLA (SEQ ID NO: 83), EASKLAS (SEQ ID NO: 29), and QGEFSCSSADCFT (SEQ ID NO: 91), respectively; a heavy chain with three CDRs comprising the amino acid sequences KYTMG (SEQ ID NO: 92), AIGATGRTVYANWAKG (SEQ ID NO: 93), and NVVDASDSDGMIAFDP (SEQ ID NO: 94), respectively and/or a light chain with three CDRs comprising the amino acid sequences QASQSVYNNKNLA (SEQ ID NO: 83), KASTLAS (SEQ ID NO: 95), and QGEFSCSSGDCVA (SEQ ID NO: 96), respectively; a heavy chain with three CDRs comprising the amino acid sequences SNAMG (SEQ ID NO: 97), SIYASGNTYYASWAKG (SEQ ID NO: 98), and LFNI (SEQ ID NO: 99), respectively and/or a light chain with three CDRs comprising the amino acid sequences QASQSVFDNKNLS (SEQ ID NO: 100), GASTLDS (SEQ ID NO: 101), and GGRDSGNIYD (SEQ ID NO: 102), respectively; a heavy chain with three CDRs comprising the amino acid sequences GSAMG (SEQ ID NO: 103), SIYVSGNTYYASWAKG (SEQ ID NO: 104), and LLNI (SEQ ID NO: 105), respectively and/or a light chain with three CDRs comprising the amino acid sequences QASQSVYDNKNLA (SEQ ID NO: 106), GASTLAS (SEQ ID NO: 58), and GGRDSDNIYD (SEQ ID NO: 107), respectively; a heavy chain with three CDRs comprising the amino acid sequences NNAMG (SEQ ID NO: 108), TIYASGNTYYASWAKG (SEQ ID NO: 109), and LFNI (SEQ ID NO: 99), respectively and/or a light chain with three CDRs comprising the amino acid sequences QASQSVYDNKNLS (SEQ ID NO: 110), AASTLAS (SEQ ID NO: 111), and GGRDSGNIYD (SEQ ID NO: 102), respectively; a heavy chain with three CDRs comprising the amino acid sequences SNAMG (SEQ ID NO: 97), SIYSSGNTYYASWARG (SEQ ID NO: 112), and LFNI (SEQ ID NO: 99), respectively and/or a light chain with three CDRs comprising the amino acid sequences QASQSVYDNKNLA (SEQ ID NO: 106), GASTVAS (SEQ ID NO: 113), and GGRDNDNIYD (SEQ ID NO: 114), respectively; a heavy chain with three CDRs comprising the amino acid sequences SNAVG (SEQ ID NO: 115), SIYSSGNSYYASWAKG (SEQ ID NO: 116), and LFNI (SEQ ID NO: 99), respectively and/or a light chain with three CDRs comprising the amino acid sequences QASQSVYDNKNLS (SEQ ID NO: 110), GASTLAS (SEQ ID NO: 58), and GGRDDDNIYD (SEQ ID NO: 117), respectively; a heavy chain with three CDRs comprising the amino acid sequences THDIS (SEQ ID NO: 37), VIARRGWTYYASWAKG (SEQ ID NO: 118), and EEFDF (SEQ ID NO: 21), respectively; a heavy chain with three CDRs comprising the amino acid sequences THDIS (SEQ ID NO: 37), VIARRGWTYYASWAKK (SEQ ID NO: 119), and EEFDF (SEQ ID NO: 21), respectively; or a light chain with three CDRs comprising the amino acid sequences QSSQSVYNNKELS (SEQ ID NO: 39), YASTLAT (SEQ ID NO: 120), and LGGYASTIDMWA (SEQ ID NO: 41), respectively.

In embodiments, monoclonal antibody comprises a VH having the amino acid sequence QSLEESG-GRLVTPGTPLTLTCTVSGFSLSSCDVNWVRQAPGK-GLEWIGVIARAGST YYASWAKGRFTVSKTSTTVYLE-IASPTIEDTATYFCVREEFDFWGQGTLVTVSS (SEQ ID NO: 121), and a VL having the amino acid sequence AVLTQTASPVSAANGGTVTITCQSSQSVYNN-NELSWFQQKPGQPPKLLINYSSTLAS GVPSRFKGSGSGTQFTLTISGVQCDDAATYYCLGG-YASIIDMWTFGGGTEVVVK (SEQ ID NO: 122); a VH having the amino acid sequence QSLEESG-GRLVTPGTPLTLTCTVSGFSLSSYDVSWVRQAPGK-GLEWIGVISRGGTTY STNWAKGRFTISKTSTTVDL-RITSPTIEDTATYFCAREEFNLWGQGTLVTVSS (SEQ ID NO: 123), and a VL having the amino acid sequence IVMTQTPSSKSVPVGDTVTINCQASESVYWNNR-LAWFQQKPGQPPKQLIYEASKLA SGVPSRFKGSGSGTQFTLTISDVVCDDAATYY-CAGYKSSSDGPAFGGGTEVVVK (SEQ ID NO: 124); a VH having the amino acid sequence QSVEESG-GRLVTPGTPLTLTCTVSGFSLSSYNMGWVRQAPGKG- LEYIGFIGTTGRAF YASWAKGRFTISKTSTTVNLKVT-SLTTEDTATYFCAGGAPGYTPFNLWGQGTLVTV SS (SEQ ID NO: 125), and a VL having the amino acid sequence QVLTQTPSSVSAAVGGTVSISCQSSQSVIS-NDLSWFQQKPGQPPRQLIYQTSKLASG VPSRFSGSGSGTQFTLTISDLKCDDAATYSCAG-GYSSSLDIYAFGGGTEVVVK (SEQ ID NO: 126); a VH having the amino acid sequence QSLEESG-GRLVTPGGSLTLTCTVSGFSLSTHDISWVRQAPGK-GLEWIGVIARRGSTY YASWAKGRFTISKT-STTVDLKITSPTIEDTATYFCAREEFDFWGQGTL VTVSS (SEQ ID NO: 127), and a VL having the amino acid sequence AVLTQTASPVSAAVGGTVTISCQSSQSVYNN-KELSWFQQKPGQPPKLLISYASTLAS GVPSRFKGSGSGTQFTLTISDLECDDAATYYCLGG-YASTIDMWAFGGGTEVVVK (SEQ ID NO: 128), a VH having the amino acid sequence QSVEESG-GRLVTPGTPLTLTCTVSGFSLGNYDGHWVRQT-PEKGLEWIGVIATIGDT YYASWAKGRFSISKT-SATVELRITSPTTEDTATYFCVRGDSRTSNEIFNLWG-QGTL V TVSS (SEQ ID NO: 129), and a VL having the amino acid sequence AVLTQTPSPVSAAVGGTLTINCQSTRSVHNNI-CLSWYQQKPGQPPKLLIYSASTLAS GVPSRFKGSGSGTQFTLAINDVQCGDAATYY-CAGCFPSKSDMYGFGGGTEVVVK (SEQ ID NO: 130); a VH having the amino acid sequence QSVEESG-GRLVTPGTPLTLTCTVSGFSLGNYDISWVRQAPGK-GLEWIGVIATVGDT YYASWAKGRFTISKT-SATVDLKITSPTTEDTATYFCVRGDSPSTNEIFGLW-GQGTLV TVSS (SEQ ID NO: 131), and a VL having the amino acid sequence AVLTQTPSPVSAAVGGTLTINCQSSRTVYNNI-CLSWYQQKLGQPPKLLIYGASTLTS GVPSR-FRGSGSGTQFTLTINDVQCGDAATYYCAGCFPST-SDMYGFGGGTEVVVK (SEQ ID NO: 132); a VH having the amino acid sequence QSVEESG-GRLVTPGTPLTLTCTVSGFSLSSYDMTWVRQAPGKG-LEYIGVISYGGSA YYASWAKGRFTISKTSTTVDLKIT-SPTTEDTATYFCARGDSDGSSELFNLWGQGTL VTVSS (SEQ ID NO: 133), and a VL having the amino acid sequence AVLTQTPSPVSAPVGGTVSIN-CQSSKSVYNNNCLSWYQQKPGQPPNLLIYGASTLAS GVPSRFKGSGSGTQFTLTINDVQCDDAATYY-CAGCFASTNDMYGFGGGSEVVVK (SEQ ID NO: 134); a VH having the amino acid sequence QPVEESG-GRLVTPGTPLTLTCTVSGFSLS √SYDMTWVRQAPGKGLEYIGVVAYGGAT YYAS-WAKGRFTISKTSTTVDLKITSPTTED-TATYFCARGDSDGSSELFNLWGQGTL VTVSS (SEQ ID NO: 135), and a VL having the amino acid sequence AVLTQTPSPVSAAVGGTVTINCQSSKSVYNNN-CLSWYQQKQGQPPKLLIYQASTPA SGVPSRFKGSGSGTQFTLTINDVQCDDAATYY-CAGCFASTSDMYGFGGGTGVVVK (SEQ ID NO: 136); a VH having the amino acid sequence QSLEESG-GRLVSPGGSLTLTCTVSGIDLSRFGVSWVRQAPGK-GLEWTGYIHTDGNV YYASWAKGRFTISKT-STTVDLKMTSLTTEDTATYFCARGGYAADLWGQA-ALVTVS S (SEQ ID NO: 137), and a VL having the amino acid sequence DPMLTQTPSSVSAAVGGTVTISCQSS-ESVYKNYLAWYQQKLGQPPKLLIGATSTLV SGVPSRFKGSGSRTQFSLTISDLECDDAATYYCVG-GYTGKNVFGGGTEVVVK (SEQ ID NO: 138); a VH having the amino acid sequence QSVEESG-GRLVTPGTPLTLTCTASGFSLSNHYIIWVRQTPGK-GLEWIGAISRRSKTDY ASWAKGRFTISKT- STTVDLKITSPTTEDTATYFCARQLDGSTSVVCDIW-GPGTLVTV SS (SEQ ID NO: 139), and a VL having the amino acid sequence QVLTQTPSPVSAAVGGTVTINCQASQNVYN-DRNLGWYQQKPGQPPKLLIYGPSTLA SGVSSRFTGSGSGTQFTLTISDLQCDDAATYYCQGE-FICSSADCCAFGGGTEVVVK (SEQ ID NO: 140); a VH having the amino acid sequence QSVEESG-GRLVTPGTPLTLTCTVSGFSLSDVTMSWVRQAPGK-GLEWIGIIGRRGRIW YANWAKGRFTISKTSPTVDLKI-ISPTSDDTATYFCARGAVSSDWNMYGMDLWGPG TLVTVSS (SEQ ID NO: 141), and a VL having the amino acid sequence QVLTQTPSSVSAPVGGTVTINCQSSQSVYNNEN-LAWYQQKLGQPPKLLIYGASTLA SGVSSR-FEGSGSGTQFALTISGVQCDDAATYYCQGEFDCS-SADCFAFGGGTEVVVK (SEQ ID NO: 142); a VH having the amino acid sequence QSVEESG-GRLVTPGTPLTLTCTVSGFSLSDVTISWVRQAPGK-GLKWTGIIGRRGRIR YADWAKGRFTISKT-STTVDLKITSPTTDDTATYFCARAY-VSSDWNIYGMDLWGPG TLVTVSS (SEQ ID NO: 143), and a VL having the amino acid sequence QVLTQ-TASPVSAPVGGTVTINCQASQSVYNNKN-LAWYQQKLGQPPKLLIYEASKL ASGVSSR-FEGSGSGTQFALTISGVQCDDAATYY-CQGEFDCSSADCFVFGGGTEVVV K (SEQ ID NO: 144); a VH having the amino acid sequence QSMEESG-GRLVTPGTPLTLTCTVSGFSLSDHAMSWVRQAPGK-GLEWIGIVGRRGRT YYASWAKGRFTISKT-STTVDLKITSPTIEDTATYFCARGYVSSDWNIYGMDL WGPG TLVTVSS (SEQ ID NO: 145), and a VL having the amino acid sequence QVLTQTPSPVSAAVGGTVTINCQASQSVYNNKN-LAWYQQKPGQPPKLLIYEASTLA SGVSSRFKGSGSGTQFTLTISGVQCD-DAATYYCQGEFDCSSADCFAFGGGTEVVVK (SEQ ID NO: 146); a VH having the amino acid sequence QSVEESGGRLVTPGTPLTLTCTASGFSLSDDAM-SWVRQAPGKGLEWIGIIGRRGKT WYAN-WAKGRFTISKTSTTVDLKITSPTTEDTATYFCAR-GYVSSDWNIYGMDLWGP GTLVTVSA (SEQ ID NO: 147), and a VL having the amino acid sequence QVLTQTPSPVSAAVGGTVTINCQASQSVYNNKN-LAWYQQKSGQPPKLLIYEASKL ASGVPSRFKGSGSGTQFTLTISGVQCD-DAATYYCQGEFSCSSADCFTFGGGTEVVV K (SEQ ID NO: 148); a VH having the amino acid sequence QSVEESGGRLVTPGTPLTLTCTASGSDIN-KYTMGWVRQAPGKGLEWVGAIGATGR TVYAN-WAKGRFTISKTSTTVDLIITSPTTEDTATYFCARNVV-DASDSDGMIAFDPW GPGTLVTVSS (SEQ ID NO: 149), and a VL having the amino acid sequence QVLTQTPSPVSAAVGGTVTINCQASQSVYNNKN-LAWYQQKPGQPPKLLIYKASTL ASGVPSRF-AGSGSGTEVTLTISDLECD-DAATYYCQGEFSCSSGDCVAFGGGTEVVV K (SEQ ID NO: 150); a VH having the amino acid sequence QSLEESG-GRLVTPGGSLTLTCTVSGIDLSSNAMGWVRQAPGE-GLEWIGSIYASGNT YYASWAKGRFAISKT-STTVDLKMTSLTAADTATYFCARLFNIWGPGTLVTVSS (SEQ ID NO: 151), and a VL having the amino acid sequence ADIVLTQT-PASVSSVVGGTVTINCQASQSVFDNKNLSWFQQKP-GQPPKQLIYGASTL DSGVPSRFKGSGSGTQFTLTISDMQCDDAATYYCG-GRDSGNIYDFGGGTEVVVK (SEQ ID NO: 152); a VH having the amino acid sequence QELKESG-GRLVTPGGSLTLSCTASGIDLSGSAMGWVRQAPGQ- GLEWIGSIYVSGNT YYASWAKGRFAISRT-
STTVDLKMTSLTAADTATYFCARLLNIWGPGTLVTVSS
(SEQ ID NO: 153), and a VL having the amino acid
sequence ADIVLTQTPSPVSIA-
VGGTVTINCQASQSVYDNKN-
LAWFQQKPGQPPKQLIYGASTL
ASGVPSRFKGSGSGTQFTLTISGMQCDDAATYYCG-
GRDSDNIYDFGGGTEVVVK (SEQ ID NO: 154); a VH
having the amino acid sequence QSVEESG-
GRLVTPGTPLTLTCTVSGIDLSNNAMGWVRQAPGE-
GLEWIGTIYASGNT YYASWAKGRFAISKT-
STTVDLKMTSLTAADTATYFCARLFNIWGPGTLVTVSS
(SEQ ID NO: 155), and a VL having the amino acid
sequence ADIVLTQSPASVS-
SAVGGTVTINCQASQSVYDNKNLSWFQQKPGQPP-
KQLIYAAST
LASGVPSRFKGSGSGTQFTLTISGMQCDDAATYYCG-
GRDSGNIYDFGGGTEVVVK (SEQ ID NO: 156); a VH
having the amino acid sequence QSLEESG-
GRLVTPGTPLTLTCTVSGIDLSS-
NAMGWVRQAPGEGLQWIGSIYSSGNTY YASWAR-
GRFAISRTSTTVDLKMTSLTAADTATYFCARLFNIW-
GPGTLVTVSS (SEQ ID NO: 157), and a VL having the
amino acid sequence ADIVVTQTPASVSAD-
VGGTVTINCQASQSVYDNKN-
LAWFQQKPGQPPKQLIYGAST
VASGVPSRFKGSGSGTQFTLTISDVQCDDAATYYCG-
GRDNDNIYDFGGGTEVVVK (SEQ ID NO: 158); a VH
having the amino acid sequence QSVEESG-
GRLVTPGTPLTLTCTVSGIDLSSNAVGWVRQAPGE-
GLEWIGSIYSSGNSY YASWAKGRFAISRT-
STTVDLKMTRLTAADTATYFCARLFNIWGPGTLVTVS
(SEQ ID NO: 159), and a VL having the amino acid
sequence ADIVLTQT-
PASVSSVVGGTVAINCQASQSVYDNKNLSWFQQK-
PGQTPKQLIYGAST
LASGVPSRFKGSGSGTQFTLTISGVQCDDAATYYCG-
GRDDDNIYDFGGGTEVVVK (SEQ ID NO: 160); a VH
having the amino acid sequence QSLEESG-
GRLVTPGGSLTLTCTVSGFSLSTHDISWVRQAPGK-
GLEWIGVIARRGWTY YASWAKGRFTISKT-
STTVDLKITSPTIEDTATYFCAREEFDFWGQGTLVTVSS
(SEQ ID NO: 161); a VH having the amino acid sequence
QSLEESGGRLVTPGGSLTLTCTVSGFSLSTHDIS-
WVRQAPGKGLEWIGVIARRGWTY YAS-
WAKKRFTISKTSTTVDLKITSPTIEDTATYFCA-
REEFDFWGQGTLVTVSS (SEQ ID NO: 162); 65D3-1 Lvl
a VL having the amino acid sequence AVLTQ-
TASPVSAAVGGTVTISCQSSQSVYNN-
KELSWFQQKPGQPPKLLISVYASTLAT
GVPSRFKGSGSGTQFTLTISDLECDDAATYYCLGG-
YASTIDMWAFGGGTEVVVK (SEQ ID NO: 163);

In embodiments, the monoclonal antibody is conjugated
to or immobilized to a solid phase support. For example, the
solid phase support is a bead, a column, a column matrix, a
multi-well plate, a particle, or a tube. For example, the
particle can be a microparticle or a nanoparticle. Such
exemplary solid phase supports can be used for any solid
phase enrichment approaches as described herein.

Aspects of the invention are also drawn towards an
immunoparticle comprising an antibody described herein.
For example, the immunoparticle can comprise an antibody
that is conjugated to a solid phase support, such as a bead,
a column, a column matrix, a multi-well plate, a particle, or
a tube. For example, the particle can be a microparticle or a
nanoparticle. For example, the bead can be a glass bead, a
magnetic bead, an agarose bead, a Sepharose bead, a silica
bead, a glass bead, or a plastic bead.

In another aspect, the invention provides a method of
detecting the presence of CFP-10 or fragment thereof in a
sample by contacting the sample with a monoclonal anti-
body as described herein, and detecting the presence or
absence of an antibody-antigen complex, thereby detecting
the presence of CFP-10 in a sample.

In still another aspect, the invention provides a method of
detecting the presence of bacteria belonging to the *Myco-
bacterium tuberculosis* complex, a group of related *Myco-
bacterium* species that can cause tuberculosis. For example,
the invention provides a method of detecting the presence of
*M. tuberculosis, M. africanum, M. bovis, M. canetti, M.
caprae, M. microti, M. mungi, M. orygis, M. pinnipedii,* or
*M. suricattae.* For example, the method can comprise con-
tacting the sample with an antibody or immunoparticle
described herein and detecting the presence or absence of an
antibody-antigen complex, thereby detecting the presence of
*Mycobacterium* species belonging to the *Mycobacterium
tuberculosis* complex, such as *Mycobacterium tuberculosis,*
in a sample.

Further, an aspect of the invention is also drawn towards
a method of diagnosing Mycobacteria infection in a subject.
For example, the invention provides methods of diagnosing
a subject infected with *M. tuberculosis, M. africanum, M.
bovis, M. canetti, M. caprae, M. microti, M. mungi, M.
orygis, M. pinnipedii,* or *M. suricattae.* In an embodiment,
the method can comprise obtaining a sample from a subject;
contacting the sample with an antibody or immunoparticle
described herein; and detecting the presence or absence of
an antibody-antigen complex, wherein the presence of an
antibody-antigen complex is indicative of Mycobacteria
infection.

Also, an aspect of the invention is drawn towards a
method of monitoring Mycobacteria infection in a subject.
For example, the invention provides methods of monitoring
subjects infected with *M. tuberculosis, M. africanum, M.
bovis, M. canetti, M. caprae, M. microti, M. mungi, M.
orygis, M. pinnipedii,* or *M. suricattae.* In an embodiment,
the method can comprise obtaining a sample from a subject;
contacting the sample with the antibody or immunoparticle
described herein; and detecting the presence or absence of
an antibody-antigen complex, thereby monitoring infection
in the subject.

In embodiments, the sample can be whole blood, lymph,
serum, plasma, urine, saliva, sputum, breath extract (mean-
ing exhaled air captured in a solution), bone marrow, aspi-
rates (nasal, lung, bronchial, tracheal), eye fluid (for
example, intraocular fluid), amniotic fluid, feces other
bodily fluids and secretions, cells, and tissue specimens and
dilutions of them. In embodiments, the sample is not spu-
tum.

In embodiments, the sample is a food sample or a sample
to be consumed by a subject.

In embodiments, *Mycobacterium tuberculosis* comprises
pulmonary or extrapulmonary tuberculosis.

In embodiments, the subject is an adult subject. In
embodiments, the subject is a pediatric subject. In embodi-
ments, the subject is HIV-positive.

Further, aspects of the invention are drawn towards a kit
comprising an antibody or immunoparticle described herein.

In embodiments, the kit can further comprise a solid phase
support, a digestion compound or compounds, wash buffers,
pipette tips, aliquot tubes, an aliquot stand, sample identi-
fication labeling, device labelling, a magnet, and instructions
for use.

Unless otherwise defined, all technical and scientific
terms used herein have the same meaning as understood by one of ordinary skill in the art to which this invention belongs. Although methods and materials similar or equivalent to those described herein can be used in the practice or testing of the invention, suitable methods and materials are described herein. All publications, patent applications, patents, and other references mentioned herein are incorporated by reference in their entirety. In the case of conflict, the specification, including definitions, will control. In addition, the materials, methods, and examples are illustrative only and are not intended to be limiting.

Other features and advantages of the invention will be apparent from and are encompassed by the following detailed description and claims.

BRIEF DESCRIPTION OF THE DRAWINGS

FIG. 12 shows IMGT Analysis of V(D)J Junctions of 17E4-1. Figure discloses SEQ ID NOS 257-258, respectively, in order of appearance.

FIG. 13 shows IMGT Analysis of V(D)J Junctions of 21H3-1. Figure discloses SEQ ID NOS 259-260, respectively, in order of appearance.

FIG. 14 shows IMGT Analysis of V(D)J Junctions of 119C10-1. Figure discloses SEQ ID NOS 261-262, respectively, in order of appearance.

FIG. 15 shows IMGT Analysis of V(D)J Junctions of 65D3-1. Figure discloses SEQ ID NOS 263-264, respectively, in order of appearance.

FIG. 16 shows CFP-10 protein sequence alignment for *Mycobacterium tuberculosis* complex species. Figure discloses SEQ ID NOS 252, 265-267, 250, 251, and 17-18, respectively, in order of appearance.

FIG. 17 shows ELISA data comparing signal detected using 65D3-1 antibodies containing the single amino acid substitutions at the indicated positions in either the heavy (H) or light (L) chain versus signal produced by comparator WT 65D3-1 antibody wells.

FIG. 18 shows protein sequence alignment of the signal peptide, framework regions (FRs) and complementary determining regions (CDRs) of the heavy and light chains of mAb 65D3-1 and its targeted mutants and mAb 67G8-2. Red (italics) and blue (underline) text indicate the FR and CDR sequences in each alignment. Green highlighted text (bold) indicates targeted mutations introduced into wild-type (WT) mAb 65D3-1 sequence to generate variant heavy (H) and light (L) chains containing amino acid substitutions at one (v1) or two (v2) positions in the second CDR of the 65D3-1 heavy or light chain. Gray highlighted text indicates amino acid variations between 65D3-1, isolated in the first mAb screening procedures, and 67G8-2, isolated in the second mAb screening attempt. Figure discloses SEQ ID NOS 253, 195, 196, 164, 254, 197, and 165, respectively, in order of appearance.

FIG. 19 shows Biacore™ 8K data for mAb 65D3-1 and its indicated targeted mutant combinations and for mAb 67G8-2.

FIG. 20 shows Biacore™ 8K assay parameters for the analysis of mAb 65D3-1 and its targeted mutants and mAb 67G8-2.

FIG. 21 shows protein sequence alignment of the signal peptide, framework regions (FRs) and complementary determining regions (CDRs) of the heavy (H) and light (L) chains of hybridoma clones that found to recognize the target 1593 peptide with high affinity. Red (italics) and blue (underline) text indicate the FR and CDR sequences in each alignment. Gray highlighted text indicates amino acids that vary from the consensus sequences at the indicated positions, or regions of variability if no consensus exists at the highlighted position. Bolded mAb identifiers indicate the clones with the highest affinity detected in each of the two mAb isolation attempts. The five grouped mAb clones are ranked from highest affinity to lowest affinity as determined by their relative ability to recover the target peptide by immunoprecipitation from serum samples spiked with CFP-10 after trypsin digestion, as analyzed by LC-MS/MS. Figure discloses SEQ ID NOS 253, 164, 166, 168, 170, 171, 254, 165, 167, 169, 255, and 172, respectively, in order of appearance.

FIG. 23 shows candidate assignments for Orycun IGH and IGL alleles comprising the VDJ and VJ regions of the $V_LC_L$ and $V_HC_1$ regions of the indicated 1593 mAb clones as determined by IMGT Analysis of V(D)J Junctions. Alleles are vertically aligned when present in more than one mAb. More than one candidate allele was identified for several clones.

FIG. 24 shows protein sequence alignment of the signal peptide, framework regions (FRs) and complementary determining regions (CDRs) of the heavy (H) and light (L) chains of hybridoma clones that found to recognize the target 2004 peptide with high affinity. Red and blue text indicate the FR and CDR sequences in each alignment. Gray highlighted text indicates amino acids that vary from the consensus sequences at the indicated positions, or regions of variability if no consensus exists at the highlighted position. All mAb clones are grouped by their ranking from highest affinity to lowest affinity as determined by the signal they produced upon analysis of their ability to detect serial dilutions of the 2004 target peptide in an indirect ELISA. Figure discloses SEQ ID NOS 173, 175, 177, 179, 181, 183, 185, 187, 189, 191, 256, 174, 176, 178, 180, 182, 184, 186, 188, 190, 192, and 194, respectively, in order of appearance.

FIG. 25 shows relative indirect ELISA signal for sample wells incubated with wells pre-incubated with four-fold serial dilutions of the 2004 target peptide (samples 1-7:10, 000, 2,500, 625, 156, 39, 10, or 2.5 pg) or with PBS (sample 8) in the presence of a constant amount of mAb. Clones are ranked by their relative signal across this dilution series as indicated by red text adjacent to the figure labels.

FIG. 26 shows candidate assignments for Orycun IGH and IGL alleles comprising the VDJ and VJ regions of the $V_LC_l$ and $V_HC_1$ regions of the indicated 2004 mAb clones as determined by IMGT Analysis of V(D)J Junctions. Alleles are vertically aligned when present in more than one mAb.

Figure 27:
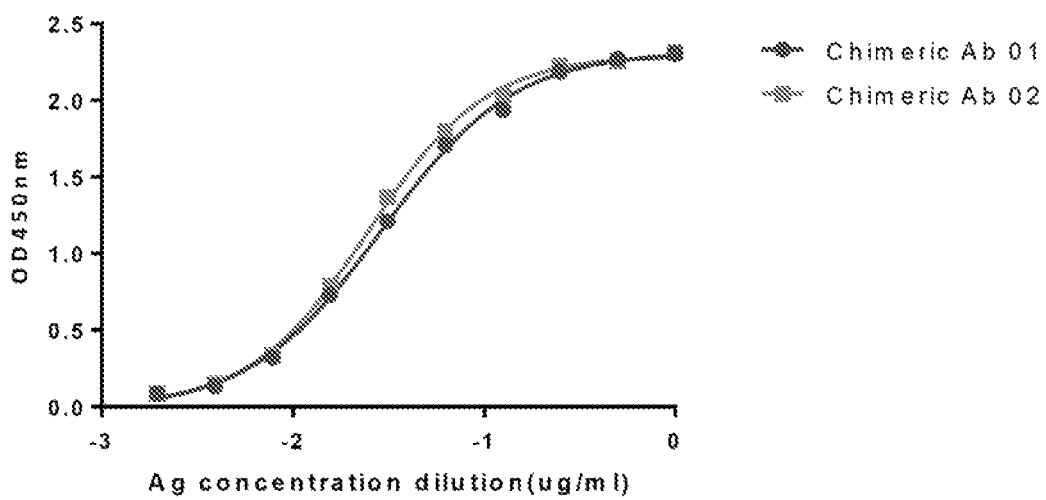

FIG. 27 shows chimeric Fab binding activity.

FIG. 28 shows NNK libraries ELISA screening results. Chimeric is marked yellow; negative control is marked green; blank is marked blue.

FIG. 29 shows SDS-PAGE results of purified IgGs.

FIG. 30 shows affinity measurement of antibodies to Peptide 1593

Figure 31:
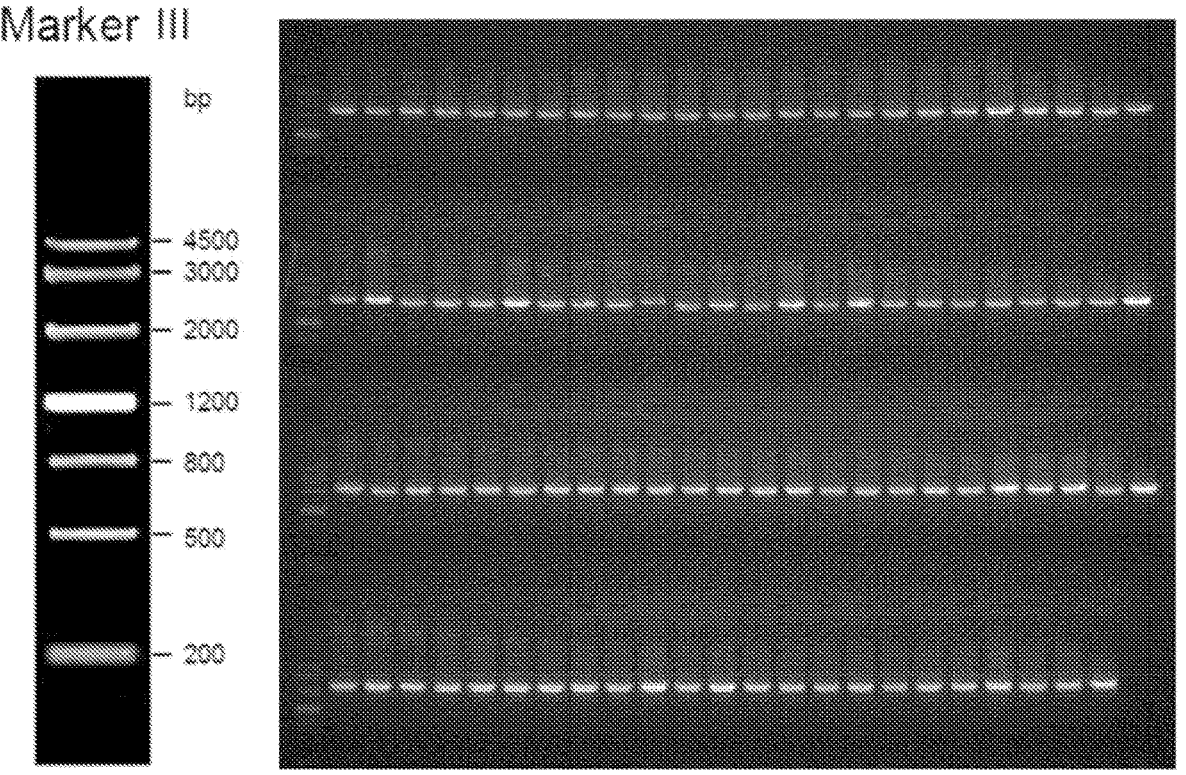

FIG. 31 shows colony PCR results of Combinatory mutagenesis library. 95 randomly picked clones of library were amplified by PCR using primers M13R-48 and M13F-47. Clones with ~2400 bp DNA band have Fab inserts.

FIG. 32 shows monoclonal phage ELISA validation of R1-R4. Negative control is marked green; blank is marked blue; clones with OD>0.5 were marked red.

FIG. 33 shows monoclonal antibody soluble expression ELISA validation of R3-R6. Chimeric is marked yellow; negative control is marked green; blank is marked blue; Top 10 clones of each plate is marked red.

Figure 34:
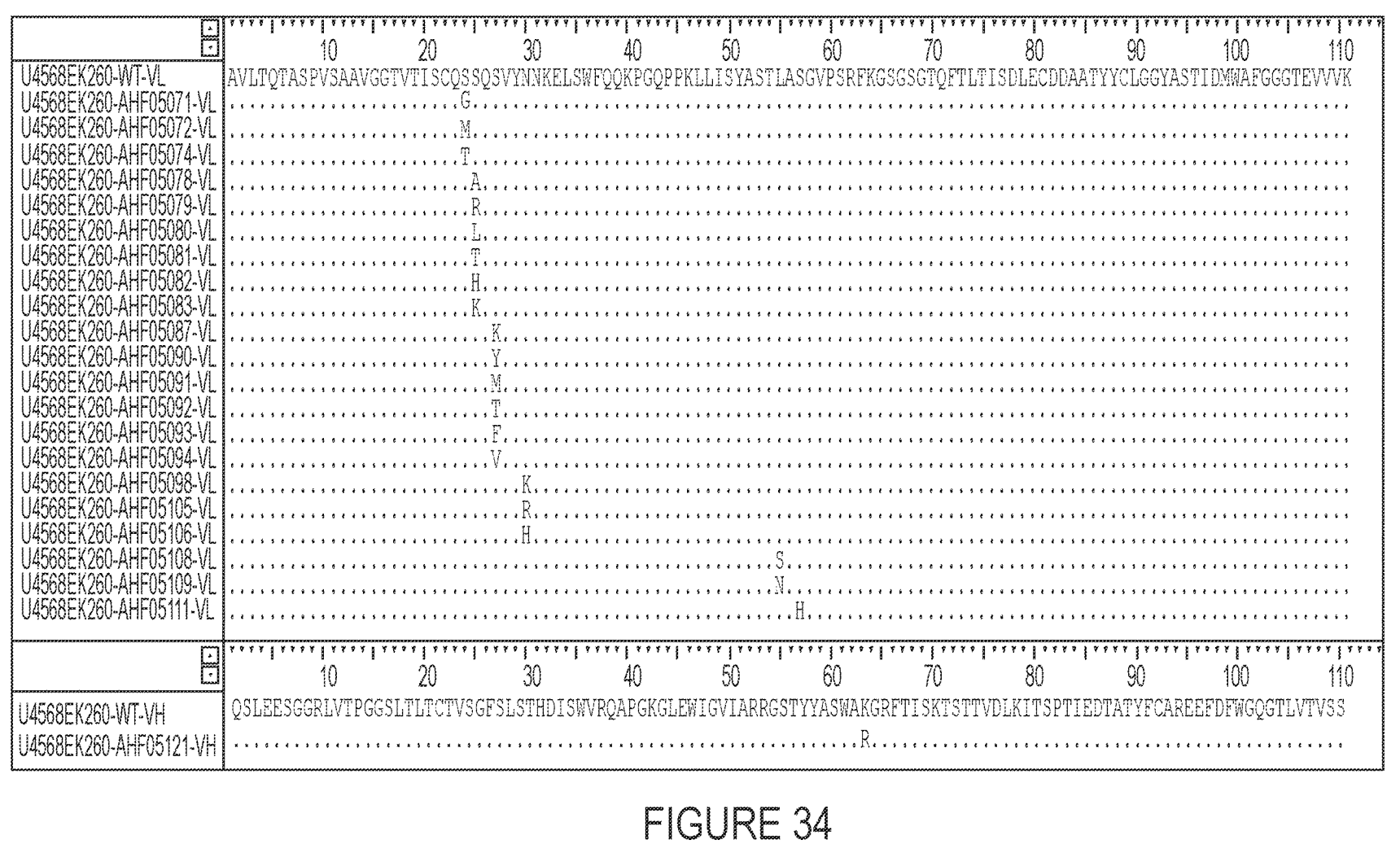

FIG. 34 shows the mutation of 22 hits. Figure discloses SEQ ID NOS 128, 207-227, 127, and 206, respectively, in order of appearance.

DETAILED DESCRIPTION

*Mycobacterium tuberculosis* actively secretes CFP-10 (culture filtrate antigen, 10 kDa) to promote pathologic responses. Loss of this factor significantly reduces virulence, a strong indication that CFP-10 is specific for virulent mycobacteria and thus, an ideal diagnostic for active TB cases. Aspects of the invention provide antibodies that bind to an epitope within CFP-10, and methods for utilizing the same to detect CFP-10 and diagnose, prognose, or monitor a subject infected with *Mycobacterium tuberculosis*. Few studies have employed monoclonal antibodies to detect *Mycobacterium tuberculosis* protein in clinical samples for direct TB diagnosis, and these demonstrate poor performance versus existing TB assays. See, for example, Feng, T. T., et al. "Novel monoclonal antibodies to ESAT-6 and CFP-10 antigens for ELISA-based diagnosis of pleural tuberculosis." *The International journal of tuberculosis and lung disease* 15.6 (2011): 804-810, and Wu, Xiaoxin, et al. "Preparation of immunochromatographic strips for rapid detection of early secreted protein ESAT-6 and culture filtrate protein CFP-10 from *Mycobacterium tuberculosis.*" *Medicine* 96.51 (2017). Current blood-based TB diagnostics instead evaluate the response of a patient's immune cells to recombinant *Mycobacterium tuberculosis* proteins, including CFP-10, as a measure of TB exposure. See, for example, Lalvani, Ajit, and Hilary S. Whitworth. "Progress in interferon-gamma release assay development and applications: an unfolding story of translational research." *Annals of translational medicine* 7.Suppl 3 (2019).

Antibodies

As used herein, the term "antibody" can refer to immunoglobulin molecules and immunologically active portions of immunoglobulin (Ig) molecules, i.e., molecules that contain an antigen binding site that specifically binds (immunoreacts with) an antigen. For example, "specifically binds" or "immunoreacts with" can refer to the antibody reacting with one or more antigenic determinants of the antigen and does not react with other polypeptides. Antibodies include, but are not limited to, polyclonal, monoclonal, and chimeric antibodies In general, antibody molecules obtained from humans relate to any of the classes IgG, IgM, IgA, IgE and IgD, which differ from one another by the nature of the heavy chain present in the molecule. Certain classes have subclasses as well, such as IgG1, IgG2, IgG3, IgG4. Furthermore, in humans, the light chain can be a kappa chain or a lambda chain. The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

The nucleic acid and amino acid sequence of the anti CFP-10 antibodies are provided herein:

TABLE 1A

Antibody 17E4-1
Variable Region nucleic acid sequences $V_H$ chain of 17E4-1 (SEQ ID NO: 1)
Signal sequence-
FR1-CDR1-FR2-CDR2-FR3-CDR3-FR4
ATGGAGACTGGGCTGCGCTGGCTTCTCCTGGTCGC

TGTGCTCAAAGGTGTCCAGTGTCAGTCGCTGGAGG

AGTCCGGGGGTCGCCTGGTAACGCCGGGGACACCC

CTGACACTCACCTGCACAGTCTCTGGATTCTCCCT

CAGCAGCTGCGACGTGAACTGGGTCCGCCAGGCTC

CAGGGAAGGGACTGGAATGGATCGGAGTCATTGCT

AGAGCTGGTAGCACATACTACGCGAGTTGGGCGAA

AGGCCGATTTACCGTCTCCAAGACCTCGACCACGG

TGTACCTGGAAATCGCCAGTCCGACGATTGAGGAC

ACGGCCACCTATTTCTGTGTCAGAGAAGAATTTGA

CTTTTGGGGCCAAGGCACCCTTGTCACCGTCTCCT

CA $V_L$ chain of 17E4-1 (SEQ ID NO: 3)
Signal sequence-
FR1-CDR1-FR2-CDR2-FR3-CDR3-FR4
ATGGACACGAGGGCCCCCACTCAGCTGCTGGGGCT

CCTGCTGCTCTGGCTCCCAGGTGCCACATTTGCCG

TABLE 1A-continued

Antibody 17E4-1
Variable Region nucleic acid sequences

CCGTGCTGACCCAGACTGCATCCCCCGTGTCTGCG

GCTAATGGAGGCACAGTCACCATCACTTGCCAGTC

CAGTCAGAGTGTCTATAATAATAATGAATTGTCGT

GGTTTCAGCAGAAACCAGGGCAGCCTCCCAAGCTC

CTGATAAATTATTCATCCACTCTGGCATCTGGGGT

CCCATCGCGGTTCAAAGGCAGTGGATCTGGGACAC

AGTTCACTCTCACCATCAGCGGCGTGCAGTGTGAC

GATGCTGCCACTTACTACTGTCTGGGCGGATATGC

TAGTATTATTGATATGTGGACTTTCGGCGGAGGGA

CCGAGGTGGTGGTCAAA

TABLE 1B

Antibody 17E4-1
Variable Region amino acid sequences

$V_H$ chain of 17E4-1 (SEQ ID NO: 2)
Signal sequence-
FR1-CDR1-FR2-CDR2-FR3-CDR3-FR4
METGLRWLLLVAVLKGVQCQSLEESGGRLVTPGTP

LTLTCTVSGFSLSSCDVNWVRQAPGKGLEWIGVIA

RAGSTYYASWAKGRFTVSKTSTTVYLEIASPTIED

TATYFCVREEFDFWGQGTLVTVSS $V_L$ chain of 17E4-1 (SEQ ID NO: 4)
Signal sequence-
FR1-CDR1-FR2-CDR2-FR3-CDR3-FR4
MDTRAPTQLLGLLLLWLPGATFAAVLTQTASPVSA

ANGGTVTITCQSSQSVYNNNELSWFQQKPGQPPKL

LINYSSTLASGVPSRFKGSGSGTQFTLTISGVQCD

DAATYYCLGGYASIIDMWTFGGGTEVVVK

TABLE 1C

Antibody 21H3-1
Variable Region nucleic acid sequences

$V_H$ chain of 21H3-1 (SEQ ID NO: 5)
Signal sequence-
FR1-CDR1-FR2-CDR2-FR3-CDR3-FR4
ATGGAGACTGGGCTGCGCTGGCTTCTCCTGGTCG

CTGTGCTCAAAGGTGTCCAGTGTCAGTCGCTGGA

GGAGTCCGGGGGTCGCCTGGTAACGCCTGGGACA

CCCCTGACACTCACCTGTACAGTCTCTGGATTCT

CCCTCAGCAGCTATGACGTGAGCTGGGTCCGCCA

GGCTCCAGGGAAGGGACTGGAATGGATCGGAGTT

ATTAGTAGAGGTGGCACCACATATTCCACAAACT

GGGCGAAAGGCCGATTCACCATCTCCAAAACCTC

TABLE 1C-continued

Antibody 21H3-1
Variable Region nucleic acid sequences

GACCACGGTGGATCTGAGAATCACCAGTCCGACA

ATTGAGGACACGGCCACCTATTTCTGTGCCAGAG

AGGAATTTAACTTGTGGGGCCAGGGCACCCTGGT

CACCGTCTCCTCA $V_L$ chain of 1F8 (SEQ ID NO: 7)
Signal sequence-
FR1-CDR1-FR2-CDR2-FR3-CDR3-FR4
ATGGACACGAGGGCCCCCACTCAGCTGCTGGGGC

TCCTGCTGCTCTGGCTCCCAGGTGCCACATTTGC

CATCGTGATGACCCAGACTCCATCTTCCAAGTCT

GTCCCTGTGGGAGACACAGTCACCATCAATTGCC

AGGCCAGTGAGAGTGTTTATTGGAACAACCGCTT

AGCCTGGTTTCAACAGAAACCAGGGCAGCCTCCC

AAGCAACTGATCTACGAAGCATCCAAACTGGCAT

CTGGGGTCCCATCGCGGTTCAAAGGCAGTGGATC

TGGGACACAGTTCACTCTCACCATCAGCGATGTG

GTGTGTGACGATGCTGCCACTTACTACTGTGCAG

GATATAAAAGTAGTAGTGATGGTCCTGCTTTCGG

CGGAGGGACCGAGGTGGTGGTCAAA

TABLE 1D

Antibody 21H3-1
Variable Region amino acid sequences

$V_H$ chain of 21H3-1 (SEQ ID NO: 6)
Signal sequence-
FR1-CDR1-FR2-CDR2-FR3-CDR3-FR4
METGLRWLLLVAVLKGVQCQSLEESGGRLVTPG

TPLTLTCTVSGFSLSSYDVSWVRQAPGKGLEWI

GVISRGGTTYSTNWAKGRFTISKTSTTVDLRIT

SPTIEDTATYFCAREEFNLWGQGTLVTVSS $V_L$ chain of 21H3-1 (SEQ ID NO: 8)
Signal sequence-
FR1-CDR1-FR2-CDR2-FR3-CDR3-FR4
MDTRAPTQLLGLLLLWLPGATFAIVMTQTPSSK

SVPVGDTVTINCQASESVYWNNRLAWFQQKPGQ

PPKQLIYEASKLASGVPSRFKGSGSGTQFTLTI

SDVVCDDAATYYCAGYKSSSDGPAFGGGTEVVVK

TABLE 1E

Antibody 119C10-1
Variable Region nucleic acid sequences

V_H chain of 119C10-1 (SEQ ID NO: 9)
Signal sequence-
FR1-CDR1-FR2-CDR2-FR3-CDR3-FR4
ATGGAGACTGGGCTGCGCTGGCTTCTCCTGGTCG

CTGTGCTCAAAGGTGTCCAGTGTCAGTCGGTGGA

GGAGTCCGGGGGTCGCCTGGTCACGCCTGGGACA

CCCCTGACACTCACCTGCACAGTCTCTGGATTCT

CCCTCAGT<u>AGCTACAACATGGGC</u>TGGGTCCGCCA

GGCTCCAGGGAAGGGGCTGGAATACATCGGA<u>TTC</u>

<u>ATTGGTACTACTGGTCGCGCATTCTACGCGAGCT</u>

<u>GGGCAAAAGGC</u>CGATTCACCATCTCCAAAACCTC

GACCACGGTGAATCTGAAAGTGACCAGTCTGACA

ACCGAGGACACGGCCACCTATTTCTGTGCCGGAG

<u>GGGCTCCTGGTTACACCCCCTTTAACTTGTGGGG</u>

CCAAGGCACCCTGGTCACCGTCTCCTCA

V_L chain of 119C10-1 (SEQ ID NO: 11)
Signal sequence-
FR1-CDR1-FR2-CDR2-FR3-CDR3-FR4
ATGGACACGAGGGCCCCCACTCAGCTGCTGGGGC

TCCTGCTGCTCTGGCTCCCAGGTGCCACATTTGC

GCAAGTGCTGACCCAGACTCCATCGTCCGTGTCT

GCGGCTGTGGGAGGCACAGTCAGCATCAGTTGC<u>C</u>

<u>AGTCCAGTCAGAGTGTTATTAGTAACGACTTATC</u>

<u>C</u>TGGTTTCAGCAGAAACCAGGGCAGCCTCCCAGG

CAACTGATCTAC<u>CAGACATCCAAACTGGC</u>ATCTG

GGGTCCCATCGCGGTTCAGTGGCAGTGGATCTGG

GACACAGTTCACTCTCACCATCAGCGACCTAAAG

TGTGACGATGCTGCCACTTATTCTTGT<u>GCAGGCG</u>

<u>GTTACAGTAGTAGTCTTGACATATATGCTTT</u>CGG

CGGAGGGACCGAGGTGGTGGTCAAA

TABLE 1F

Antibody 119C10-1
Variable Region amino acid sequences

V_H chain of 119C10-1 (SEQ ID NO: 10)
Signal sequence-
FR1-CDR1-FR2-CDR2-FR3-CDR3-FR4
METGLRWLLLVAVLKGVQCQSVEESGGRLVTPGTP LTLTCTVSGFSLSS<u>YNMGW</u>VRQAPGKGLEYIG<u>FIG</u>

<u>TTGRAFYASWAKG</u>RFTISKTSTTVNLKVTSLTTED

TATYFCAGG<u>APGYTPFNL</u>WGQGTLVTVSS

TABLE 1F-continued

Antibody 119C10-1
Variable Region amino acid sequences

V_L chain of 119C10-1 (SEQ ID NO: 12)
Signal sequence-
FR1-CDR1-FR2-CDR2-FR3-CDR3-FR4
MDTRAPTQLLGLLLLWLPGATFAQVLTQTPSSVSA AVGGTVSISC<u>QSSQSVISNDLS</u>WFQQKPGQPPRQL

IYQTSKLASGVPSRFSGSGSGTQFTLTISDLKCDD

AATYSC<u>AGGYSSSLDIYA</u>FGGGTEVVVK

TABLE 1G

Antibody 65D3-1
Variable Region nucleic acid sequences

V_H chain of 65D3-1 (SEQ ID NO: 13)
Signal sequence-
FR1-CDR1-FR2-CDR2-FR3-CDR3-FR4
ATGGAGACTGGGCTGCGCTGGCTTCTCCTGGTCGCTGT

GCTCAAAGGTGTCCAGTGTCAGTCGCTGGAGGAGTCCG

GGGGTCGCCTGGTAACGCCTGGAGGATCCCTGACACTC

ACCTGCACAGTCTCTGGATTCTCCCTCAGC<u>ACCCACGA</u>

<u>CATCAGCTGGGTCCGCCAGGCTCCAGGGAAGGGACTGG</u>

AATGGATCGGA<u>GTCATTGCCAGACGTGGCAGCACATAC</u>

<u>TACGCGAGTTGGGCAAAAGGC</u>CGATTCACCATCTCCAA

GACCTCGACCACGGTGGATCTGAAAATCACCAGTCCGA

CAATTGAAGACACGGCCACCTATTTCTGTGCCAGA<u>GAA</u>

<u>GAATTTGACTTTT</u>GGGGCCAGGGCACCCTGGTCACCGT

CTCCTCA

V_L chain of 65D3-1 (SEQ ID NO: 15)
Signal sequence-
FR1-CDR1-FR2-CDR2-FR3-CDR3-FR4
ATGGACACGAGGGCCCCCACTCAGCTGCTGGGGCTCCT

GCTGCTCTGGCTCCCAGGTGCCACATTTGCCGCCGTGC

TGACCCAGACTGCATCCCCCGTGTCTGCGGCTGTTGGA

GGCACAGTCACCATCAGTTGC<u>CAGTCCAGTCAGAGTGT</u>

<u>TTATAATAACAAAGAATTATCC</u>TGGTTTCAGCAGAAAC

CAGGGCAGCCTCCCAAACTCCTGATCTCT<u>TATGCATCC</u>

<u>ACTCTGGCATCT</u>GGGGTCCCATCGCGGTTCAAAGGCAG

TGGATCTGGGACACAGTTCACTCTCACCATCAGCGACC

TGGAGTGTGACGATGCTGCCACTTACTACTGT<u>CTAGGC</u>

<u>GGTTATGCTAGTACTATTGATATGTGGGCT</u>TTCGGCGG

AGGGACCGAGGTGGTGGTCAAA

TABLE 1H

Antibody 65D3-1
Variable Region chain amino acid sequences

V_H chain of 65D3-1 (SEQ ID NO: 14)
Signal sequence-
FR1-CDR1-FR2-CDR2-FR3-CDR3-FR4
METGLRWLLLLVAVLKGVQCQSLEESGGRLVTPGGSLTLTC

TVSGFSLSTHDISWVRQAPGKGLEWIGVIARRGSTYYASW

AKGRFTISKTSTTVDLKITSPTIEDTATYFCAREEFDFWG

QGTLVTVSS

V_L chain of 65D3-1 (SEQ ID NO: 16)
Signal sequence-
FR1-CDR1-FR2-CDR2-FR3-CDR3-FR4
MDTRAPTQLLGLLLLWLPGATFAAVLTQTASPVSAAVGG

TVTISCQSSQSVYNNKELSWFQQKPGQPPKLLISYASTL

ASGVPSRFKGSGSGTQFTLTISDLECDDAATYYCLGGYA

STIDMWAFGGGTEVVVK

TABLE 1I

Antibody 67G8-2
Variable Region chain amino acid sequences

V_H chain of 67G8-2 (SEQ ID NO: 164)
Signal sequence-
FR1-CDR1-FR2-CDR2-FR3-CDR3-FR4
METGLRWLLLLVAVLKGVQCQSVEESGGRLVTPGTPLTLTCT

VSGFSLGNYDGHWVRQTPEKGLEWIGVIATIGDTYYASWAK

GRFSISKTSATVELRITSPTTEDTATYFCVRGDSRTSNEIF

NLWGQGTLVTVSS

V_L chain of 67G8-2 (SEQ ID NO: 165)
Signal sequence-
FR1-CDR1-FR2-CDR2-FR3-CDR3-FR4
MDTRAPTQLLGLLLLWLPGATFAAVLTQTPSPVSAAVGGTL

TINCQSTRSVHNNICLSWYQQKPGQPPKLLIYSASTLASGV

PSRFKGSGSGTQFTLAINDVQCGDAATYYCAGCFPSKSDMY

GFGGGTEVVVK

TABLE 1J

Antibody 135A6-1
Variable Region chain amino acid sequences

V_H chain of 135A6-1 (SEQ ID NO: 166)
Signal sequence-
FR1-CDR1-FR2-CDR2-FR3-CDR3-FR4
METGLRWLLLLVAVLKGVQCQSVEESGGRLVTPGTPLTLTCTVSG

FSLGNYDISWVRQAPGKGLEWIGVIATVGDTYYASWAKGRFTIS

KTSATVDLKITSPTTEDTATYFCVRGDSPSTNEIFGLWGQGTLV

TVSS

V_L chain of 135A6-1 (SEQ ID NO: 167)
Signal sequence-
FR1-CDR1-FR2-CDR2-FR3-CDR3-FR4
MDTRAPTQLLGLLLLWLPGATFAAVLTQTPSPVSAAVGGTLTIN

CQSSRTVYNNICLSWYQQKLGQPPKLLIYGASTLTSGVPSRFRG

TABLE 1J-continued

Antibody 135A6-1
Variable Region chain amino acid sequences

SGSGTQFTLTINDVQCGDAATYYCAGCFPSTSDMYGFGGGTEVV

VK

TABLE 1K

Antibody 101G10-2
Variable Region chain amino acid sequences

V_H chain of 101G10-2 (SEQ ID NO: 168)
Signal sequence-
FR1-CDR1-FR2-CDR2-FR3-CDR3-FR4
MEAGLRWLLLLVAVLKGVQCQSVEESGGRLVTPGTPLTLTC

TVSGFSLSSYDMTWVRQAPGKGLEYIGVISYGGSAYYASW

AKGRFTISKTSTTVDLKITSPTTEDTATYFCARGDSDGSS

ELFNLWGQGTLVTVSS
V_L chain of 101G10-2 (SEQ ID NO: 169)
Signal sequence-
FR1-CDR1-FR2-CDR2-FR3-CDR3-FR4
MDTRAPTQLLGLLLLWLPGAAFAAVLTQTPSPVSAPVGGT

VSINCQSSKSVYNNNCLSWYQQKPGQPPNLLIYGASTLAS

GVPSRFKGSGSGTQFTLTINDVQCDDAATYYCAGCFASTN

DMYGFGGGSEVVVK

TABLE 1L

Antibody 125D9-1
Variable Region chain amino acid sequences

V_H chain of 125D9-1 (SEQ ID NO: 170)
Signal sequence-
FR1-CDR1-FR2-CDR2-FR3-CDR3-FR4
MEAGLRWLLLLVAVLKGVQCQPVEESGGRLVTPGTPLT

LTCTVSGFSLSSYDMTWVRQAPGKGLEYIGVVAYGGA

TYYASWAKGRFTISKTSTTVDLKITSPTTEDTATYFC

ARGDSDGSSELFNLWGQGTLVTVSS

V_L chain of 125D9-1 (SEQ ID NO: 255)
Signal sequence-
FR1-CDR1-FR2-CDR2-FR3-CDR3-FR4
MDTRAPTQLLGLLLLWLPGATFAAVLTQTPSPVSAAVG

GTVTINCQSSKSVYNNNCLSWYQQKQGQPPKLLIYQAS

TPASGVPSRFKGSGSGTQFTLTINDVQCDDAATYYCAG

CFASTSDMYGFGGGTGVVVK

TABLE 1M

Antibody 91B4-1
Variable Region chain amino acid sequences

V_H chain of 91B4-1 (SEQ ID NO: 171)
Signal sequence-
FR1-CDR1-FR2-CDR2-FR3-CDR3-FR4
METGLRWLLLLVAVLKGVQCQSLEESGGRLVSPGGSLTLTCTVS

GIDLSRFGVSWVRQAPGKGLEWTGYIHTDGNVYYASWAKGRFT

TABLE 1M-continued

Antibody 91B4-1
Variable Region chain amino acid sequences

ISKTSTTVDLKMTSLTTEDTATYFCARGGYAADLWGQAALVTV

SS $V_L$ chain of 91B4-1 (SEQ ID NO: 172)
Signal sequence-
FR1-CDR1-FR2-CDR2-FR3-CDR3-FR4
MDTRAPTQLLGLLLLWLPGAKCDPMLTQTPSSVSAAVGGTVTIS

CQSSESVYKNYLAWYQQKLGQPPKLLIGATSTLVSGVPSRFKGS

GSRTQFSLTISDLECDDAATYYCVGGYTGKNVFGGGTEVVVK

TABLE 1N

Antibody 70A12-1
Variable Region chain amino acid sequences $V_H$ chain of 70A12-1 (SEQ ID NO: 173)
Signal sequence-
FR1-CDR1-FR2-CDR2-FR3-CDR3-FR4
METGLRWLLLVAVLKGVQCQSVEESGGRLVTPGTPLTLTCTAS

GFSLSNHYIIWVRQTPGKGLEWIGAISRRSKTDYASWAKGRFT

ISKTSTTVDLKITSPTTEDTATYFCARQLDGSTSVVCDIWGPG

TLVTVSS $V_L$ chain of 70A12-1 (SEQ ID NO: 174)
Signal sequence-
FR1-CDR1-FR2-CDR2-FR3-CDR3-FR4
MDTRAPTQLLGLLLLWLPGATFAQVLTQTPSPVSAAVGGTVTI

NCQASQNVYNDRNLGWYQQKPGQPPKLLIYGPSTLASGVSSRF

TGSGSGTQFTLTISDLQCDDAATYYCQGEFICSSADCCAFGGG

TEVVVK

TABLE 1O

Antibody 6D10-1
Variable Region chain amino acid sequences $V_H$ chain of 6D10-1 (SEQ ID NO: 175)
Signal sequence-
FR1-CDR1-FR2-CDR2-FR3-CDR3-FR4
METGLRWLLLVAVLKGVQCQSVEESGGRLVTPGTPLTLTCTVSGFSL

SDVTMSWVRQAPGKGLEWIGIIGRRGRIWYANWAKGRFTISKTSPTV

DLKIISPTSDDTATYFCARGAVSSDWNMYGMDLWGPGTLVTVSS $V_L$ chain of 6D10-1 (SEQ ID NO: 176)
Signal sequence-
FR1-CDR1-FR2-CDR2-FR3-CDR3-FR4
MDTRAPTQLLGLLLLWLPGATFAQVLTQTPSVSAPVGGTVTINCQS

SQSVYNNENLAWYQQKLGQPPKLLIYGASTLASGVSSRFEGSGSGTQ

FALTISGVQCDDAATYYCQGEFDCSSADCFAFGGGTEVVVK

TABLE 1P

Antibody 5B7-1
Variable Region chain amino acid sequences $V_H$ chain of 5B7-1 (SEQ ID NO: 177)
Signal sequence-
FR1-CDR1-FR2-CDR2-FR3-CDR3-FR4
METGLRWLLLVAVLKGVQCQSVEESGGRLVTPGTPLTLTCTVS

GFSLSDVTISWVRQAPGKGLKWTGIIGRRGRIRYADWAKGRFT

ISKTSTTVDLKITSPTTDDTATYFCARAYVSSDWNIYGMDLWG

PGTLVTVSS $V_L$ chain of 5B7-1 (SEQ ID NO: 178)
Signal sequence-
FR1-CDR1-FR2-CDR2-FR3-CDR3-FR4
MDTRAPTQLLGLLLLWLPGATFAQVLTQTASPVSAPVGGTVTIN

CQASQSVYNNKNLAWYQQKLGQPPKLLIYEASKLASGVSSRFEG

SGSGTQFALTISGVQCDDAATYYCQGEFDCSSADCFVFGGGTEV

VVK

TABLE 1Q

Antibody 55H8-1
Variable Region chain amino acid sequences $V_H$ chain of 55H8-1 (SEQ ID NO: 179)
Signal sequence-
FR1-CDR1-FR2-CDR2-FR3-CDR3-FR4
METGLRWLLLVAVLKGVQCQSMEESGGRLVTPGTPLTLTCT

VSGFSLSDHAMSWVRQAPGKGLEWIGIVGRRGRTYYASWAK

GRFTISKTSTTVDLKITSPTIEDTATYFCARGYVSSDWNIY

GMDLWGPGTLVTVSS $V_L$ chain of 55H8-1 (SEQ ID NO: 180)
Signal sequence-
FR1-CDR1-FR2-CDR2-FR3-CDR3-FR4
MDTRAPTQLLGLLLLWLPGATFAQVLTQTPSPVSAAVGGTVT

INCQASQSVYNNKNLAWYQQKPGQPPKLLIYEASTLASGVSS

RFKGSGSGTQFTLTISGVQCDDAATYYCQGEFDCSSADCFAF

GGGTEVVVK

TABLE 1R

Antibody 10G3-1
Variable Region chain amino acid sequences $V_H$ chain of 10G3-1 (SEQ ID NO: 181)
Signal sequence-
FR1-CDR1-FR2-CDR2-FR3-CDR3-FR4
METGLRWLLLVAVLKGVQCQSVEESGGRLVTPGTPLTLTCT

ASGFSLSDDAMSWVRQAPGKGLEWIGIIGRRGKTWYANWAK

GRFTISKTSTTVDLKITSPTTEDTATYFCARGYVSSDWNIY

GMDLWGPGTLVTVSA

TABLE 1R-continued

---

Antibody 10G3-1
Variable Region chain amino acid sequences

---

$V_L$ chain of 10G3-1 (SEQ ID NO: 182)
Signal sequence-
FR1-CDR1-FR2-CDR2-FR3-CDR3-FR4
MDTRAPTQLLGLLLLWLPGATFAQVLTQTPSPVSAAVGGTV

TINCQASQSVYNNKNLAWYQQKSGQPPKLLIYEASKLASGV

PSRFKGSGSGTQFTLTISGVQCDDAATYYCQGEFSCSSADC

FTFGGGTEVVVK

---

TABLE 1S

---

Antibody 76C4-1
Variable Region chain amino acid sequences

---

$V_H$ chain of 76C4-1 (SEQ ID NO: 183)
Signal sequence-
FR1-CDR1-FR2-CDR2-FR3-CDR3-FR4
METGLRWLLLVAVLKGGQCQSVEESGGRLVTPGTPLTL

TCTASGSDINKYTMGWVRQAPGKGLEWVGAIGATGRTV

YANWAKGRFTISKTSTTVDLIITSPTTEDTATYFCARN

VVDASDSDGMIAFDPWGPGTLVTVSS $V_L$ chain of 76C4-1 (SEQ ID NO: 184)
Signal sequence-
FR1-CDR1-FR2-CDR2-FR3-CDR3-FR4
MDTRAPTQLLGLLLLWLPGATFAQVLTQTPSPVSAAVGG

TVTINCQASQSVYNNKNLAWYQQKPGQPPKLLIYKASTL

ASGVPSRFAGSGSGTEVTLTISDLECDDAATYYCQGEFS

CSSGDCVAFGGGTEVVVK

---

TABLE 1T

---

Antibody 3E9-1
Variable Region chain amino acid sequences

---

$V_H$ chain of 3E9-1 (SEQ ID NO: 185)
Signal sequence-
FR1-CDR1-FR2-CDR2-FR3-CDR3-FR4
METGLRWLLLVAVLKGVQCQSLEESGGRLVTPGGS

LTLTCTVSGIDLSSNAMGWVRQAPGEGLEWIGSIY

ASGNTYYASWAKGRFAISKTSTTVDLKMTSLTAAD

TATYFCARLFNIWGPGTLVTVSS $V_L$ chain of 3E9-1 (SEQ ID NO: 186)
Signal sequence-
FR1-CDR1-FR2-CDR2-FR3-CDR3-FR4
MDTRAPTQLLGLLLLWLPGARCADIVLTQTPASVS

SVVGGTVTINCQASQSVFDNKNLSWFQQKPGQPPK

QLIYGASTLDSGVPSRFKGSGSGTQFTLTISDMQC

DDAATYYCGGRDSGNIYDFGGGTEVVVK

---

TABLE 1U

---

Antibody 76H12-1
Variable Region chain amino acid sequences

---

$V_H$ chain of 76H12-1 (SEQ ID NO: 187)
Signal sequence-
FR1-CDR1-FR2-CDR2-FR3-CDR3-FR4
METGLRWLLLVAVLKGVQCQELKESGGRLVTPGGSL

TLSCTASGIDLSGSAMGWVRQAPGQGLEWIGSIYVS

GNTYYASWAKGRFAISRTSTTVDLKMTSLTAADTAT

YFCARLLNIWGPGTLVTVSS $V_L$ chain of 76H12-1 (SEQ ID NO: 188)
Signal sequence-
FR1-CDR1-FR2-CDR2-FR3-CDR3-FR4
MDTRAPTQLLGLLLLWLPGARCADIVLTQTPSPVSIA

VGGTVTINCQASQSVYDNKNLAWFQQKPGQPPKQLIY

GASTLASGVPSRFKGSGSGTQFTLTISGMQCDDAATY

YCGGRDSDNIYDFGGGTEVVVK

---

TABLE 1V

---

Antibody 74D3-1
Variable Region chain amino acid sequences

---

$V_H$ chain of 74D3-1 (SEQ ID NO: 189)
Signal sequence-
FR1-CDR1-FR2-CDR2-FR3-CDR3-FR4
METGLRWLLLVAVLKGVQCQSVEESGGRLVTPGTP

LTLTCTVSGIDLSNNAMGWVRQAPGEGLEWIGTIY

ASGNTYYASWAKGRFAISKTSTTVDLKMTSLTAAD

TATYFCARLFNIWGPGTLVTVSS $V_L$ chain of 74D3-1 (SEQ ID NO: 190)
Signal sequence-
FR1-CDR1-FR2-CDR2-FR3-CDR3-FR4
MDTRAPTQLLGLLLLWLPGARCADIVLTQSPASVS

SAVGGTVTINCQASQSVYDNKNLSWFQQKPGQPPK

QLIYAASTLASGVPSRFKGSGSGTQFTLTISGMQC

DDAATYYCGGRDSGNIYDFGGGTEVVVK

---

TABLE 1W

---

Antibody 4G6-1
Variable Region chain amino acid sequences

---

$V_H$ chain of 4G6-1 (SEQ ID NO: 191)
Signal sequence-
FR1-CDR1-FR2-CDR2-FR3-CDR3-FR4
METGLRWLLLVAVLKGVQCQSLEESGGRLVTPGT

PLTLTCTVSGIDLSSNAMGWVRQAPGEGLQWIGS

IYSSGNTYYASWARGRFAISRTSTTVDLKMTSLT

AADTATYFCARLFNIWGPGTLVTVSS

TABLE 1W-continued

```
            Antibody 4G6-1
 Variable Region chain amino acid sequences

VL chain of 4G6-1 (SEQ ID NO: 192)
Signal sequence-
FR1-CDR1-FR2-CDR2-FR3-CDR3-FR4
MDTRAPTQLLGLLLLWLPGARCADIVVTQTPASVS

ADVGGTVTINCQASQSVYDNKNLAWFQQKPGQPPK

QLIYGASTVASGVPSRFKGSGSGTQFTLTISDVQC

DDAATYYCGGRDNDNIYDFGGGTEVVVK
```

TABLE 1X

```
           Antibody 21F10-1
 Variable Region chain amino acid sequences

VH chain of 21F10-1 (SEQ ID NO: 193)
Signal sequence-
FR1-CDR1-FR2-CDR2-FR3-CDR3-FR4
METGLRWLLLVAVLKGVQCQSVEESGGRLVTPGTPL

TLTCTVSGIDLSSNAVGWVRQAPGEGLEWIGSIYSS

GNSYYASWAKGRFAISRTSTTVDLKMTRLTAADTAT

YFCARLFNIWGPGTLVTVS

VL chain of 21F10-1 (SEQ ID NO: 194)
Signal sequence-
FR1-CDR1-FR2-CDR2-FR3-CDR3-FR4
MDTRAPTQLLGLLLLWLPGARCADIVLTQTPASVSSV

VGGTVAINCQASQSVYDNKNLSWFQQKPGQTPKQLIY

GASTLASGVPSRFKGSGSGTQFTLTISGVQCDDAATY

YCGGRDDDNIYDFGGGTEVVVK
```

TABLE 1Y

```
           Antibody 65D3-1 Hv1
 Variable Region chain amino acid sequences

VH chain of 65D3-1 Hv1 (SEQ ID NO: 195)
Signal sequence-
FR1-CDR1-FR2-CDR2-FR3-CDR3-FR4
METGLRWLLLVAVLKGVQCQSLEESGGRLVTPGGSLTL

TCTVSGFSLSTHDISWVRQAPGKGLEWIGVIARRGWTY

YASWAKGRFTISKTSTTVDLKITSPTIEDTATYFCARE

EFDFWGQGTLVTVSS
```

*W indicates targeted mutation introduced into wild-type mAb
65D3-1 sequence

TABLE 1Z

```
           Antibody 65D3-1 Hv2
 Variable Region chain amino acid sequences

VH chain of 65D3-1 Hv2 (SEQ ID NO: 196)
Signal sequence-
FR1-CDR1-FR2-CDR2-FR3-CDR3-FR4
METGLRWLLLVAVLKGVQCQSLEESGGRLVTPGGSLTL

TCTVSGFSLSTHDISWVRQAPGKGLEWIGVIARRGWTY
```

TABLE 1Z-continued

```
           Antibody 65D3-1 Hv2
 Variable Region chain amino acid sequences

YASWAKKRFTISKTSTTVDLKITSPTIEDTATYFCARE

EFDEWGQGTLVTVSS
```

*W and K indicates targeted mutations introduced into wild-type
mAb 65D3-1 sequence

TABLE 1AA

```
           Antibody 65D3-1 Lv1
 Variable Region chain amino acid sequences

VL chain of 65D3-1 Lv1 (SEQ ID NO: 197)
Signal sequence-
FR1-CDR1-FR2-CDR2-FR3-CDR3-FR4
MDTRAPTQLLGLLLLWLPGATFAAVLTQTASPVSAAVG

GTVTISCQSSQSVYNNKELSWFQQKPGQPPKLLISYAS

TLATGVPSRFKGSGSGTQFTLTISDLECDDAATYYCLG

GYASTIDMWAFGGGTEVVVK
```

*T indicates targeted mutation introduced into wild-type mAb
65D3-1 sequence

A CFP-10 protein or a derivative, fragment, analog, homolog or ortholog thereof, can be utilized as an immunogen in the generation of antibodies that immunospecifically bind these protein components. As described herein, the immunogens used in the generation of antibodies to CFP-10 comprise peptide 1593 (TDAATLAQEAGNFERC; SEQ ID NO: 198; which can also be referred to as peptide 1593.75 or 1594) and peptide 2004 (TQIDQVESTAGSLQGQWRC; SEQ ID NO199). The target peptides, excluding the C-terminal linker cysteine as indicated by the bold and underline "C", matched sequences within CFP-10. Specifically, peptide 1593 matched amino acids 6 to 20, and peptide 2004 matched amino acids 27 to 44. The use of a peptide immunogen is utilized to address several critical issues associated with the use of antibodies developed using native CFP-10 protein to detect CFP-10 in clinical samples. First, full-length CFP-10 exhibits substantial homology with protein homologs secreted by related mycobacteria, many of which also cause respiratory infections that exhibit symptoms similar to those caused by active *Mycobacterium tuberculosis* infections. However, peptides derived from these CFP-10 proteins can contain unique amino sequences that permit specific identification of their species of origin. These sequences don't necessarily need to be displayed as accessible epitopes on native CFP-10 protein, and antibodies that recognize these linear epitopes do not necessarily need to be generated at appreciable levels when using native CFP-10 protein as the immunogen. Second, even if these epitopes are displayed on the surface of native CFP-10 in an accessible fashion, these sequences may be blocked in clinical samples by interactions with specific host antibodies or interactions with other host proteins. Without wishing to be bound by theory, these confounding effects are eliminated when diagnostic samples are digested to liberate target peptides. Thus, the use of peptide-specific antibodies to recognize target peptides produced by specific digestion of diagnostic samples, has synergistic effects to increase the detection sensitivity and specificity for a target biomarker.

Those skilled in the art will recognize that it is possible to determine, without undue experimentation, if a monoclonal antibody has the same specificity as a monoclonal antibody of the invention by ascertaining whether the former prevents the latter from binding to CFP-10 protein or fragment thereof. Without wishing to be bound by theory, if the monoclonal antibody being tested competes with the monoclonal antibody of the invention, as shown by a decrease in binding by the monoclonal antibody of the invention, then the two monoclonal antibodies can bind to the same, or to a closely related, epitope. Competition assays are well known to those of skill in the art.

Another way to determine whether a monoclonal antibody has the specificity of a monoclonal antibody of the invention is to pre-incubate the monoclonal antibody of the invention with the CFP-10 polypeptide with which it is normally reactive, and then add the monoclonal antibody being tested to determine if the monoclonal antibody being tested is inhibited in its ability to bind CFP-10. If the monoclonal antibody being tested is inhibited then, it has the same, or functionally equivalent, epitopic specificity as the monoclonal antibody of the invention.

As used herein, the term "epitope" can include any protein determinant that can specifically bind to an immunoglobulin, a single-chain variable fragment (scFv), or a T-cell receptor. Epitopic determinants can consist of chemically active surface groupings of molecules such as amino acids or sugar side chains and can have specific three-dimensional structural characteristics, as well as specific charge characteristics. For example, antibodies can be raised against N-terminal or C-terminal peptides of a polypeptide.

Without wishing to be bound by theory, the antibodies and fragments described herein bind a distinct epitope. As described herein, a peptide is used as the immunogen in the production of the antibodies, and therefore the epitope can comprise a linear amino acid sequence therein. In embodiments, the linear amino acid sequence is 2, 3, 4, 5, 6, 7, 8, 9, 10, or greater than 10 amino acids in length. In some embodiments, the linear amino acid sequence can be 11, 12, 13, 14, 15, or 20 amino acids in length. In embodiments, the linear amino acid sequence is 5 or 6 amino acids in length. In embodiments, the antibodies described herein can bind to the same or overlapping segment of the peptide immunogen. In other embodiments, the antibodies described herein can bind distinct, non-overlapping peptide sequences.

If two or more antibodies bind to the same or overlapping segment of a peptide immunogen, they can be considered to compete with each other for binding to the peptide immunogen. The term "competes with," when referring to a pair of antibodies, can refer to a first antibody that detectably competes with a second antibody (or other molecule) in a binding assay using, for example, recombinant immunogen or cell-surface expressed immunogens. For example, a first antibody can block or attenuate the binding of a second antibody, if this second bound to an epitope that overlapped with the epitope that was bound by the first antibody. Further, if the epitope of the second antibody is directly adjacent to the epitope bound by the first antibody, then the first antibody can block or attenuate the binding of the second antibody by spatial exclusion or steric effects.

As used herein, the terms "immunological binding," and "immunological binding properties" can refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ allows for the cancellation of parameters not related to affinity, and is equal to the dissociation constant $K_d$. (See, generally, Davies et al. (1990) Annual Rev Biochem 59:439-473). An antibody of the invention is said to specifically bind to CFP-10 epitope when the equilibrium binding constant ($K_d$) is ≤1 μM, ≤100 nM, ≤10 nM, or ≤100 pM to about 1 pM, as measured by assays such as radioligand binding assays or similar assays known to those skilled in the art.

Monoclonal antibodies as described herein can undergo affinity maturation, for example, to increase the strength or affinity of immunological binding. "Affinity maturation" can refer to a process in which an antibody is evolved from a reference antibody (also referred to as a parent antibody), such as by mutation of one or more amino acid residues, to have increased activity for a target antigen than a corresponding form of the reference antibody has for the same target antigen. Hence, the evolved antibody is optimized compared to the reference or template antibody.

Reference to an affinity matured antibody can refer to an antibody that has an increased activity for a target antigen relative to a reference antibody. For example, the affinity matured antibody can exhibit increased binding to the target antigen compared to the reference or parent antibody. The affinity matured antibody can bind to the same epitope as the reference antibody.

An optimized antibody can refer to an antibody, or portion thereof, that has an increased activity for a target protein or antigen compared to a reference antibody, for example, improved binding affinity for a target protein and/or an improved functional activity. The antibody can be optimized by virtue of one or more amino acid modifications (amino acid deletion, replacement or insertion) compared to a parent antibody not containing the one or more amino acid modifications. An activity, for example binding affinity, can be increased by at or about 1.5-fold to 1000-fold, such as at least or about 2-fold to 100-fold, for example at or about 1.5-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold or more compared to an activity of the parent antibody (e.g. germline antibody not containing the modification(s)).

Various procedures known within the art can be used for the production of polyclonal or monoclonal antibodies directed against a protein of the invention, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, NY, incorporated herein by reference).

Antibodies can be purified by well-known techniques, such as affinity chromatography using protein A or protein G, which provide primarily the IgG fraction of immune serum. Subsequently, or alternatively, the specific antigen that is the target of the immunoglobulin sought, or an epitope thereof, can be immobilized on a column to purify the immune specific antibody by immunoaffinity chromatography. Purification of immunoglobulins is discussed, for example, by D. Wilkinson (The Scientist, published by The Scientist, Inc., Philadelphia PA, Vol. 14, No. 8 (Apr. 17, 2000), pp. 25-28).

The antibodies described herein can be detected by appropriate assays, e.g., conventional types of immunoassays. For example, an assay can be performed in which CFP-10 or fragment thereof is affixed to a solid phase. Incubation is maintained for a sufficient period of time to allow the antibody in a sample to bind to the immobilized polypeptide on the solid phase. After this first incubation, the solid phase is separated from the sample. The solid phase is washed to remove unbound materials and interfering substances such as non-specific proteins which can also be present in the sample. The solid phase containing the antibody of interest bound to the immobilized polypeptide is subsequently incubated with a second, labeled antibody or antibody bound to a coupling agent such as biotin or avidin. This second antibody can be another anti-CFP-10 antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

The term "monoclonal antibody" or "MAb" or "monoclonal antibody composition", as used herein, can refer to a population of antibody molecules that contain only one molecular species of antibody molecule consisting of a unique light chain gene product and a unique heavy chain gene product. For example, the complementarity determining regions (CDRs) of the monoclonal antibody are identical in the molecules of the population. MAbs contain an antigen binding site that can be immunoreactive with an epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, can be immunized with an immunizing agent to elicit lymphocytes that can produce antibodies that will specifically bind to the immunizing agent. Alternatively, the lymphocytes can be immunized in vitro.

The immunizing agent can include the protein antigen, a fragment thereof or a fusion protein thereof. For example, peripheral blood lymphocytes can be used if cells of human origin are required for uses described herein, or spleen cells or lymph node cells can be used if non-human mammalian sources required for uses described herein. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines can be transformed mammalian cells, such as myeloma cells of rodent, bovine and human origin. For example, rat or mouse myeloma cell lines can be employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas can include hypoxanthine, aminopterin, and thymidine ("HAT medium"), which substances prevent the growth of HGPRT-deficient cells.

Immortalized cell lines can be those that fuse efficiently, support stable high-level expression of antibody by the selected antibody-producing cells, and are sensitive to a medium such as HAT medium. Immortalized cell lines can be murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. The binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art.

"Affinity" or "binding affinity" can refer to the strength with which an antibody molecule or portion thereof binds to an epitope on a target protein or antigen. Affinity can be measured by the equilibrium binding constant ($K_A$) or the equilibrium dissociation constant ($K_D$)). The low affinity antibody-antigen interactions are weak and the molecules tend to separate rapidly, while the high affinity antibody-antigen binding is strong and the molecules remain in the bound state for an extended period of time. For example, the affinity of the antibody for the target protein is, in equilibrium binding constant ($K_A$), about $10^6$ M$^{-1}$ or more, about $10^7$ M$^{-1}$ or more, about $10^8$ M$^{-1}$ or more, or about $10^9$ M$^{-1}$ $10^{10}$ M$^{-1}$, $10^{11}$ M$^{-1}$ or $10^{12}$ M$^{-1}$. Furthermore, the antibody can have an equilibrium dissociation constant ($K_D$) of about $10^{-4}$ M to $10^{-5}$ M, about $10^{-5}$ M to $10^{-6}$ M, about $10^{-6}$ M to $10^{-7}$ M, about $10^{-7}$ M to $10^{-8}$ M, about $10^{-8}$ M, about $10^{-9}$ M, about $10^{-10}$ M, about $10^{-11}$ M, about $10^{-12}$ M or about $10^{-13}$ M or about greater than $10^{-13}$ M. Low dissociation constants can also be characterized. Without wishing to be bound by theory, a low dissociation constant can be that the antibody is characterized by a higher binding affinity. For example, antibodies with a dissociation constant of nM, or nM or less, are considered as high affinity antibodies. Such affinities are known in the art and can be determined, e.g., by equilibrium dialysis; by surface plasmon resonance (SPR) using a BIAcore instrument according to the general procedures outlined by the manufacturer; radioimmunoassays using radiolabeled target antigens; or by other methods known to the person skilled in the art. Affinity data are described, for example, in Scatchard et al., Ann N. Y. Acad. Analysis can be performed using the method of ScL, 51:660 (1949). Further, the binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that can specifically bind to genes encoding the heavy and light chains of murine antibodies). The hybridoma cells of the invention can be a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody described herein or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies can be prepared by using trioma technique; the human B-cell hybridoma technique (see Kozbor, et al., 1983 Immunol Today 4:72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies can be utilized and can be produced by using human hybridomas (see Cote, et al., 1983. Proc Natl Acad Sci USA 80:2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

"Humanized antibodies" can be antibodies from a non-human species (such as mouse), whose amino acid sequences (for example, in the CDR regions) have been modified to increase their similarity to antibody variants produced naturally in humans. Antibodies can be humanized by methods known in the art, such as CDR-grafting. See also, Safdari et al., (2013) *Biotechnol Genet Eng Rev.;* 29:175-86. In addition, humanized antibodies can be produced in transgenic plants, as an inexpensive production alternative to existing mammalian systems. For example, the transgenic plant can be a tobacco plant, i.e., Nicotiania *benthamiana*, and *Nicotiana* tabaccum. The antibodies are purified from the plant leaves. Stable transformation of the plants can be achieved through the use of *Agrobacterium tumefaciens* or particle bombardment. For example, nucleic acid expression vectors containing at least the heavy and light chain sequences are expressed in bacterial cultures, i.e., *A. tumefaciens* strain BLA4404, via transformation. Infiltration of the plants can be accomplished via injection.

Soluble leaf extracts can be prepared by grinding leaf tissue in a mortar and by centrifugation. Isolation and purification of the antibodies can be readily performed by many of the methods known to the skilled artisan in the art. Other methods for antibody production in plants are described in, for example, Fischer et al., Vaccine, 2003, 21:820-5; and Ko et al, Current Topics in Microbiology and Immunology, Vol. 332, 2009, pp. 55-78. As such, the invention further provides any cell or plant comprising a vector that encodes the antibody described herein, or produces the antibody of the invention.

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies can additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides the modifications is then obtained as progeny by crossbreeding intermediate transgenic animals containing fewer than the full complement of the modifications. An embodiment of such a nonhuman animal can be a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds immunospecifically to the relevant epitope with high affinity, are disclosed in PCT publication WO 99/53049.

The antibody can be expressed by a vector containing a DNA segment encoding the single chain antibody described herein. A vector can refer to a system that can carry a foreign gene and can be rendered in a host cell. These include plasmid vectors, recombinant viral vectors, recombinant bacterial vectors, pseudovirions, virus-like particles, and the like.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

The "recombinant viral vector" can refer to a vector that can carry a foreign gene based on a recombinant virus, and includes, for example, a recombinant adenovirus vector, a recombinant poxvirus vector, a baculovirus vector, and the like.

The "recombinant bacterial vector" can refer to a vector that can carry a foreign gene constructed based on a recombinant bacterium, and includes, for example, a *Listeria* vector, an attenuated *Salmonella* vector, and the like.

Vectors can include viral vectors, fusion proteins and chemical conjugates. Retroviral vectors include moloney murine leukemia viruses. DNA viral vectors can be used. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cell's cytoplasm. Avipoxvirus vectors result in only a short-term expression of the nucleic acid. Adenovirus vectors, adeno-associated virus vectors and herpes simplex virus (HSV) vectors can be used to introduce the nucleic acid into neural cells. The adenovirus vector results in a shorter-term expression (about 2 months) than adeno-associated virus (about 4 months), which in turn is shorter than HSV vectors. The vector chosen will depend upon the target cell. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any target cell. For example, stereotaxic injection can be used to direct the vectors (e.g. adenovirus, HSV) to a required location for uses described herein. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and can be useful in delivering the vector to the target cell. (See Bobo et al., Proc. Natl. Acad. Sci. USA 91:2076-2080 (1994); Morrison et al., Am. J. Physiol. 266:292-305 (1994)).

These vectors can be used to express large quantities of antibodies that can be used in a variety of ways. For example, to detect the presence of CFP1-in a sample. The antibody can also be used to try to bind to and disrupt the function of CFP-10.

In an embodiment, the antibodies of the invention are full-length antibodies, containing an Fc region similar to wild-type Fc regions that bind to Fc receptors.

Heteroconjugate antibodies are also within the scope of the invention. Heteroconjugate antibodies are composed of two covalently joined antibodies. The antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In some embodiments, the antibody described herein can be modified with respect to effector function, so as to enhance, e.g., the effectiveness of the antibody in neutralizing or preventing mycobacterial infection. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176:1191-1195 (1992) and Shopes, J. Immunol., 148:2918-2922 (1992)). Alternatively, an antibody can be engineered that has dual Fc regions and can thereby have enhanced complement lysis and ADCC capabilities. (See Stevenson et al., Anti-Cancer Drug Design, 3:219-230 (1989)). In an embodiment, the antibody of the invention has modifications of the Fc region, such that the Fc region does not bind to the Fc receptors. In an embodiment, the Fc receptor is Fcγ receptor. In embodiments, the antibodies have modification of the Fc region such that the Fc region does not bind to Fcγ, but still binds to neonatal Fc receptor.

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Immunoconjugates can also comprise an antibody conjugated with a label. In some embodiments, the label comprises a chromogen. Each chromogen listed is reactive with the corresponding enzyme to produce a signal which reports the presence of the immunoconjugate. The superscript notation (*) indicates that the chromogen fluoresces, rather than produces a color change. Non-limiting examples of chromagens and their corresponding enzyme are listed herein.

| Chromagen | Enzyme |
|---|---|
| *4-Methylumbelliferyl phosphate | alkaline phosphatase |
| * bis (4-Methylumbelliferyl phosphate) | or |
| 3-0-methylfluorescein | acid phosphatase |
| *Flavone-3-diphosphate tetraammonium salt | |
| p-nitrophenyl phosphate 2Na | |
| *Tyramine hydrochloride | peroxidase |
| *3-(p-hydroxyphenyl) Propionic acid | |
| *p-Hydroxyphenethyl alcohol | |
| 2,2'-Azino-Di-3-Ethylbenzothiazoline | |
| Sulfonic acid (ABTS) | |
| ortho-phenylenediamine 2HCl | |
| O-dianisidine | |
| *5-aminosalicylic acid | |
| p-cresol | |
| 3,3'-dimethyloxybenzidine | |
| 3-methyl-2-benzothiazolinehydrazone | |
| 3,3',5,5'-Tetramethylbenzidine (TMB) | |
| o-nitrophenyl-β-D-galactopyranoside | β-D-galactosidase |
| 4-methylumbelliferyl phosphate | |
| β-D-galactoside | |
| 2,2'-Azino-Di-3-Ethylbenzothiazoline | Glucose oxidase |
| Sulfonic acid (ABTS) | |

In some embodiments, the label comprises a binding moiety (e.g., biotin-avidin, biotin-streptavidin or sugar-lectin, myc tag, his tag and the like). In some embodiments, the label comprises a colored dye compound, such as a fluorescent dye. Non-limiting examples of fluorescent dye compounds include fluorescein, ethidium bromide, rhodamine, Texas Red, Phycoerythrin (RPE), and cyanine. In some embodiments, the label comprises a fluorescent compound (e.g., GFP, RFP, YFP, BFP, and the like). In some embodiments, the label consists of a nanoparticle, where the size, composition and geometry of the particle can determine the absorption and emission properties of the nanoparticle, which can be altered by interaction with other particles with overlapping emission and absorption spectra that can undergo other interactions (e.g. plasmonic resonance). In some embodiments, the label comprises a chemiluminescent compound (e.g., N-(4-Aminobutyl)-N-ethylisoluminol, 4-Aminophthalhydrazide, Disodium 2-chloro-5-(4-methoxyspiro[1,2-dioxetane-3,2'-(5-chlorotricyclo[3.3.1.13.7]decan])-4-yl]-1-phenyl phosphate). In some embodiments, the label comprises an enzymatic compound (e.g., β-D-galactosidase or peroxidase).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

For example, the antibody can be coupled (i.e., physically linked) to a detectable substance for the detection of CFP-10 or fragment thereof. Non-limiting examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Coupling can be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. Covalent binding can be used, and achieved by, for example, direct condensation of existing side chains or by the incorporation of external bridging molecules. Many bivalent or polyvalent linking agents are useful in coupling protein molecules, such as the antibodies of the invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987)). Linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Linkers can include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo- LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described herein contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is prone to disruption in vitro, resulting in less conjugate available. Sulfo-NHS, for example, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82:3688 (1985); Hwang et al., Proc. Natl Acad. Sci. USA, 77:4030 (1980); and U.S. Pat. Nos. 4,485,045 and 4,544,545. Liposomes with enhanced circulation time are disclosed in U.S. Pat. No. 5,013,556.

Useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the required diameter for uses described herein. Fab' fragments of the antibody of the invention can be conjugated to the liposomes as described in Martin et al., J. Biol. Chem., 257:286-288 (1982) via a disulfide-interchange reaction.

Use of Antibodies Against CFP-10

Antibodies directed against CFP-10 or a fragment thereof can be used in methods known within the art relating to the detection, localization and/or quantitation of CFP-10 or fragment thereof (e.g., for use in measuring levels of the CFP-10 protein within appropriate physiological samples, for use in diagnostic methods, for use in imaging the protein, and the like). In a given embodiment, antibodies specific to CFP-10, or derivative, fragment, analog or homolog thereof, that contain the antibody derived antigen binding domain, can be utilized as active compounds or antigen-binding agents.

An antibody specific for CFP-10 can be used to isolate a CFP-10 polypeptide by standard techniques, such as immunoaffinity, chromatography or immunoprecipitation. Antibodies directed against an CFP-10 protein (or a fragment thereof) can be used diagnostically to monitor protein levels in a biological sample, such as a tissue or fluid, as part of a clinical testing procedure, e.g., to, for example, determine the efficacy of a given treatment regimen or diagnose a given disease or infection.

In other embodiments, antibodies directed against a CFP-10 protein (or fragment thereof) can be used to detect *Mycobacterium* species in a composition to be ingested by a subject (i.e., for food safety purposes). In some embodiments, antibodies directed against a CFP-10 protein (or fragment thereof) can be used to detect *Mycobacterium* species in a sample collected from an animal (for example, as part of livestock or wildlife management efforts or veterinary care). For example, such compositions can be useful in identifying animals infected with mycobacteria whereby such animals are raised or hunted for meat or employed to produce dairy products.

In embodiments, detection can be facilitated by coupling (i.e., physically linking) the antibody to a detectable substance. Examples of detectable substances include those described herein.

Antibodies of the invention, including polyclonal, monoclonal, humanized and fully human antibodies, can be used as diagnostic agents. Such agents can be employed to diagnose a CFP-10-related disease or pathology in a subject, such as Mycobacteria infection.

An effective amount of an antibody of the invention can refer to an amount needed to achieve an objective, such as detection of CFP-10 protein or diagnosis of Mycobacteria infection. As noted herein, this can be due to a binding interaction between the antibody and its target antigen. The effective amount required will furthermore depend on the binding affinity of the antibody for its specific antigen.

An antibody according to the invention can be used as an agent for detecting the presence of CFP-10 (or a protein or a protein fragment thereof) in a sample. For example, the antibody contains a detectable label. Antibodies can be polyclonal or monoclonal. In embodiments, the antibody is an intact antibody. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

The detection method of the invention can be used to detect an analyte in a biological sample in vitro as well as in vivo. For example, in vitro techniques for detection of an analyte protein include enzyme linked immunosorbent assays (ELISAs), Western blots, immunoprecipitations, and immunofluorescence. Procedures for conducting immunoassays are described, for example in "ELISA: Theory and Practice: Methods in Molecular Biology", Vol. 42, J. R. Crowther (Ed.) Human Press, Totowa, NJ, 1995; "Immunoassay", E. Diamandis and T. Christopoulus, Academic Press, Inc., San Diego, CA, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Screening Assays and Methods

The invention provides screening assays and methods for identifying therapeutics and/or prophylactics, i.e., candidate or test compounds or agents (e.g., peptides, peptidomimetics, small molecules or other drugs) that can be used to prevent or treat a Mycobacteria infection. The invention also encompasses the candidates and/or compounds identified using the screening assays described herein.

The term "screening" can refer to determining whether a candidate and/or test compound has capabilities or characteristics of preventing or slowing down (lessening) the targeted pathologic condition stated herein, such as Mycobacteria infection, namely *M. tuberculosis* infection or any complications thereof. In some embodiments, the peptide antibodies described herein can be uses in immunoassays to evaluate approaches that specifically inhibit the expression or secretion of the CFP-10 virulence factor. For example, the antibody can be used in assays that utilize denatured protein (e.g. Western blots). In other embodiments, the peptide antibody described herein can be useful in preclinical studies to evaluate the efficacy of candidate drugs, since it can rapidly quantitate the level of a virulence factor indicative of active TB in disease in small blood samples. Without wishing to be bound by theory, the level of CFP-10 can be serially analyzed during TB treatment in most pre-clinical animal models of human TB (e.g. guinea pigs, rabbits, and non-human primates). The ability to examine the longitudinal response to treatment in the same animal can be highly valuable, but samples required by other tests for such analyses (e.g., bronchoalveolar lavage fluid or tissue biopsies) can be challenging to obtain and cannot be collected with the same frequency as blood samples. This ability can be very useful in studies designed to evaluate dose responses and treatment intervals.

The candidate and/or test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12:145).

A "small molecule" as used herein, is meant to refer to a composition that has a molecular weight of less than about 5 kDa and, for example, less than about 4 kDa. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90:6909; Erb, et al., 1994. Proc. Natl. Acad. Sci. U.S.A. 91:11422; Zuckermann, et al., 1994. J. Med. Chem. 37:2678; Cho, et al., 1993. Science 261:1303; Carrell, et al., 1994. Angew. Chem. Int. Ed. Engl. 33:2059; Carell, et al., 1994. Angew. Chem. Int. Ed. Engl. 33:2061; and Gallop, et al., 1994. J. Med. Chem. 37:1233.

Libraries of compounds can be presented in solution (see e.g., Houghten, 1992. Biotechniques 13:412-421), or on beads (see Lam, 1991. Nature 354:82-84), on chips (see Fodor, 1993. Nature 364:555-556), bacteria (see U.S. Pat. No. 5,223,409), spores (see U.S. Pat. No. 5,233,409), plasmids (see Cull, et al., 1992. Proc. Natl. Acad. Sci. USA 89:1865-1869) or on phage (see Scott and Smith, 1990. Science 249:386-390; Devlin, 1990. Science 249:404-406; Cwirla, et al., 1990. Proc. Natl. Acad. Sci. U.S.A. 87:6378-6382; Felici, 1991. J. Mol. Biol. 222:301-310; and U.S. Pat. No. 5,233,409.).

Those skilled in the art will recognize that, in any of the screening methods disclosed herein, the antibody can be a CFP-10-specific antibody, such as monoclonal antibody 17E4-1, 21H3-1, 119C10-1, or 65D3-1 or any variant thereof. Additionally, the antigen can be CFP-10 protein, or a portion or fragment thereof.

The screening methods disclosed herein can be performed as a cell-based assay or as a cell-free assay. The cell-free assays of the invention are amenable to use of both the soluble form or the membrane-bound form of the proteins and fragments thereof. In the case of cell-free assays comprising the membrane-bound forms of the proteins, it can be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether) n, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

The invention further pertains to new agents identified by any of the aforementioned screening assays and uses thereof for treatments as described herein.

Diagnostic Assays and Methods

Aspects of the invention are also drawn to diagnostic assays and methods for detecting the presence or absence of CFP-10 in a sample, thereby diagnosing, prognosing, or monitoring a *Mycobacterium* species infection. For example, the invention provides a method of detecting in a sample the presence of *M. tuberculosis, M. africanum, M. bovis, M. canetti, M. caprae, M. microti, M. mungi, M. orygis, M. pinnipedii,* or *M. suricattae.*

The term "diagnosing" can refer to determining the presence or absence of a disease or condition, such as an infection, for example a Mycobacterial infection. Additionally, the term can refer to determining the level or severity of a disease or condition, as well as monitoring of the disease or condition to determine its response to a therapeutic regimen.

The term "monitoring" can refer to the observation of a disease over time. Monitoring of a subject's disease state can be performed by continuously measuring certain parameters and/or by repeatedly performing a medical test. In some embodiments of the invention, a subject's disease state is monitored by repeatedly obtaining samples from the subject, assaying the samples using the method disclosed herein and comparing the results of the assays with one another and/or with a reference value to identify any change in the subject's disease state.

The term "prognosing" can refer to an assessment of the future outcome of a disease, such as a *Mycobacterium* species infection, or the likelihood of developing a disease. A prognosis can include a prediction of the likelihood of recovery from a disease, or a prediction of the likelihood of developing a disease.

The terms "*Mycobacterium tuberculosis*," "TB," "Mtb," "*M. tuberculosis*" and "pathogenic *Mycobacterium tuberculosis*" can be used interchangeably. The term *Mycobacterium tuberculosis* can refer to a pathogenic (e.g. virulent) bacterial species in the family Mycobacteriaceae and a causative agent of tuberculosis (TB). One of skill in the art understands that there are multiple isolates of the same bacteria and that there are multiple strains (isolates) of *M. tuberculosis.* Each of the various isolates of *M. tuberculosis* can be detected using the systems and methods described herein.

*Mycobacterium bovis* is another *mycobacterium* that can cause TB disease in humans, and is also found in cattle and other animals such as bison, elk, and deer. People can be infected with *M. bovis* by eating or drinking contaminated, unpasteurized dairy products. The pasteurization process, which destroys disease-causing organisms in milk by rapidly heating and then cooling the milk, eliminates *M. bovis* from milk products.

Infection can also occur from direct contact with a wound, such as what can occur during slaughter or hunting, or by inhaling the bacteria in air exhaled by animals infected with *M. bovis*. Direct transmission from animals to humans through the air is rare, but *M. bovis* can be spread directly from person to person when people with the disease in their lungs cough or sneeze.

*Mycobacterium africanum* is a species of *mycobacterium* that is found in West African countries, where it is estimated to cause up to 40% of pulmonary tuberculosis.

Other species that are causative agents of human and animal tuberculosis include, but are not limited to, *M. canetti, M. caprae, M. microti, M. mungi, M. orygis, M. pinnipedii,* and *M. suricattae*. Together, the *Mycobacterium* species described herein make up the *Mycobacterium tuberculosis* complex (MTC or MTBC), which is a genetically related group of *Mycobacterium* species that can cause tuberculosis in humans and other animals.

The term "pathogenic" can refer to a bacterium that can cause disease in a host. If not properly treated, TB disease can be fatal. TB-causing bacteria can attack the lungs, but can attack any part of the body such as the kidney, spine, and brain. According to the Center for Disease Control (CDC) "extrapulmonary TB" refers to TB disease in any part of the body other than the lungs (for example, kidney, spine, brain, or lymph nodes). "Pulmonary TB" can refer to TB disease that occurs in the lungs, and can produce a cough that lasts 3 weeks or longer. Most TB disease is pulmonary.

"Latent" TB infection occurs when an individual is persistently infected with a TB-causing *mycobacterium*, but does not develop active TB disease in which the pathogen replicates and spreads to cause tissue damage. In some embodiments, diagnostic assays and methods described herein are useful for detecting a TB infection (for example with the presence or absence of CFP-10 in a sample), but the infection is not latent TB.

Aspects are drawn to methods for detecting the presence or absence of CFP-10 in a sample using mass spectrometry-based methods.

One embodiment of a method for detecting the presence or absence of CFP-10 in a sample involves obtaining a sample from a subject and contacting the sample with a monoclonal antibody according to the invention such that the presence of the CFP-10 is detected in the sample.

The term "detecting" can refer to identifying the presence or absence of substance(s) (e.g., antigen, such as CFP-10) in a sample, quantifying the amount of substance(s) (e.g., antigen, such as CFP-10) in the sample, qualifying the type of substance; and/or quantifying the activity level of substance(s) in the sample. The term can also refer to identifying the presence or absence of a microorganism in a sample, such as a pathogenic *Mycobacterium* species in a food sample or in a sample obtained from a subject.

The terms "patient", "host", or "subject" can refer to any entity that can benefit from embodiments described herein. For example, the subject is a vertebrate animal, which can denote any animal species (for example, a mammalian species, such as a human being). In embodiments, a "patient" can refer to any animal host including without limitation any mammalian host. For example, the term can refer to any mammalian host, the latter including but not limited to, human and non-human primates, bovines, canines, caprines, cavines, corvines, epines, equines, felines, hircines, lapines, leporines, lupines, murines, ovines, porcines, ranines, racines, vulpines, and the like, including livestock, zoological specimens, exotics, as well as companion animals, pets, and any animal under the care of a veterinary practitioner. A patient can be of any age who is, or is suspected to be, afflicted with Mycobacteria infection, such as *M. tuberculosis*. Thus, the term "subject" can refer to a mammal, such as a human, but can also be another animal such as a domestic animal (e.g., a dog, cat, or the like), a farm animal (e.g., a cow, a sheep, a pig, a horse, a chicken, a duck, or the like) or a laboratory animal (e.g., a monkey, a rat, a mouse, a rabbit, a guinea pig, or the like). A subject includes one who is, or is suspected to be, afflicted with Mycobacteria infection, such as *M. tuberculosis.*

In embodiments, the subject is, or is suspected to be, afflicted with Mycobacteria infection and also HIV infection. According to the Center for Disease Control (CDC) "HIV infection" refers to infection with the human immunodeficiency virus, the virus that causes AIDS (acquired immunodeficiency syndrome). A person with both latent TB infection and HIV infection is at very high risk for developing TB disease. According to the World Health Organization (WHO), people living with HIV are 19 times more likely to develop active TB disease than people without HIV. HIV and TB form a lethal combination, each speeding the other's progress. In 2018 about 251,000 people died of HIV-associated TB. In 2018, there were an estimated 862,000 new cases of TB amongst people who were HIV-positive, 72% of whom were living in Africa. Without wishing to be bound by theory, the antibodies described herein can detect *Mycobacterium tuberculosis* in the presence of HIV. Conventional TB diagnostics exhibit reduced sensitivity when analyzing specimens obtained from HIV-affected individuals, which can result from dysregulation of the prevalence, type, and activity of immune cells in granulomas that form at Mtb infection foci. Granulomas are a hallmark of TB, where they can play a critical role in confining and suppressing the proliferation of Mtb bacilli. These structures consist of an organized collection of immune cells that form in response to Mtb infection, and consist of Mtb-infected macrophages, recruited macrophages and differentiated epithelioid cells surrounded by a layer of lymphocytes. HIV infection can cause granuloma homeostasis by dysregulating T cell and macrophage function, resulting in granuloma disorganization and a reduced ability of these structures to contain the associated Mtb infection. This can allow the development of disseminated TB where Mtb bacilli have spread to extrapulmonary tissues, and a resulting a reduction of Mtb bacilli in lung tissue can explain the difficulty encountered in diagnosing HIV patients using sputum samples. See, for example, Diedrich, C. R., J. O'Hern, and R. J. Wilkinson. "HIV-1 and the *Mycobacterium tuberculosis* granuloma: A systematic review and meta-analysis." *Tuberculosis* 98 (2016): 62-76.

In embodiments, the subject afflicted with, or suspected to be afflicted with Mycobacteria infection is a pediatric subject. A pediatric subject can refer to a subject between the time from birth through adolescence (*Stedman's Medical Dictionary, 27th Edition*). TB diagnosis can be challenging in children, since 1 million children develop TB and 239,000 die of TB-related causes each year, with 80% of such deaths estimated to occur in children <5 years old, and 96% estimated to occur in children who do not receive TB treatment. See, for example, Dodd, Peter J., et al. "The global burden of tuberculosis mortality in children: a mathematical modelling study." *The Lancet Global health* 5.9 (2017): e898-e906. Missed diagnoses can be responsible for undertreatment since children with TB, for example those co-infected with HIV, frequently exhibit non-specific symptoms; initially have paucibacillary disease, where there are few bacilli present in diagnostic samples; and can present with disseminated TB (miliary TB or TB meningitis), where Mtb bacilli have escaped immune containment in the lungs, which can rapidly progress in absence of appropriate treatment, See, for example, Thomas, Tania A. "Tuberculosis in children." *Pediatric Clinics* 64.4 (2017): 893-909; Marais, Ben J., et al. "A refined symptom-based approach to diagnose pulmonary tuberculosis in children." *Pediatrics* 118.5 (2006): e1350-e1359; Edwards, D. J., F. Kitetele, and A. Van Rie. "Agreement between clinical scoring systems used for the diagnosis of pediatric tuberculosis in the HIV era." *The International Journal of Tuberculosis and Lung Disease* 11.3 (2007): 263-269; and Zar, Heather J., Tom G. Connell, and Mark Nicol. "Diagnosis of pulmonary tuberculosis in children: new advances." *Expert review of anti-infective therapy* 8.3 (2010): 277-288. This clinical presentation, combined with the difficulty of obtaining respiratory samples from young children, makes it challenging to diagnose pediatric TB and monitor its treatment response using standard sputum-based methods. See, for example, Nicol, Mark P., and Heather J. Zar. "New specimens and laboratory diagnostics for childhood pulmonary TB: progress and prospects." *Paediatric respiratory reviews* 12.1 (2011): 16-21; Thomas, Tania A. "Tuberculosis in children." *Pediatric Clinics* 64.4 (2017): 893-909; and Zar, Heather J., et al. "Induced sputum versus gastric lavage for microbiological confirmation of pulmonary tuberculosis in infants and young children: a prospective study." *The Lancet* 365.9454 (2005): 130-134.

In certain embodiments, the antibody is a labeled antibody. As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

The term "sample" can refer to any sample that can contain an analyte of interest, such as CFP-10 or a fragment thereof. A sample can be a non-biological sample or a biological sample, and encompasses clinical specimens (diagnostic samples collected as part of standard clinical procedures). Non-biological samples include those prepared in vitro comprising varying concentrations of a target molecule of interest in solution. Biological samples include, without limitation, whole blood, lymph, serum, plasma, urine, saliva, sputum, breath extract (meaning exhaled air captured in a solution), bone marrow, aspirates (nasal, lung, bronchial, tracheal), eye fluid, amniotic fluid, feces other bodily fluids and secretions, cells, and tissue specimens and dilutions of them. As used herein, the term "body fluid" means any fluid that can be isolated from the body of an individual. For example, "body fluid" can include blood, plasma, serum, bile, saliva, urine, tears, perspiration, and the like. In embodiments, the sample comprises a body fluid sample from human; for example plasma or serum. For example, the bodily fluid can be obtained from a vertebrate mammal, such as, a human having, suspected of having, and/or at risk for developing, an infection. Any suitable biological sample can be used. For example, a biological sample can be a specimen obtained from a subject or can be derived from such a subject. A subject can provide a plurality of biological samples, including a solid biological sample, from for example, a biopsy or a tissue. In some cases, a sample can be a tissue section or cells that are placed in or adapted to tissue culture. A biological sample also can be a biological fluid such as urine, blood, plasma, serum, saliva, tears, or mucus, or such a sample absorbed onto a paper or polymer substrate. A biological sample can be further fractionated, for example, to a fraction containing particular cell types. In some embodiments, a sample can be a combination of samples from a subject (e.g., a combination of a tissue and fluid sample). In some cases, serum or plasma is obtained from the subject using techniques known in the art.

The term "biological sample" can refer to tissues, cells and biological fluids isolated from a subject, as well as tissues, cells and fluids present within a subject. Included within the usage of the term "biological sample", therefore, is blood and a fraction or component of blood including blood serum, blood plasma, or lymph. The definition can also include a sample that has been manipulated in any way after its procurement, such as by treatment with reagents, solubilization, or enrichment for certain components, such as proteins or polynucleotides.

In embodiments, the biological sample can be isolated from or obtained from a subject. As used herein, the phrase "obtaining a biological sample" or "isolating a biological sample" can refer to any process for directly or indirectly acquiring a biological sample from a subject. For example, a biological sample can be obtained (e.g., at a point-of-care facility, e.g., a physician's office, a hospital, laboratory facility) by procuring a tissue or fluid sample (e.g., blood draw, marrow sample, spinal tap) from a subject. Alternatively, a biological sample can be obtained by receiving the biological sample (e.g., at a laboratory facility) from one or more persons who procured the sample directly from the subject. Further, the biological sample can be obtained, such as directly or indirectly, from an animal, such as for livestock or wildlife management efforts or veterinary care.

In one embodiment, the sample contains protein molecules from the subject. In one embodiment, the biological sample is a peripheral blood leukocyte sample isolated by conventional means from a subject. In another embodiment, the biological sample is blood serum isolated by conventional means from a subject.

In embodiments, the sample is not sputum. Sputum is expectorated matter, especially mucus or mucopurulent matter expectorated in diseases of the air passages (*Stedman's Medical Dictionary, 27th edition*). Currently, sputum is examined for TB bacteria using a smear, a test to see whether there are TB bacteria in a subject's phlegm. To do this test, lab works smear the sputum on a glass slide, stain the slide with a special stain, and look for any TB bacteria on the slide. This test can take 1 day to get the results. Part of the sputum can also be used to do a culture, which can take 2 to 4 weeks in most laboratories. Sputum-based TB assays are directly influenced by Mtb abundance in the collected sample, and it can be difficult to obtain diagnostically useful sputum samples from children, HIV-infected individuals, and individuals with extrapulmonary, disseminated or paucibacillary TB. For example, mycobacterial culture is positive in only 30-62% of pediatric TB cases. See, for example, Zar, Heather J., et al. "Induced sputum versus gastric lavage for microbiological confirmation of pulmonary tuberculosis in infants and young children: a prospective study." *The Lancet* 365.9454 (2005): 130-134. Molecular diagnostics that utilize sputum samples, such as Xpert RIF/MTB and Xpert Ultra enable rapid diagnosis but are also less sensitive in children. See, for example, Nemes, Elisa, et al. "Diagnostic Accuracy of Early Secretory Antigenic Target-6-Free Interferon-gamma Release Assay Compared to QuantiFERON-TB Gold In-tube." *Clinical Infectious Diseases* 69.10 (2019): 1724-1730.

In embodiments, the sample is a food sample. A "food sample" can refer to a food preparation or a portion of a food preparation. Food preparations encompass fresh preparations, preparations stored under modified atmosphere, vacuum-packed preparations, frozen preparations, fermented preparations, smoked preparations and dry preparations. Example of food preparations include meat preparations (including beef meat, bison meat, deer meat, calf meat, pork meat, horse meat, lamb meat, mutton meat, goat meat, rabbit meat, turkey meat, chicken meat, duck meat, guinea fowl meat, as sausages, minced, or ground), fish preparations (including salmon, trout) vegetable preparations (including cabbage, gherkin, bean, grape leaf, lemons, garlic, Swiss chard, beet, carrot, celery, mushroom, cucumber, courgette, broad bean, turnip, onion, peas, sweet pepper, pumpkin, radish, escarole, tomato, orange, olives, or mixes such as pickles), cereals preparations (including rice, soy, wheat) and milk (yogurt, cheese, kefir).

Many of the major disease-causing mycobacteria, such as *Mycobacterium tuberculosis*, and members of the *Mycobacterium avium* complex (MAC) of non-tuberculous mycobacteria (NTM) are slow-growing. The length of time that it takes to culture these species can decrease their utility as diagnostic tests since such extended culture times can increase the risk of disease transmission or disease progression resulting in tissue damage in the absence of appropriate therapy.

The detection methods described herein can be used to detect CFP-10 or a fragment thereof in a biological sample in vitro as well as in vivo. For example, in vitro techniques for detection of CFP-10 include enzyme linked immunosorbent assays (ELISAs), Western blots, immunoprecipitations, and immunofluorescence. Furthermore, in vivo techniques for detection of CFP-10 include introducing into a subject a labeled anti-CFP-10 antibody. For example, the antibody can be labeled with a radioactive marker whose presence and location in a subject can be detected by standard imaging techniques.

As described herein, the antibodies can be linked to a labeling agent (alternatively termed "label") such as a fluorescent molecule (such as a fluorescent bead), a binding partner, a solid support, or other agents that are known in the art to facilitate separation. Non-limiting examples of such agents are described herein.

For example, the peptide-specific antibody can be immobilized on a column, bead or other surface for use as a peptide-specific affinity capture reagent. In an embodiment, the anti-peptide antibody is immobilized on commercially available protein A-derivatized POROS chromatography media (Applied Biosystems) and covalently fixed on this support by covalent crosslinking with dimethyl pimelimidate according to the manufacturer's instructions. The resulting solid phase media can bind the monitor peptide specifically from a peptide mixture (e.g., a tryptic digest of serum or plasma).

As used herein, the terms "purification", "purifying", and "enriching" do not refer to removing materials from the sample other than the analyte(s) of interest. Instead, these terms refer to a procedure that enriches the amount of one or more analytes of interest relative to other components in the sample that can interfere with detection of the analyte of interest.

Purification of the sample by various means can allow relative reduction of one or more interfering substances, e.g., one or more substances that can or cannot interfere with the detection of selected analyte by mass spectrometry. Relative reduction as this term is used does not require that any substance, present with the analyte of interest in the material to be purified, is entirely removed by purification.

The term "immunopurification" or "immunopurify" can refer to a purification procedure that utilizes antibodies, including polyclonal or monoclonal antibodies, such as those described herein, to enrich the one or more analytes of interest. Immunopurification can be performed using any of the immunopurification methods well known in the art. Often the immunopurification procedure utilizes antibodies bound, conjugated or otherwise attached to a solid support, for example a bead, column, well, tube, gel, capsule, particle or the like.

Immunopurification can include without limitation procedures often referred to in the art as immunoprecipitation, as well as procedures often referred to in the art as affinity chromatography or immunoaffinity chromatography.

The term "immunoparticle" can refer to a capsule, bead, gel particle or the like that has antibodies bound, conjugated or otherwise attached to its surface (for example, on and/or in the particle). In certain embodiments, immunoparticles are sepharose or agarose beads. In alternative embodiments, immunoparticles comprise glass, plastic or silica beads, or silica gel.

As used herein, the term "anti-CFP-10 antibody" can refer to any polyclonal or monoclonal antibody that has an affinity for CFP-10, epitope thereof, or peptide fragment thereof. In various embodiments the specificity of the antibodies to chemical species other than CFP-10 can vary; for example, in certain embodiments the anti-CFP-10 antibodies are specific for CFP-10 and thus have little or no affinity for chemical species other than CFP-10, whereas in other embodiments the anti-CFP-10 antibodies are non-specific and thus bind certain chemical species other than CFP-10.

The antibodies and fragments as described herein can be utilized with any solid phase enrichment approach. The term "solid phase enrichment" or "solid phase extraction" or "SPE" can refer to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase can be retained by the solid phase resulting in a purification of the analyte in the mobile phase. In other instances, the analyte, such as CFP-10, can be retained by the solid phase, allowing undesired components of the mobile phase to pass through or around the solid phase. In these instances, a second mobile phase is then used to elute the retained analyte off of the solid phase for further processing or analysis. SPE, including TFLC, can operate via a unitary or mixed mode mechanism. Mixed mode mechanisms utilize ion exchange and hydrophobic retention in the same column; for example, the solid phase of a mixed-mode SPE column can exhibit strong anion exchange and hydrophobic retention; or can exhibit strong cation exchange and hydrophobic retention.

To facilitate separation of the antibody-protein complex from unbound protein in the sample, the antibody can be linked to an agent that facilitates separation, such as a binding partner (e.g., biotin, oligonucleotide, aptamer), a solid support (such as a bead or matrix, including a microarray or multiwell plate); or any other agent known in the art.

Linking can be covalent or noncovalent, and can be direct or indirect. Methods for linking antibodies to such agents are well known in the art. See, e.g. Kennedy et al. (1976) Clin. Chim. Acta 70:1-31, and Schurs et al. (1977) Clin. Chim. Acta 81:1-40 (describing coupling techniques, including the glutaraldehyde method, the periodate method, the dimaleimide method, the m-maleimidobenzyl-N-hydroxy-succinimide ester method, each of which methods are incorporated by reference herein).

Methods for separating an antibody-protein complex from a sample are known in the art and include use of a capture agent that binds a binding partner (e.g., avidin to capture a biotin-linked antibody; an oligonucleotide to capture an oligonucleotide linked to an antibody; Physical separation can also be used, such as sedimentation, filtration, FACS (for example, using beads that are labeled with a spectral signature), and magnetic separation (when the antibody is linked to a matrix with magnetic properties, such as a magnetic bead).

Many binding partners are known in the art (e.g., a dinitrophenyl group, digoxigenin, fluorophores, Oregon Green dyes, Alexa Fluor 488 (Molecular Probes), fluorescein, a dansyl group, Marina Blue (Molecular Probes), tetramethylrhodamine, Texas Red (Molecular Probes), BODIPY (4,4-difluoro-4-bora-3a,4a-diaza-s-indacene; U.S. Pat. No. 4,774,339) dyes, etc) that can be used in the invention. Antibodies that can be used as capture reagents can specifically bind to binding agents are commercially available from vendors such as Molecular Probes, Eugene, Oreg. These antibodies include antibodies that can specifically bind to a dinitrophenyl group, a digoxigenin, a fluorophore, Oregon Green dyes, Alexa Fluor 488 (Molecular Probes), fluorescein, a dansyl group, Marina Blue (Molecular Probes), tetrahmethylrhodamine, Texas Red (Molecular Probes), and a BODIPY dye (Molecular Probes). Any suitable ligand and anti-ligand can also be used.

Oligonucleotides can be used as binding partner and capture reagents. Oligonucleotides include nucleic acids such as DNA, RNA, and mixed RNA/DNA molecules. The oligonucleotide that is used as the affinity label can hybridize to the sequence of the oligonucleotide present on the capture reagent. Those of skill in the art will recognize that many different oligonucleotide sequences can be designed that will hybridize to each other. Important considerations for designing such oligonucleotide pairs include the actual nucleotide sequence, the length of the oligonucleotides, the hybridization conditions (e.g., temperature, salt concentration, presence of organic chemicals, etc.) and the melting temperature of the oligonucleotide.

Solid supports suitable for immobilizing (linking) antibodies or proteins from a sample (and modifications to render solid supports suitable for immobilizing antibodies) are well known in the art. Examples of a solid support include: a bead (including magnetized beads), microwell plate, and a protein microarray (See, e.g. U.S. Pat. No. 6,365,418). Thus, for example, CdSe-CdS core-shell nanocrystals enclosed in a silica shell can be easily derivatized for coupling to a biological molecule. Bruchez et al. (1998) Science 281:2013-2016. Similarly, highly fluorescent quantum dots (zinc sulfide-capped cadmium selenide) have been covalently coupled to biomolecules for use in ultrasensitive biological detection. Warren and Nie (1998) Science 281: 2016-2018. Fluorescently labeled beads are commercially available from Luminex and Quantum Dot.

The bound protein (or in some embodiments, polypeptide fragments) can be released from the antibody-protein complex using conventional immunoaffinity elution conditions such as acidic pH, ionic strength, detergents or a combination thereof. In embodiments, peptide or protein is de-salted for subsequent fractionation, characterization, or other analysis.

In more than one embodiment, it can be desirable to immobilize either the antibody or the antigen, for example, to facilitate separation of complexed from uncomplexed forms of one or both. Observation of the antibody-antigen complex can be accomplished in any vessel suitable for containing the reactants. Examples of such vessels include microtiter plates, test tubes, and micro centrifuge tubes. In one embodiment, a fusion protein can be provided that adds a domain that allows one or both of the proteins to be bound to a matrix. For example, GST antibody fusion proteins or GST antigen fusion proteins can be adsorbed onto glutathione sepharose beads (Sigma Chemical, St. Louis, MO) or glutathione derivatized microtiter plates, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined directly or indirectly. Alternatively, the complexes can be dissociated from the matrix, and the level of antibody-antigen complex formation can be determined using standard techniques.

Other techniques for immobilizing proteins on matrices can also be used in the assays of the invention. For example, the antibody or the antigen (e.g. the 1593 peptide or 65D3-1 antibody) can be immobilized utilizing conjugation of biotin and streptavidin. Biotinylated antibody or antigen molecules can be prepared from biotin NHS (N hydroxy succinimide) using techniques well known within the art (e.g., biotinylation kit, Pierce Chemicals, Rockford, Ill.), and immobilized in the wells of streptavidin coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described herein for the GST immobilized complexes, include immunodetection of complexes using such other antibodies reactive with the antibody or antigen.

In some embodiments, the methods of the invention further comprise treating the sample with a protein cleaving agent, whereby polypeptide fragments are generated. In one embodiment, the sample is contacted with a protein cleaving agent prior to contacting a sample with an anti-CFP-10 antibody. In another embodiment, protein is contacted with a protein cleaving agent after separation of protein from an antibody-protein complex.

Protein cleaving agent treatment generates protein cleavage fragments (such as polypeptides), which can facilitate subsequent mass spectral analysis of the amount of protein and the identity of proteins in a sample(s). Treatment with a protein cleaving agent treatment can facilitate the analysis of proteins whose molecular masses exceed 25 kDa. Protein cleaving reagent treatment also can facilitate accessibility and/or access of antibodies to a cognate epitope. Protein cleaving agents are well known in the art, and are further discussed herein. In some embodiments, one protein cleaving agent is used. In other embodiments, more than one protein cleaving reagent is used. In some embodiments, more than one type of protein cleaving agent is used with respect to a single sample (e.g., two or more types of proteases, two or more types of chemical cleavage agents, or a combination of one or more protease and one or more chemical cleavage agent). Conditions for treatment with a protein cleaving agent are well known in the art.

In one embodiment, a protein cleaving agent is a protease. Example of proteases that can be used as protein cleaving agents, include, but are not limited to: chymotrypsin, trypsin (arg, lys cleavage sequence), thermolysin (phe, leu, iso, val cleavage sequence), V8 protease, Endoproteinase Glu-C, Endoproteinase Asp-N, Endoproteinase Lys-C, Endoproteinase Arg-C, Endoproteinase Arg-N, Factor Xa protease, thrombin, enterokinase, V5 protease, and the tobacco etch virus protease. Proteases useful in the methods of the invention can be genetically engineered and/or chemically modified to prevent autolysis. It is appreciated that an enzymatic protein cleaving agent (such as a protease) can be modified to facilitate removal of the protease from the polypeptide cleavage products following polypeptide cleavage. Such modifications are known in the art and include: (1) bead-bound (e.g., latex, silica or magnetic bead) protease, (2) haptenated protease, (3) affinity depletion of the protease (with, for example, a bead-bound anti-protease, or bead-bound non-cleavable substrate) and/or (4) size exclusion chromatography. The activity of a protease can be inhibited, for example, by treating with heat, a protease inhibitor, a metal chelator (e.g., EGTA, EDTA), etc.

In another embodiment, a protein cleaving agent is a chemical cleaving agent, such as chemical substances and compounds that cleave polypeptides and peptide bonds. Nonlimiting examples of chemical cleaving agents include cyanogen bromide (which cleaves at methionine residues), hydroxylamine (which cleaves between an Asn and a Gly residue), and acid pH (which can cleave an Asp-Pro bond) (see e.g., Ausubel et al., supra).

In still further embodiments, phosphatases (e.g., alkaline phosphatase, acid phosphatase, protein serine phosphatase, protein tyrosine phosphatase, protein threonine phosphatase, etc.), lipases, and other enzymes can be employed as protein cleaving agents.

In another aspect, the invention provides methods for characterizing a protein using mass spectrometry, comprising: (a) reducing the complexity of a sample using any of the methods described herein, whereby proteins are enriched and/or purified; and (b) analyzing the proteins (interchangeably termed "products") which are isolated, purified, prepared and/or separated using any of the methods herein, wherein the analyzing is by mass spectrometry. Mass spectrometry methods are well known in the art. For example, in some embodiments, the mass spectrometry method is matrix-assisted laser desorption/ionization ("MALDI") mass spectrometry; surface-enhanced laser desorption ionization ("SELDI"); and/or tandem mass spectrometry (e.g., MS/MS, MS/MS/MS, ESI-MS/MS). In some embodiments, tandem mass spectrometry is carried out using a laser desorption/ionization mass spectrometer that is further coupled to a quadrupole time-of-flight mass spectrometer QqTOF MS (see e.g., Krutchmsky et al, WO 99/38185). Methods such as MALDI-QqTOFMS (Krutchinsky et al., WO 99/38185; Shevchenko et al. (2000) Anal. Chem. 72:2132-2141), ESI-QqTOF MS (Figeys et al. (1998) Rapid Comm'ns. Mass Spec. 12-1435-144) and chip capillary electrophoresis (chip-CE)-QqTOF MS (Li et al. (2000) Anal. Chem. 72:599-609) have been described previously. Mass spectrometers and techniques for using them in methods of the invention are well known to those of skill in the art. A person skilled in the art understands that any of the components of a mass spectrometer (e.g., desorption source, mass analyzer, detect, etc.) can be combined with other suitable components described herein or those known in the art. For additional information regarding mass spectrometers, see, e.g., Principles of Instrumental Analysis, 3rd ed., Skoog, Saunders College Publishing, Philadelphia, 1985; and Kirk-Othmer Encyclopedia of Chemical Technology, 4th ed. Vol. 15 (John Wiley & Sons, New York 1995), pp. 1071-1094.

Kits

The antibodies of the invention can also be included in kits for detecting the presence of CFP-10 or a fragment thereof in a sample. For example, the kit can comprise a means for obtaining a sample from a subject and/or a vessel for storing the collected sample for a period of time; an agent that can detect CFP-10 (e.g., an anti-CFP-10 monoclonal antibody) in a sample; means for determining the amount of CFP-10 in the sample; and means for comparing the amount of CFP-10 in the sample with a standard. The compound or agent can be packaged in a suitable container. The kit can further comprise instructions for using the kit to detect CFP-10 in a sample.

In an embodiment, the kit can be used in conjunction with capital equipment (such as a mass spectrometer) for the detection of Mycobacteria spp., for example, active pulmonary or extrapulmonary tuberculosis, even in cases with HIV coinfection. The assay kit can include reagents for use in sample preparation. These reagents can include commercially available materials such as, but not limited to: nanoparticles, digestion compounds, and wash buffers for rinsing. Other components within the kit can include pipette tips, aliquot tubes (sometimes referred to as 'vials' or 'Eppendorf tubes'), an aliquot stand for tube management, sample identification labeling, and device labelling, such as Instructions for Use (IFU). The kit can further consist of reusable capital components including a magnet for separation of nanoparticles and/or additional disposable components.

EXAMPLES

Example 1

Two groups of four New Zealand Rabbits were immunized with Keyhole limpet hemocyanin (KLH) conjugated with synthetic peptides containing sequences specific for the 10 kDa culture filtrate protein (CFP-10/EsxB) of *Mycobacterium tuberculosis* via a cysteine residue added to the C-terminus of each peptide.

Peptide 1593 (TDAATLAOEAGNEER (SEQ ID NO: 17)

Figure 1:
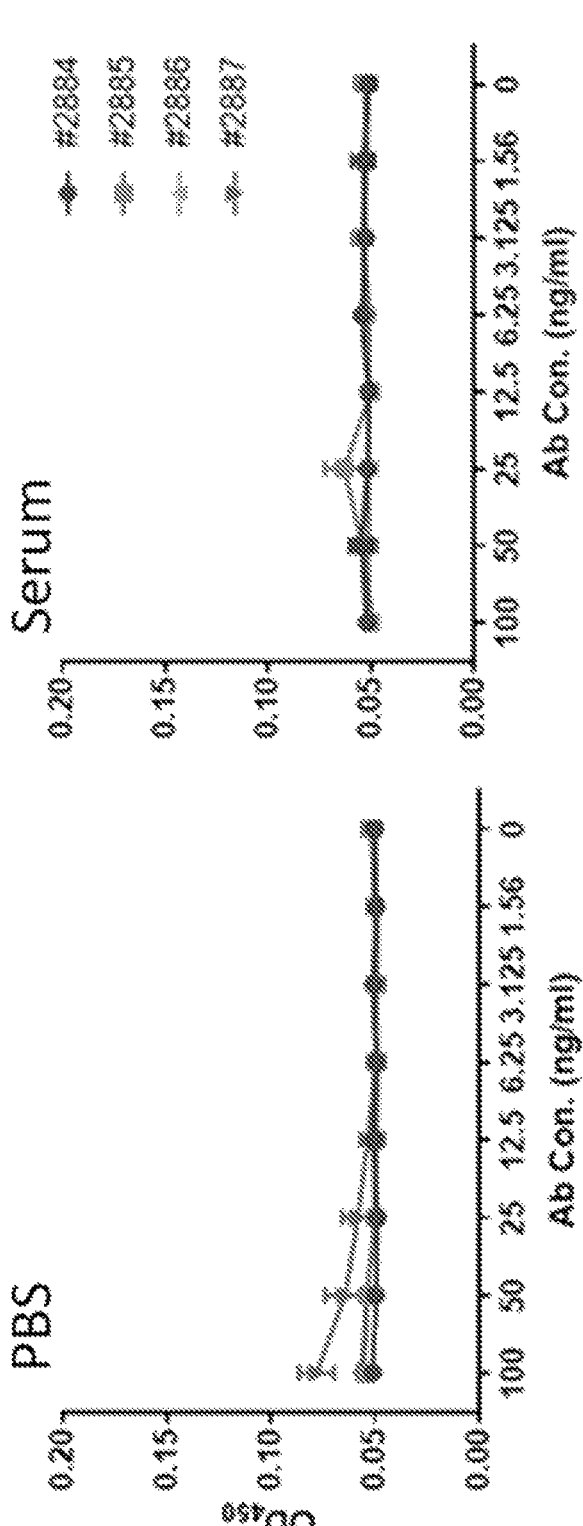
FIG. 1 shows indirect ELISAs (100 μl) for reactivity to CFP-10 protein.
Figure 2:
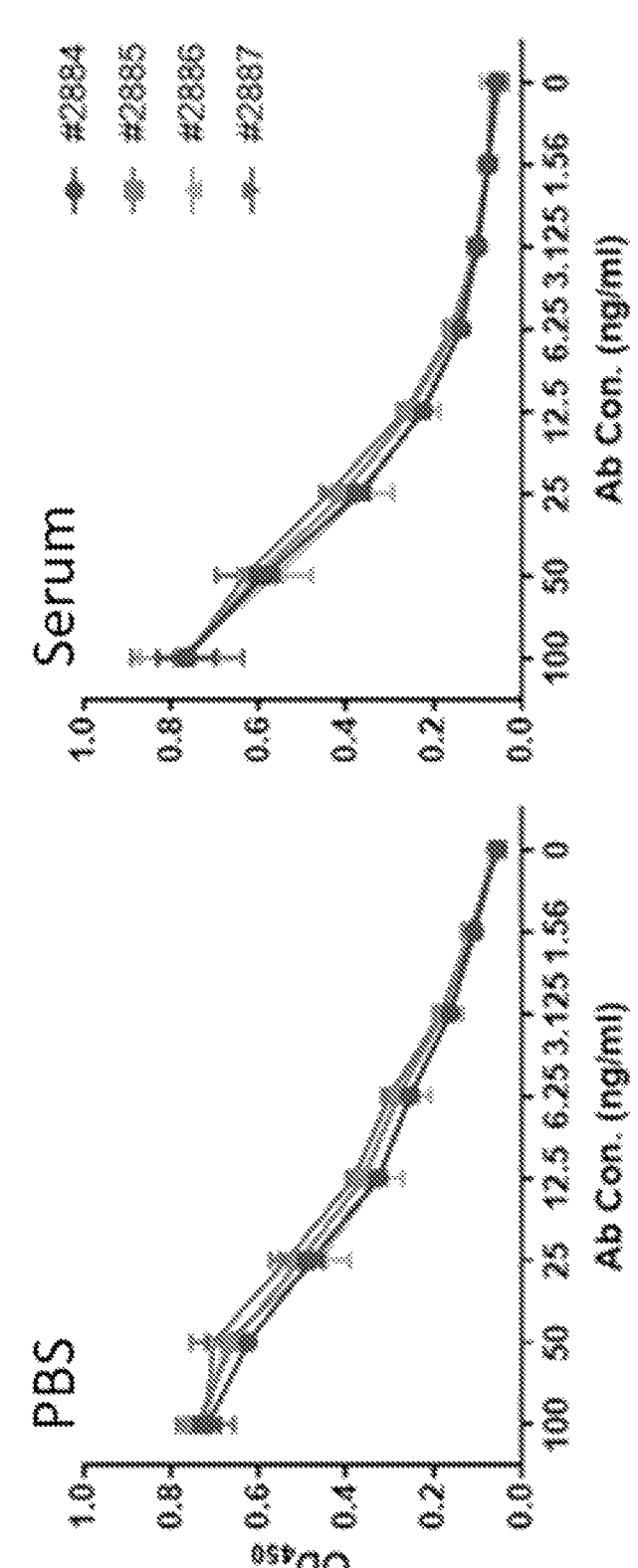
FIG. 2 shows indirect ELISAs (100 μl) for reactivity to 1593 peptide.
Figure 3:
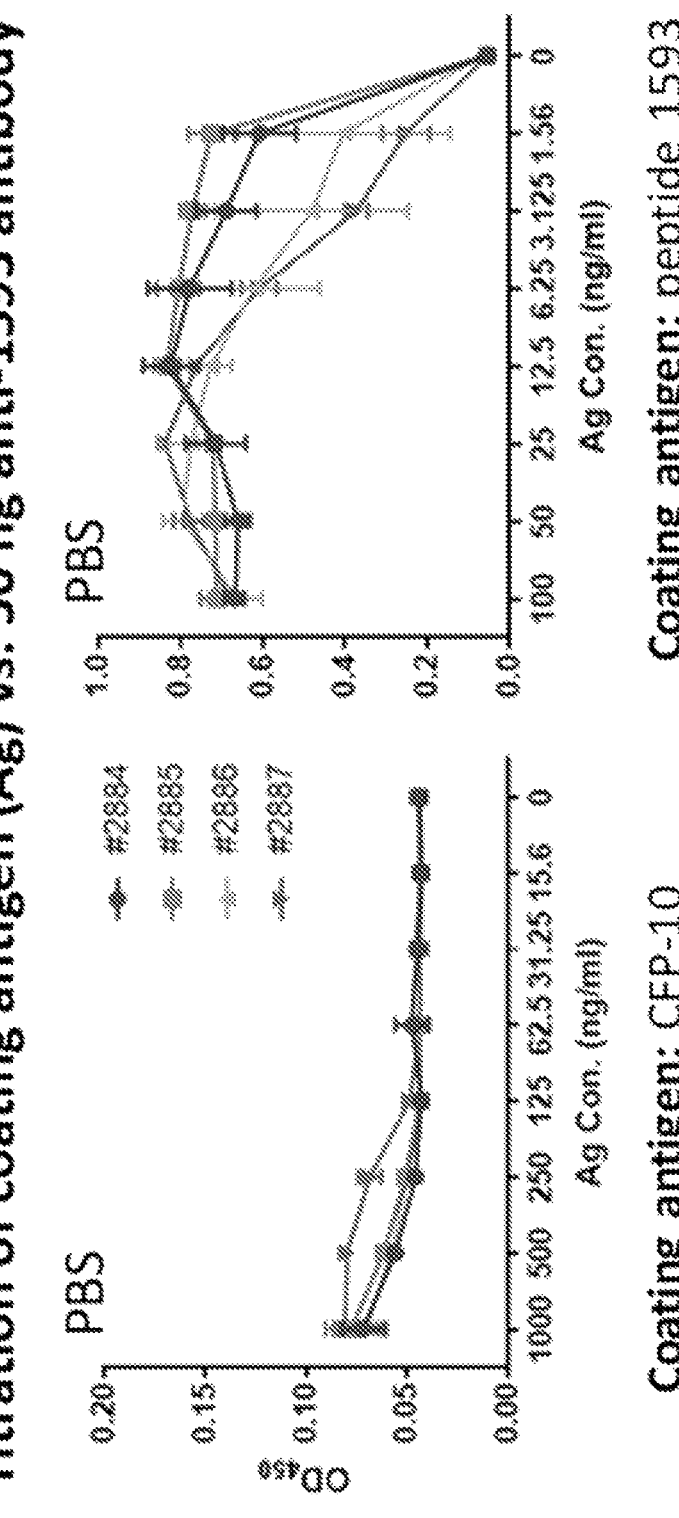
FIG. 3 shows indirect ELISAs (100 μl) for reactivity to low conc. antigen.

Rabbits 2884, 2885, 2886 and 2887 were immunized and boosted twice with KLH protein conjugated with the target peptide TDAATLAQEAGNFERC (SEQ ID NO: 198) (peptide 1593), which-excluding the C-terminal linker cysteine-matched the N-terminal amino acid sequence of CFP-10 (aa 6 to 20). Serum derived from these rabbits was assayed for its reactivity with both full-length recombinant CFP-10 protein and synthetic peptide 1593 in indirect ELISAs that were performed using either phosphate buffered saline (PBS) or healthy human serum (Serum) as the incubation matrix. Serum from rabbits 2884-2887 demonstrated poor affinity for recombinant CFP-10 protein (FIG. 1) in ELISAs adjusted for serum antibody concentration but demonstrated good reactivity in ELISAs where peptide 1593 was used as the target antigen (FIG. 2). These analyses, however, reflected the serum reactivity to high concentrations of the target antigens that are much greater than those that should be encountered in serum samples of patients with active TB cases. Indirect ELISAs were thus performed with serial dilutions of the target antigens and a constant antibody concentration (FIG. 3). Serum from all four rabbits demonstrated weak reactivity for full-length CFP-10 protein, but variable reactivity to decreasing amounts of peptide 1593. Serum from rabbits 2884 and 2885 demonstrating greater reactivity to serial dilutions of peptide 1593 than serum from rabbits 2886 and 2887, although all the serum samples exhibited significant reactivity to the lowest antigen concentration assayed in this experiment (1.56 ng/ml; 156 pg total protein) which was lower than the level we have detected in most serum samples drawn from individuals with active tuberculosis (TB) cases.

Figure 4:
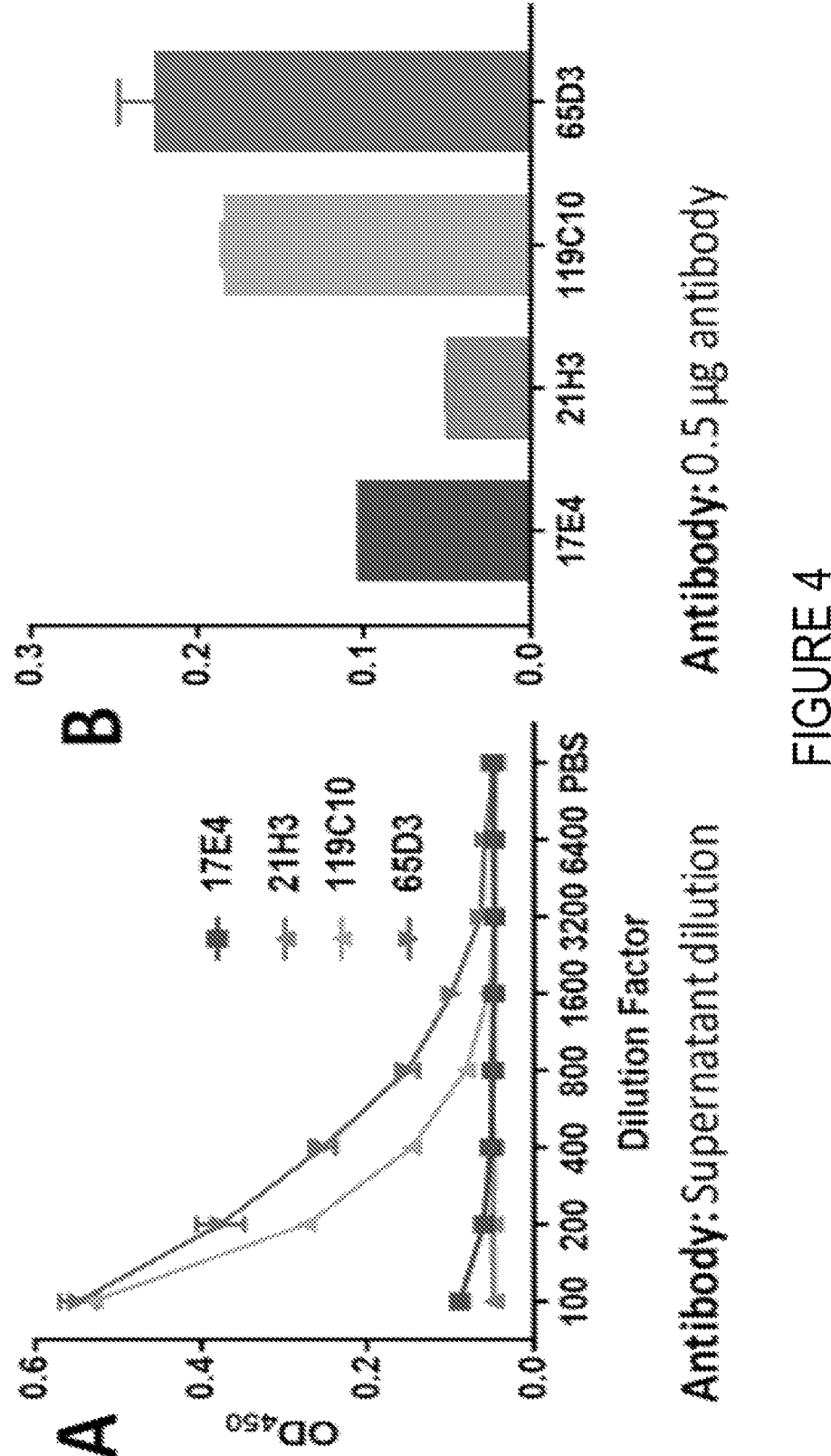
FIG. 4 shows indirect ELISAs (100 μl) for reactivity to 1593 peptide.
Figure 5:
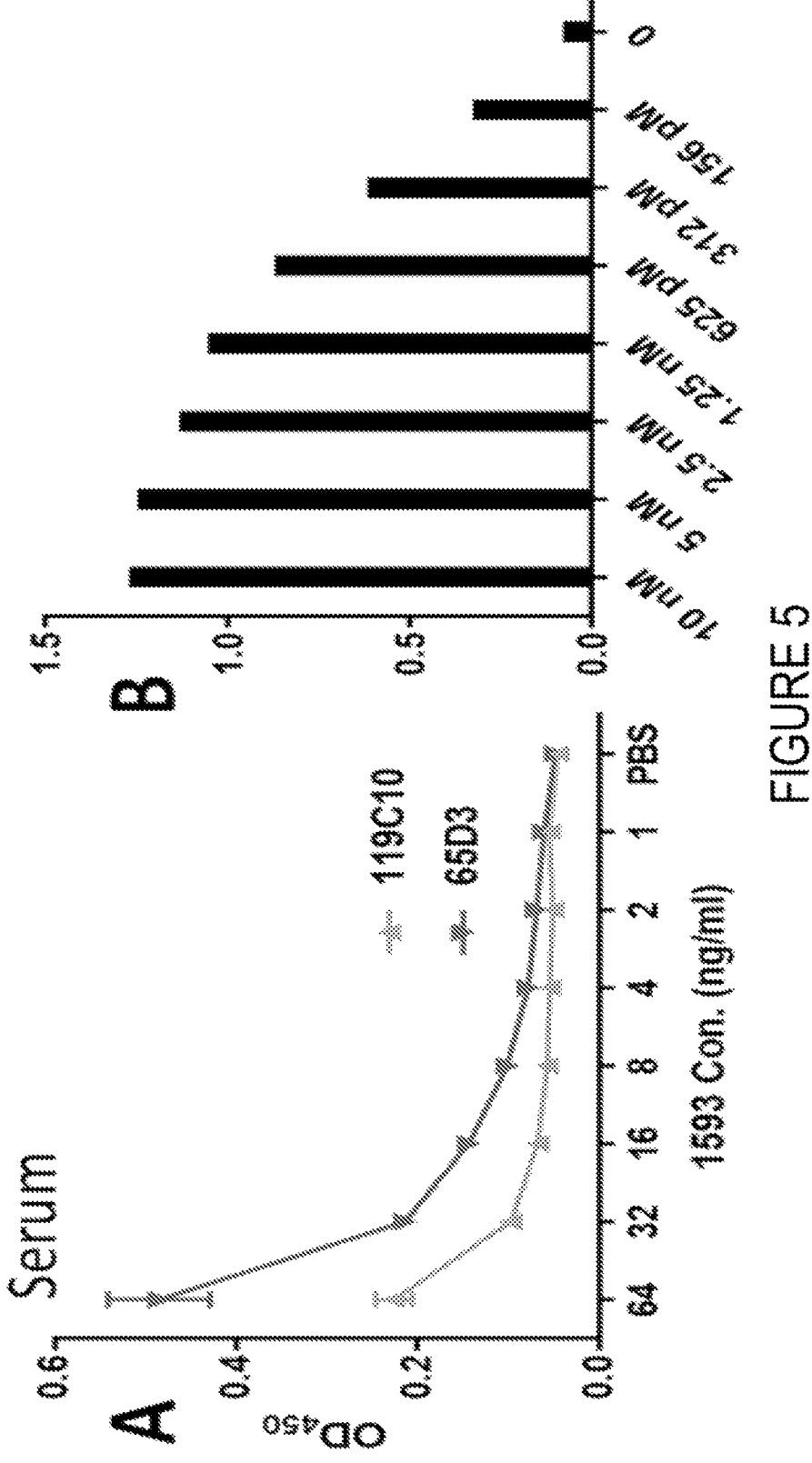
FIG. 5 shows indirect ELISAs (100 μl) for reactivity to 1593 peptide
Figure 6:
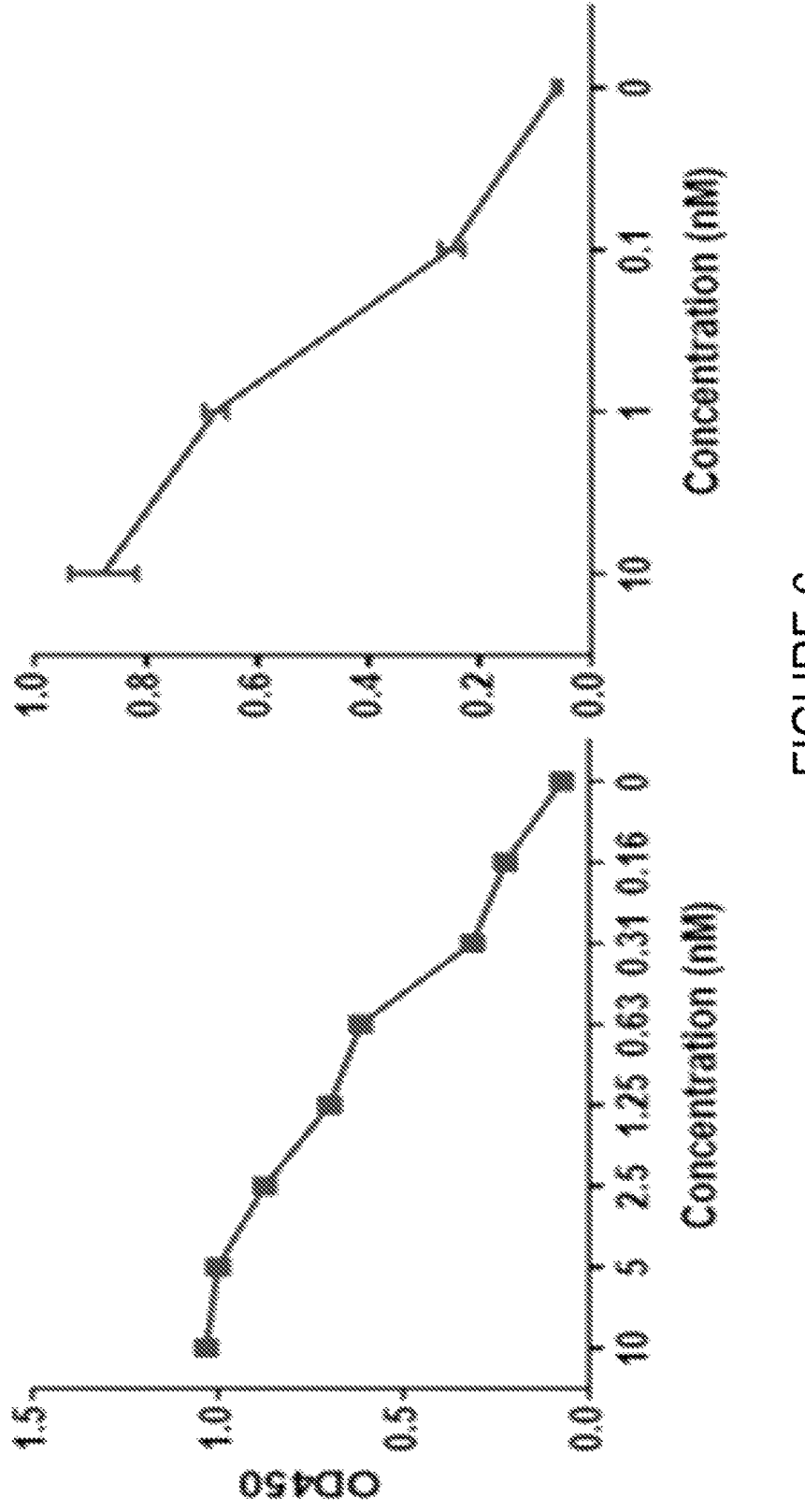
FIG. 6 shows indirect ELISAs (100 μl) for reactivity to 1593 peptide.

Based on this data, we chose rabbit 2885 to produce monoclonal antibodies. Screening of the clone library identified four clones whose supernatants demonstrated reactivity to peptide 1593. However, Indirect ELISAs revealed that the supernatants of only two of these clones exhibited good reactivity for 100 μg of peptide 1593, with the supernatant of clone 65D3 performing better than that of clone 119C10 (FIG. 4A), and adjusting for the antibody concentrations in the supernatants of these clones did not markedly alter these results (FIG. 4B). We next analyzed the response of the 119C10 and 65D3 against a serial dilution of low concentration peptide 1593, incubating 100 ng of each antibody in 100 μL healthy human serum during antigen detection. Under these conditions only 65D3 showed a reasonable response curve (FIG. 5A), since the 119C10 signal fell to baseline early in the 1593 peptide serial dilution curve. Repeating this ELISA using an approximation of the physiological range of our target antigen indicated that the 65D3 antibody exhibited good performance across the full range of expected antigen concentrations (FIG. 5A), and this result was largely replicated in subsequent assays (FIG. 6).

Figure 7:
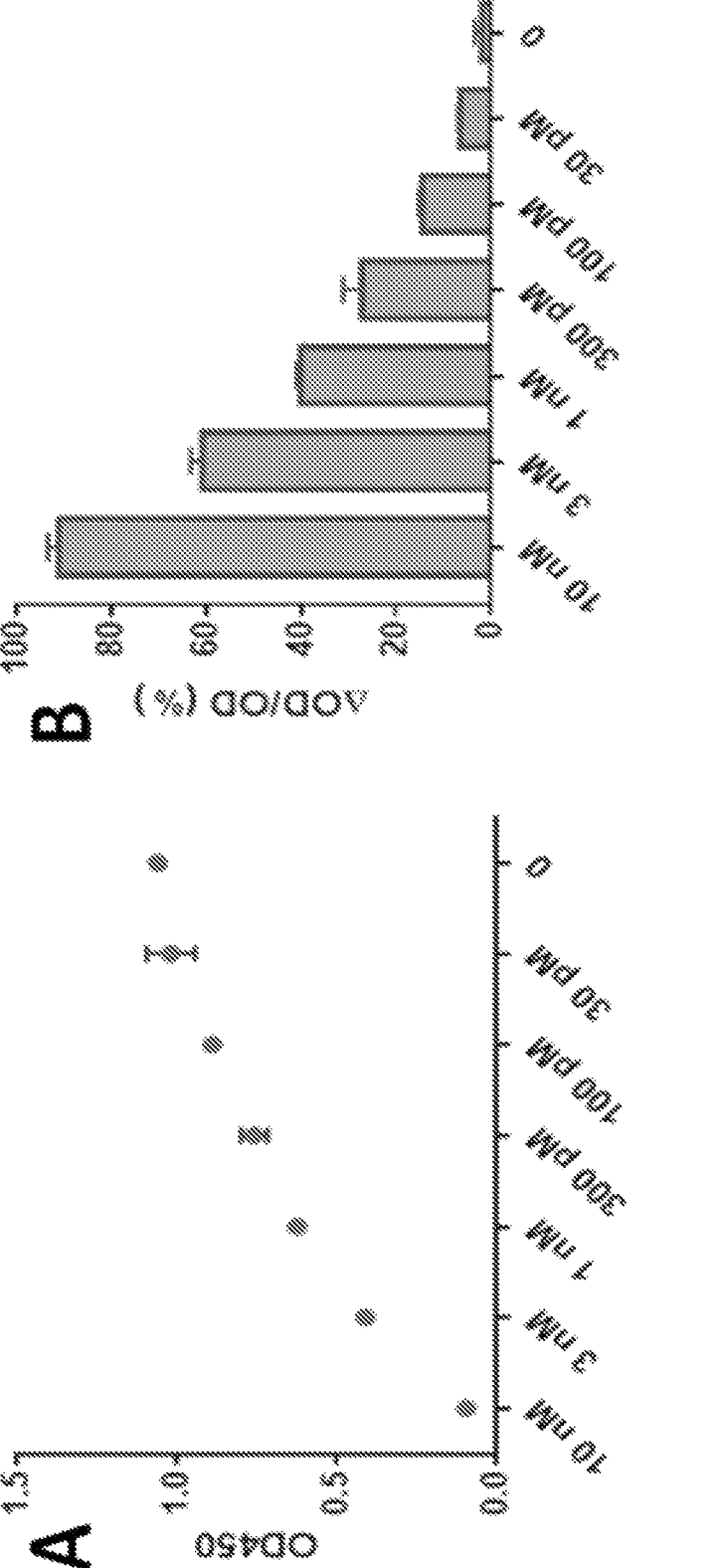
FIG. 7 shows competitive indirect ELISA for reactivity to 1593 peptide (N=3).

Antibody binding behavior observed by indirect ELISA represents an artificial situation since the antigen of interest is immobilized on a surface which confines its conformational interactions with the binding antibody flexibility. Antibodies also bind in proximity to multiple copies of the antigen, which could influence apparent binding behavior since after antigen-antibody dissociation an antibody would be in proximity to a high local concentration of its target antigen, favoring the rapid formation of a new antigen-antibody complex. Competitive indirect ELISAs were therefore performed to address the effect of soluble 1593 peptide on the biding behavior of the 65D3 antibody. In these assays, assay wells were coated with 100 μL of a 6 nM concentration of peptide 1593 and then incubated with 50 ng/mL 65D3 antibody in 100 μL serial dilutions containing 10 nM to 30 pM of peptide 1593 (FIG. 7A). In this assay, the signal observed in the absence of soluble peptide 1593 (0 pM) was progressively blocked by increasing concentrations of soluble peptide 1593, attaining 40% and 90% suppression at 1 nM and 10 nM concentrations, respectively (FIG. 7B).

Figure 8:
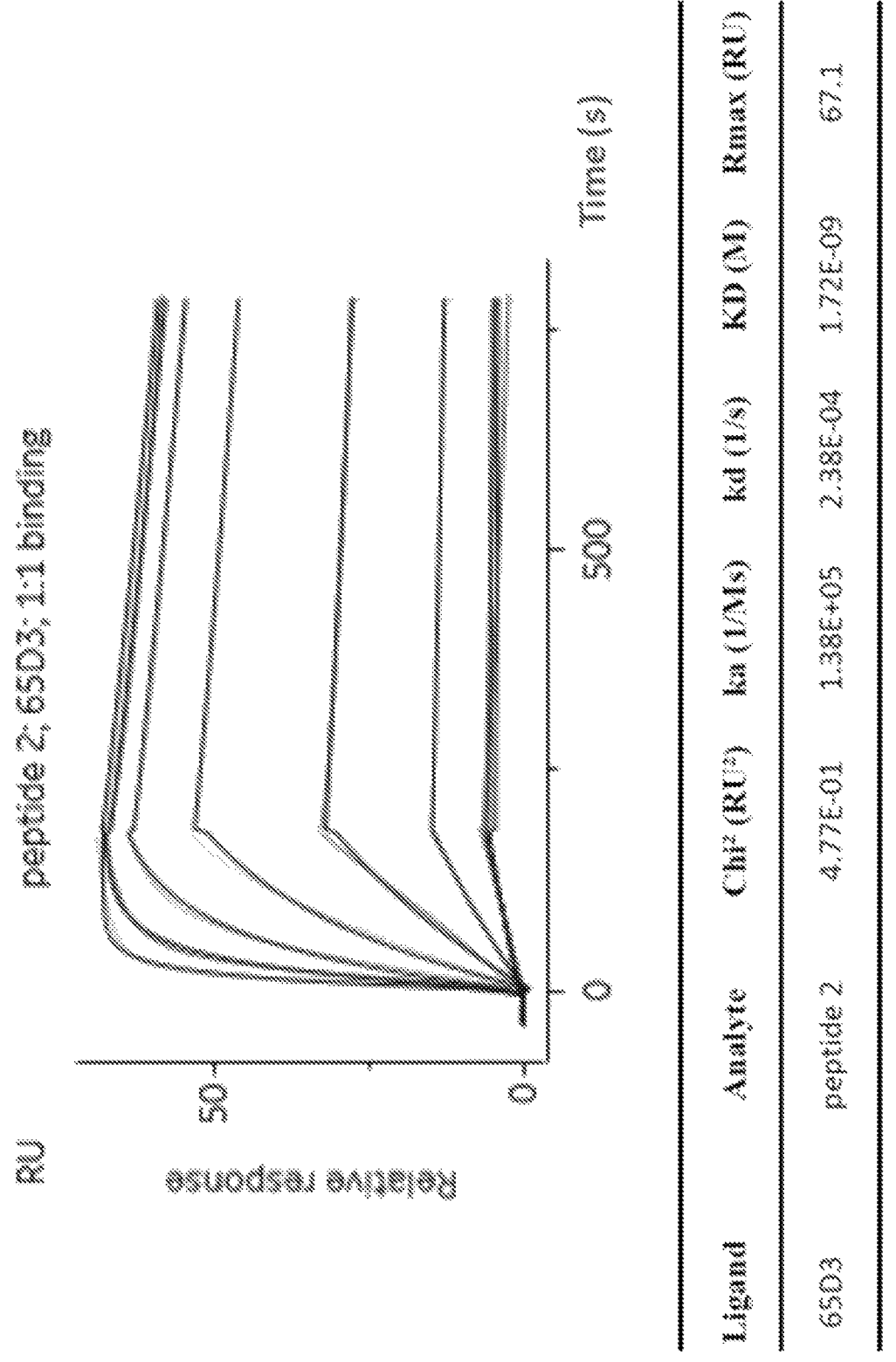
FIG. 8 shows Biacore™ analysis of 65D3 antibody and peptide 1593 binding.

Binding affinity of the 65D3 antibody to peptide 1593 was next measured on a Biacore™ 8K with an 66D3 immobilization level of 11390.5 RU and association and dissociation contact times of 180 and 600 seconds, respectively, at a flow rate of 30 μL/min and peptide 1593 concentrations of 7.8, 15.6, 31.2, 62.5, 125, 250, and 500 nM (FIG. 8). This analysis indicated that the affinity of the 65D3 antibody for peptide 1593 was 1.72 nM.

Peptide 2004 (TQIDQVESTAGSLQGQWR (SEO ID NO: 18))

Figure 9:
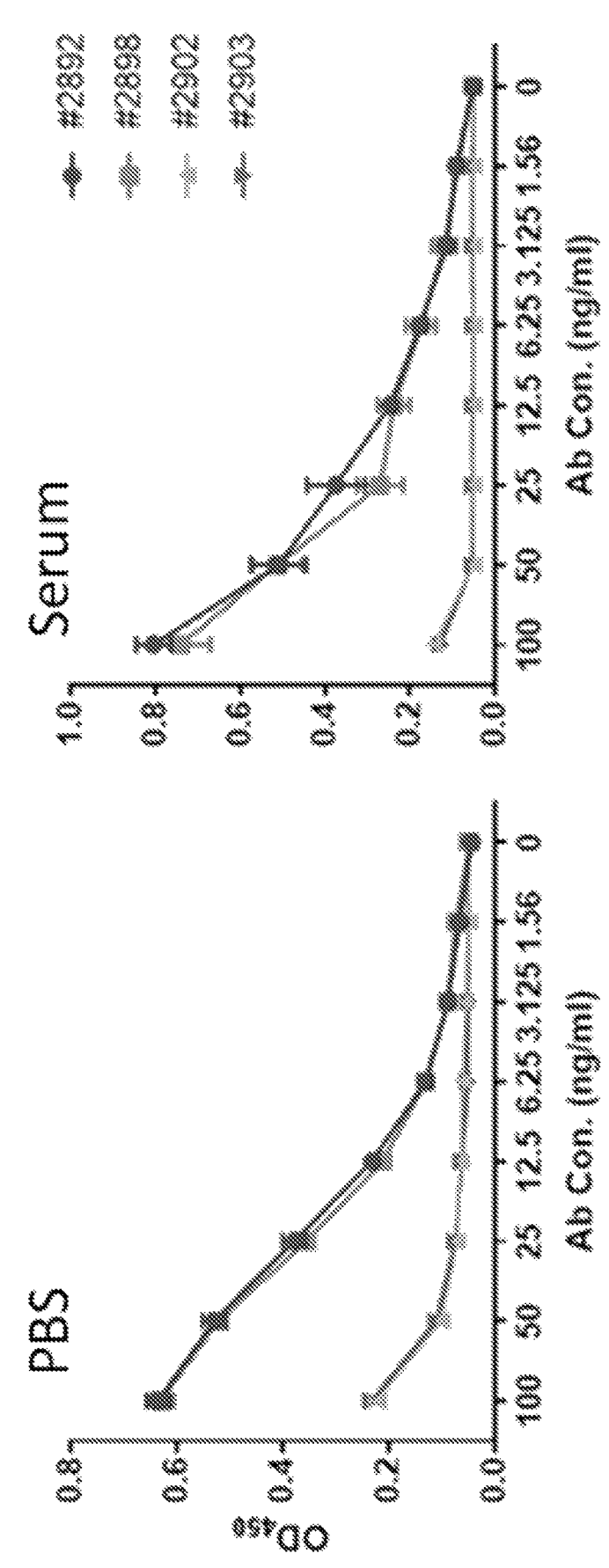
FIG. 9 shows indirect ELISAs (100 μl) for reactivity to CFP-10 protein.
Figure 10:
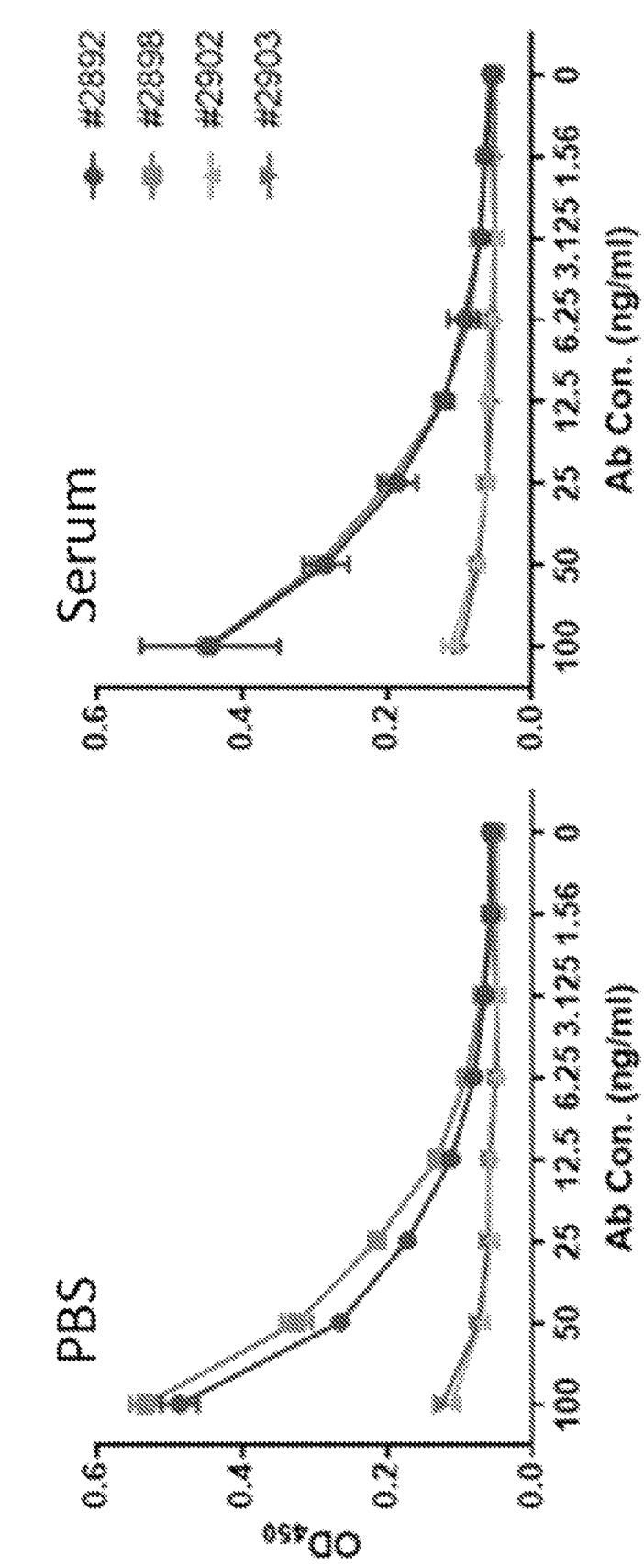
FIG. 10 shows indirect ELISAs (100 μl) for reactivity to 1593 peptide.

Rabbits 2892, 2898, 2902 and 2903 were immunized and boosted twice with KLH protein conjugated with the target peptide TQIDQVESTAGSLQGQWRC (SEQ ID NO: 199) (peptide 2004), which—excluding the C-terminal linker cysteine—matched amino acids 27 to 44 of the CFP-10 protein sequence. Serum derived from these rabbits was assayed for its reactivity with both full-length with both full-length recombinant CFP-10 protein and synthetic peptide 1593 in indirect ELISAs that were performed using either phosphate buffered saline (PBS) or healthy human serum (Serum) as the incubation matrix. Serum from rabbits 2892 and 2898 exhibited moderate affinity for recombinant CFP-10 protein (FIG. 9) after incubation in either PBS or serum in indirect ELISAs adjusted for serum antibody concentration. Serum from rabbits 2902 and 2903 demonstrate poor affinity for CFP-10 when assayed in PBS, and this performance deteriorated further when assays were conducted in serum. Serum from rabbits 2892 and 2898, but not 2902 and 2903, also demonstrated moderate affinity for peptide 2004 (FIG. 10), although binding activity appeared modestly decreased from that observed with full-length CFP-10 protein and appeared to more rapidly decrease when assayed with lower antibody concentrations.

Figure 11:
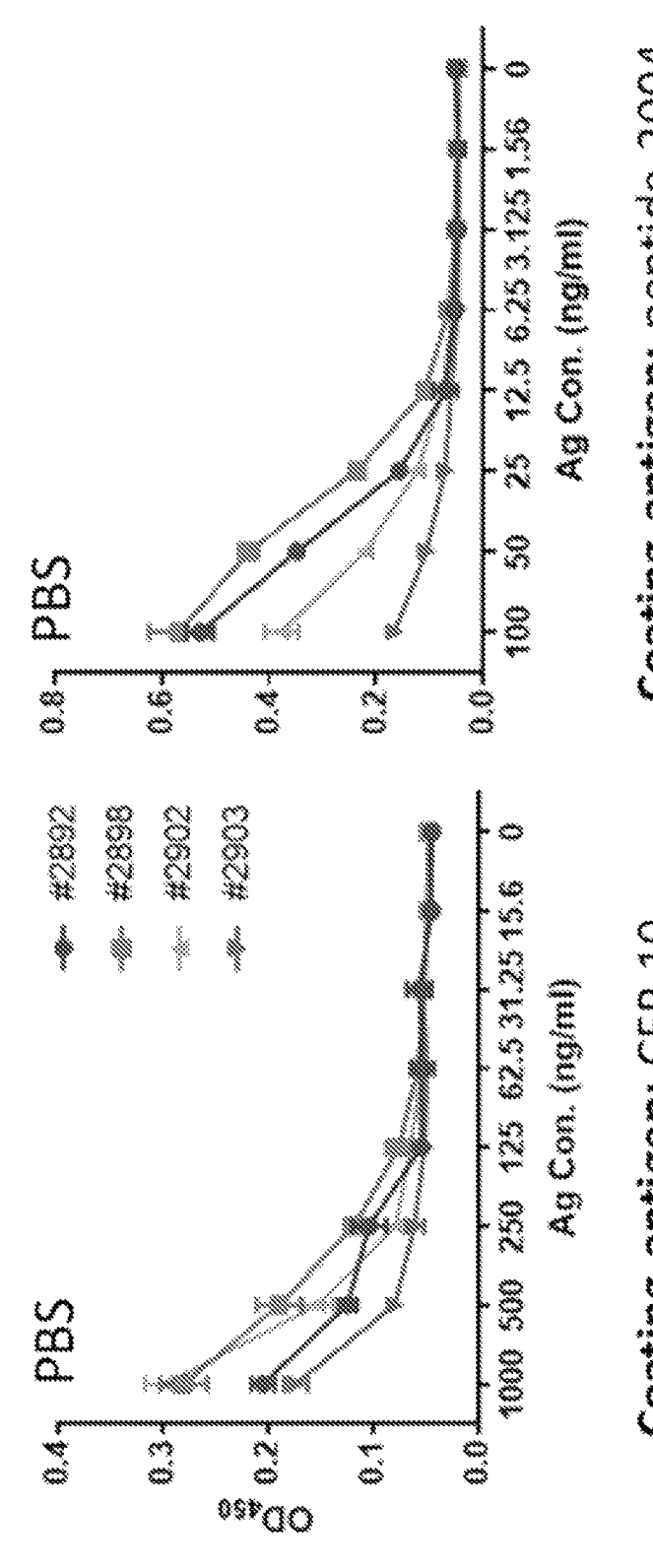
FIG. 11 shows indirect ELISAs (100 μl) for reactivity to 1593 peptide.
Figure 22:
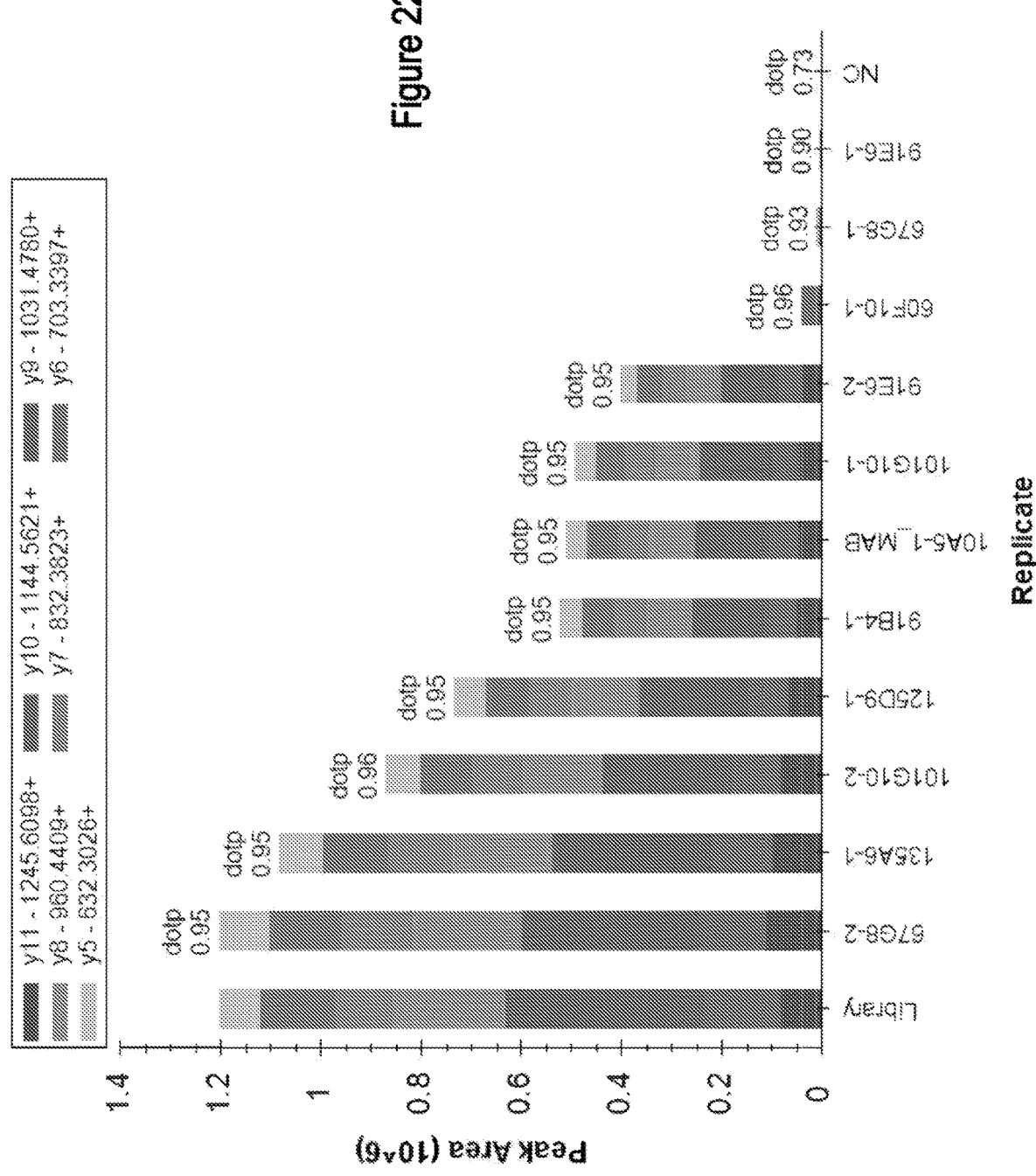
FIG. 22 shows relative LC-MS/MS mass spectrometry signal analysis for the 1593 target peptide after its immunoprecipitation with equivalent amounts of the indicated mAbs. The "Library" column indicates the expected contribution of the indicated y-ions of 1593, as indicated by their respective colors. The dot product (dotp) values above each column indicate the similarity of the target ions detected from peptides captured with each mAb during their immunoprecipitation for trypsin-digested serum samples to library-derived target peptide ions.

Indirect ELISAs were next performed with serial antigen dilutions and a constant antibody concentration (FIG. 11). Results from this analysis demonstrated poor antigen binding activity from all four serum samples.

Example 2 Affinity Measurement of 65D3

Samples:

| Samples | MW (KDa) | Concentration (mg/ml) |
|---|---|---|
| 65D3 | 150 KD | 1.841 |
| Peptide 2 | 2 KD | 5 |

Instrument and Reagents:

Biacore™ 8K, 29215379-2177839 (GE Healthcare).

Series S Sensor Chip CM5, Cat. No. BR-1005-30 (Lot. No. 10270193) (GE Healthcare)

10 mM sodium acetate, pH 4.5, Cat. No. BR-1003-50, (Lot. No. 20623) (GE Healthcare).

Amine coupling kit, Cat. No. BR-1000-50 (Lot. No 2087132) (GE Healthcare).

NHS: 100 mM N-hydroxysuccinimide in $H_2O$

EDC: 400 mM 1-ethyl-3-(3-dimethylaminopropyl) carbodiimide in $H_2O$

Ethanolamine: 1 M ethanolamine hydrochloride, adjusted to pH 8.5 with NaOH.

HBS-EP$^+$: 10 mM HEPES, 150 mM NaCl, 3 mM EDTA, 0.05% Tween 20, pH 7.4 (Lot. No. BCBX4905) (GE Healthcare)

Methods

Immobilization of 65D3 onto CM5 Sensor Chip

The immobilization of 65D3 were performed under 25 degrees Celsius while HBS-EP$^+$ was used as the running buffer. The sensor chip surface of flow cells 1 and 2 were activated by freshly mixed 50 mmol/L N-Hydroxysuccinimide (NHS) and 200 mmol/L 1-ethyl-3-(3-dimethylaminopropyl) carbodiimide hydrochloride (EDC) for 420s (10 μL/min). Afterwards, 65D3 diluted in 10 mmol/L NaAC (pH 4.5) was injected into the flow cell 2 to achieve conjugation of MAX Response Unit respectively, while flow cell 1 was set as blank. After the amine coupling reaction, the remaining active coupling sites on chip surface were blocked with 420 s injection of 1 mol/L ethanolamine hydrochloride.

Affinity Measurement

The assay was performed at 25° C. and the running buffer was HBS-EP⁺. Diluted peptide was injected over the surface as association phase, followed by injecting running buffer as dissociation phase. Running configuration was listed as the table below.

| IMMOBILIZATION | |
| --- | --- |
| Ligand | 65D3 |
| Immobilization level (Ru) | 11390.5 |
| ASSOCIATION AND DISSOCIATION | |
| Association contact time(s) | 180 |
| Dissociation contact time(s) | 600 |
| Flow rate (μl/min) | 30 |
| Sample concentrations (nM) | 7.8125, 15.625, 31.25, 62.5, 125, 250, 500 |

Results

All the data were processed using the Biacore™ Evaluation software version 1.1 Flow cell 1 and blank injection of buffer in each cycle were used as double reference for Response Units subtraction.

See FIG. 8 for affinity measurement of 65D3 to peptide 2. In this experiment, the affinity of 65D3 to peptide 2 was 1.72E-09 M.

Example 3—Affinity Maturation of 65D3

Affinity maturation can be performed to enhance the affinity of antibodies to peptide 1593 according to, for example, the strategy of NKK saturation mutagenesis and phage display.

Amino Acid Sequences of Parental Antibody

Antigen: Peptide 2 (Peptide 1593) and Biotin-Peptide 2

SfiI enzyme (NEB, Cat #: R0123S)

NheI-HF enzyme (NEB, Cat #: R3131S)

Ampicillin stock, 100 mg/ml

80% Glycerol

20% Glucose

2×YT: 16 g Tryptone, 10 g Yeast extract and 5 g NaCl dissolved in 1 L ddH2O

Host strain: *E. coli* SS320, TG1

M13KO7 helper phage (NEB, Cat. No.: N0315S)

pCDNA3.4 expression vector and Expi293F cell (prepared by GenScript)

Biological safety cabinet (Thermo Scientific, Model. 1384)

Zhichu CO2 shaker incubator (Shanghai Zhichu Instrument, Model. ZCZY-BS8)

Expi293F medium (Gibco, Cat. No. A14351-01)

ExpiFectamine293 Transfection Kit (Gibco, Cat. No. A14525)

TPP Tubespin Bioreactor 50 (Cat. No. 87050)

125-ml shake flask (Corning, Cat. No. 431143)

500-ml shake flask (Corning, Cat. No. 431145)

Protein-A resin (GenScript, Cat. No. L0443)

Binding buffer: 0.15 M NaCl, 20 mM Na2HPO4, pH 7.0

Elution buffer: 0.1 M Glycine-HCl, pH 2.5

Neutralization buffer: 1 M Tris-HCl, pH 9.0

IPTG 0.1 mM

Coating buffer: 0.05 M NaHCO₃, pH 9.6

PBS: 137 mM NaCl, 2.7 mM KCl, 4.3 mM Na2HPO4, 1.4 mM KH2PO4, pH 7.4

ELISA microtiter plate (Corning, Cat. No.: 9018)

Blocking buffer (MPBS): PBS buffer, pH 7.4, with 3% skimmed milk

Washing buffer (PBST): PBS buffer, pH 7.4, with 0.05% Tween20

Elution buffer: 0.1M TEA, trimethylamine (for phage display panning)

1M Tris-HCl (pH7.4)

HRP conjugated Goat Anti-Human IgG-F(ab')₂ antibody (Jackson ImmunoResearch, Cat #: 109-035-097)

HRP conjugated Anti-M13 monoclonal antibody (Sino Biological, Cat #: 11973-MM05T-H)

Tetramethylbenzidine (TMB, GenScript);

1M HCl (GenScript)

Biacore T200/Biacore 8K (GE Healthcare)

Series S Sensor Chip CM5 (GE Healthcare, Cat. No.: BR-1005-30)

HBS-EP: 10 mM HEPES, 500 mM NaCl, 3 mM EDTA, 0.05% Tween 20, pH 7.4

10 mM Glycine-HCl

Methods 3.1 Construction and Production of Chimeric Fab Antibodies

The DNA sequences encoding the antibody heavy and light chains were synthesized and inserted into FASEBA vector to construct expression plasmids of Fab chimeric. Then the FASEBA vector was transferred into TG1 competent, and after selecting positive clones for culture, IPTG induced Fab chimeric antibody expression.

3.2 Binding Confirmation of Chimeric Fab Antibodies

The affinity of chimeric Fab antibodies binding to Peptide 1593 was individually determined using ELISA. Microtiter ELISA plates were coated with 10 μg/ml BSA (expression detection) or 1, 0.5, 0.25, 0.125, 0.0625, 0.03125, 0.015625, 0.007813, 0.003906, 0.001953 μg/ml antigen protein (binding evaluation) in 100 μl coating buffer at 4° C. overnight, and subsequently incubated with blocking buffer at 37° C. for 1 hour. Then the plates were washed with washing buffer and incubated with 100 μl antibody-containing supernatants at RT for 2 hours. Next the plates were washed with washing buffer and incubated with 100 μl secondary antibody (0.1 μg/ml goat anti-human IgG F(ab')₂-HRP for 45 minutes. After washing, the reaction was developed with 100 μl TMB substrate for 10 minutes at room temperature and stopped by adding 50 μl of 1 M HCl. The absorbance values were measured at 450 nm using a spectrometer.

3.3 Construction of NNK Library

Totally 63 residues in CDR region were selected optimization, their conformational adjacent residues were defined and mutated by NNK method. Each individual NNK library was generated per residue based on the FASEBA platform with a theoretical diversity at 20. 48 clones were randomly selected from each NNK library for expression in *E. coli* TG1 in 96-deep-well plates were selected for sequencing. Then unique clones the crude protein secreted in medium was analyzed by ELISA against BSA and antigen protein for the assessment of expression and binding specificity, respectively. The "beneficial mutants" that increased antibody affinity, yet without compromising antibody expression, were confirmed by ELISA again. Clones with improved affinity were selected for IgG construction.

3.4 FASEBA Screening

This screening process selected 92 clones from each plate of the 63 NNK libraries for expression in *E. coli* in 96-deep-well plates. The crude protein secreted in medium was analyzed by ELISA against antigen protein for the assessment of binding specificity. Clones with significantly improved ELISA signal were selected for sequencing. And the beneficial mutants were obtained.

3.5 Construction and Production of IgGs

The variable domains of heavy chain (VH) and light chain (VL) encoding the parental antibody and its affinity-matured antibody were synthesized and inserted into pCDNA3.4 vector to construct full length IgG expressing vectors, respectively. The heavy and light chain expressing plasmids were used for transfection. The recombinant IgGs secreted to the medium were purified using protein A affinity chromatography. Finally, the concentration and purified antibodies were assessed by OD280 and SDS-PAGE, respectively.

3.6 Affinity Measurement

Antibody affinity to antigen protein was determined using a Surface Plasmon Resonance (SPR) biosensor, Biacore (GE Healthcare). Antibodies were immobilized on the sensor chip through amine coupling method. Antigen was used as the analyte. The data of dissociation (kd) and association (ka) rate constants were obtained using Biacore evaluation software. The equilibrium dissociation constants (KD) were calculated from the ratio of kd over ka.

3.7 Construction of Combinatorial Mutagenesis Phage Display Library

The combinatorial mutagenesis phage display library consists of a set of predefined DNA parts strategically assembled in a specific arrangement for downstream synthetic biology. The variant slots are synthesized using advanced and high-throughput platforms. The library quality is ensured through Sanger sequencing of 20 random colonies and guarantee a minimal positive rate of 80%, 10 μg clonal plasmids will be delivered. The design of combinatorial mutagenesis phage display library was shown in Table 2.

TABLE 2

The design of combinatorial mutagenesis phage display library.

| | CDR1 | CDR2 | | | | CDR3 |
|---|---|---|---|---|---|---|
| | 31 | 60 | 62 | 63 | 64 | 99 |
| VH | H | S | A | K | G | F |
| mutation AA | S, D, N | G, Y, H, F, D, N | other 19 AAs | other 19 AAs | other 19 AAs | other 19 AAs |

3.8 Phage Display Library Panning Selection

The phage display library (size: 4.48×106) were rescued, amplification and precipitated with PEG/NaCl and re-suspended in PBS for panning. The Phage panning was carried out using soluble phase panning with Biotin-Peptide 1593, and the panning procedures were performed using a standard procedure developed by GenScript. Two different panning strategies were performed as below.

3.8.1 Normal Phage Panning (R1-R4)

Phage particles (input 2×1012 pfu/pool) and Dynabeads™ M280 streptavidin were diluted/blocked in 5% BSA-PBS incubated for 1 hour with slowly rotating. Then added Biotin-peptide2 into the blocked libraries and incubated for 1 hour with slow rotation. Next the antigen and antibody binding libraries were transferred to Dynabeads and incubated for 30 min with slow rotation.

3.8.2 Competition Panning (R5-R6)

Phage particles (2×1011 pfu/pool) and M280 streptavidin Dynabeads™ were diluted/blocked in 5% BSA-PBS incubated for 1 hour with slow rotation. Biotin-peptide2 (1593) was then added into the blocked libraries and incubated for 1 hour with slow rotation, added peptide2 into the binding libraries and incubated for 30 min with slow rotation. Next the antigen and antibody binding libraries were transferred to Dynabeads and incubated for 30 min with slow rotation.

3.8.3 Bound Phage Collection (the Same Steps)

After capture, unbound/nonspecifically bound phages were removed by decanting and washing with 0.05% PBST for 8-15 times and 3-5 times with PBS. The bound phage were eluted by TEA and neutralized with 1M Tris-HCl (pH7.4). The phage eluate was used to infect 10 ml exponentially growing E. coli TG1 at 37° C. Phage particles were prepared for subsequent rounds of panning, by amplification and rescue using M13K07 helper phage as per standard procedures. The former round amplified phage was used as the input phage for next round panning. The infected TGI were plated on the 2YT-Amp+ plates at round 1-6. Single colonies were picked and binding activity were validated by monoclonal ELISA.

3.9 Monoclonal ELISA Screening and DNA Sequencing 3.9.1 Phage ELISA Screening

Individual colonies were grown in 96-deep-well plate and rescued by M13KO7 helper phage at 30° C. overnight. Meantime, 96-well ELISA microtiter plates were coated with lug/ml Peptide 1593 in coating buffer overnight at 4° C. The plates were blocked with 3% MPBS. After rinsing, 50 μl phage supernatant from each overnight culture deep well and 50 μl 0.1% PBST was added to the plate for 2 hours incubation at RT. After rinsing plates three times with wash buffer, the HRP-conjugated anti-M13 monoclonal antibody was added to the plates for 45 minutes at RT. The plates were washed for an additional 6 times and the substrate solution was added to the wells for the signal developing reaction, and absorption was measured at 450 nm using a spectrometer. The phage binders with significantly improved ELISA signal were selected for DNA sequencing and beneficial mutants were obtained.

3.9.2 Soluble Expression ELISA Screening

Individual colonies were grown in 96-deep-well plate and induced for expression at 30° C. overnight. Simultaneously, 96-well ELISA microtiter plates were coated with 0.015 μg/ml Peptide 1593 in coating buffer overnight at 4° C. These plates were blocked with 3% MPBS. After rinsing, 50 μl expression supernatant from each overnight culture deep well and 50 μl 0.1% PBST was added to the plate for a 2 hour incubation at RT. After rinsing plates three times with wash buffer, the HRP-conjugated Goat Anti-Human IgG-F (ab')2 antibody was added to the plates for 45 minutes at RT. The plates were washed for additional 6 times and the substrate solution was added to the wells for the signal developing reaction. The absorption was measured at 450 nm using a spectrometer. Clones with significantly improved ELISA signal were selected for DNA sequencing and beneficial mutants were obtained.

4. Results 4.1 Binding Confirmation of Chimeric Fab Antibody by ELISA

The results indicated that chimeric Fab antibody was binding with the Ag. The Ab-Ag binding activity validated by ELISA in Table 3 and FIG. 27. The Peptide 1593 concentration of 0.015 μg/ml was selected for further test.

TABLE 3

| Chimeric Fab binding activity. | | |
| --- | --- | --- |
| Ag concentration dilution (ug/ml) | Chimeric Ab 01 | Chimeric Ab 02 |
| 1 | 2.301 | 2.311 |
| 0.5 | 2.272 | 2.253 |
| 0.25 | 2.184 | 2.225 |
| 0.125 | 1.936 | 2.035 |
| 0.0625 | 1.708 | 1.800 |
| 0.03125 | 1.212 | 1.367 |
| 0.015625 | 0.730 | 0.789 |
| 0.0078125 | 0.319 | 0.341 |
| 0.00390625 | 0.133 | 0.147 |
| 0.00953125 | 0.084 | 0.084 |
| Blank | 0.051 | 0.050 |
| NC | 0.052 | 0.052 |

See, for example, FIG. 27 for chimeric Fab binding activity.

4.2 NNK Library Construction

In total, 63 residues were selected for CDR region optimization, as shown in Table 4 and Table 5, so that 63 NNK libraries were constructed. Each individual NNK library that was generated per residue based on the FASEBA platform had a theoretical diversity of 20. The QC results are shown in Table 5.

TABLE 4

| Residues selected for NNK library construction. | | | | | |
| --- | --- | --- | --- | --- | --- |
| L-CDR1 | L-CDR2 | L-CDR3 | H-CDR1 | H-CDR2 | H-CDR3 |
| L1-L13 | L14-L20 | L21-32 | H1-H10 | H11-H26 | H27-H31 |

TABLE 5

| | | | | The QC results of 63 NNK libraries | | | |
| --- | --- | --- | --- | --- | --- | --- | --- |
| Library | Mutation site | Clone for sequencing | Analysis | Mutants (unique clones) | WT | Bad sequence | mutant ratio (unique/ analysis) |
| L1 | Q | 24 | 21 | 13 | 0 | 2 | 62% |
| L2 | S | 24 | 24 | 14 | 1 | 2 | 58% |
| L3 | S | 24 | 22 | 11 | 2 | 1 | 50% |
| L4 | Q | 24 | 19 | 11 | 2 | 0 | 58% |
| L5 | S | 24 | 23 | 12 | 3 | 4 | 52% |
| L6 | V | 24 | 18 | 12 | 0 | 1 | 67% |
| L7 | Y | 24 | 20 | 10 | 0 | 1 | 50% |
| L8 | N | 24 | 20 | 12 | 1 | 0 | 60% |
| L9 | N | 24 | 22 | 13 | 1 | 0 | 59% |
| L10 | K | 24 | 21 | 13 | 1 | 1 | 62% |
| L11 | E | 24 | 22 | 12 | 0 | 0 | 59% |
| L12 | L | 24 | 21 | 10 | 2 | 2 | 48% |
| L13 | S | 24 | 17 | 8 | 3 | 0 | 47% |
| L14 | Y | 24 | 21 | 10 | 2 | 2 | 48% |
| L15 | A | 24 | 14 | 10 | 0 | 1 | 71% |
| L16 | S | 24 | 20 | 10 | 3 | 1 | 50% |
| L17 | T | 24 | 20 | 10 | 1 | 3 | 50% |
| L18 | L | 24 | 16 | 11 | 2 | 2 | 69% |
| L19 | A | 24 | 17 | 9 | 2 | 1 | 53% |
| L20 | S | 24 | 20 | 11 | 3 | 0 | 55% |
| L21 | L | 24 | 21 | 12 | 2 | 1 | 57% |
| L22 | G | 24 | 22 | 14 | 3 | 1 | 64% |
| L23 | G | 24 | 19 | 9 | 4 | 0 | 47% |
| L24 | Y | 24 | 19 | 10 | 5 | 2 | 53% |
| L25 | A | 24 | 18 | 6 | 6 | 2 | 33% |
| L26 | S | 24 | 20 | 8 | 6 | 1 | 30% |
| L27 | T | 24 | 21 | 9 | 4 | 1 | 43% |
| L28 | I | 24 | 20 | 11 | 1 | 0 | 55% |
| L29 | D | 24 | 23 | 10 | 2 | 1 | 43% |
| L30 | M | 24 | 19 | 10 | 2 | 0 | 53% |
| L31 | W | 24 | 17 | 11 | 3 | 0 | 65% |
| L32 | A | 24 | 22 | 11 | 5 | 2 | 50% |
| H1 | G | 24 | 24 | 12 | 4 | 1 | 50% |
| H2 | F | 24 | 24 | 8 | 6 | 1 | 33% |
| H3 | S | 24 | 23 | 11 | 2 | 0 | 48% |
| H4 | L | 24 | 24 | 9 | 4 | 1 | 38% |
| H5 | S | 24 | 21 | 7 | 2 | 2 | 33% |
| H6 | T | 24 | 24 | 10 | 1 | 1 | 42% |
| H7 | H | 24 | 23 | 13 | 0 | 0 | 57% |
| H8 | D | 24 | 24 | 12 | 1 | 1 | 50% |
| H9 | I | 24 | 24 | 11 | 1 | 2 | 46% |
| H10 | S | 24 | 23 | 11 | 0 | 0 | 48% |
| H11 | V | 24 | 21 | 14 | 3 | 2 | 67% |
| H12 | I | 24 | 23 | 11 | 1 | 1 | 48% |
| H13 | A | 24 | 20 | 11 | 0 | 2 | 55% |
| H14 | R | 24 | 24 | 12 | 3 | 1 | 50% |
| H15 | R | 24 | 23 | 13 | 2 | 0 | 57% |
| H16 | G | 24 | 24 | 11 | 6 | 1 | 46% |
| H17 | S | 24 | 24 | 12 | 3 | 0 | 50% |
| H18 | T | 24 | 23 | 15 | 1 | 0 | 65% |
| H19 | Y | 24 | 23 | 12 | 2 | 2 | 52% |

TABLE 5-continued

| | | | | Mutants (unique clones) | WT | Bad sequence | mutant ratio (unique/ analysis) |
|---|---|---|---|---|---|---|---|
| Library | Mutation site | Clone for sequencing | Analysis | | | | |
| H20 | Y | 24 | 24 | 12 | 1 | 0 | 50% |
| H21 | A | 24 | 23 | 11 | 1 | 3 | 48% |
| H22 | S | 24 | 21 | 10 | 4 | 3 | 48% |
| H23 | W | 24 | 23 | 10 | 2 | 2 | 43% |
| H24 | A | 24 | 19 | 11 | 2 | 1 | 58% |
| H25 | K | 24 | 23 | 10 | 2 | 4 | 43% |
| H26 | G | 24 | 24 | 9 | 6 | 2 | 38% |
| H27 | E | 24 | 22 | 10 | 1 | 6 | 45% |
| H28 | E | 24 | 24 | 11 | 1 | 3 | 46% |
| H29 | F | 24 | 19 | 11 | 0 | 0 | 58% |
| H30 | D | 24 | 21 | 11 | 1 | 0 | 52% |
| H31 | F | 24 | 23 | 12 | 2 | 0 | 52% |

Notes:
Mutants: unique clones; mutant ratio = mutants/analysis 4.3 Identification of Optimized Binders from NNK Libraries From each NNK library, over 90 clones were randomly selected, grown and tested for Peptide 1593 binding activity by ELISA. 63 NNK libraries were screened to identify binders with high affinity by ELISA, and details are listed in FIG. 28 and Table 6. This data was used to select the most obvious points of improvement for gene synthesis for production of purified antibodies (Table 7).

TABLE 6

Hits selected from the 63 NNK libraries by ELISA.

| NO. | well ID | OD450 nm | sequence ID | mutation | WT | WT OD450 nm | ratio |
|---|---|---|---|---|---|---|---|
| 1 | L2-H01 | 1.025 | AHF05067 | G | S | 0.834 | 1.230 |
| 2 | L2-B03 | 1.008 | AHF05068 | T | S | 0.834 | 1.209 |
| 3 | L2-G04 | 1.146 | AHF05069 | M | S | 0.834 | 1.375 |
| 4 | L2-G06 | 1.037 | AHF05070 | S | S | 0.834 | 1.244 |
| 5 | L2-A07 | 1.111 | AHF05071 | G | S | 0.834 | 1.333 |
| 6 | L2-E07 | 1.093 | AHF05072 | M | S | 0.834 | 1.311 |
| 7 | L2-D08 | 0.994 | AHF05073 | S | S | 0.834 | 1.193 |
| 8 | L2-F08 | 1.075 | AHF05074 | T | S | 0.834 | 1.290 |
| 9 | L2-H08 | 1.054 | AHF05075 | S | S | 0.834 | 1.265 |
| 10 | L2-A12 | 0.995 | AHF05076 | S | S | 0.834 | 1.194 |
| 11 | L3-D02 | 0.97 | AHF05077 | H | S | 0.807 | 1.203 |
| 12 | L3-H02 | 0.972 | AHF05078 | A | S | 0.807 | 1.205 |
| 13 | L3-C04 | 0.963 | AHF05079 | R | S | 0.807 | 1.194 |
| 14 | L3-D05 | 0.954 | AHF05080 | L | S | 0.807 | 1.183 |
| 15 | L3-H05 | 0.956 | AHF05081 | T | S | 0.807 | 1.185 |
| 16 | L3-A07 | 0.95 | AHF05082 | H | S | 0.807 | 1.178 |
| 17 | L3-D07 | 0.982 | AHF05083 | K | S | 0.807 | 1.218 |
| 18 | L3-H07 | 1.028 | AHF05084 | S | S | 0.807 | 1.275 |
| 19 | L3-C08 | 0.995 | AHF05085 | R | S | 0.807 | 1.234 |
| 20 | L3-C09 | 1.037 | AHF05086 | R | S | 0.807 | 1.286 |
| 21 | L5-C02 | 1.159 | AHF05087 | K | S | 0.777 | 1.492 |
| 22 | L5-F02 | 1.158 | AHF05088 | M | S | 0.777 | 1.490 |
| 23 | L5-C04 | 1.098 | AHF05089 | Y | S | 0.777 | 1.413 |
| 24 | L5-F04 | 1.117 | AHF05090 | Y | S | 0.777 | 1.438 |
| 25 | L5-F05 | 1.14 | AHF05091 | M | S | 0.777 | 1.467 |
| 26 | L5-A06 | 1.111 | AHF05092 | T | S | 0.777 | 1.430 |
| 27 | L5-C08 | 1.112 | AHF05093 | F | S | 0.777 | 1.431 |
| 28 | L5-F08 | 1.092 | AHF05094 | V | S | 0.777 | 1.405 |
| 29 | L5-C09 | 1.076 | AHF05095 | stop codon | S | 0.777 | 1.385 |
| 30 | L5-G10 | 1.117 | AHF05096 | stop codon | S | 0.777 | 1.438 |
| 31 | L8-F07 | 1.161 | AHF05097 | stop codon | N | 0.763 | 1.523 |
| 32 | L8-B10 | 1.043 | AHF05098 | K | N | 0.763 | 1.368 |
| 33 | L8-C04 | 1.026 | AHF05099 | K | N | 0.763 | 1.346 |
| 34 | L8-C10 | 1.024 | AHF05100 | R | N | 0.763 | 1.343 |
| 35 | L8-B05 | 1.019 | AHF05101 | H | N | 0.763 | 1.336 |
| 36 | L8-F11 | 1.009 | AHF05102 | stop codon | N | 0.763 | 1.323 |
| 37 | L8-F04 | 1.006 | AHF05103 | R | N | 0.763 | 1.319 |
| 38 | L8-A06 | 0.974 | AHF05104 | R | N | 0.763 | 1.277 |
| 39 | L8-H06 | 0.958 | AHF05105 | R | N | 0.763 | 1.256 |

TABLE 6-continued

| | | | Hits selected from the 63 NNK libraries by ELISA. | | | | |
|---|---|---|---|---|---|---|---|
| NO. | well ID | OD450 nm | sequence ID | mutation | WT | WT OD450 nm | ratio |
| 40 | L8-C02 | 0.957 | AHF05106 | H | N | 0.763 | 1.255 |
| 41 | L18-F02 | 0.934 | AHF05107 | L | L | 0.746 | 1.252 |
| 42 | L18-E05 | 0.968 | AHF05108 | S | L | 0.746 | 1.298 |
| 43 | L18-F06 | 0.937 | AHF05109 | N | L | 0.746 | 1.256 |
| *44* | *L20-H04* | *0.977* | *AHF05110* | *T* | *S* | *0.477* | *2.048* |
| 45 | L20-H06 | 0.596 | AHF05111 | H | S | 0.477 | 1.249 |
| *46* | *H17-C4* | *1.282* | *AHF05120* | *W* | *S* | *0.623* | *2.058* |
| 47 | H25-E2 | 0.872 | AHF05121 | R | K | 0.622 | 1.402 |
| 48 | H25-B9 | 0.813 | AHF05122 | K | K | 0.622 | 1.307 |
| *49* | *H26-F4* | *1.091* | *AHF05123* | *K* | *G* | *0.837* | *1.303* |

The mutant sites *marked*.

TABLE 7

| | Antibody heavy and light chain combination. | | |
|---|---|---|---|
| Mutant Antibody | light chain mutant site | Heavy chain mutant site | |
| variant 1 | L-S57T | H-S55W | H-G64K |
| variant 2 | L-S57T | H-S55W | NA |
| variant 3 | NA | H-S55W | NA |

4.4 IgG Production of the Potential Affinity-Matured Antibody

According to the sequence analysis, two heavy chains and one light chain were designed. Three mutant IgGs and the wild-type IgG were expressed and purified. The SDS-PAGE data for these IgGs are shown in FIG. 29.

4.5 Affinity Measurement of Final Leads IgGs

The BIAcore setup parameters and the affinity data of Peptide 1593 to the final lead combination antibodies and wild-type antibody are summarized in Tables 8-9, and the BIAcore data curves are shown in FIG. 30.

TABLE 8

| Details, parameters of antibodies affinity validation. | |
|---|---|
| Immobilization | |
| Ligand | antibodies |
| Immobilization level (Ru) | ~6000 |
| Association & Dissociation | |
| Association contact time(s) | 180 |
| Dissociation contact time(s) | 600 |
| Flow rate (μl/min) | 30 |
| Sample concentrations (nM) | 1.5625, 3.125, 6.25, 12.5, 25, 50, 100 |

TABLE 9

| | | | | | | |
|---|---|---|---|---|---|---|
| | | Affinity measurement of antibodies to peptide 1593 | | | | |
| Ligand | Analyte | Chi$^2$ (RU$^2$) | ka (1/Ms) | kd (1/s) | KD (M) | Rmax (RU) |
| S55W&G46K-VH + S57T-VL | Peptide 2 (peptide 1593) | 1.49E−01 | 1.04E+05 | 2.70E−04 | 2.60E−09 | 61.9 |
| S55W-VH + S57T-VL | Peptide 2 (peptide 1593) | 2.57E−01 | 1.20E+05 | 3.93E−04 | 3.27E−09 | 42.6 |
| S55W-VH + VL | Peptide 2 (peptide 1593) | 1.07E−01 | 1.28E+05 | 2.60E−04 | 2.03E−09 | 41.2 |
| VH + VL | Peptide 2 (peptide 1593) | 5.32E−01 | 2.25E+05 | 1.70E−04 | 7.55E−10 | 69.3 |

FIG. 30 shows the affinity measurement of antibodies to Peptide 1593.

4.6 Combinatorial Phage Library QC

TABLE 10

| | | | General information of Combinatory mutagenesis library. | | | | | |
|---|---|---|---|---|---|---|---|
| Design Library Size | Library Size (titer) | Insert clones | total clones | Insert rate | Analysis sequences | total sequences | In-frame rate |
| 4.48E+06 | 7.64E+08 | 95 | 95 | 100.00% | 39 | 48 | 81.25% |

FIG. 31 shows colony PCR results of Combinatory mutagenesis library.

4.7 Panning Streamline and Results Summary

TABLE 11

| | | Round | Input (pfu) | Output (pfu) | Amplification (pfu/ml) |
|---|---|---|---|---|---|
| | Panning streamline and results summary | | | | |
| | Antigen | | | | |
| 1 ug/ml | Biotin-peptide 1593 | R1 | 2.00E+12 | 9.50E+06 | 3.00E+13 |
| 1 ug/ml | Biotin-peptide 1593 | R2 | 2.00E+12 | 8.70E+06 | 6.60E+12 |
| 1 ug/ml | Biotin-peptide 1593 | R3 | 2.00E+12 | 8.00E+06 | 9.70E+12 |
| 1 ug/ml | Biotin-peptide 1593 | R4 | 2.00E+12 | 9.00E+06 | 2.73E+13 |
| 0.1 ug/ml | Biotin-pep. 1593 | R5 | 2.00E+11 | 3.09E+07 | 2.77E+13 |
| 0.01 ug/ml | Biotin-pep. 1593 | R6 | 2.00E+11 | 6.30E+07 | NA |
| 0.001 ug/ml | Biotin-pep. 1593 | R6 | 2.00E+11 | 2.30E+07 | NA |
| 0.001 ug/ml | Biotin-pep. 1593, 001 ug/ml pep. 1593 competition | R6 | 2.00E+11 | 6.00E+06 | NA |

4.8 Polyclonal Phage ELISA Results

TABLE 12

Polyclonal phage ELISA validation of R0-R2

| | 1 | 2 | 3 | 4 | 5 | 6 | 7 | 8 | 9 | 10 | 11 | 12 | Phage library |
|---|---|---|---|---|---|---|---|---|---|---|---|---|---|
| | | | | | | Diluted | | | | | | | |
| | 1E+12 | 1E+11 | 1E+10 | 1E+09 | 1E+08 | 1.00E+07 | 1.00E+06 | 1.00E+05 | 1.00E+4 | 1.00E+03 | blank | blank | |
| A | 0.359 | 0.195 | 0.088 | 0.071 | 0.07 | 0.076 | 0.074 | 0.065 | 0.063 | 0.083 | 0.06 | 0.063 | R0 |
| B | 0.298 | 0.239 | 0.11 | 0.064 | 0.063 | 0.065 | 0.073 | 0.061 | 0.062 | 0.006 | 0.056 | 0.067 | R0 |

| | 1 | 2 | 3 | 4 | 5 | 6 | 7 | 8 | 9 | 10 | 11 | 12 | Phage library |
|---|---|---|---|---|---|---|---|---|---|---|---|---|---|
| | | | | | | Diluted | | | | | | | |
| | 3E+12 | 3E+11 | 3E+10 | 3E+09 | 3E+08 | 3.00E+07 | 3.00E+06 | 3.00E+05 | 3.00E+4 | 3.00E+03 | blank | blank | |
| A | 0.799 | 0.213 | 0.122 | 0.078 | 0.065 | 0.063 | 0.065 | 0.06 | 0.06 | 0.068 | 0.075 | 0.083 | R1 |
| B | 0.543 | 0.255 | 0.083 | 0.066 | 0.069 | 0.066 | 0.077 | 0.074 | 0.074 | 0.068 | 0.069 | 0.099 | R1 |

| | 1 | 2 | 3 | 4 | 5 | 6 | 7 | 8 | 9 | 10 | 11 | 12 | Phage library |
|---|---|---|---|---|---|---|---|---|---|---|---|---|---|
| | | | | | | Diluted | | | | | | | |
| | 1.32E+12 | 2.64E+11 | 5.28E+10 | 1.06E+10 | 2.11E+09 | 4.22E+08 | 8.45E+07 | 1.69E+07 | 3.38E+6 | 6.76E+05 | blank | blank | |
| A | 0.582 | 0.190 | 0.118 | 0.073 | 0.070 | 0.064 | 0.067 | 0.068 | 0.079 | 0.074 | 0.065 | 0.076 | R2 |
| B | 0.483 | 0.198 | 0.096 | 0.080 | 0.083 | 0.066 | 0.066 | 0.078 | 0.111 | 0.090 | 0.070 | 0.080 | R2 |

4.9 Monoclonal Phage ELISA Results

After 1-4 rounds panning, more than 90 colonies were picked from each pool and validated by monoclonal phage ELISA. Monoclonal phage ELISA details are shown in FIG. 32. ELISA plates were coated with lug/ml Biotin-peptide 1593 (100 μl/well) and incubated at 4° C. for overnight. Negative control: non-related phage supernatant. Blank: 2YT medium. FIG. 32 shows monoclonal phage ELISA validation of R1-R4

4.10 Monoclonal Soluble Expression ELISA Results

After 3-6 rounds of panning, more than 90 colonies were picked of each pool and validated by monoclonal soluble expression ELISA. Monoclonal soluble expression ELISA details are shown in FIG. 33. ELISA plates were coated with 0.015 μg/ml peptide 1593 (100 μl/well) and incubated at 4° C. for overnight. Negative control: non-related expression supernatant. Blank: 2YT medium. FIG. 33 shows monoclonal soluble expression ELISA validation of R3-R6.

Sequences of Antibodies

The sequences are shown in the format of 'Leader Sequence-VH/VL-rIgGCH/rIgKCL-Stop codon**'.

Amino Acid Sequence

Heavy Chain:

```
>U4568EK260-S55W&G64K-VH
                                        (SEQ ID NO: 200)
MGWNYIIFFLAATATGVHSQSLEESGGRLVTPGGSLTLTCTVSGFSLSTH

DISWVRQAPGKGLEWIGVIARRGWTYYASWAKKRFTISKTSTTVDLKITS

PTIEDTATYFCAREEFDFWGQGTLVTVSSGQPKAPSVFPLAPCCGDTPSS

TVTLGCLVKGYLPEPVTVTWNSGTLTNGVRTFPSVRQSSGLYSLSSVVSV

TSSSQPVTCNVAHPATNTKVDKTVAPSTCSKPTCPPPELLGGPSVFIFPP

KPKDTLMISRTPEVTCVVVDVSQDDPEVQFTWYINNEQVRTARPPLREQQ

FNSTIRVVSTLPIAHQDWLRGKEFKCKVHNKALPAPIEKTISKARGQPLE

PKVYTMGPPREELSSRSVSLTCMINGFYPSDISVEWEKNGKAEDNYKTTP

AVLDSDGSYFLYSKLSVPTSEWQRGDVFTCSVMHEALHNHYTQKSISRSP

GK**
```

-continued

>U4568EK260-S55W-VH (SEQ ID NO: 201)

MGWNYIIFFLAATATGVHS*QSLEESGGRLVTPGGSLTLTCTVSGESLSTH*

*DISWVRQAPGKGLEWIGVIARRGWTYYASWAKGRFTISKTSTTVDLKITS*

*PTIEDTATYFCAREEFDFWGQGTLVTVSS*GQPKAPSVFPLAPCCGDTPSS

TVTLGCLVKGYLPEPVTVTWNSGTLTNGVRTFPSVRQSSGLYSLSSVVSV

TSSSQPVTCNVAHPATNTKVDKTVAPSTCSKPTCPPPELLGGPSVFIFPP

KPKDTLMISRTPEVTCVVVDVSQDDPEVQFTWYINNEQVRTARPPLREQQ

FNSTIRVVSTLPIAHQDWLRGKEFKCKVHNKALPAPIEKTISKARGQPLE

PKVYTMGPPREELSSRSVSLTCMINGFYPSDISVEWEKNGKAEDNYKTTP

AVLDSDGSYFLYSKLSVPTSEWQRGDVFTCSVMHEALHNHYTQKSISRSP

GK**

Light Chain:

>U4568EK260-S57T-VL (SEQ ID NO: 202)

MRAPAQIFGFLLLLFPGIRC*AVLTQTASPVSAAVGGTVTISCQSSQSVYN*

*NKELSWFQQKPGQPPKLLISYASTLATGVPSRFKGSGSGTQFTLTISDLE*

*CDDAATYYCLGGYASTIDMWAFGGGTEVVVK*GDPVAPTVLIFPPAADQVA

TGTVTIVCVANKYFPDVTVTWEVDGTTQTTGIENSKTPQNSADCTYNLSS

TLTLTSTQYNSHKEYTCKVTQGTTSVVQSFNRGDC*

DNA Sequence:
Heavy Chain:

>U4568EK260-S55W&G64K-VH (SEQ ID NO: 203)

ATGGGATGGAACTATATCATTTTCTTTTTGGCAGCAACAGCTACAGGTGT

CCACTCC*CAGAGCCTCGAGGAGAGCGGCGGCAGACTGGTGACCCCTGGCG*

*GATCTCTGACCCTGACATGTACCGTGTCCGGCTTCAGCCTGAGCACCCAC*

*GATATCAGCTGGGTCAGACAGGCCCCTGGCAAGGGCCTGGAATGGATCGG*

*CGTGATCGCCCGGAGAGGATGGACATACTACGCCTCTTGGGCTAAGAAAA*

*GATTTACAATTAGCAAGACCTCCACTACCGTGGACCTGAAGATCACCAGC*

*CCCACAATCGAGGACACCGCCACCTACTTCTGCGCCCGGGAAGAGTTCGA*

*CTTCTGGGGACAGGGCACCCTGGTGACAGTGTCTAGC*GGCCAGCCCAAGG

CACCTAGCGTGTTCCCACTGGCACCATGCTGTGGGGACACCCCATCTAGT

ACTGTCACCCTGGGCTGCCTGGTGAAAGGGTATCTGCCCGAGCCTGTCAC

AGTGACTTGGAACAGCGGAACCCTGACAAATGGCGTCCGAACATTTCCTT

CCGTGCGGCAGTCAAGCGGCCTGTACTCTCTGTCCTCTGTGGTCAGTGTG

ACAAGTTCAAGCCAGCCAGTCACTTGTAACGTGGCACATCCCGCCACTAA

TACCAAGGTCGATAAAACTGTGGCCCCCTCAACCTGCAGCAAGCCTACAT

GTCCACCTCCAGAGCTGCTGGGAGGACCTTCCGTGTTCATCTTTCCCCCT

AAGCCAAAAGACACCCTGATGATTTCTCGCACCCCCGAAGTCACATGCGT

GGTCGTGGATGTGAGTCAGGACGATCCTGAGGTCCAGTTCACCTGGTATA

TCAACAATGAACAGGTGAGGACAGCACGACCACCACTGCGAGAGCAGCAG

-continued

TTTAACTCAACTATCCGAGTCGTGAGCACCCTGCCAATTGCTCACCAGGA

CTGGCTGAGGGGCAAGGAGTTCAAGTGCAAAGTGCATAACAAGGCCCTGC

CAGCACCCATCGAGAAGACAATTTCTAAAGCCCGCGGACAGCCTCTGGAA

CCAAAGGTGTACACTATGGGCCCTCCAAGAGAGGAACTGTCCTCTAGGAG

CGTCTCCCTGACCTGTATGATCAACGGGTTTTATCCCTCCGACATTTCTG

TGGAGTGGGAAAAGAACGGAAAAGCCGAGGATAATTACAAGACAACTCCA

GCTGTGCTGGACAGTGATGGATCATATTTCCTGTACAGCAAACTGTCCGT

GCCCACTAGTGAATGGCAGAGAGGCGATGTCTTTACCTGTTCAGTGATGC

ACGAGGCACTGCACAATCACTACACTCAGAAGTCCATCTCAAGAAGCCCA

GGGAAA*TGATAA*

>U4568EK260-S55W-VH (SEQ ID NO: 204)

ATGGGATGGAACTATATCATTTTCTTTTTGGCAGCAACAGCTACAGGTGT

CCACTCC*CAGAGCCTGGAAGAGAGCGGCGGAAGACTCGTGACCCCTGGAG*

*GATCTCTGACCCTGACATGTACCGTGTCCGGCTTTAGCCTGAGCACACAC*

*GATATCAGCTGGGTGCGGCAGGCCCCTGGCAAGGGCCTGGAATGGATCGG*

*CGTGATCGCCAGACGGGGCTGGACCTACTACGCCAGCTGGGCTAAAGGCA*

*GATTCACCATTTCTAAGACCTCCACCACAGTGGACCTGAAGATCACCAGC*

*CCCACAATCGAGGACACCGCCACATACTTCTGCGCCAGAGAGGAGTTCGA*

*CTTCTGGGGCCAGGGCACCCTGGTCACAGTGTCTAGC*GGCCAGCCCAAGG

CACCTAGCGTGTTCCCACTGGCACCATGCTGTGGGGACACCCCATCTAGT

ACTGTCACCCTGGGCTGCCTGGTGAAAGGGTATCTGCCCGAGCCTGTCAC

AGTGACTTGGAACAGCGGAACCCTGACAAATGGCGTCCGAACATTTCCTT

CCGTGCGGCAGTCAAGCGGCCTGTACTCTCTGTCCTCTGTGGTCAGTGTG

ACAAGTTCAAGCCAGCCAGTCACTTGTAACGTGGCACATCCCGCCACTAA

TACCAAGGTCGATAAAACTGTGGCCCCCTCAACCTGCAGCAAGCCTACAT

GTCCACCTCCAGAGCTGCTGGGAGGACCTTCCGTGTTCATCTTTCCCCCT

AAGCCAAAAGACACCCTGATGATTTCTCGCACCCCCGAAGTCACATGCGT

GGTCGTGGATGTGAGTCAGGACGATCCTGAGGTCCAGTTCACCTGGTATA

TCAACAATGAACAGGTGAGGACAGCACGACCACCACTGCGAGAGCAGCAG

TTTAACTCAACTATCCGAGTCGTGAGCACCCTGCCAATTGCTCACCAGGA

CTGGCTGAGGGGCAAGGAGTTCAAGTGCAAAGTGCATAACAAGGCCCTGC

CAGCACCCATCGAGAAGACAATTTCTAAAGCCCGCGGACAGCCTCTGGAA

CCAAAGGTGTACACTATGGGCCCTCCAAGAGAGGAACTGTCCTCTAGGAG

CGTCTCCCTGACCTGTATGATCAACGGGTTTTATCCCTCCGACATTTCTG

TGGAGTGGGAAAAGAACGGAAAAGCCGAGGATAATTACAAGACAACTCCA

-continued

GCTGTGCTGGACAGTGATGGATCATATTTCCTGTACAGCAAACTGTCCGT

GCCCACTAGTGAATGGCAGAGAGGCGATGTCTTTACCTGTTCAGTGATGC

ACGAGGCACTGCACAATCACTACACTCAGAAGTCCATCTCAAGAAGCCCA

GGGAAA*TGATAA*

Light Chain:

>U4568EK260-S57T-VL
(SEQ ID NO: 205)

ATGAGGGCTCCTGCACAGATTTTTGGCTTCTTGTTGCTCTTGTTTCCAGG

TATCAGATGT*GCTGTGCTCACCCAGACCGCCAGCCCTGTGTCCGCCGCTG*

*TGGGCGGCACAGTGACCATCAGCTGTCAGTCCAGCCAGAGCGTGTACAAC*

*AACAAGGAGCTGAGCTGGTTCCAGCAGAAACCTGGCCAGCCTCCAAAGCT*

*GCTGATCAGCTACGCCTCTACCCTGGCCACCGGCGTGCCCAGCAGATTCA*

*AGGGCTCTGGCAGCGGCACCCAATTTACCCTGACAATCTCTGATCTGGAA*

*TGCGACGACGCCGCCACATACTACTGCCTGGGCGGATATGCCAGCACAAT*

*CGACATGTGGGCCTTCGGCGGAGGAACCGAGGTGGTGGTCAA*GGGGGATC

CTGTGGCACCAACTGTCCTGATCTTTCCACCCGCTGCAGACCAGGTGGCA

ACTGGCACCGTCACAATTGTCTGCGTGGCCAATAAGTACTTTCCAGACGT

GACTGTGACCTGGGAGGTGGATGGCACTACCCAGACAACTGGGATTGAAA

ACAGCAAAACTCCCCAGAACTCCGCTGATTGTACCTATAACCTGTCTAGT

ACACTGACTCTGACCAGTACACAGTACAATTCACACAAGGAATATACCTG

TAAGGTGACCCAGGGCACAACAAGCGTCGTCCAGTCTTTCAACAGGGGGG

ATTGC*TAATAA*

Example 4

Amino Acid Sequence of Variable Region:
Heavy Chain:

>U4568EK260-AHF05121-VH
(SEQ ID NO: 206)

QSLEESGGRLVTPGGSLTLTCTVSGFSLSTHDISWVRQAPGKGLEWIGVI

ARRGSTYYASWARGRFTISKTSTTVDLKITSPTIEDTATYFCAREEFDFW

GQGTLVTVSS

Light Chain:

>U4568EK260-AHF05071-VL
(SEQ ID NO: 207}

AVLTQTASPVSAAVGGTVTISCQGSQSVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05072-VL
(SEQ ID NO: 208)

AVLTQTASPVSAAVGGTVTISCQMSQSVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05074-VL
(SEQ ID NO:209)

AVLTQTASPVSAAVGGTVTISCQTSQSVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05078-VL
(SEQ ID NO: 201)

AVLTQTASPVSAAVGGTVTISCQSAQSVYNNKELSWFQQKPGQPPKLLIS

YASTLASGVPSRFKGSGSGTQFTLTISDLECDDAATYYCLGGYASTIDMW

AFGGGTEVVVK

TABLE 13

| | | | | | | | |
|---|---|---|---|---|---|---|---|
| | | | The ELISA results of 22 hits | | | | |
| NO. | well ID | OD450 nm | sequence ID | mutation | WT | WT OD450 nm | ratio |
| 1 | L2-A07 | 1.111 | AHF05071 | G | S | 0.834 | 1.33 |
| 2 | L2-E07 | 1.093 | AHF05072 | M | S | 0.834 | 1.31 |
| 3 | L2-F08 | 1.075 | AHF05074 | T | S | 0.834 | 1.29 |
| 4 | L3-H02 | 0.972 | AHF05078 | A | S | 0.807 | 1.21 |
| 5 | L3-C04 | 0.963 | AHF05079 | R | S | 0.807 | 1.19 |
| 6 | L3-D05 | 0.954 | AHF05080 | L | S | 0.807 | 1.18 |
| 7 | L3-H05 | 0.956 | AHF05081 | T | S | 0.807 | 1.19 |
| 8 | L3-A07 | 0.950 | AHF05082 | H | S | 0.807 | 1.18 |
| 9 | L3-D07 | 0.982 | AHF05083 | K | S | 0.807 | 1.22 |
| 10 | L5-C02 | 1.159 | AHF05087 | K | S | 0.777 | 1.49 |
| 11 | L5-F04 | 1.117 | AHF05090 | Y | S | 0.777 | 1.44 |
| 12 | L5-F05 | 1.140 | AHF05091 | M | S | 0.777 | 1.47 |
| 13 | L5-A06 | 1.111 | AHF05092 | T | S | 0.777 | 1.43 |
| 14 | L5-C08 | 1.112 | AHF05093 | F | S | 0.777 | 1.43 |
| 15 | L5-F08 | 1.092 | AHF05094 | V | S | 0.777 | 1.41 |
| 16 | L8-B10 | 1.043 | AHF05098 | K | N | 0.763 | 1.37 |
| 17 | L8-H06 | 0.958 | AHF05105 | R | N | 0.763 | 1.26 |
| 18 | L8-C02 | 0.957 | AHF05106 | H | N | 0.763 | 1.26 |
| 19 | L18-E05 | 0.968 | AHF05108 | S | L | 0.746 | 1.30 |
| 20 | L18-F06 | 0.937 | AHF05109 | N | L | 0.746 | 1.26 |
| 21 | L20-H06 | 0.596 | AHF05111 | H | S | 0.477 | 1.25 |
| 22 | H25-E2 | 0.872 | AHF05121 | R | K | 0.622 | 1.40 |

See also, for example, FIG. 34.

-continued

>U4568EK260-AHF05079-VL (SEQ ID NO: 211)
AVLTQTASPVSAAVGGTVTISCQSRQSVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05080-VL (SEQ ID NO: 212)
AVLTQTASPVSAAVGGTVTISCQSLQSVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05081-VL (SEQ ID NO: 213)
AVLTQTASPVSAAVGGTVTISCQSTQSVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05082-VL (SEQ ID NO: 214)
AVLTQTASPVSAAVGGTVTISCQSHQSVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05083-VL (SEQ ID NO: 215)
AVLTQTASPVSAAVGGTVTISCQSKQSVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05087-VL (SEQ ID NO: 216)
AVLTQTASPVSAAVGGTVTISCQSSQKVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05090-VL (SEQ ID NO: 217)
AVLTQTASPVSAAVGGTVTISCQSSQYVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05091-VL (SEQ ID NO: 218)
AVLTQTASPVSAAVGGTVTISCQSSQMVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05092-VL (SEQ ID NO: 219)
AVLTQTASPVSAAVGGTVTISCQSSQTVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05093-VL (SEQ ID NO: 220)
AVLTQTASPVSAAVGGTVTISCQSSQFVYNNKELSWFQQKPGQPPKLLIS

YASTLASGVPSRFKGSGSGTQFTLTISDLECDDAATYYCLGGYASTIDMW

AFGGGTEVVVK

-continued

>U4568EK260-AHF05094-VL (SEQ ID NO: 221)
AVLTQTASPVSAAVGGTVTISCQSSQVVYNNKELSWFQQKPGQPPKLLIS

YASTLASGVPSRFKGSGSGTQFTLTISDLECDDAATYYCLGGYASTIDMW

AFGGGTEVVVK

>U4568EK260-AHF05098-VL (SEQ ID NO: 222)
AVLTQTASPVSAAVGGTVTISCQSSQSVYKNKELSWFQQKPGQPPKLLIS

YASTLASGVPSRFKGSGSGTQFTLTISDLECDDAATYYCLGGYASTIDMW

AFGGGTEVVVK

>U4568EK260-AHF05105-VL (SEQ ID NO: 223)
AVLTQTASPVSAAVGGTVTISCQSSQSVYRNKELSWFQQKPGQPPKLLIS

YASTLASGVPSRFKGSGSGTQFTLTISDLECDDAATYYCLGGYASTIDMW

AFGGGTEVVVK

>U4568EK260-AHF05106-VL (SEQ ID NO: 224)
AVLTQTASPVSAAVGGTVTISCQSSQSVYHNKELSWFQQKPGQPPKLLIS

YASTLASGVPSRFKGSGSGTQFTLTISDLECDDAATYYCLGGYASTIDMW

AFGGGTEVVVK

>U4568EK260-AHF05108-VL (SEQ ID NO: 225)
AVLTQTASPVSAAVGGTVTISCQSSQSVYNNKELSWFQQKPGQPPKLLIS

YASTSASGVPSRFKGSGSGTQFTLTISDLECDDAATYYCLGGYASTIDMW

AFGGGTEVVVK

>U4568EK260-AHF05109-VL (SEQ ID NO: 226)
AVLTQTASPVSAAVGGTVTISCQSSQSVYNNKELSWFQQKPGQPPKLLIS

YASTNASGVPSRFKGSGSGTQFTLTISDLECDDAATYYCLGGYASTIDMW

AFGGGTEVVVK

>U4568EK260-AHF05111-VL (SEQ ID NO: 227)
AVLTQTASPVSAAVGGTVTISCQSSQSVYNNKELSWFQQKPGQPPKLLIS

YASTLAHGVPSRFKGSGSGTQFTLTISDLECDDAATYYCLGGYASTIDMW

AFGGGTEVVVK

DNA Sequence of Variable Region:
Heavy Chain:

>U4568EK260-AHF05121-VH (SEQ ID NO: 228)
CAGAGCCTGGAGGAAAGCGGTGGTCGTCTGGTGACCCCGGGTGGTAGCCT

GACCCTGACCTGCACCGTTAGCGGTTTCAGCCTGAGCACCCACGACATCA

GCTGGGTGCGTCAAGCGCCGGGCAAGGGTCTGGAGTGGATCGGTGTTATT

GCGCGTCGTGGCAGCACCTACTATGCGAGCTGGGCGCGGGGCCGTTTCAC

CATTAGCAAAACCAGCACCACCGTGGACCTGAAAATCACCAGCCCGACCA

TTGAAGATACCGCGACCTACTTTTGCGCGCGTGAGGAATTCGATTTTTGG

GGTCAGGGCACCCTGGTGACCGTTAGCAGC

Light Chain:

>U4568EK260-AHF05071-VL (SEQ ID NO: 229)

GCGGTGCTGACCCAGACCGCGAGCCCGGTTAGCGCGGCGGTGGGTGGCAC

CGTTACCATCAGCTGCCAGGGTAGCCAAAGCGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05072-VL (SEQ ID NO: 230)

GCGGTGCTGACCCAGACCGCGAGCCCGGTTAGCGCGGCGGTGGGGGCACC

GTTACCATCAGCTGCCAGATGAGCCAAAGCGTTTACAACAACAAGGAGCT

GAGCTGGTTCCAGCAAAAGCCGGGTCAGCCGCCGAAACTGCTGATTAGCT

ATGCGAGCACCCTGGCGAGCGGTGTGCCGAGCCGTTTCAAAGGCAGCGGT

AGCGGCACCCAATTTACCCTGACCATCAGCGACCTGGAGTGCGACGATGC

GGCGACCTACTATTGCCTGGGTGGCTACGCGAGCACCATTGATATGTGGG

CGTTTGGTGGCGGTACCGAAGTGGTTGTGAAG

>U4568EK260-AHF05074-VL (SEQ ID NO: 231)

GCGGTGCTGACCCAGACCGCGAGCCCGGTTAGCGCGGCGGTGGGTGGCAC

CGTTACCATCAGCTGCCAGACTAGCCAAAGCGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05078-VL (SEQ ID NO: 232)

GCGGTGCTGACCCAGACCGCGAGCCCGGTTAGCGCGGCGGTGGGTGGCAC

CGTTACCATCAGCTGCCAGAGCGCGCAAAGCGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05079-VL (SEQ ID NO: 233)

GCGGTGCTGACCCAGACCGCGAGCCCGGTTAGCGCGGCGGTGGGTGGCAC

CGTTACCATCAGCTGCCAGAGCAGGCAAAGCGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05080-VL (SEQ ID NO: 234)

GCGGTGCTGACCCAGACCGCGAGCCCGGTTAGCGCGGCGGTGGGGGCACC

GTTACCATCAGCTGCCAGAGCCTGCAAAGCGTTTACAACAACAAGGAGCT

GAGCTGGTTCCAGCAAAAGCCGGGTCAGCCGCCGAAACTGCTGATTAGCT

ATGCGAGCACCCTGGCGAGCGGTGTGCCGAGCCGTTTCAAAGGCAGCGGT

AGCGGCACCCAATTTACCCTGACCATCAGCGACCTGGAGTGCGACGATGC

GGCGACCTACTATTGCCTGGGTGGCTACGCGAGCACCATTGATATGTGGG

CGTTTGGTGGCGGTACCGAAGTGGTTGTGAAG

>U4568EK260-AHF05081-VL (SEQ ID NO[]: 235)

GCGGTGCTGACCCAGACCGCGAGCCCGGTTAGCGCGGCGGTGGGTGGCAC

CGTTACCATCAGCTGCCAGAGCACTCAAAGCGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05082-VL (SEQ ID NO: 236)

GCGGTGCTGACCCAGACCGCGAGCCCGGTTAGCGCGGCGGTGGGTGGCAC

CGTTACCATCAGCTGCCAGAGCCATCAAAGCGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05083-VL (SEQ ID NO: 237)

GCGGTGCTGACCCAGACCGCGAGCCCGGTTAGCGCGGCGGTGGGTGGCAC

CGTTACCATCAGCTGCCAGAGCAAGCAAAGCGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05087-VL (SEQ ID NO: 238)

GCGGTGCTGACCCAGACCGCGAGCCCGGTTAGCGCGGCGGTGGGTGGCAC

CGTTACCATCAGCTGCCAGAGCAGCCAAAAGGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

-continued

CGGCGACCTACTATTGCCTGGGTGGCTACGCGAGCACCATTGATATGTGG

GCGTTTGGTGGCGGTACCGAAGTGGTTGTGAAG

>U4568EK260-AHF05090-VL
(SEQ ID NO: 239)
GCGGTGCTGACCCAGACCGCGAGCCCGGTTAGCGCGGCGGTGGGTGGCAC

CGTTACCATCAGCTGCCAGAGCAGCCAATATGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05091-VL
(SEQ ID NO: 240)
GCGGTGCTGACCCAGACCGCGAGCCCGGTTAGCGCGGCGGTGGGTGGCAC

CGTTACCATCAGCTGCCAGAGCAGCCAAATGGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05092-VL
(SEQ ID NO: 241)
GCGGTGCTGACCCAGACCGCGAGCCCGGTTAGCGCGGCGGTGGGTGGCAC

CGTTACCATCAGCTGCCAGAGCAGCCAAACGGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05093-VL
(SEQ ID NO: 242)
GCGGTGCTGACCCAGACCGCGAGCCCGGTTAGCGCGGCGGTGGGTGGCAC

CGTTACCATCAGCTGCCAGAGCAGCCAATTTGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05094-VL
(SEQ ID NO: 243)
GCGGTGCTGACCCAGACCGCGAGCCCGGTTAGCGCGGCGGTGGGTGGCAC

CGTTACCATCAGCTGCCAGAGCAGCCAAGTGGTTTACAACAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

-continued

CGGCGACCTACTATTGCCTGGGTGGCTACGCGAGCACCATTGATATGTGG

GCGTTTGGTGGCGGTACCGAAGTGGTTGTGAAG

>U4568EK260-AHF05098-VL
(SEQ ID NO: 244)
GCGGTGCTGACCCAGACCGCGAGCCCGGTTAGCGCGGCGGTGGGTGGCAC

CGTTACCATCAGCTGCCAGAGCAGCCAAAGCGTTTACAAGAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05105-VL
(SEQ ID NO: 245)
GCGGTGCTGACCCAGACCGCGAGCCCGGTTAGCGCGGCGGTGGGTG

GCACCGTTACCATCAGCTGCCAGAGCAGCCAAAGCGTTTACCGGAACAAG

GAGCTGAGCTGGTTCCAGCAAAAGCCGGGTCAGCCGCCGAAACTGCTGAT

TAGCTATGCGAGCACCCTGGCGAGCGGTGTGCCGAGCCGTTTCAAAGGCA

GCGGTAGCGGCACCCAATTTACCCTGACCATCAGCGACCTGGAGTGCGAC

GATGCGGCGACCTACTATTGCCTGGGTGGCTACGCGAGCACCATTGATAT

GTGGGCGTTTGGTGGCGGTACCGAAGTGGTTGTGAAG

>U4568EK260-AHF05106-VL
(SEQ ID NO: 246)
GCGGTGCTGACCCAGACCGCGAGCCCGGTTAGCGCGGCGGTGGGTGGCAC

CGTTACCATCAGCTGCCAGAGCAGCCAAAGCGTTTACCATAACAAGGAGC

TGAGCTGGTTCCAGCAAAAGCCGGGTCAGCCGCCGAAACTGCTGATTAGC

TATGCGAGCACCCTGGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05108-VL
(SEQ ID NO: 247)
GCGGTGCTGACCCAGACCGCGAGCCCGGTTAGCGCGGCGGTGGGTGGCAC

CGTTACCATCAGCTGCCAGAGCAGCCAAAGCGTTTACAACAACAAGGAGC

TGAGCTGGTTCCAGCAAAAGCCGGGTCAGCCGCCGAAACTGCTGATTAGC

TATGCGAGCACCAGTGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05109-VL
(SEQ ID NO: 248)
GCGGTGCTGACCCAGACCGCGAGCCCGGTTAGCGCGGCGGTGGGTGGCAC

CGTTACCATCAGCTGCCAGAGCAGCCAAAGCGTTTACAACAACAAGGAGC

TGAGCTGGTTCCAGCAAAAGCCGGGTCAGCCGCCGAAACTGCTGATTAGC

-continued

TATGCGAGCACCAATGCGAGCGGTGTGCCGAGCCGTTTCAAAGGCAGCGG

TAGCGGCACCCAATTTACCCTGACCATCAGCGACCTGGAGTGCGACGATG

CGGCGACCTACTATTGCCTGGGTGGCTACGCGAGCACCATTGATATGTGG

GCGTTTGGTGGCGGTACCGAAGTGGTTGTGAAG

>U4568EK260-AHF05111-VL (SEQ ID NO: 249)
GCGGTGCTGACCCAGACCGCGAGCCCGGTTAGCGCGGCGGTGGGTGGCAC

CGTTACCATCAGCTGCCAGAGCAGCCAAAGCGTTTACAACAACAAGGAGC

TGAGCTGGTTCCAGCAAAAGCCGGGTCAGCCGCCGAAACTGCTGATTAGC

TATGCGAGCACCCTGGCGCATGGTGTGCCGAGCCGTTTCAAAGGCAGCGG

TAGCGGCACCCAATTTACCCTGACCATCAGCGACCTGGAGTGCGACGATG

-continued

CGGCGACCTACTATTGCCTGGGTGGCTACGCGAGCACCATTGATATGTGG

GCGTTTGGTGGCGGTACCGAAGTGGTTGTGAAG

Example 5

Antigen name: Peptide 2 (peptide 1593)
Antigen sequence: TDAATLAQEAGNFERC (SEQ ID NO: 198)
Immunogen: Peptide-KLH conjugates
Host strain: New Zealand Rabbits
QC Results:
Indirect ELISA:
Coating Antigen: TDAATLAQEAGNFERC (SEQ ID NO: 198) (U5912EJ300-1)
Coating Concentration: 1 µg/ml, 100 µl/well
Coating Buffer: Phosphate Buffered Saline, pH 7.4
Secondary Antibody: Anti-Rabbit IgG Fc Monoclonal Secondary Antibody (Min X Hu, Ms, Rt, Sh, Bv, Gt, Camel) (HRP conjugate) (GenScript, Cat. No. A01856)

TABLE 14

ELISA results of supernatant:

| Cell lines | Supernatant Dilution | | | | | | | Negative Control | Titer | Concentration (µg/ml) |
|---|---|---|---|---|---|---|---|---|---|---|
| | Undiluted | 0.049 | 0.063 | 1:90 | 1:270 | 1:810 | 1:2,430 | | | |
| 60F10-1 | 3.102 | 2.160 | 0.797 | 0.329 | 0.158 | 0.105 | 0.074 | 0.060 | 1:270 | 27.542 |
| 67G8-1 | 2.850 | 1.291 | 0.579 | 0.201 | 0.101 | 0.083 | 0.071 | 0.060 | 1:90 | 20.154 |
| 67G8-2 | 3.218 | 3.298 | 3.386 | 3.101 | 2.333 | 1.315 | 0.616 | 0.060 | >1:2,430 | 12.654 |
| 91B4-1 | 3.117 | 3.284 | 3.334 | 3.045 | 2.275 | 1.298 | 0.618 | 0.060 | >1:2,430 | 5.460 |
| 91E6-1 | 2.615 | 1.204 | 0.453 | 0.192 | 0.130 | 0.074 | 0.063 | 0.060 | 1:270 | 27.444 |
| 91E6-2 | 3.128 | 3.567 | 3.521 | 3.434 | 3.369 | 3.275 | 2.466 | 0.060 | >1:2,430 | 46.100 |
| 101G10-1 | 3.356 | 3.537 | 3.426 | 3.395 | 3.343 | 3.056 | 2.188 | 0.060 | >1:2,430 | 22.686 |
| 101G10-2 | 3.226 | 3.393 | 3.334 | 3.222 | 3.214 | 3.101 | 2.411 | 0.060 | >1:2,430 | 25.781 |
| 125D9-1 | 3.203 | 3.483 | 3.403 | 3.367 | 3.308 | 3.265 | 2.853 | 0.060 | >1:2,430 | 39.051 |
| 135A6-1 | 3.274 | 3.348 | 3.455 | 3.455 | 3.223 | 2.683 | 1.687 | 0.060 | >1:2,430 | 21.702 |

The titer is the highest dilution with S/N (Signal/Negative)>=2.1, the OD450 in negative control is the average of two technical replicates.
QC Results:
Indirect ELISA:
Coating Antigen: TDAATLAQEAGNFERC (SEQ ID NO: 198)
Coating Concentration: 1 µg/ml, 100 µl/well.
Coating Buffer: Phosphate Buffered Saline, pH 7.4
Secondary Antibody: Anti-Rabbit IgG Fc Monoclonal Secondary Antibody (Min X Hu, Ms, Rt, Sh, Bv, Gt, Camel) (HRP conjugate) (GenScript, Cat. No. A01856)

TABLE 15

ELISA results of recombinant MonoRab antibody:

| | Concentration (ng/ml) | | | | | | | | | | |
|---|---|---|---|---|---|---|---|---|---|---|---|
| | 1,000.00 | 500.00 | 250.00 | 125.00 | 62.50 | 31.25 | 15.62 | 7.81 | 3.90 | 1.95 | Blank |
| | Dilution | | | | | | | | | | |
| | 1:1,000 | 1:2,000 | 1:4,000 | 1:8,000 | 1:16,000 | 1:32,000 | 1:64,000 | 1:128,000 | 1:256,000 | 1:512,000 | Blank | Titer |
| 67G8-2 | 2.854 | 2.835 | 2.797 | 2.757 | 2.606 | 2.451 | 2.143 | 1.658 | 1.209 | 0.876 | 0.049 | >1:512,000 |

The titer is the highest dilution with S/B (Signal/Blank)
>=2.1, the OD450 in blank is the average of two technical
replicates. The starting concentration of 1 mg/ml and the
corresponding dilution ratio is calculated based on the actual
concentrations.

OTHER EMBODIMENTS

While the invention has been described in conjunction
with the detailed description thereof, the foregoing description is intended to illustrate and not limit the scope of the
invention, which is defined by the scope of the appended
claims. Other aspects, advantages, and modifications are
within the scope of the following claims.

---

What is claimed is:

1. An isolated monoclonal antibody, wherein said monoclonal antibody binds to an epitope of the culture filtrate antigen-10 (CFP-10) or peptide fragment thereof, wherein said monoclonal antibody comprises:

a heavy chain with three CDRs comprising the amino acid sequences NYDGH (SEQ ID NO: 42), VIATIGDTYYASWAKG (SEQ ID NO: 43), and GDSRTSNEIFNL (SEQ ID NO: 44), respectively and a light chain with three CDRs comprising the amino acid sequences QSTRSVHNNICLS (SEQ ID NO: 45), SASTLAS (SEQ ID NO: 46), and AGCFPSKSDMYG (SEQ ID NO: 47), respectively.

2. The monoclonal antibody of claim 1, wherein said epitope comprises

```
                                        (SEQ ID NO: 17)
    TDAATLAQEAGNFER or (SEQ ID NO: 18)
    TQIDQVESTAGSLQGQWR.
```

3. The monoclonal antibody of claim 1, comprising:
a VH having the amino acid sequence of

```
                                        (SEQ ID NO: 129)
QSVEESGGRLVTPGTPLTLTCTVSGFSLGNYDGHWVRQTPEKGLEWIGV

IATIGDTYYASWAKGRFSISKTSATVELRITSPTTEDTATYFCVRGDSR

TSNEIFNLWGQGTLVTVSS,
``` and
a VL having the amino acid sequence of

```
                                        (SEQ ID NO: 130)
AVLTQTPSPVSAAVGGTLTINCQSTRSVHNNICLSWYQQKPGQPPKLLI

YSASTLASGVPSRFKGSGSGTQFTLAINDVQCGDAATYYCAGCFPSKSD

MYGFGGGTEVVVK.
```

4. The monoclonal antibody of claim 1, wherein the monoclonal antibody is immobilized to a solid phase support.

5. The monoclonal antibody of claim 4, wherein the solid phase support is a bead, a column, a multi-well plate, a tube.

6. A method of detecting the presence of Mycobacteria in a sample, the method comprising:
contacting the sample with the antibody of claim 1; and
detecting the presence or absence of an antibody-antigen complex, thereby detecting the presence of Mycobacteria in a sample.

7. A method of diagnosing Mycobacteria infection in a subject, the method comprising:
obtaining a sample from a subject;
contacting the sample with the antibody of claim 1; and
detecting the presence or absence of an antibody-antigen complex, wherein the presence of an antibody-antigen complex is indicative of Mycobacteria infection.

8. A method of monitoring Mycobacteria infection in a subject, the method comprising:
obtaining a sample from a subject;
contacting the sample with the antibody of claim 1; and
detecting the presence or absence of an antibody-antigen complex, thereby monitoring infection in the subject.

9. The method of claim 6, 7, or 8, wherein the sample comprises serum or plasma.

10. The method of claim 6, 7, or 8, wherein the sample is not sputum.

11. The method of claim 6, 7, or 8, wherein the sample is a food sample.

12. The method of claim 6, 7, or 8, wherein Mycobacteria comprises *M. tuberculosis, M. africanum, M. bovis, M. canetti, M. caprae, M. microti, M. mungi, M. orygis, M. pinnipedii*, or *M. suricattae*.

13. The method of claim 6, 7, or 8, wherein *Mycobacterium tuberculosis* comprises pulmonary or extrapulmonary tuberculosis.

14. The method of claim 6, 7, or 8, wherein the subject is HIV-positive.

15. The method of claim 6, 7, or 8 in the subject is a pediatric subject.

* * * * *

SEQUENCE LISTING

<160> NUMBER OF SEQ ID NOS: 267

<210> SEQ ID NO 1
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggagactg ggctgcgctg gcttctcctg gtcgctgtgc tcaaaggtgt ccagtgtcag      60
tcgctggagg agtccggggg tcgcctggta acgccgggga cacccctgac actcacctgc     120
acagtctctg gattctccct cagcagctgc gacgtgaact gggtccgcca ggctccaggg     180
aagggactgg aatggatcgg agtcattgct agagctggta gcacatacta cgcgagttgg     240
gcgaaaggcc gatttaccgt ctccaagacc tcgaccacgg tgtacctgga aatcgccagt     300
ccgacgattg aggacacggc cacctatttc tgtgtcagag aagaatttga cttttggggc     360
caaggcaccc ttgtcaccgt ctcctca                                        387

<210> SEQ ID NO 2
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Cys Asp Val Asn Trp Val Arg Gln Ala Pro Gly Lys Gly Leu Glu
    50                  55                  60

Trp Ile Gly Val Ile Ala Arg Ala Gly Ser Thr Tyr Tyr Ala Ser Trp
65                  70                  75                  80

Ala Lys Gly Arg Phe Thr Val Ser Lys Thr Ser Thr Thr Val Tyr Leu
                85                  90                  95

Glu Ile Ala Ser Pro Thr Ile Glu Asp Thr Ala Thr Tyr Phe Cys Val
            100                 105                 110

Arg Glu Glu Phe Asp Phe Trp Gly Gln Gly Thr Leu Val Thr Val Ser
            115                 120                 125

Ser

<210> SEQ ID NO 3
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggacacga gggcccccac tcagctgctg gggctcctgc tgctctggct cccaggtgcc          60
acatttgccg ccgtgctgac ccagactgca tcccccgtgt ctgcggctaa tggaggcaca         120
gtcaccatca cttgccagtc cagtcagagt gtctataata taatgaatt gtcgtggttt          180 cagcagaaac cagggcagcc tcccaagctc ctgataaatt attcatccac tctggcatct         240
ggggtcccat cgcggttcaa aggcagtgga tctgggacac agttcactct caccatcagc         300
ggcgtgcagt gtgacgatgc tgccacttac tactgtctgg cggatatgc tagtattatt          360 gatatgtgga ctttcggcgg agggaccgag gtggtggtca aa                            402

<210> SEQ ID NO 4
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Ala Ser Pro
                20                  25                  30

Val Ser Ala Ala Asn Gly Gly Thr Val Thr Ile Thr Cys Gln Ser Ser
            35                  40                  45

Gln Ser Val Tyr Asn Asn Asn Glu Leu Ser Trp Phe Gln Gln Lys Pro
        50                  55                  60

Gly Gln Pro Pro Lys Leu Leu Ile Asn Tyr Ser Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Leu Gly Gly Tyr Ala Ser Ile Ile Asp Met Trp Thr Phe Gly Gly Gly
        115                 120                 125

Thr Glu Val Val Val Lys
        130

<210> SEQ ID NO 5
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggagactg ggctgcgctg gcttctcctg gtcgctgtgc tcaaaggtgt ccagtgtcag          60

```
tcgctggagg agtccggggg tcgcctggta acgcctggga cacccctgac actcacctgt     120
acagtctctg gattctccct cagcagctat gacgtgagct gggtccgcca ggctccaggg     180
aagggactgg aatggatcgg agttattagt agaggtggca ccacatattc cacaaactgg     240
gcgaaaggcc gattcaccat ctccaaaacc tcgaccacgg tggatctgag aatcaccagt     300
ccgacaattg aggacacggc cacctatttc tgtgccagag aggaatttaa cttgtggggc     360
cagggcaccc tggtcaccgt ctcctca                                          387
```

```
<210> SEQ ID NO 6
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Asp Val Ser Trp Val Arg Gln Ala Pro Gly Lys Gly Leu Glu
    50                  55                  60

Trp Ile Gly Val Ile Ser Arg Gly Gly Thr Thr Tyr Ser Thr Asn Trp
65                  70                  75                  80

Ala Lys Gly Arg Phe Thr Ile Ser Lys Thr Ser Thr Thr Val Asp Leu
                85                  90                  95

Arg Ile Thr Ser Pro Thr Ile Glu Asp Thr Ala Thr Tyr Phe Cys Ala
            100                 105                 110

Arg Glu Glu Phe Asn Leu Trp Gly Gln Gly Thr Leu Val Thr Val Ser
        115                 120                 125

Ser
```

```
<210> SEQ ID NO 7
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggacacga gggcccccac tcagctgctg gggctcctgc tgctctggct cccaggtgcc      60
acatttgcca tcgtgatgac ccagactcca tcttccaagt ctgtccctgt gggagacaca     120
gtcaccatca attgccaggc cagtgagagt gtttattgga caaccgctt agcctggttt      180 caacagaaac cagggcagcc tcccaagcaa ctgatctacg aagcatccaa actggcatct     240
ggggtcccat cgcggttcaa aggcagtgga tctgggacac agttcactct caccatcagc     300
gatgtggtgt gtgacgatgc tgccacttac tactgtgcag atataaaag tagtagtgat      360 ggtcctgctt tcggcggagg gaccgaggtg gtggtcaaa                            399
```

```
<210> SEQ ID NO 8
<211> LENGTH: 133
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 8

Met Asp Thr Arg Ala Pro Thr Gln Leu Leu Gly Leu Leu Leu Trp
1               5                   10                  15

Leu Pro Gly Ala Thr Phe Ala Ile Val Met Thr Gln Thr Pro Ser Ser
            20                  25                  30

Lys Ser Val Pro Val Gly Asp Thr Val Thr Ile Asn Cys Gln Ala Ser
        35                  40                  45

Glu Ser Val Tyr Trp Asn Asn Arg Leu Ala Trp Phe Gln Gln Lys Pro
    50                  55                  60

Gly Gln Pro Pro Lys Gln Leu Ile Tyr Glu Ala Ser Lys Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Val Cys Asp Asp Ala Ala Thr Tyr Tyr Cys
            100                 105                 110

Ala Gly Tyr Lys Ser Ser Ser Asp Gly Pro Ala Phe Gly Gly Gly Thr
        115                 120                 125

Glu Val Val Val Lys
    130

<210> SEQ ID NO 9
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atggagactg ggctgcgctg gcttctcctg gtcgctgtgc tcaaaggtgt ccagtgtcag     60
tcggtggagg agtccggggg tcgcctggtc acgcctggga cacccctgac actcacctgc    120
acagtctctg gattctccct cagtagctac aacatgggct gggtccgcca ggctccaggg    180 aagggggctgg aatacatcgg attcattggt actactggtc gcgcattcta cgcgagctgg    240
gcaaaaggcc gattcaccat ctccaaaacc tcgaccacgg tgaatctgaa agtgaccagt    300
ctgacaaccg aggacacggc cacctatttc tgtgccggag gggctcctgg ttacacccccc    360 tttaacttgt ggggccaagg caccctggtc accgtctcct ca                       402

<210> SEQ ID NO 10
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Asn Met Gly Trp Val Arg Gln Ala Pro Gly Lys Gly Leu Glu
```

-continued

```
     50              55              60

Tyr Ile Gly Phe Ile Gly Thr Thr Gly Arg Ala Phe Tyr Ala Ser Trp
65              70              75              80

Ala Lys Gly Arg Phe Thr Ile Ser Lys Thr Ser Thr Thr Val Asn Leu
            85              90              95

Lys Val Thr Ser Leu Thr Thr Glu Asp Thr Ala Thr Tyr Phe Cys Ala
            100             105             110

Gly Gly Ala Pro Gly Tyr Thr Pro Phe Asn Leu Trp Gly Gln Gly Thr
        115             120             125

Leu Val Thr Val Ser Ser
    130
```

```
<210> SEQ ID NO 11
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atggacacga gggcccccac tcagctgctg gggctcctgc tgctctggct cccaggtgcc      60
acatttgcgc aagtgctgac ccagactcca tcgtccgtgt ctgcggctgt gggaggcaca     120
gtcagcatca gttgccagtc cagtcagagt gttattagta cgacttatc ctggtttcag      180 cagaaaccag ggcagcctcc caggcaactg atctaccaga catccaaact ggcatctggg     240
gtcccatcgc ggttcagtgg cagtggatct gggacacagt tcactctcac catcagcgac     300
ctaaagtgtg acgatgctgc cacttattct tgtgcaggcg gttacagtag tagtcttgac     360
atatatgctt tcggcggagg gaccgaggtg gtggtcaaa                           399
```

```
<210> SEQ ID NO 12
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asp Thr Arg Ala Pro Thr Gln Leu Leu Gly Leu Leu Leu Leu Trp
1               5               10              15

Leu Pro Gly Ala Thr Phe Ala Gln Val Leu Thr Gln Thr Pro Ser Ser
            20              25              30

Val Ser Ala Ala Val Gly Gly Thr Val Ser Ile Ser Cys Gln Ser Ser
        35              40              45

Gln Ser Val Ile Ser Asn Asp Leu Ser Trp Phe Gln Gln Lys Pro Gly
    50              55              60

Gln Pro Pro Arg Gln Leu Ile Tyr Gln Thr Ser Lys Leu Ala Ser Gly
65              70              75              80

Val Pro Ser Arg Phe Ser Gly Ser Gly Ser Gly Thr Gln Phe Thr Leu
            85              90              95

Thr Ile Ser Asp Leu Lys Cys Asp Asp Ala Ala Thr Tyr Ser Cys Ala
            100             105             110

Gly Gly Tyr Ser Ser Ser Leu Asp Ile Tyr Ala Phe Gly Gly Gly Thr
        115             120             125

Glu Val Val Val Lys
    130
```

```
<210> SEQ ID NO 13
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atggagactg ggctgcgctg gcttctcctg gtcgctgtgc tcaaaggtgt ccagtgtcag      60
tcgctggagg agtccggggg tcgcctggta acgcctggag gatccctgac actcacctgc     120
acagtctctg gattctccct cagcacccac gacatcagct gggtccgcca ggctccaggg     180
aagggactgg aatggatcgg agtcattgcc agacgtggca gcacatacta cgcgagttgg     240
gcaaaaggcc gattcaccat ctccaagacc tcgaccacgg tggatctgaa aatcaccagt     300
ccgacaattg aagacacggc cacctatttc tgtgccagag aagaatttga ctttttggggc     360 cagggcaccc tggtcaccgt ctcctca                                         387

<210> SEQ ID NO 14
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Gly Ser Leu Thr Leu Thr Cys Thr Val Ser Gly Phe Ser Leu Ser
        35                  40                  45

Thr His Asp Ile Ser Trp Val Arg Gln Ala Pro Gly Lys Gly Leu Glu
    50                  55                  60

Trp Ile Gly Val Ile Ala Arg Arg Gly Ser Thr Tyr Tyr Ala Ser Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Ile Glu Asp Thr Ala Thr Tyr Phe Cys Ala
            100                 105                 110

Arg Glu Glu Phe Asp Phe Trp Gly Gln Gly Thr Leu Val Thr Val Ser
        115                 120                 125

Ser

<210> SEQ ID NO 15
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atggacacga gggcccccac tcagctgctg gggctcctgc tgctctggct cccaggtgcc      60
acatttgccg ccgtgctgac ccagactgca tcccccgtgt ctgcggctgt ggaggcaca      120 gtcaccatca gttgccagtc cagtcagagt gtttataata caaagaatt atcctggttt      180
```

-continued cagcagaaac cagggcagcc tcccaaactc ctgatctctt atgcatccac tctggcatct          240
ggggtcccat cgcggttcaa aggcagtgga tctgggacac agttcactct caccatcagc          300
gacctggagt gtgacgatgc tgccacttac tactgtctag gcggttatgc tagtactatt          360
gatatgtggg ctttcggcgg agggaccgag gtggtggtca aa                            402

<210> SEQ ID NO 16
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Ala Ser Pro
                20                  25                  30

Val Ser Ala Ala Val Gly Gly Thr Val Thr Ile Ser Cys Gln Ser Ser
            35                  40                  45

Gln Ser Val Tyr Asn Asn Lys Glu Leu Ser Trp Phe Gln Gln Lys Pro
        50                  55                  60

Gly Gln Pro Pro Lys Leu Leu Ile Ser Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
                100                 105                 110

Leu Gly Gly Tyr Ala Ser Thr Ile Asp Met Trp Ala Phe Gly Gly Gly
            115                 120                 125

Thr Glu Val Val Val Lys
        130

<210> SEQ ID NO 17
<211> LENGTH: 15
<212> TYPE: PRT
<213> ORGANISM: Unknown
<220> FEATURE:
<223> OTHER INFORMATION: Description of Unknown:
      peptide 1593 sequence

<400> SEQUENCE: 17

Thr Asp Ala Ala Thr Leu Ala Gln Glu Ala Gly Asn Phe Glu Arg
1               5                   10                  15

<210> SEQ ID NO 18
<211> LENGTH: 18
<212> TYPE: PRT
<213> ORGANISM: Unknown
<220> FEATURE:
<223> OTHER INFORMATION: Description of Unknown:
      peptide 2004 sequence

<400> SEQUENCE: 18

Thr Gln Ile Asp Gln Val Glu Ser Thr Ala Gly Ser Leu Gln Gly Gln
1               5                   10                  15

Trp Arg

<210> SEQ ID NO 19

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Cys Asp Val Asn
1               5

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Ile Ala Arg Ala Gly Ser Thr Tyr Tyr Ala Ser Trp Ala Lys Gly
1               5                   10                  15

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Glu Phe Asp Phe
1               5

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Ser Gln Ser Val Tyr Asn Asn Asn Glu Leu Ser
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Ser Ser Thr Leu Ala Ser
1               5

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Leu Gly Gly Tyr Ala Ser Ile Ile Asp Met Trp Thr
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Tyr Asp Val Ser
1               5

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Val Ile Ser Arg Gly Gly Thr Thr Tyr Ser Thr Asn Trp Ala Lys Gly
1               5                   10                  15

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Glu Phe Asn Leu
1               5

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ala Ser Glu Ser Val Tyr Trp Asn Asn Arg Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Ala Ser Lys Leu Ala Ser
1               5

<210> SEQ ID NO 30
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 30

Ala Gly Tyr Lys Ser Ser Ser Asp Gly Pro Ala
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Tyr Asn Met Gly
1               5

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Ile Gly Thr Thr Gly Arg Ala Phe Tyr Ala Ser Trp Ala Lys Gly
1               5                   10                  15

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ala Pro Gly Tyr Thr Pro Phe Asn Leu
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Ser Gln Ser Val Ile Ser Asn Asp Leu Ser
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Thr Ser Lys Leu Ala Ser
1               5

```
<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Gly Gly Tyr Ser Ser Ser Leu Asp Ile Tyr Ala
1               5                   10

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr His Asp Ile Ser
1               5

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Ile Ala Arg Arg Gly Ser Thr Tyr Tyr Ala Ser Trp Ala Lys Gly
1               5                   10                  15

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ser Ser Gln Ser Val Tyr Asn Asn Lys Glu Leu Ser
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Ala Ser Thr Leu Ala Ser
1               5

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41
```

```
Leu Gly Gly Tyr Ala Ser Thr Ile Asp Met Trp Ala
1               5                   10

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Tyr Asp Gly His
1               5

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Ile Ala Thr Ile Gly Asp Thr Tyr Tyr Ala Ser Trp Ala Lys Gly
1               5                   10                  15

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Asp Ser Arg Thr Ser Asn Glu Ile Phe Asn Leu
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ser Thr Arg Ser Val His Asn Asn Ile Cys Leu Ser
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Ala Ser Thr Leu Ala Ser
1               5

<210> SEQ ID NO 47
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 47

Ala Gly Cys Phe Pro Ser Lys Ser Asp Met Tyr Gly
1               5                   10

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asn Tyr Asp Ile Ser
1               5

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Ile Ala Thr Val Gly Asp Thr Tyr Tyr Ala Ser Trp Ala Lys Gly
1               5                   10                  15

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Asp Ser Pro Ser Thr Asn Glu Ile Phe Gly Leu
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ser Ser Arg Thr Val Tyr Asn Asn Ile Cys Leu Ser
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ala Ser Thr Leu Thr Ser
1               5
```

```
<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Gly Cys Phe Pro Ser Thr Ser Asp Met Tyr Gly
1               5                   10

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Tyr Asp Met Thr
1               5

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Ile Ser Tyr Gly Gly Ser Ala Tyr Tyr Ala Ser Trp Ala Lys Gly
1               5                   10                  15

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Asp Ser Asp Gly Ser Ser Glu Leu Phe Asn Leu
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Ser Ser Lys Ser Val Tyr Asn Asn Asn Cys Leu Ser
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 58

Gly Ala Ser Thr Leu Ala Ser
1               5

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Gly Cys Phe Ala Ser Thr Asn Asp Met Tyr Gly
1               5                   10

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Val Ala Tyr Gly Gly Ala Thr Tyr Tyr Ala Ser Trp Ala Lys Gly
1               5                   10                  15

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Ala Ser Thr Pro Ala Ser
1               5

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Gly Cys Phe Ala Ser Thr Ser Asp Met Tyr Gly
1               5                   10

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Phe Gly Val Ser
1               5

<210> SEQ ID NO 64
<211> LENGTH: 16
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 64

Tyr Ile His Thr Asp Gly Asn Val Tyr Tyr Ala Ser Trp Ala Lys Gly
1               5                   10                  15

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Gly Tyr Ala Ala Asp Leu
1               5

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Ser Ser Glu Ser Val Tyr Lys Asn Tyr Leu Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Thr Ser Thr Leu Val Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Val Gly Gly Tyr Thr Gly Lys Asn Val
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asn His Tyr Ile Ile
1               5

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Ile Ser Arg Arg Ser Lys Thr Asp Tyr Ala Ser Trp Ala Lys Gly
1               5                   10                  15

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Leu Asp Gly Ser Thr Ser Val Val Cys Asp Ile
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Ala Ser Gln Asn Val Tyr Asn Asp Arg Asn Leu Gly
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Pro Ser Thr Leu Ala Ser
1               5

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gly Glu Phe Ile Cys Ser Ser Ala Asp Cys Cys Ala
1               5                   10

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 75

Asp Val Thr Met Ser
1               5

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Ile Gly Arg Arg Gly Arg Ile Trp Tyr Ala Asn Trp Ala Lys Gly
1               5                   10                  15

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Ala Val Ser Ser Asp Trp Asn Met Tyr Gly Met Asp Leu
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Ser Ser Gln Ser Val Tyr Asn Asn Glu Asn Leu Ala
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Gly Glu Phe Asp Cys Ser Ser Ala Asp Cys Phe Ala
1               5                   10

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Val Thr Ile Ser
1               5

<210> SEQ ID NO 81
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ile Ile Gly Arg Arg Gly Arg Ile Arg Tyr Ala Asp Trp Ala Lys Gly
1               5                   10                  15

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Tyr Val Ser Ser Asp Trp Asn Ile Tyr Gly Met Asp Leu
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Ala Ser Gln Ser Val Tyr Asn Asn Lys Asn Leu Ala
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Gly Glu Phe Asp Cys Ser Ser Ala Asp Cys Phe Val
1               5                   10

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp His Ala Met Ser
1               5

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ile Val Gly Arg Arg Gly Arg Thr Tyr Tyr Ala Ser Trp Ala Lys Gly
```

1              5              10              15

```
<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Tyr Val Ser Ser Asp Trp Asn Ile Tyr Gly Met Asp Leu
1               5                   10

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Ala Ser Thr Leu Ala Ser
1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Asp Ala Met Ser
1               5

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ile Ile Gly Arg Arg Gly Lys Thr Trp Tyr Ala Asn Trp Ala Lys Gly
1               5                   10                  15

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Gly Glu Phe Ser Cys Ser Ser Ala Asp Cys Phe Thr
1               5                   10

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 92

Lys Tyr Thr Met Gly
1               5

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Ile Gly Ala Thr Gly Arg Thr Val Tyr Ala Asn Trp Ala Lys Gly
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asn Val Val Asp Ala Ser Asp Ser Asp Gly Met Ile Ala Phe Asp Pro
1               5                   10                  15

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Lys Ala Ser Thr Leu Ala Ser
1               5

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Gly Glu Phe Ser Cys Ser Ser Gly Asp Cys Val Ala
1               5                   10

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Asn Ala Met Gly
1               5

<210> SEQ ID NO 98

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Ile Tyr Ala Ser Gly Asn Thr Tyr Tyr Ala Ser Trp Ala Lys Gly
1               5                   10                  15

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Leu Phe Asn Ile
1

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Ala Ser Gln Ser Val Phe Asp Asn Lys Asn Leu Ser
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ala Ser Thr Leu Asp Ser
1               5

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Arg Asp Ser Gly Asn Ile Tyr Asp
1               5                   10

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103
```

-continued

```
Gly Ser Ala Met Gly
1               5

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ile Tyr Val Ser Gly Asn Thr Tyr Tyr Ala Ser Trp Ala Lys Gly
1               5                   10                  15

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Leu Asn Ile
1

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Ala Ser Gln Ser Val Tyr Asp Asn Lys Asn Leu Ala
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Gly Arg Asp Ser Asp Asn Ile Tyr Asp
1               5                   10

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asn Asn Ala Met Gly
1               5

<210> SEQ ID NO 109
<211> LENGTH: 16
<212> TYPE: PRT
<213> ORGANISM: Artificial Sequence
<220> FEATURE:
```

<223> OTHER INFORMATION: Description of Artificial Sequence: Synthetic
     peptide

<400> SEQUENCE: 109

Thr Ile Tyr Ala Ser Gly Asn Thr Tyr Tyr Ala Ser Trp Ala Lys Gly
1               5                   10                  15

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 110

Gln Ala Ser Gln Ser Val Tyr Asp Asn Lys Asn Leu Ser
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 111

Ala Ala Ser Thr Leu Ala Ser
1               5

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 112

Ser Ile Tyr Ser Ser Gly Asn Thr Tyr Tyr Ala Ser Trp Ala Arg Gly
1               5                   10                  15

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 113

Gly Ala Ser Thr Val Ala Ser
1               5

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 114

Gly Gly Arg Asp Asn Asp Asn Ile Tyr Asp
1               5                   10

```
<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ser Asn Ala Val Gly
1               5

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Ile Tyr Ser Ser Gly Asn Ser Tyr Tyr Ala Ser Trp Ala Lys Gly
1               5                   10                  15

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Gly Arg Asp Asp Asp Asn Ile Tyr Asp
1               5                   10

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Val Ile Ala Arg Arg Gly Trp Thr Tyr Tyr Ala Ser Trp Ala Lys Gly
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Val Ile Ala Arg Arg Gly Trp Thr Tyr Tyr Ala Ser Trp Ala Lys Lys
1               5                   10                  15

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120
```

-continued

```
Tyr Ala Ser Thr Leu Ala Thr
1               5

<210> SEQ ID NO 121
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Cys Asp
            20                  25                  30

Val Asn Trp Val Arg Gln Ala Pro Gly Lys Gly Leu Glu Trp Ile Gly
        35                  40                  45

Val Ile Ala Arg Ala Gly Ser Thr Tyr Tyr Ala Ser Trp Ala Lys Gly
    50                  55                  60

Arg Phe Thr Val Ser Lys Thr Ser Thr Thr Val Tyr Leu Glu Ile Ala
65                  70                  75                  80

Ser Pro Thr Ile Glu Asp Thr Ala Thr Tyr Phe Cys Val Arg Glu Glu
                85                  90                  95

Phe Asp Phe Trp Gly Gln Gly Thr Leu Val Thr Val Ser Ser
                100                 105                 110

<210> SEQ ID NO 122
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ala Val Leu Thr Gln Thr Ala Ser Pro Val Ser Ala Ala Asn Gly Gly
1               5                   10                  15

Thr Val Thr Ile Thr Cys Gln Ser Ser Gln Ser Val Tyr Asn Asn Asn
            20                  25                  30

Glu Leu Ser Trp Phe Gln Gln Lys Pro Gly Gln Pro Pro Lys Leu Leu
        35                  40                  45

Ile Asn Tyr Ser Ser Thr Leu Ala Ser Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Leu Gly Gly Tyr Ala Ser Ile
                85                  90                  95

Ile Asp Met Trp Thr Phe Gly Gly Gly Thr Glu Val Val Val Lys
                100                 105                 110

<210> SEQ ID NO 123
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123
```

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asp
            20                  25                  30

Val Ser Trp Val Arg Gln Ala Pro Gly Lys Gly Leu Glu Trp Ile Gly
        35                  40                  45

Val Ile Ser Arg Gly Gly Thr Thr Tyr Ser Thr Asn Trp Ala Lys Gly
    50                  55                  60

Arg Phe Thr Ile Ser Lys Thr Ser Thr Thr Val Asp Leu Arg Ile Thr
65                  70                  75                  80

Ser Pro Thr Ile Glu Asp Thr Ala Thr Tyr Phe Cys Ala Arg Glu Glu
                85                  90                  95

Phe Asn Leu Trp Gly Gln Gly Thr Leu Val Thr Val Ser Ser
            100                 105                 110
```

<210> SEQ ID NO 124
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Ile Val Met Thr Gln Thr Pro Ser Ser Lys Ser Val Pro Val Gly Asp
1               5                   10                  15

Thr Val Thr Ile Asn Cys Gln Ala Ser Glu Ser Val Tyr Trp Asn Asn
            20                  25                  30

Arg Leu Ala Trp Phe Gln Gln Lys Pro Gly Gln Pro Pro Lys Gln Leu
        35                  40                  45

Ile Tyr Glu Ala Ser Lys Leu Ala Ser Gly Val Pro Ser Arg Phe Lys
    50                  55                  60

Gly Ser Gly Ser Gly Thr Gln Phe Thr Leu Thr Ile Ser Asp Val Val
65                  70                  75                  80

Cys Asp Asp Ala Ala Thr Tyr Tyr Cys Ala Gly Tyr Lys Ser Ser Ser
                85                  90                  95

Asp Gly Pro Ala Phe Gly Gly Gly Thr Glu Val Val Val Lys
            100                 105                 110
```

<210> SEQ ID NO 125
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asn
            20                  25                  30

Met Gly Trp Val Arg Gln Ala Pro Gly Lys Gly Leu Glu Tyr Ile Gly
        35                  40                  45

Phe Ile Gly Thr Thr Gly Arg Ala Phe Tyr Ala Ser Trp Ala Lys Gly
    50                  55                  60

Arg Phe Thr Ile Ser Lys Thr Ser Thr Thr Val Asn Leu Lys Val Thr
65                  70                  75                  80
```

-continued

Ser Leu Thr Thr Glu Asp Thr Ala Thr Tyr Phe Cys Ala Gly Gly Ala
                85                      90                      95

Pro Gly Tyr Thr Pro Phe Asn Leu Trp Gly Gln Gly Thr Leu Val Thr
            100                     105                     110

Val Ser Ser
        115

<210> SEQ ID NO 126
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Leu Thr Gln Thr Pro Ser Ser Val Ser Ala Ala Val Gly Gly
1               5                   10                  15

Thr Val Ser Ile Ser Cys Gln Ser Ser Gln Ser Val Ile Ser Asn Asp
            20                  25                  30

Leu Ser Trp Phe Gln Gln Lys Pro Gly Gln Pro Pro Arg Gln Leu Ile
        35                  40                  45

Tyr Gln Thr Ser Lys Leu Ala Ser Gly Val Pro Ser Arg Phe Ser Gly
    50                  55                  60

Ser Gly Ser Gly Thr Gln Phe Thr Leu Thr Ile Ser Asp Leu Lys Cys
65                  70                  75                  80

Asp Asp Ala Ala Thr Tyr Ser Cys Ala Gly Gly Tyr Ser Ser Ser Leu
                85                  90                  95

Asp Ile Tyr Ala Phe Gly Gly Gly Thr Glu Val Val Val Lys
            100                 105                 110

<210> SEQ ID NO 127
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Ser Thr His Asp
            20                  25                  30

Ile Ser Trp Val Arg Gln Ala Pro Gly Lys Gly Leu Glu Trp Ile Gly
        35                  40                  45

Val Ile Ala Arg Arg Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Ile Glu Asp Thr Ala Thr Tyr Phe Cys Ala Arg Glu Glu
                85                  90                  95

Phe Asp Phe Trp Gly Gln Gly Thr Leu Val Thr Val Ser Ser
            100                 105                 110

<210> SEQ ID NO 128
<211> LENGTH: 111
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 128

```
Ala Val Leu Thr Gln Thr Ala Ser Pro Val Ser Ala Ala Val Gly Gly
1               5                   10                  15

Thr Val Thr Ile Ser Cys Gln Ser Ser Gln Ser Val Tyr Asn Asn Lys
            20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110
```

<210> SEQ ID NO 129
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Gly Asn Tyr Asp
            20                  25                  30

Gly His Trp Val Arg Gln Thr Pro Glu Lys Gly Leu Glu Trp Ile Gly
        35                  40                  45

Val Ile Ala Thr Ile Gly Asp Thr Tyr Tyr Ala Ser Trp Ala Lys Gly
    50                  55                  60

Arg Phe Ser Ile Ser Lys Thr Ser Ala Thr Val Glu Leu Arg Ile Thr
65                  70                  75                  80

Ser Pro Thr Thr Glu Asp Thr Ala Thr Tyr Phe Cys Val Arg Gly Asp
                85                  90                  95

Ser Arg Thr Ser Asn Glu Ile Phe Asn Leu Trp Gly Gln Gly Thr Leu
            100                 105                 110

Val Thr Val Ser Ser
        115
```

<210> SEQ ID NO 130
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Ala Val Leu Thr Gln Thr Pro Ser Pro Val Ser Ala Ala Val Gly Gly
1               5                   10                  15

Thr Leu Thr Ile Asn Cys Gln Ser Thr Arg Ser Val His Asn Asn Ile
            20                  25                  30

Cys Leu Ser Trp Tyr Gln Gln Lys Pro Gly Gln Pro Pro Lys Leu Leu
```

-continued

```
                35                  40                  45

Ile Tyr Ser Ala Ser Thr Leu Ala Ser Gly Val Pro Ser Arg Phe Lys
        50                  55                  60

Gly Ser Gly Ser Gly Thr Gln Phe Thr Leu Ala Ile Asn Asp Val Gln
65                  70                  75                  80

Cys Gly Asp Ala Ala Thr Tyr Tyr Cys Ala Gly Cys Phe Pro Ser Lys
                85                  90                  95

Ser Asp Met Tyr Gly Phe Gly Gly Gly Thr Glu Val Val Val Lys
            100                 105                 110

<210> SEQ ID NO 131
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Ser Val Glu Glu Ser Gly Gly Arg Leu Val Thr Pro Gly Thr Pro
1                   5                   10                  15

Leu Thr Leu Thr Cys Thr Val Ser Gly Phe Ser Leu Gly Asn Tyr Asp
            20                  25                  30

Ile Ser Trp Val Arg Gln Ala Pro Gly Lys Gly Leu Glu Trp Ile Gly
        35                  40                  45

Val Ile Ala Thr Val Gly Asp Thr Tyr Tyr Ala Ser Trp Ala Lys Gly
    50                  55                  60

Arg Phe Thr Ile Ser Lys Thr Ser Ala Thr Val Asp Leu Lys Ile Thr
65                  70                  75                  80

Ser Pro Thr Thr Glu Asp Thr Ala Thr Tyr Phe Cys Val Arg Gly Asp
                85                  90                  95

Ser Pro Ser Thr Asn Glu Ile Phe Gly Leu Trp Gly Gln Gly Thr Leu
            100                 105                 110

Val Thr Val Ser Ser
        115

<210> SEQ ID NO 132
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Ala Val Leu Thr Gln Thr Pro Ser Pro Val Ser Ala Ala Val Gly Gly
1                   5                   10                  15

Thr Leu Thr Ile Asn Cys Gln Ser Ser Arg Thr Val Tyr Asn Asn Ile
            20                  25                  30

Cys Leu Ser Trp Tyr Gln Gln Lys Leu Gly Gln Pro Pro Lys Leu Leu
        35                  40                  45

Ile Tyr Gly Ala Ser Thr Leu Thr Ser Gly Val Pro Ser Arg Phe Arg
    50                  55                  60

Gly Ser Gly Ser Gly Thr Gln Phe Thr Leu Thr Ile Asn Asp Val Gln
65                  70                  75                  80

Cys Gly Asp Ala Ala Thr Tyr Tyr Cys Ala Gly Cys Phe Pro Ser Thr
                85                  90                  95

Ser Asp Met Tyr Gly Phe Gly Gly Gly Thr Glu Val Val Val Lys
```

-continued

```
              100             105             110
```

<210> SEQ ID NO 133
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asp
            20                  25                  30

Met Thr Trp Val Arg Gln Ala Pro Gly Lys Gly Leu Glu Tyr Ile Gly
        35                  40                  45

Val Ile Ser Tyr Gly Gly Ser Ala Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Asp
                85                  90                  95

Ser Asp Gly Ser Ser Glu Leu Phe Asn Leu Trp Gly Gln Gly Thr Leu
            100                 105                 110

Val Thr Val Ser Ser
        115
```

<210> SEQ ID NO 134
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

```
Ala Val Leu Thr Gln Thr Pro Ser Pro Val Ser Ala Pro Val Gly Gly
1               5                   10                  15

Thr Val Ser Ile Asn Cys Gln Ser Ser Lys Ser Val Tyr Asn Asn Asn
            20                  25                  30

Cys Leu Ser Trp Tyr Gln Gln Lys Pro Gly Gln Pro Pro Asn Leu Leu
        35                  40                  45

Ile Tyr Gly Ala Ser Thr Leu Ala Ser Gly Val Pro Ser Arg Phe Lys
    50                  55                  60

Gly Ser Gly Ser Gly Thr Gln Phe Thr Leu Thr Ile Asn Asp Val Gln
65                  70                  75                  80

Cys Asp Asp Ala Ala Thr Tyr Tyr Cys Ala Gly Cys Phe Ala Ser Thr
                85                  90                  95

Asn Asp Met Tyr Gly Phe Gly Gly Gly Ser Glu Val Val Val Lys
            100                 105                 110
```

<210> SEQ ID NO 135
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

-continued

```
Gln Pro Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asp
                20                  25                  30

Met Thr Trp Val Arg Gln Ala Pro Gly Lys Gly Leu Glu Tyr Ile Gly
            35                  40                  45

Val Val Ala Tyr Gly Gly Ala Thr Tyr Tyr Ala Ser Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Asp
                85                  90                  95

Ser Asp Gly Ser Ser Glu Leu Phe Asn Leu Trp Gly Gln Gly Thr Leu
            100                 105                 110

Val Thr Val Ser Ser
        115
```

<210> SEQ ID NO 136
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

```
Ala Val Leu Thr Gln Thr Pro Ser Pro Val Ser Ala Ala Val Gly Gly
1               5                   10                  15

Thr Val Thr Ile Asn Cys Gln Ser Ser Lys Ser Val Tyr Asn Asn Asn
                20                  25                  30

Cys Leu Ser Trp Tyr Gln Gln Lys Gln Gly Gln Pro Pro Lys Leu Leu
            35                  40                  45

Ile Tyr Gln Ala Ser Thr Pro Ala Ser Gly Val Pro Ser Arg Phe Lys
        50                  55                  60

Gly Ser Gly Ser Gly Thr Gln Phe Thr Leu Thr Ile Asn Asp Val Gln
65                  70                  75                  80

Cys Asp Asp Ala Ala Thr Tyr Tyr Cys Ala Gly Cys Phe Ala Ser Thr
                85                  90                  95

Ser Asp Met Tyr Gly Phe Gly Gly Gly Thr Gly Val Val Val Lys
            100                 105                 110
```

<210> SEQ ID NO 137
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

```
Gln Ser Leu Glu Glu Ser Gly Gly Arg Leu Val Ser Pro Gly Gly Ser
1               5                   10                  15

Leu Thr Leu Thr Cys Thr Val Ser Gly Ile Asp Leu Ser Arg Phe Gly
                20                  25                  30

Val Ser Trp Val Arg Gln Ala Pro Gly Lys Gly Leu Glu Trp Thr Gly
            35                  40                  45

Tyr Ile His Thr Asp Gly Asn Val Tyr Tyr Ala Ser Trp Ala Lys Gly
        50                  55                  60
```

-continued

```
Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Arg Gly Gly
                85                  90                  95

Tyr Ala Ala Asp Leu Trp Gly Gln Ala Ala Leu Val Thr Val Ser Ser
            100                 105                 110

<210> SEQ ID NO 138
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Pro Met Leu Thr Gln Thr Pro Ser Ser Val Ser Ala Ala Val Gly
1               5                   10                  15

Gly Thr Val Thr Ile Ser Cys Gln Ser Ser Glu Ser Val Tyr Lys Asn
                20                  25                  30

Tyr Leu Ala Trp Tyr Gln Gln Lys Leu Gly Gln Pro Pro Lys Leu Leu
        35                  40                  45

Ile Gly Ala Thr Ser Thr Leu Val Ser Gly Val Pro Ser Arg Phe Lys
    50                  55                  60

Gly Ser Gly Ser Arg Thr Gln Phe Ser Leu Thr Ile Ser Asp Leu Glu
65                  70                  75                  80

Cys Asp Asp Ala Ala Thr Tyr Tyr Cys Val Gly Gly Tyr Thr Gly Lys
                85                  90                  95

Asn Val Phe Gly Gly Gly Thr Glu Val Val Val Lys
            100                 105

<210> SEQ ID NO 139
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn His Tyr
                20                  25                  30

Ile Ile Trp Val Arg Gln Thr Pro Gly Lys Gly Leu Glu Trp Ile Gly
        35                  40                  45

Ala Ile Ser Arg Arg Ser Lys Thr Asp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gln Leu
                85                  90                  95

Asp Gly Ser Thr Ser Val Val Cys Asp Ile Trp Gly Pro Gly Thr Leu
            100                 105                 110

Val Thr Val Ser Ser
        115

<210> SEQ ID NO 140
```

```
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Leu Thr Gln Thr Pro Ser Pro Val Ser Ala Ala Val Gly Gly
1               5                   10                  15

Thr Val Thr Ile Asn Cys Gln Ala Ser Gln Asn Val Tyr Asn Asp Arg
            20                  25                  30

Asn Leu Gly Trp Tyr Gln Gln Lys Pro Gly Gln Pro Pro Lys Leu Leu
        35                  40                  45

Ile Tyr Gly Pro Ser Thr Leu Ala Ser Gly Val Ser Ser Arg Phe Thr
    50                  55                  60

Gly Ser Gly Ser Gly Thr Gln Phe Thr Leu Thr Ile Ser Asp Leu Gln
65                  70                  75                  80

Cys Asp Asp Ala Ala Thr Tyr Tyr Cys Gln Gly Glu Phe Ile Cys Ser
                85                  90                  95

Ser Ala Asp Cys Cys Ala Phe Gly Gly Gly Thr Glu Val Val Val Lys
            100                 105                 110

<210> SEQ ID NO 141
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asp Val Thr
            20                  25                  30

Met Ser Trp Val Arg Gln Ala Pro Gly Lys Gly Leu Glu Trp Ile Gly
        35                  40                  45

Ile Ile Gly Arg Arg Gly Arg Ile Trp Tyr Ala Asn Trp Ala Lys Gly
    50                  55                  60

Arg Phe Thr Ile Ser Lys Thr Ser Pro Thr Val Asp Leu Lys Ile Ile
65                  70                  75                  80

Ser Pro Thr Ser Asp Asp Thr Ala Thr Tyr Phe Cys Ala Arg Gly Ala
                85                  90                  95

Val Ser Ser Asp Trp Asn Met Tyr Gly Met Asp Leu Trp Gly Pro Gly
            100                 105                 110

Thr Leu Val Thr Val Ser Ser
        115

<210> SEQ ID NO 142
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Leu Thr Gln Thr Pro Ser Ser Val Ser Ala Pro Val Gly Gly
1               5                   10                  15
```

-continued

```
Thr Val Thr Ile Asn Cys Gln Ser Ser Gln Ser Val Tyr Asn Asn Glu
             20                  25                  30

Asn Leu Ala Trp Tyr Gln Gln Lys Leu Gly Gln Pro Pro Lys Leu Leu
             35                  40                  45

Ile Tyr Gly Ala Ser Thr Leu Ala Ser Gly Val Ser Ser Arg Phe Glu
         50                  55                  60

Gly Ser Gly Ser Gly Thr Gln Phe Ala Leu Thr Ile Ser Gly Val Gln
65                  70                  75                  80

Cys Asp Asp Ala Ala Thr Tyr Tyr Cys Gln Gly Glu Phe Asp Cys Ser
                 85                  90                  95

Ser Ala Asp Cys Phe Ala Phe Gly Gly Gly Thr Glu Val Val Val Lys
             100                 105                 110
```

<210> SEQ ID NO 143
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asp Val Thr
             20                  25                  30

Ile Ser Trp Val Arg Gln Ala Pro Gly Lys Gly Leu Lys Trp Thr Gly
         35                  40                  45

Ile Ile Gly Arg Arg Gly Arg Ile Arg Tyr Ala Asp Trp Ala Lys Gly
         50                  55                  60

Arg Phe Thr Ile Ser Lys Thr Ser Thr Thr Val Asp Leu Lys Ile Thr
65                  70                  75                  80

Ser Pro Thr Thr Asp Asp Thr Ala Thr Tyr Phe Cys Ala Arg Ala Tyr
                 85                  90                  95

Val Ser Ser Asp Trp Asn Ile Tyr Gly Met Asp Leu Trp Gly Pro Gly
             100                 105                 110

Thr Leu Val Thr Val Ser Ser
         115
```

<210> SEQ ID NO 144
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

```
Gln Val Leu Thr Gln Thr Ala Ser Pro Val Ser Ala Pro Val Gly Gly
1               5                   10                  15

Thr Val Thr Ile Asn Cys Gln Ala Ser Gln Ser Val Tyr Asn Asn Lys
             20                  25                  30

Asn Leu Ala Trp Tyr Gln Gln Lys Leu Gly Gln Pro Pro Lys Leu Leu
             35                  40                  45

Ile Tyr Glu Ala Ser Lys Leu Ala Ser Gly Val Ser Ser Arg Phe Glu
         50                  55                  60

Gly Ser Gly Ser Gly Thr Gln Phe Ala Leu Thr Ile Ser Gly Val Gln
65                  70                  75                  80
```

-continued

```
Cys Asp Asp Ala Ala Thr Tyr Tyr Cys Gln Gly Glu Phe Asp Cys Ser
                85                      90                      95

Ser Ala Asp Cys Phe Val Phe Gly Gly Gly Thr Glu Val Val Val Lys
            100                     105                 110
```

```
<210> SEQ ID NO 145
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145
```

```
Gln Ser Met Glu Glu Ser Gly Gly Arg Leu Val Thr Pro Gly Thr Pro
1               5                   10                  15

Leu Thr Leu Thr Cys Thr Val Ser Gly Phe Ser Leu Ser Asp His Ala
            20                  25                  30

Met Ser Trp Val Arg Gln Ala Pro Gly Lys Gly Leu Glu Trp Ile Gly
        35                  40                  45

Ile Val Gly Arg Arg Gly Arg Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Ile Glu Asp Thr Ala Thr Tyr Phe Cys Ala Arg Gly Tyr
                85                      90                  95

Val Ser Ser Asp Trp Asn Ile Tyr Gly Met Asp Leu Trp Gly Pro Gly
            100                     105                 110

Thr Leu Val Thr Val Ser Ser
        115
```

```
<210> SEQ ID NO 146
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146
```

```
Gln Val Leu Thr Gln Thr Pro Ser Pro Val Ser Ala Ala Val Gly Gly
1               5                   10                  15

Thr Val Thr Ile Asn Cys Gln Ala Ser Gln Ser Val Tyr Asn Asn Lys
            20                  25                  30

Asn Leu Ala Trp Tyr Gln Gln Lys Pro Gly Gln Pro Pro Lys Leu Leu
        35                  40                  45

Ile Tyr Glu Ala Ser Thr Leu Ala Ser Gly Val Ser Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Gln Gly Glu Phe Asp Cys Ser
                85                      90                  95

Ser Ala Asp Cys Phe Ala Phe Gly Gly Gly Thr Glu Val Val Val Lys
            100                     105                 110
```

```
<210> SEQ ID NO 147
<211> LENGTH: 119
<212> TYPE: PRT
<213> ORGANISM: Artificial Sequence
<220> FEATURE:
```

-continued

<223> OTHER INFORMATION: Description of Artificial Sequence: Synthetic
     polypeptide

<400> SEQUENCE: 147

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asp Asp Ala
            20                  25                  30

Met Ser Trp Val Arg Gln Ala Pro Gly Lys Gly Leu Glu Trp Ile Gly
        35                  40                  45

Ile Ile Gly Arg Arg Gly Lys Thr Trp Tyr Ala Asn Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Tyr
                85                  90                  95

Val Ser Ser Asp Trp Asn Ile Tyr Gly Met Asp Leu Trp Gly Pro Gly
            100                 105                 110

Thr Leu Val Thr Val Ser Ala
        115

<210> SEQ ID NO 148
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 148

Gln Val Leu Thr Gln Thr Pro Ser Pro Val Ser Ala Ala Val Gly Gly
1               5                   10                  15

Thr Val Thr Ile Asn Cys Gln Ala Ser Gln Ser Val Tyr Asn Asn Lys
            20                  25                  30

Asn Leu Ala Trp Tyr Gln Gln Lys Ser Gly Gln Pro Pro Lys Leu Leu
        35                  40                  45

Ile Tyr Glu Ala Ser Lys Leu Ala Ser Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Gln Gly Glu Phe Ser Cys Ser
                85                  90                  95

Ser Ala Asp Cys Phe Thr Phe Gly Gly Gly Thr Glu Val Val Val Lys
            100                 105                 110

<210> SEQ ID NO 149
<211> LENGTH: 121
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 149

Gln Ser Val Glu Glu Ser Gly Gly Arg Leu Val Thr Pro Gly Thr Pro
1               5                   10                  15

Leu Thr Leu Thr Cys Thr Ala Ser Gly Ser Asp Ile Asn Lys Tyr Thr
            20                  25                  30

Met Gly Trp Val Arg Gln Ala Pro Gly Lys Gly Leu Glu Trp Val Gly

-continued

```
                35                    40                    45
Ala Ile Gly Ala Thr Gly Arg Thr Val Tyr Ala Asn Trp Ala Lys Gly
    50                    55                    60

Arg Phe Thr Ile Ser Lys Thr Ser Thr Thr Val Asp Leu Ile Ile Thr
65                    70                    75                    80

Ser Pro Thr Thr Glu Asp Thr Ala Thr Tyr Phe Cys Ala Arg Asn Val
                85                    90                    95

Val Asp Ala Ser Asp Ser Asp Gly Met Ile Ala Phe Asp Pro Trp Gly
                100                   105                   110

Pro Gly Thr Leu Val Thr Val Ser Ser
        115                   120

<210> SEQ ID NO 150
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Val Leu Thr Gln Thr Pro Ser Pro Val Ser Ala Ala Val Gly Gly
1                   5                     10                    15

Thr Val Thr Ile Asn Cys Gln Ala Ser Gln Ser Val Tyr Asn Asn Lys
                20                    25                    30

Asn Leu Ala Trp Tyr Gln Gln Lys Pro Gly Gln Pro Pro Lys Leu Leu
        35                    40                    45

Ile Tyr Lys Ala Ser Thr Leu Ala Ser Gly Val Pro Ser Arg Phe Ala
        50                    55                    60

Gly Ser Gly Ser Gly Thr Glu Val Thr Leu Thr Ile Ser Asp Leu Glu
65                    70                    75                    80

Cys Asp Asp Ala Ala Thr Tyr Tyr Cys Gln Gly Glu Phe Ser Cys Ser
                85                    90                    95

Ser Gly Asp Cys Val Ala Phe Gly Gly Gly Thr Glu Val Val Val Lys
                100                   105                   110

<210> SEQ ID NO 151
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Ser Leu Glu Glu Ser Gly Gly Arg Leu Val Thr Pro Gly Gly Ser
1                   5                     10                    15

Leu Thr Leu Thr Cys Thr Val Ser Gly Ile Asp Leu Ser Ser Asn Ala
                20                    25                    30

Met Gly Trp Val Arg Gln Ala Pro Gly Glu Gly Leu Glu Trp Ile Gly
        35                    40                    45

Ser Ile Tyr Ala Ser Gly Asn Thr Tyr Tyr Ala Ser Trp Ala Lys Gly
        50                    55                    60

Arg Phe Ala Ile Ser Lys Thr Ser Thr Thr Val Asp Leu Lys Met Thr
65                    70                    75                    80

Ser Leu Thr Ala Ala Asp Thr Ala Thr Tyr Phe Cys Ala Arg Leu Phe
                85                    90                    95

Asn Ile Trp Gly Pro Gly Thr Leu Val Thr Val Ser Ser
```

-continued 100             105

<210> SEQ ID NO 152
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Ala Asp Ile Val Leu Thr Gln Thr Pro Ala Ser Val Ser Ser Val Val
1               5                   10                  15

Gly Gly Thr Val Thr Ile Asn Cys Gln Ala Ser Gln Ser Val Phe Asp
            20                  25                  30

Asn Lys Asn Leu Ser Trp Phe Gln Gln Lys Pro Gly Gln Pro Pro Lys
        35                  40                  45

Gln Leu Ile Tyr Gly Ala Ser Thr Leu Asp Ser Gly Val Pro Ser Arg
    50                  55                  60

Phe Lys Gly Ser Gly Ser Gly Thr Gln Phe Thr Leu Thr Ile Ser Asp
65                  70                  75                  80

Met Gln Cys Asp Asp Ala Ala Thr Tyr Tyr Cys Gly Gly Arg Asp Ser
                85                  90                  95

Gly Asn Ile Tyr Asp Phe Gly Gly Gly Thr Glu Val Val Val Lys
            100                 105                 110

<210> SEQ ID NO 153
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Glu Leu Lys Glu Ser Gly Gly Arg Leu Val Thr Pro Gly Gly Ser
1               5                   10                  15

Leu Thr Leu Ser Cys Thr Ala Ser Gly Ile Asp Leu Ser Gly Ser Ala
            20                  25                  30

Met Gly Trp Val Arg Gln Ala Pro Gly Gln Gly Leu Glu Trp Ile Gly
        35                  40                  45

Ser Ile Tyr Val Ser Gly Asn Thr Tyr Tyr Ala Ser Trp Ala Lys Gly
    50                  55                  60

Arg Phe Ala Ile Ser Arg Thr Ser Thr Thr Val Asp Leu Lys Met Thr
65                  70                  75                  80

Ser Leu Thr Ala Ala Asp Thr Ala Thr Tyr Phe Cys Ala Arg Leu Leu
                85                  90                  95

Asn Ile Trp Gly Pro Gly Thr Leu Val Thr Val Ser Ser
            100                 105

<210> SEQ ID NO 154
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Ala Asp Ile Val Leu Thr Gln Thr Pro Ser Pro Val Ser Ile Ala Val
1               5                   10                  15

```
Gly Gly Thr Val Thr Ile Asn Cys Gln Ala Ser Gln Ser Val Tyr Asp
        20                  25                  30

Asn Lys Asn Leu Ala Trp Phe Gln Gln Lys Pro Gly Gln Pro Pro Lys
        35                  40                  45

Gln Leu Ile Tyr Gly Ala Ser Thr Leu Ala Ser Gly Val Pro Ser Arg
    50                  55                  60

Phe Lys Gly Ser Gly Ser Gly Thr Gln Phe Thr Leu Thr Ile Ser Gly
65                  70                  75                  80

Met Gln Cys Asp Asp Ala Ala Thr Tyr Tyr Cys Gly Gly Arg Asp Ser
                85                  90                  95

Asp Asn Ile Tyr Asp Phe Gly Gly Gly Thr Glu Val Val Val Lys
            100                 105                 110

<210> SEQ ID NO 155
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Asn Asn Ala
        20                  25                  30

Met Gly Trp Val Arg Gln Ala Pro Gly Glu Gly Leu Glu Trp Ile Gly
        35                  40                  45

Thr Ile Tyr Ala Ser Gly Asn Thr Tyr Tyr Ala Ser Trp Ala Lys Gly
    50                  55                  60

Arg Phe Ala Ile Ser Lys Thr Ser Thr Thr Val Asp Leu Lys Met Thr
65                  70                  75                  80

Ser Leu Thr Ala Ala Asp Thr Ala Thr Tyr Phe Cys Ala Arg Leu Phe
                85                  90                  95

Asn Ile Trp Gly Pro Gly Thr Leu Val Thr Val Ser Ser
            100                 105

<210> SEQ ID NO 156
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Ala Asp Ile Val Leu Thr Gln Ser Pro Ala Ser Val Ser Ser Ala Val
1               5                   10                  15

Gly Gly Thr Val Thr Ile Asn Cys Gln Ala Ser Gln Ser Val Tyr Asp
        20                  25                  30

Asn Lys Asn Leu Ser Trp Phe Gln Gln Lys Pro Gly Gln Pro Pro Lys
        35                  40                  45

Gln Leu Ile Tyr Ala Ala Ser Thr Leu Ala Ser Gly Val Pro Ser Arg
    50                  55                  60

Phe Lys Gly Ser Gly Ser Gly Thr Gln Phe Thr Leu Thr Ile Ser Gly
65                  70                  75                  80

Met Gln Cys Asp Asp Ala Ala Thr Tyr Tyr Cys Gly Gly Arg Asp Ser
                85                  90                  95
```

```
Gly Asn Ile Tyr Asp Phe Gly Gly Gly Thr Glu Val Val Val Lys
            100             105             110

<210> SEQ ID NO 157
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Gly Trp Val Arg Gln Ala Pro Gly Glu Gly Leu Gln Trp Ile Gly
            35                  40                  45

Ser Ile Tyr Ser Ser Gly Asn Thr Tyr Tyr Ala Ser Trp Ala Arg Gly
        50                  55                  60

Arg Phe Ala Ile Ser Arg Thr Ser Thr Thr Val Asp Leu Lys Met Thr
65                  70                  75                  80

Ser Leu Thr Ala Ala Asp Thr Ala Thr Tyr Phe Cys Ala Arg Leu Phe
                85                  90                  95

Asn Ile Trp Gly Pro Gly Thr Leu Val Thr Val Ser Ser
            100             105

<210> SEQ ID NO 158
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Ala Asp Ile Val Val Thr Gln Thr Pro Ala Ser Val Ser Ala Asp Val
1               5                   10                  15

Gly Gly Thr Val Thr Ile Asn Cys Gln Ala Ser Gln Ser Val Tyr Asp
            20                  25                  30

Asn Lys Asn Leu Ala Trp Phe Gln Gln Lys Pro Gly Gln Pro Pro Lys
        35                  40                  45

Gln Leu Ile Tyr Gly Ala Ser Thr Val Ala Ser Gly Val Pro Ser Arg
    50                  55                  60

Phe Lys Gly Ser Gly Ser Gly Thr Gln Phe Thr Leu Thr Ile Ser Asp
65                  70                  75                  80

Val Gln Cys Asp Asp Ala Ala Thr Tyr Tyr Cys Gly Gly Arg Asp Asn
                85                  90                  95

Asp Asn Ile Tyr Asp Phe Gly Gly Gly Thr Glu Val Val Val Lys
            100             105             110

<210> SEQ ID NO 159
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159
```

-continued

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Val Gly Trp Val Arg Gln Ala Pro Gly Glu Gly Leu Glu Trp Ile Gly
        35                  40                  45

Ser Ile Tyr Ser Ser Gly Asn Ser Tyr Tyr Ala Ser Trp Ala Lys Gly
    50                  55                  60

Arg Phe Ala Ile Ser Arg Thr Ser Thr Thr Val Asp Leu Lys Met Thr
65                  70                  75                  80

Arg Leu Thr Ala Ala Asp Thr Ala Thr Tyr Phe Cys Ala Arg Leu Phe
                85                  90                  95

Asn Ile Trp Gly Pro Gly Thr Leu Val Thr Val Ser
            100                 105
```

<210> SEQ ID NO 160
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

```
Ala Asp Ile Val Leu Thr Gln Thr Pro Ala Ser Val Ser Ser Val Val
1               5                   10                  15

Gly Gly Thr Val Ala Ile Asn Cys Gln Ala Ser Gln Ser Val Tyr Asp
            20                  25                  30

Asn Lys Asn Leu Ser Trp Phe Gln Gln Lys Pro Gly Gln Thr Pro Lys
            35                  40                  45

Gln Leu Ile Tyr Gly Ala Ser Thr Leu Ala Ser Gly Val Pro Ser Arg
    50                  55                  60

Phe Lys Gly Ser Gly Ser Gly Thr Gln Phe Thr Leu Thr Ile Ser Gly
65                  70                  75                  80

Val Gln Cys Asp Asp Ala Ala Thr Tyr Tyr Cys Gly Gly Arg Asp Asp
                85                  90                  95

Asp Asn Ile Tyr Asp Phe Gly Gly Gly Thr Glu Val Val Val Lys
            100                 105                 110
```

<210> SEQ ID NO 161
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

```
Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Ser Thr His Asp
            20                  25                  30

Ile Ser Trp Val Arg Gln Ala Pro Gly Lys Gly Leu Glu Trp Ile Gly
        35                  40                  45

Val Ile Ala Arg Arg Gly Trp Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80
```

-continued

```
Ser Pro Thr Ile Glu Asp Thr Ala Thr Tyr Phe Cys Ala Arg Glu Glu
                85                  90                  95

Phe Asp Phe Trp Gly Gln Gly Thr Leu Val Thr Val Ser Ser
            100                 105                 110

<210> SEQ ID NO 162
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Ser Thr His Asp
                20                  25                  30

Ile Ser Trp Val Arg Gln Ala Pro Gly Lys Gly Leu Glu Trp Ile Gly
            35                  40                  45

Val Ile Ala Arg Arg Gly Trp Thr Tyr Tyr Ala Ser Trp Ala Lys Lys
        50                  55                  60

Arg Phe Thr Ile Ser Lys Thr Ser Thr Thr Val Asp Leu Lys Ile Thr
65                  70                  75                  80

Ser Pro Thr Ile Glu Asp Thr Ala Thr Tyr Phe Cys Ala Arg Glu Glu
                85                  90                  95

Phe Asp Phe Trp Gly Gln Gly Thr Leu Val Thr Val Ser Ser
            100                 105                 110

<210> SEQ ID NO 163
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Ala Val Leu Thr Gln Thr Ala Ser Pro Val Ser Ala Ala Val Gly Gly
1               5                   10                  15

Thr Val Thr Ile Ser Cys Gln Ser Ser Gln Ser Val Tyr Asn Asn Lys
                20                  25                  30

Glu Leu Ser Trp Phe Gln Gln Lys Pro Gly Gln Pro Pro Lys Leu Leu
            35                  40                  45

Ile Ser Tyr Ala Ser Thr Leu Ala Thr Gly Val Pro Ser Arg Phe Lys
        50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 164
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 164

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Thr Leu Thr Cys Thr Val Ser Gly Phe Ser Leu Gly
            35                  40                  45

Asn Tyr Asp Gly His Trp Val Arg Gln Thr Pro Glu Lys Gly Leu Glu
        50                  55                  60

Trp Ile Gly Val Ile Ala Thr Ile Gly Asp Thr Tyr Tyr Ala Ser Trp
65                  70                  75                  80

Ala Lys Gly Arg Phe Ser Ile Ser Lys Thr Ser Ala Thr Val Glu Leu
                85                  90                  95

Arg Ile Thr Ser Pro Thr Thr Glu Asp Thr Ala Thr Tyr Phe Cys Val
            100                 105                 110

Arg Gly Asp Ser Arg Thr Ser Asn Glu Ile Phe Asn Leu Trp Gly Gln
        115                 120                 125

Gly Thr Leu Val Thr Val Ser Ser
        130                 135
```

<210> SEQ ID NO 165
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
                20                  25                  30

Val Ser Ala Ala Val Gly Gly Thr Leu Thr Ile Asn Cys Gln Ser Thr
            35                  40                  45

Arg Ser Val His Asn Asn Ile Cys Leu Ser Trp Tyr Gln Gln Lys Pro
        50                  55                  60

Gly Gln Pro Pro Lys Leu Leu Ile Tyr Ser Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Ala Ile Asn Asp Val Gln Cys Gly Asp Ala Ala Thr Tyr Tyr Cys
            100                 105                 110

Ala Gly Cys Phe Pro Ser Lys Ser Asp Met Tyr Gly Phe Gly Gly Gly
        115                 120                 125

Thr Glu Val Val Val Lys
        130
```

<210> SEQ ID NO 166
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

```
Met Glu Thr Gly Leu Arg Trp Leu Leu Leu Val Ala Val Leu Lys Gly
1               5                   10                  15
```

```
1                    5                        10                          15

Val Gln Cys Gln Ser Val Glu Glu Ser Gly Gly Arg Leu Val Thr Pro
                 20                      25                      30

Gly Thr Pro Leu Thr Leu Thr Cys Thr Val Ser Gly Phe Ser Leu Gly
             35                      40                      45

Asn Tyr Asp Ile Ser Trp Val Arg Gln Ala Pro Gly Lys Gly Leu Glu
         50                      55                      60

Trp Ile Gly Val Ile Ala Thr Val Gly Asp Thr Tyr Tyr Ala Ser Trp
65                       70                      75                      80

Ala Lys Gly Arg Phe Thr Ile Ser Lys Thr Ser Ala Thr Val Asp Leu
                 85                      90                      95

Lys Ile Thr Ser Pro Thr Thr Glu Asp Thr Ala Thr Tyr Phe Cys Val
             100                     105                     110

Arg Gly Asp Ser Pro Ser Thr Asn Glu Ile Phe Gly Leu Trp Gly Gln
             115                     120                     125

Gly Thr Leu Val Thr Val Ser Ser
        130                     135
```

<210> SEQ ID NO 167
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

```
Met Asp Thr Arg Ala Pro Thr Gln Leu Leu Gly Leu Leu Leu Leu Trp
1                    5                        10                          15

Leu Pro Gly Ala Thr Phe Ala Ala Val Leu Thr Gln Thr Pro Ser Pro
                 20                      25                      30

Val Ser Ala Ala Val Gly Gly Thr Leu Thr Ile Asn Cys Gln Ser Ser
             35                      40                      45

Arg Thr Val Tyr Asn Asn Ile Cys Leu Ser Trp Tyr Gln Gln Lys Leu
         50                      55                      60

Gly Gln Pro Pro Lys Leu Leu Ile Tyr Gly Ala Ser Thr Leu Thr Ser
65                       70                      75                      80

Gly Val Pro Ser Arg Phe Arg Gly Ser Gly Ser Gly Thr Gln Phe Thr
                 85                      90                      95

Leu Thr Ile Asn Asp Val Gln Cys Gly Asp Ala Ala Thr Tyr Tyr Cys
             100                     105                     110

Ala Gly Cys Phe Pro Ser Thr Ser Asp Met Tyr Gly Phe Gly Gly Gly
             115                     120                     125

Thr Glu Val Val Val Lys
        130
```

<210> SEQ ID NO 168
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

```
Met Glu Ala Gly Leu Arg Trp Leu Leu Leu Val Ala Val Leu Lys Gly
1                    5                        10                          15

Val Gln Cys Gln Ser Val Glu Glu Ser Gly Gly Arg Leu Val Thr Pro
```

-continued

```
        20              25              30

Gly Thr Pro Leu Thr Leu Thr Cys Thr Val Ser Gly Phe Ser Leu Ser
        35              40              45

Ser Tyr Asp Met Thr Trp Val Arg Gln Ala Pro Gly Lys Gly Leu Glu
    50              55              60

Tyr Ile Gly Val Ile Ser Tyr Gly Gly Ser Ala Tyr Tyr Ala Ser Trp
65              70              75              80

Ala Lys Gly Arg Phe Thr Ile Ser Lys Thr Ser Thr Thr Val Asp Leu
                85              90              95

Lys Ile Thr Ser Pro Thr Thr Glu Asp Thr Ala Thr Tyr Phe Cys Ala
                100             105             110

Arg Gly Asp Ser Asp Gly Ser Ser Glu Leu Phe Asn Leu Trp Gly Gln
        115             120             125

Gly Thr Leu Val Thr Val Ser Ser
    130             135
```

<210> SEQ ID NO 169
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

```
Met Asp Thr Arg Ala Pro Thr Gln Leu Leu Gly Leu Leu Leu Leu Trp
1               5               10              15

Leu Pro Gly Ala Ala Phe Ala Ala Val Leu Thr Gln Thr Pro Ser Pro
                20              25              30

Val Ser Ala Pro Val Gly Gly Thr Val Ser Ile Asn Cys Gln Ser Ser
            35              40              45

Lys Ser Val Tyr Asn Asn Asn Cys Leu Ser Trp Tyr Gln Gln Lys Pro
    50              55              60

Gly Gln Pro Pro Asn Leu Leu Ile Tyr Gly Ala Ser Thr Leu Ala Ser
65              70              75              80

Gly Val Pro Ser Arg Phe Lys Gly Ser Gly Ser Gly Thr Gln Phe Thr
                85              90              95

Leu Thr Ile Asn Asp Val Gln Cys Asp Asp Ala Ala Thr Tyr Tyr Cys
            100             105             110

Ala Gly Cys Phe Ala Ser Thr Asn Asp Met Tyr Gly Phe Gly Gly Gly
        115             120             125

Ser Glu Val Val Val Lys
    130
```

<210> SEQ ID NO 170
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

```
Met Glu Ala Gly Leu Arg Trp Leu Leu Leu Val Ala Val Leu Lys Gly
1               5               10              15

Val Gln Cys Gln Pro Val Glu Glu Ser Gly Gly Arg Leu Val Thr Pro
                20              25              30

Gly Thr Pro Leu Thr Leu Thr Cys Thr Val Ser Gly Phe Ser Leu Ser
```

```
                35                  40                  45

Ser Tyr Asp Met Thr Trp Val Arg Gln Ala Pro Gly Lys Gly Leu Glu
    50                  55                  60

Tyr Ile Gly Val Val Ala Tyr Gly Gly Ala Thr Tyr Tyr Ala Ser Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
                100                 105                 110

Arg Gly Asp Ser Asp Gly Ser Ser Glu Leu Phe Asn Leu Trp Gly Gln
            115                 120                 125

Gly Thr Leu Val Thr Val Ser Ser
    130                 135
```

<210> SEQ ID NO 171
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Ser Pro
                20                  25                  30

Gly Gly Ser Leu Thr Leu Thr Cys Thr Val Ser Gly Ile Asp Leu Ser
            35                  40                  45

Arg Phe Gly Val Ser Trp Val Arg Gln Ala Pro Gly Lys Gly Leu Glu
    50                  55                  60

Trp Thr Gly Tyr Ile His Thr Asp Gly Asn Val Tyr Tyr Ala Ser Trp
65                  70                  75                  80

Ala Lys Gly Arg Phe Thr Ile Ser Lys Thr Ser Thr Thr Val Asp Leu
                85                  90                  95

Lys Met Thr Ser Leu Thr Thr Glu Asp Thr Ala Thr Tyr Phe Cys Ala
                100                 105                 110

Arg Gly Gly Tyr Ala Ala Asp Leu Trp Gly Gln Ala Ala Leu Val Thr
            115                 120                 125

Val Ser Ser
    130
```

<210> SEQ ID NO 172
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

```
Met Asp Thr Arg Ala Pro Thr Gln Leu Leu Gly Leu Leu Leu Leu Trp
1               5                   10                  15

Leu Pro Gly Ala Lys Cys Asp Pro Met Leu Thr Gln Thr Pro Ser Ser
                20                  25                  30

Val Ser Ala Ala Val Gly Gly Thr Val Thr Ile Ser Cys Gln Ser Ser
            35                  40                  45

Glu Ser Val Tyr Lys Asn Tyr Leu Ala Trp Tyr Gln Gln Lys Leu Gly
```

-continued

```
            50                    55                    60

Gln Pro Pro Lys Leu Leu Ile Gly Ala Thr Ser Thr Leu Val Ser Gly
65                    70                    75                    80

Val Pro Ser Arg Phe Lys Gly Ser Gly Ser Arg Thr Gln Phe Ser Leu
                  85                    90                    95

Thr Ile Ser Asp Leu Glu Cys Asp Asp Ala Ala Thr Tyr Tyr Cys Val
              100                   105                   110

Gly Gly Tyr Thr Gly Lys Asn Val Phe Gly Gly Gly Thr Glu Val Val
          115                   120                   125

Val Lys
    130

<210> SEQ ID NO 173
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Met Glu Thr Gly Leu Arg Trp Leu Leu Leu Val Ala Val Leu Lys Gly
1                 5                    10                    15

Val Gln Cys Gln Ser Val Glu Glu Ser Gly Gly Arg Leu Val Thr Pro
              20                    25                    30

Gly Thr Pro Leu Thr Leu Thr Cys Thr Ala Ser Gly Phe Ser Leu Ser
          35                    40                    45

Asn His Tyr Ile Ile Trp Val Arg Gln Thr Pro Gly Lys Gly Leu Glu
      50                    55                    60

Trp Ile Gly Ala Ile Ser Arg Arg Ser Lys Thr Asp Tyr Ala Ser Trp
65                    70                    75                    80

Ala Lys Gly Arg Phe Thr Ile Ser Lys Thr Ser Thr Thr Val Asp Leu
                  85                    90                    95

Lys Ile Thr Ser Pro Thr Thr Glu Asp Thr Ala Thr Tyr Phe Cys Ala
              100                   105                   110

Arg Gln Leu Asp Gly Ser Thr Ser Val Val Cys Asp Ile Trp Gly Pro
          115                   120                   125

Gly Thr Leu Val Thr Val Ser Ser
    130                   135

<210> SEQ ID NO 174
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Met Asp Thr Arg Ala Pro Thr Gln Leu Leu Gly Leu Leu Leu Leu Trp
1                 5                    10                    15

Leu Pro Gly Ala Thr Phe Ala Gln Val Leu Thr Gln Thr Pro Ser Pro
                  20                    25                    30

Val Ser Ala Ala Val Gly Gly Thr Val Thr Ile Asn Cys Gln Ala Ser
          35                    40                    45

Gln Asn Val Tyr Asn Asp Arg Asn Leu Gly Trp Tyr Gln Gln Lys Pro
      50                    55                    60

Gly Gln Pro Pro Lys Leu Leu Ile Tyr Gly Pro Ser Thr Leu Ala Ser
```

-continued

```
65                  70                  75                  80

Gly Val Ser Ser Arg Phe Thr Gly Ser Gly Ser Gly Thr Gln Phe Thr
                85                  90                  95

Leu Thr Ile Ser Asp Leu Gln Cys Asp Asp Ala Ala Thr Tyr Tyr Cys
                100                 105                 110

Gln Gly Glu Phe Ile Cys Ser Ser Ala Asp Cys Cys Ala Phe Gly Gly
            115                 120                 125

Gly Thr Glu Val Val Val Lys
    130                 135

<210> SEQ ID NO 175
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Asp Val Thr Met Ser Trp Val Arg Gln Ala Pro Gly Lys Gly Leu Glu
    50                  55                  60

Trp Ile Gly Ile Ile Gly Arg Arg Gly Arg Ile Trp Tyr Ala Asn Trp
65                  70                  75                  80

Ala Lys Gly Arg Phe Thr Ile Ser Lys Thr Ser Pro Thr Val Asp Leu
                85                  90                  95

Lys Ile Ile Ser Pro Thr Ser Asp Asp Thr Ala Thr Tyr Phe Cys Ala
                100                 105                 110

Arg Gly Ala Val Ser Ser Asp Trp Asn Met Tyr Gly Met Asp Leu Trp
            115                 120                 125

Gly Pro Gly Thr Leu Val Thr Val Ser Ser
    130                 135

<210> SEQ ID NO 176
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
                20                  25                  30

Val Ser Ala Pro Val Gly Gly Thr Val Thr Ile Asn Cys Gln Ser Ser
        35                  40                  45

Gln Ser Val Tyr Asn Asn Glu Asn Leu Ala Trp Tyr Gln Gln Lys Leu
    50                  55                  60

Gly Gln Pro Pro Lys Leu Leu Ile Tyr Gly Ala Ser Thr Leu Ala Ser
65                  70                  75                  80

Gly Val Ser Ser Arg Phe Glu Gly Ser Gly Ser Gly Thr Gln Phe Ala
```

-continued

```
                   85                  90                  95

Leu Thr Ile Ser Gly Val Gln Cys Asp Asp Ala Ala Thr Tyr Tyr Cys
                  100                 105                 110

Gln Gly Glu Phe Asp Cys Ser Ser Ala Asp Cys Phe Ala Phe Gly Gly
         115                 120                 125

Gly Thr Glu Val Val Val Lys
     130                 135

<210> SEQ ID NO 177
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Met Glu Thr Gly Leu Arg Trp Leu Leu Leu Val Ala Val Leu Lys Gly
1               5                  10                  15

Val Gln Cys Gln Ser Val Glu Glu Ser Gly Gly Arg Leu Val Thr Pro
             20                  25                  30

Gly Thr Pro Leu Thr Leu Thr Cys Thr Val Ser Gly Phe Ser Leu Ser
         35                  40                  45

Asp Val Thr Ile Ser Trp Val Arg Gln Ala Pro Gly Lys Gly Leu Lys
     50                  55                  60

Trp Thr Gly Ile Ile Gly Arg Arg Gly Arg Ile Arg Tyr Ala Asp Trp
65                  70                  75                  80

Ala Lys Gly Arg Phe Thr Ile Ser Lys Thr Ser Thr Thr Val Asp Leu
                 85                  90                  95

Lys Ile Thr Ser Pro Thr Thr Asp Asp Thr Ala Thr Tyr Phe Cys Ala
                 100                 105                 110

Arg Ala Tyr Val Ser Ser Asp Trp Asn Ile Tyr Gly Met Asp Leu Trp
         115                 120                 125

Gly Pro Gly Thr Leu Val Thr Val Ser Ser
     130                 135

<210> SEQ ID NO 178
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Met Asp Thr Arg Ala Pro Thr Gln Leu Leu Gly Leu Leu Leu Leu Trp
1               5                  10                  15

Leu Pro Gly Ala Thr Phe Ala Gln Val Leu Thr Gln Thr Ala Ser Pro
             20                  25                  30

Val Ser Ala Pro Val Gly Gly Thr Val Thr Ile Asn Cys Gln Ala Ser
         35                  40                  45

Gln Ser Val Tyr Asn Asn Lys Asn Leu Ala Trp Tyr Gln Gln Lys Leu
     50                  55                  60

Gly Gln Pro Pro Lys Leu Leu Ile Tyr Glu Ala Ser Lys Leu Ala Ser
65                  70                  75                  80

Gly Val Ser Ser Arg Phe Glu Gly Ser Gly Ser Gly Thr Gln Phe Ala
                 85                  90                  95

Leu Thr Ile Ser Gly Val Gln Cys Asp Asp Ala Ala Thr Tyr Tyr Cys
```

```
                  100              105              110
Gln Gly Glu Phe Asp Cys Ser Ser Ala Asp Cys Phe Val Phe Gly Gly
        115              120              125

Gly Thr Glu Val Val Val Lys
    130              135

<210> SEQ ID NO 179
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Met Glu Thr Gly Leu Arg Trp Leu Leu Leu Val Ala Val Leu Lys Gly
1               5               10              15

Val Gln Cys Gln Ser Met Glu Glu Ser Gly Gly Arg Leu Val Thr Pro
            20              25              30

Gly Thr Pro Leu Thr Leu Thr Cys Thr Val Ser Gly Phe Ser Leu Ser
        35              40              45

Asp His Ala Met Ser Trp Val Arg Gln Ala Pro Gly Lys Gly Leu Glu
    50              55              60

Trp Ile Gly Ile Val Gly Arg Arg Gly Arg Thr Tyr Tyr Ala Ser Trp
65              70              75              80

Ala Lys Gly Arg Phe Thr Ile Ser Lys Thr Ser Thr Val Asp Leu
            85              90              95

Lys Ile Thr Ser Pro Thr Ile Glu Asp Thr Ala Thr Tyr Phe Cys Ala
        100             105             110

Arg Gly Tyr Val Ser Ser Asp Trp Asn Ile Tyr Gly Met Asp Leu Trp
        115             120             125

Gly Pro Gly Thr Leu Val Thr Val Ser Ser
    130             135

<210> SEQ ID NO 180
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Met Asp Thr Arg Ala Pro Thr Gln Leu Leu Gly Leu Leu Leu Leu Trp
1               5               10              15

Leu Pro Gly Ala Thr Phe Ala Gln Val Leu Thr Gln Thr Pro Ser Pro
            20              25              30

Val Ser Ala Ala Val Gly Gly Thr Val Thr Ile Asn Cys Gln Ala Ser
        35              40              45

Gln Ser Val Tyr Asn Asn Lys Asn Leu Ala Trp Tyr Gln Gln Lys Pro
    50              55              60

Gly Gln Pro Pro Lys Leu Leu Ile Tyr Glu Ala Ser Thr Leu Ala Ser
65              70              75              80

Gly Val Ser Ser Arg Phe Lys Gly Ser Gly Ser Gly Thr Gln Phe Thr
            85              90              95

Leu Thr Ile Ser Gly Val Gln Cys Asp Asp Ala Ala Thr Tyr Tyr Cys
        100             105             110

Gln Gly Glu Phe Asp Cys Ser Ser Ala Asp Cys Phe Ala Phe Gly Gly
```

-continued

```
                115                 120                 125

Gly Thr Glu Val Val Val Lys
    130                 135

<210> SEQ ID NO 181
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Thr Leu Thr Cys Thr Ala Ser Gly Phe Ser Leu Ser
        35                  40                  45

Asp Asp Ala Met Ser Trp Val Arg Gln Ala Pro Gly Lys Gly Leu Glu
    50                  55                  60

Trp Ile Gly Ile Ile Gly Arg Arg Gly Lys Thr Trp Tyr Ala Asn Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
                100                 105                 110

Arg Gly Tyr Val Ser Ser Asp Trp Asn Ile Tyr Gly Met Asp Leu Trp
        115                 120                 125

Gly Pro Gly Thr Leu Val Thr Val Ser Ala
    130                 135

<210> SEQ ID NO 182
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
                20                  25                  30

Val Ser Ala Ala Val Gly Gly Thr Val Thr Ile Asn Cys Gln Ala Ser
        35                  40                  45

Gln Ser Val Tyr Asn Asn Lys Asn Leu Ala Trp Tyr Gln Gln Lys Ser
    50                  55                  60

Gly Gln Pro Pro Lys Leu Leu Ile Tyr Glu Ala Ser Lys Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
                100                 105                 110

Gln Gly Glu Phe Ser Cys Ser Ser Ala Asp Cys Phe Thr Phe Gly Gly
        115                 120                 125

Gly Thr Glu Val Val Val Lys
```

-continued

```
     130              135
```

<210> SEQ ID NO 183
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

```
Met Glu Thr Gly Leu Arg Trp Leu Leu Leu Val Ala Val Leu Lys Gly
1               5                   10                  15

Gly Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Ser Asp Ile Asn
        35                  40                  45

Lys Tyr Thr Met Gly Trp Val Arg Gln Ala Pro Gly Lys Gly Leu Glu
    50                  55                  60

Trp Val Gly Ala Ile Gly Ala Thr Gly Arg Thr Val Tyr Ala Asn Trp
65                  70                  75                  80

Ala Lys Gly Arg Phe Thr Ile Ser Lys Thr Ser Thr Thr Val Asp Leu
                85                  90                  95

Ile Ile Thr Ser Pro Thr Thr Glu Asp Thr Ala Thr Tyr Phe Cys Ala
            100                 105                 110

Arg Asn Val Val Asp Ala Ser Asp Ser Asp Gly Met Ile Ala Phe Asp
        115                 120                 125

Pro Trp Gly Pro Gly Thr Leu Val Thr Val Ser Ser
    130                 135                 140
```

<210> SEQ ID NO 184
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ala Ser
        35                  40                  45

Gln Ser Val Tyr Asn Asn Lys Asn Leu Ala Trp Tyr Gln Gln Lys Pro
    50                  55                  60

Gly Gln Pro Pro Lys Leu Leu Ile Tyr Lys Ala Ser Thr Leu Ala Ser
65                  70                  75                  80

Gly Val Pro Ser Arg Phe Ala Gly Ser Gly Ser Gly Thr Glu Val Thr
                85                  90                  95

Leu Thr Ile Ser Asp Leu Glu Cys Asp Asp Ala Ala Thr Tyr Tyr Cys
            100                 105                 110

Gln Gly Glu Phe Ser Cys Ser Ser Gly Asp Cys Val Ala Phe Gly Gly
        115                 120                 125

Gly Thr Glu Val Val Val Lys
    130                 135
```

```
<210> SEQ ID NO 185
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Gly Ser Leu Thr Leu Thr Cys Thr Val Ser Gly Ile Asp Leu Ser
        35                  40                  45

Ser Asn Ala Met Gly Trp Val Arg Gln Ala Pro Gly Glu Gly Leu Glu
    50                  55                  60

Trp Ile Gly Ser Ile Tyr Ala Ser Gly Asn Thr Tyr Tyr Ala Ser Trp
65                  70                  75                  80

Ala Lys Gly Arg Phe Ala Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Leu Phe Asn Ile Trp Gly Pro Gly Thr Leu Val Thr Val Ser Ser
            115                 120                 125

<210> SEQ ID NO 186
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Met Asp Thr Arg Ala Pro Thr Gln Leu Leu Gly Leu Leu Leu Leu Trp
1               5                   10                  15

Leu Pro Gly Ala Arg Cys Ala Asp Ile Val Leu Thr Gln Thr Pro Ala
            20                  25                  30

Ser Val Ser Ser Val Val Gly Gly Thr Val Thr Ile Asn Cys Gln Ala
        35                  40                  45

Ser Gln Ser Val Phe Asp Asn Lys Asn Leu Ser Trp Phe Gln Gln Lys
    50                  55                  60

Pro Gly Gln Pro Pro Lys Gln Leu Ile Tyr Gly Ala Ser Thr Leu Asp
65                  70                  75                  80

Ser Gly Val Pro Ser Arg Phe Lys Gly Ser Gly Ser Gly Thr Gln Phe
                85                  90                  95

Thr Leu Thr Ile Ser Asp Met Gln Cys Asp Asp Ala Ala Thr Tyr Tyr
            100                 105                 110

Cys Gly Gly Arg Asp Ser Gly Asn Ile Tyr Asp Phe Gly Gly Gly Thr
            115                 120                 125

Glu Val Val Val Lys
    130

<210> SEQ ID NO 187
<211> LENGTH: 128
<212> TYPE: PRT
<213> ORGANISM: Artificial Sequence
<220> FEATURE:
<223> OTHER INFORMATION: Description of Artificial Sequence: Synthetic
```

```
    polypeptide

<400> SEQUENCE: 187

Met Glu Thr Gly Leu Arg Trp Leu Leu Leu Val Ala Val Leu Lys Gly
1               5                   10                  15

Val Gln Cys Gln Glu Leu Lys Glu Ser Gly Gly Arg Leu Val Thr Pro
            20                  25                  30

Gly Gly Ser Leu Thr Leu Ser Cys Thr Ala Ser Gly Ile Asp Leu Ser
        35                  40                  45

Gly Ser Ala Met Gly Trp Val Arg Gln Ala Pro Gly Gln Gly Leu Glu
    50                  55                  60

Trp Ile Gly Ser Ile Tyr Val Ser Gly Asn Thr Tyr Tyr Ala Ser Trp
65                  70                  75                  80

Ala Lys Gly Arg Phe Ala Ile Ser Arg Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Leu Leu Asn Ile Trp Gly Pro Gly Thr Leu Val Thr Val Ser Ser
        115                 120                 125

<210> SEQ ID NO 188
<211> LENGTH: 133
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 188

Met Asp Thr Arg Ala Pro Thr Gln Leu Leu Gly Leu Leu Leu Leu Trp
1               5                   10                  15

Leu Pro Gly Ala Arg Cys Ala Asp Ile Val Leu Thr Gln Thr Pro Ser
            20                  25                  30

Pro Val Ser Ile Ala Val Gly Gly Thr Val Thr Ile Asn Cys Gln Ala
        35                  40                  45

Ser Gln Ser Val Tyr Asp Asn Lys Asn Leu Ala Trp Phe Gln Gln Lys
    50                  55                  60

Pro Gly Gln Pro Pro Lys Gln Leu Ile Tyr Gly Ala Ser Thr Leu Ala
65                  70                  75                  80

Ser Gly Val Pro Ser Arg Phe Lys Gly Ser Gly Ser Gly Thr Gln Phe
                85                  90                  95

Thr Leu Thr Ile Ser Gly Met Gln Cys Asp Asp Ala Ala Thr Tyr Tyr
            100                 105                 110

Cys Gly Gly Arg Asp Ser Asp Asn Ile Tyr Asp Phe Gly Gly Gly Thr
        115                 120                 125

Glu Val Val Val Lys
    130

<210> SEQ ID NO 189
<211> LENGTH: 128
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 189

Met Glu Thr Gly Leu Arg Trp Leu Leu Leu Val Ala Val Leu Lys Gly
1               5                   10                  15
```

-continued

```
Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
            35                  40                  45

Asn Asn Ala Met Gly Trp Val Arg Gln Ala Pro Gly Glu Gly Leu Glu
        50                  55                  60

Trp Ile Gly Thr Ile Tyr Ala Ser Gly Asn Thr Tyr Tyr Ala Ser Trp
65                  70                  75                  80

Ala Lys Gly Arg Phe Ala Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Leu Phe Asn Ile Trp Gly Pro Gly Thr Leu Val Thr Val Ser Ser
        115                 120                 125
```

<210> SEQ ID NO 190
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

```
Met Asp Thr Arg Ala Pro Thr Gln Leu Leu Gly Leu Leu Leu Leu Trp
1               5                   10                  15

Leu Pro Gly Ala Arg Cys Ala Asp Ile Val Leu Thr Gln Ser Pro Ala
            20                  25                  30

Ser Val Ser Ser Ala Val Gly Gly Thr Val Thr Ile Asn Cys Gln Ala
            35                  40                  45

Ser Gln Ser Val Tyr Asp Asn Lys Asn Leu Ser Trp Phe Gln Gln Lys
        50                  55                  60

Pro Gly Gln Pro Pro Lys Gln Leu Ile Tyr Ala Ala Ser Thr Leu Ala
65                  70                  75                  80

Ser Gly Val Pro Ser Arg Phe Lys Gly Ser Gly Ser Gly Thr Gln Phe
                85                  90                  95

Thr Leu Thr Ile Ser Gly Met Gln Cys Asp Asp Ala Ala Thr Tyr Tyr
            100                 105                 110

Cys Gly Gly Arg Asp Ser Gly Asn Ile Tyr Asp Phe Gly Gly Gly Thr
            115                 120                 125

Glu Val Val Val Lys
        130
```

<210> SEQ ID NO 191
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ile Asp Leu Ser
            35                  40                  45
```

```
Ser Asn Ala Met Gly Trp Val Arg Gln Ala Pro Gly Glu Gly Leu Gln
    50                  55                  60

Trp Ile Gly Ser Ile Tyr Ser Ser Gly Asn Thr Tyr Tyr Ala Ser Trp
65                  70                  75                  80

Ala Arg Gly Arg Phe Ala Ile Ser Arg Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Leu Phe Asn Ile Trp Gly Pro Gly Thr Leu Val Thr Val Ser Ser
        115                 120                 125
```

<210> SEQ ID NO 192
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

```
Met Asp Thr Arg Ala Pro Thr Gln Leu Leu Gly Leu Leu Leu Leu Trp
1                   5                   10                  15

Leu Pro Gly Ala Arg Cys Ala Asp Ile Val Val Thr Gln Thr Pro Ala
                20                  25                  30

Ser Val Ser Ala Asp Val Gly Gly Thr Val Thr Ile Asn Cys Gln Ala
            35                  40                  45

Ser Gln Ser Val Tyr Asp Asn Lys Asn Leu Ala Trp Phe Gln Gln Lys
    50                  55                  60

Pro Gly Gln Pro Pro Lys Gln Leu Ile Tyr Gly Ala Ser Thr Val Ala
65                  70                  75                  80

Ser Gly Val Pro Ser Arg Phe Lys Gly Ser Gly Ser Gly Thr Gln Phe
                85                  90                  95

Thr Leu Thr Ile Ser Asp Val Gln Cys Asp Asp Ala Ala Thr Tyr Tyr
            100                 105                 110

Cys Gly Gly Arg Asp Asn Asp Asn Ile Tyr Asp Phe Gly Gly Gly Thr
        115                 120                 125

Glu Val Val Val Lys
    130
```

<210> SEQ ID NO 193
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

```
Met Glu Thr Gly Leu Arg Trp Leu Leu Leu Val Ala Val Leu Lys Gly
1                   5                   10                  15

Val Gln Cys Gln Ser Val Glu Glu Ser Gly Gly Arg Leu Val Thr Pro
                20                  25                  30

Gly Thr Pro Leu Thr Leu Thr Cys Thr Val Ser Gly Ile Asp Leu Ser
            35                  40                  45

Ser Asn Ala Val Gly Trp Val Arg Gln Ala Pro Gly Glu Gly Leu Glu
    50                  55                  60

Trp Ile Gly Ser Ile Tyr Ser Ser Gly Asn Ser Tyr Tyr Ala Ser Trp
65                  70                  75                  80
```

-continued

```
Ala Lys Gly Arg Phe Ala Ile Ser Arg Thr Ser Thr Thr Val Asp Leu
            85                  90                  95

Lys Met Thr Arg Leu Thr Ala Ala Asp Thr Ala Thr Tyr Phe Cys Ala
            100                 105                 110

Arg Leu Phe Asn Ile Trp Gly Pro Gly Thr Leu Val Thr Val Ser
        115                 120                 125

<210> SEQ ID NO 194
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Met Asp Thr Arg Ala Pro Thr Gln Leu Leu Gly Leu Leu Leu Leu Trp
1               5                   10                  15

Leu Pro Gly Ala Arg Cys Ala Asp Ile Val Leu Thr Gln Thr Pro Ala
            20                  25                  30

Ser Val Ser Ser Val Val Gly Gly Thr Val Ala Ile Asn Cys Gln Ala
        35                  40                  45

Ser Gln Ser Val Tyr Asp Asn Lys Asn Leu Ser Trp Phe Gln Gln Lys
    50                  55                  60

Pro Gly Gln Thr Pro Lys Gln Leu Ile Tyr Gly Ala Ser Thr Leu Ala
65                  70                  75                  80

Ser Gly Val Pro Ser Arg Phe Lys Gly Ser Gly Ser Gly Thr Gln Phe
            85                  90                  95

Thr Leu Thr Ile Ser Gly Val Gln Cys Asp Asp Ala Ala Thr Tyr Tyr
            100                 105                 110

Cys Gly Gly Arg Asp Asp Asp Asn Ile Tyr Asp Phe Gly Gly Gly Thr
        115                 120                 125

Glu Val Val Val Lys
    130

<210> SEQ ID NO 195
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Gly Ser Leu Thr Leu Thr Cys Thr Val Ser Gly Phe Ser Leu Ser
        35                  40                  45

Thr His Asp Ile Ser Trp Val Arg Gln Ala Pro Gly Lys Gly Leu Glu
    50                  55                  60

Trp Ile Gly Val Ile Ala Arg Arg Gly Trp Thr Tyr Tyr Ala Ser Trp
65                  70                  75                  80

Ala Lys Gly Arg Phe Thr Ile Ser Lys Thr Ser Thr Thr Val Asp Leu
            85                  90                  95

Lys Ile Thr Ser Pro Thr Ile Glu Asp Thr Ala Thr Tyr Phe Cys Ala
            100                 105                 110
```

```
Arg Glu Glu Phe Asp Phe Trp Gly Gln Gly Thr Leu Val Thr Val Ser
        115                 120                 125

Ser

<210> SEQ ID NO 196
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Gly Ser Leu Thr Leu Thr Cys Thr Val Ser Gly Phe Ser Leu Ser
        35                  40                  45

Thr His Asp Ile Ser Trp Val Arg Gln Ala Pro Gly Lys Gly Leu Glu
    50                  55                  60

Trp Ile Gly Val Ile Ala Arg Arg Gly Trp Thr Tyr Tyr Ala Ser Trp
65                  70                  75                  80

Ala Lys Lys Arg Phe Thr Ile Ser Lys Thr Ser Thr Thr Val Asp Leu
                85                  90                  95

Lys Ile Thr Ser Pro Thr Ile Glu Asp Thr Ala Thr Tyr Phe Cys Ala
            100                 105                 110

Arg Glu Glu Phe Asp Phe Trp Gly Gln Gly Thr Leu Val Thr Val Ser
        115                 120                 125

Ser

<210> SEQ ID NO 197
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Ala Ser Pro
            20                  25                  30

Val Ser Ala Ala Val Gly Gly Thr Val Thr Ile Ser Cys Gln Ser Ser
        35                  40                  45

Gln Ser Val Tyr Asn Asn Lys Glu Leu Ser Trp Phe Gln Gln Lys Pro
    50                  55                  60

Gly Gln Pro Pro Lys Leu Leu Ile Ser Tyr Ala Ser Thr Leu Ala Thr
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Leu Gly Gly Tyr Ala Ser Thr Ile Asp Met Trp Ala Phe Gly Gly Gly
        115                 120                 125

Thr Glu Val Val Val Lys
```

-continued

130

```
<210> SEQ ID NO 198
<211> LENGTH: 16
<212> TYPE: PRT
<213> ORGANISM: Unknown
<220> FEATURE:
<223> OTHER INFORMATION: Description of Unknown:
      peptide 1593 sequence

<400> SEQUENCE: 198

Thr Asp Ala Ala Thr Leu Ala Gln Glu Ala Gly Asn Phe Glu Arg Cys
1               5                   10                  15

<210> SEQ ID NO 199
<211> LENGTH: 19
<212> TYPE: PRT
<213> ORGANISM: Unknown
<220> FEATURE:
<223> OTHER INFORMATION: Description of Unknown:
      peptide 2004 sequence

<400> SEQUENCE: 199

Thr Gln Ile Asp Gln Val Glu Ser Thr Ala Gly Ser Leu Gln Gly Gln
1               5                   10                  15

Trp Arg Cys

<210> SEQ ID NO 200
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Met Gly Trp Asn Tyr Ile Ile Phe Phe Leu Ala Ala Thr Ala Thr Gly
1               5                   10                  15

Val His Ser Gln Ser Leu Glu Glu Ser Gly Gly Arg Leu Val Thr Pro
            20                  25                  30

Gly Gly Ser Leu Thr Leu Thr Cys Thr Val Ser Gly Phe Ser Leu Ser
        35                  40                  45

Thr His Asp Ile Ser Trp Val Arg Gln Ala Pro Gly Lys Gly Leu Glu
    50                  55                  60

Trp Ile Gly Val Ile Ala Arg Arg Gly Trp Thr Tyr Tyr Ala Ser Trp
65                  70                  75                  80

Ala Lys Lys Arg Phe Thr Ile Ser Lys Thr Ser Thr Thr Val Asp Leu
                85                  90                  95

Lys Ile Thr Ser Pro Thr Ile Glu Asp Thr Ala Thr Tyr Phe Cys Ala
                100                 105                 110

Arg Glu Glu Phe Asp Phe Trp Gly Gln Gly Thr Leu Val Thr Val Ser
            115                 120                 125

Ser Gly Gln Pro Lys Ala Pro Ser Val Phe Pro Leu Ala Pro Cys Cys
        130                 135                 140

Gly Asp Thr Pro Ser Ser Thr Val Thr Leu Gly Cys Leu Val Lys Gly
145                 150                 155                 160

Tyr Leu Pro Glu Pro Val Thr Val Thr Trp Asn Ser Gly Thr Leu Thr
                165                 170                 175

Asn Gly Val Arg Thr Phe Pro Ser Val Arg Gln Ser Ser Gly Leu Tyr
            180                 185                 190
```

-continued

```
Ser Leu Ser Ser Val Val Ser Val Thr Ser Ser Ser Gln Pro Val Thr
        195                 200                 205

Cys Asn Val Ala His Pro Ala Thr Asn Thr Lys Val Asp Lys Thr Val
    210                 215                 220

Ala Pro Ser Thr Cys Ser Lys Pro Thr Cys Pro Pro Pro Glu Leu Leu
225                 230                 235                 240

Gly Gly Pro Ser Val Phe Ile Phe Pro Pro Lys Pro Lys Asp Thr Leu
                245                 250                 255

Met Ile Ser Arg Thr Pro Glu Val Thr Cys Val Val Val Asp Val Ser
                260                 265                 270

Gln Asp Asp Pro Glu Val Gln Phe Thr Trp Tyr Ile Asn Asn Glu Gln
            275                 280                 285

Val Arg Thr Ala Arg Pro Pro Leu Arg Glu Gln Gln Phe Asn Ser Thr
    290                 295                 300

Ile Arg Val Val Ser Thr Leu Pro Ile Ala His Gln Asp Trp Leu Arg
305                 310                 315                 320

Gly Lys Glu Phe Lys Cys Lys Val His Asn Lys Ala Leu Pro Ala Pro
                325                 330                 335

Ile Glu Lys Thr Ile Ser Lys Ala Arg Gly Gln Pro Leu Glu Pro Lys
            340                 345                 350

Val Tyr Thr Met Gly Pro Pro Arg Glu Glu Leu Ser Ser Arg Ser Val
            355                 360                 365

Ser Leu Thr Cys Met Ile Asn Gly Phe Tyr Pro Ser Asp Ile Ser Val
    370                 375                 380

Glu Trp Glu Lys Asn Gly Lys Ala Glu Asp Asn Tyr Lys Thr Thr Pro
385                 390                 395                 400

Ala Val Leu Asp Ser Asp Gly Ser Tyr Phe Leu Tyr Ser Lys Leu Ser
                405                 410                 415

Val Pro Thr Ser Glu Trp Gln Arg Gly Asp Val Phe Thr Cys Ser Val
                420                 425                 430

Met His Glu Ala Leu His Asn His Tyr Thr Gln Lys Ser Ile Ser Arg
            435                 440                 445

Ser Pro Gly Lys
    450
```

```
<210> SEQ ID NO 201
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201
```

```
Met Gly Trp Asn Tyr Ile Ile Phe Phe Leu Ala Ala Thr Ala Thr Gly
1               5                   10                  15

Val His Ser Gln Ser Leu Glu Glu Ser Gly Gly Arg Leu Val Thr Pro
            20                  25                  30

Gly Gly Ser Leu Thr Leu Thr Cys Thr Val Ser Gly Phe Ser Leu Ser
            35                  40                  45

Thr His Asp Ile Ser Trp Val Arg Gln Ala Pro Gly Lys Gly Leu Glu
    50                  55                  60

Trp Ile Gly Val Ile Ala Arg Arg Gly Trp Thr Tyr Tyr Ala Ser Trp
65                  70                  75                  80

Ala Lys Gly Arg Phe Thr Ile Ser Lys Thr Ser Thr Thr Val Asp Leu
                85                  90                  95
```

```
Lys Ile Thr Ser Pro Thr Ile Glu Asp Thr Ala Thr Tyr Phe Cys Ala
            100                 105                 110

Arg Glu Glu Phe Asp Phe Trp Gly Gln Gly Thr Leu Val Thr Val Ser
            115                 120                 125

Ser Gly Gln Pro Lys Ala Pro Ser Val Phe Pro Leu Ala Pro Cys Cys
            130                 135                 140

Gly Asp Thr Pro Ser Ser Thr Val Thr Leu Gly Cys Leu Val Lys Gly
145                 150                 155                 160

Tyr Leu Pro Glu Pro Val Thr Val Thr Trp Asn Ser Gly Thr Leu Thr
                165                 170                 175

Asn Gly Val Arg Thr Phe Pro Ser Val Arg Gln Ser Ser Gly Leu Tyr
            180                 185                 190

Ser Leu Ser Ser Val Val Ser Val Thr Ser Ser Gln Pro Val Thr
            195                 200                 205

Cys Asn Val Ala His Pro Ala Thr Asn Thr Lys Val Asp Lys Thr Val
    210                 215                 220

Ala Pro Ser Thr Cys Ser Lys Pro Thr Cys Pro Pro Glu Leu Leu
225                 230                 235                 240

Gly Gly Pro Ser Val Phe Ile Phe Pro Pro Lys Pro Lys Asp Thr Leu
                245                 250                 255

Met Ile Ser Arg Thr Pro Glu Val Thr Cys Val Val Val Asp Val Ser
                260                 265                 270

Gln Asp Asp Pro Glu Val Gln Phe Thr Trp Tyr Ile Asn Asn Glu Gln
            275                 280                 285

Val Arg Thr Ala Arg Pro Pro Leu Arg Glu Gln Gln Phe Asn Ser Thr
            290                 295                 300

Ile Arg Val Val Ser Thr Leu Pro Ile Ala His Gln Asp Trp Leu Arg
305                 310                 315                 320

Gly Lys Glu Phe Lys Cys Lys Val His Asn Lys Ala Leu Pro Ala Pro
                325                 330                 335

Ile Glu Lys Thr Ile Ser Lys Ala Arg Gly Gln Pro Leu Glu Pro Lys
                340                 345                 350

Val Tyr Thr Met Gly Pro Pro Arg Glu Glu Leu Ser Ser Arg Ser Val
            355                 360                 365

Ser Leu Thr Cys Met Ile Asn Gly Phe Tyr Pro Ser Asp Ile Ser Val
    370                 375                 380

Glu Trp Glu Lys Asn Gly Lys Ala Glu Asp Asn Tyr Lys Thr Thr Pro
385                 390                 395                 400

Ala Val Leu Asp Ser Asp Gly Ser Tyr Phe Leu Tyr Ser Lys Leu Ser
                405                 410                 415

Val Pro Thr Ser Glu Trp Gln Arg Gly Asp Val Phe Thr Cys Ser Val
                420                 425                 430

Met His Glu Ala Leu His Asn His Tyr Thr Gln Lys Ser Ile Ser Arg
            435                 440                 445

Ser Pro Gly Lys
    450
```

<210> SEQ ID NO 202
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Met Arg Ala Pro Ala Gln Ile Phe Gly Phe Leu Leu Leu Leu Phe Pro
1               5                   10                  15

Gly Ile Arg Cys Ala Val Leu Thr Gln Thr Ala Ser Pro Val Ser Ala
            20                  25                  30

Ala Val Gly Gly Thr Val Thr Ile Ser Cys Gln Ser Ser Gln Ser Val
        35                  40                  45

Tyr Asn Asn Lys Glu Leu Ser Trp Phe Gln Gln Lys Pro Gly Gln Pro
    50                  55                  60

Pro Lys Leu Leu Ile Ser Tyr Ala Ser Thr Leu Ala Thr Gly Val Pro
65                  70                  75                  80

Ser Arg Phe Lys Gly Ser Gly Ser Gly Thr Gln Phe Thr Leu Thr Ile
                85                  90                  95

Ser Asp Leu Glu Cys Asp Asp Ala Ala Thr Tyr Tyr Cys Leu Gly Gly
            100                 105                 110

Tyr Ala Ser Thr Ile Asp Met Trp Ala Phe Gly Gly Gly Thr Glu Val
        115                 120                 125

Val Val Lys Gly Asp Pro Val Ala Pro Thr Val Leu Ile Phe Pro Pro
    130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
        195                 200                 205

Tyr Asn Ser His Lys Glu Tyr Thr Cys Lys Val Thr Gln Gly Thr Thr
    210                 215                 220

Ser Val Val Gln Ser Phe Asn Arg Gly Asp Cys
225                 230                 235

<210> SEQ ID NO 203
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
atgggatgga actatatcat tttctttttg gcagcaacag ctacaggtgt ccactcccag      60
agcctcgagg agagcggcgg cagactggtg acccctggcg gatctctgac cctgacatgt     120
accgtgtccg gcttcagcct gagcacccac gatatcagct gggtcagaca ggcccctggc     180
aagggcctgg aatggatcgg cgtgatcgcc cggagaggat ggacatacta cgcctcttgg     240
gctaagaaaa gatttacaat tagcaagacc tccactaccg tggacctgaa gatcaccagc     300
cccacaatcg aggacaccgc cacctacttc tgcgcccggg aagagttcga cttctgggga     360
cagggcaccc tggtgacagt gtctagcggc cagcccaagg cacctagcgt gttcccactg     420
gcaccatgct gtgggggacac cccatctagt actgtcaccc tgggctgcct ggtgaaaggg     480
tatctgcccg agcctgtcac agtgacttgg aacagcggaa ccctgacaaa tggcgtccga     540
acatttcctt ccgtgcggca gtcaagcggc ctgtactctc tgtcctctgt ggtcagtgtg     600
acaagttcaa gccagccagt cacttgtaac gtggcacatc ccgccactaa taccaaggtc     660

-continued gataaaactg tggcccctc aacctgcagc aagcctacat gtccacctcc agagctgctg          720
ggaggacctt ccgtgttcat ctttcccct aagccaaaag acaccctgat gatttctcgc          780 accccgaag tcacatgcgt ggtcgtggat gtgagtcagg acgatcctga ggtccagttc          840
acctggtata tcaacaatga acaggtgagg acagcacgac caccactgcg agagcagcag          900
tttaactcaa ctatccgagt cgtgagcacc ctgccaattg ctcaccagga ctggctgagg          960
ggcaaggagt tcaagtgcaa agtgcataac aaggccctgc cagcacccat cgagaagaca          1020
atttctaaag cccgcggaca gcctctggaa ccaaaggtgt acactatggg ccctccaaga          1080
gaggaactgt cctctaggag cgtctccctg acctgtatga tcaacgggtt ttatccctcc          1140
gacatttctg tggagtggga aaagaacgga aaagccgagg ataattacaa gacaactcca          1200
gctgtgctgg acagtgatgg atcatatttc ctgtacagca aactgtccgt gcccactagt          1260
gaatggcaga gaggcgatgt ctttacctgt tcagtgatgc acgaggcact gcacaatcac          1320
tacactcaga agtccatctc aagaagccca gggaaatgat aa                            1362

<210> SEQ ID NO 204
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
atgggatgga actatatcat tttctttttg gcagcaacag ctacaggtgt ccactcccag           60
agcctggaag agagcggcgg aagactcgtg accctggag gatctctgac cctgacatgt          120
accgtgtccg gctttagcct gagcacacac gatatcagct gggtgcggca ggcccctggc          180
aagggcctgg aatggatcgg cgtgatcgcc agacggggct ggacctacta cgccagctgg          240
gctaaaggca gattcaccat ttctaagacc tccaccacag tggacctgaa gatcaccagc          300
cccacaatcg aggacaccgc cacatacttc tgcgccagag aggagttcga cttctggggc          360 cagggcacccc tggtcacagt gtctagcggc cagcccaagg cacctagcgt gttcccactg          420
gcaccatgct gtgggggacac cccatctagt actgtcaccc tgggctgcct ggtgaaaggg          480
tatctgcccg agcctgtcac agtgacttgg aacagcggaa ccctgacaaa tggcgtccga          540
acatttcctt ccgtgcggca gtcaagcggc ctgtactctc tgtcctctgt ggtcagtgtg          600
acaagttcaa gccagccagt cacttgtaac gtggcacatc ccgccactaa taccaaggtc          660
gataaaactg tggcccctc aacctgcagc aagcctacat gtccacctcc agagctgctg          720
ggaggacctt ccgtgttcat ctttcccct aagccaaaag acaccctgat gatttctcgc          780 accccgaag tcacatgcgt ggtcgtggat gtgagtcagg acgatcctga ggtccagttc          840
acctggtata tcaacaatga acaggtgagg acagcacgac caccactgcg agagcagcag          900
tttaactcaa ctatccgagt cgtgagcacc ctgccaattg ctcaccagga ctggctgagg          960
ggcaaggagt tcaagtgcaa agtgcataac aaggccctgc cagcacccat cgagaagaca          1020
atttctaaag cccgcggaca gcctctggaa ccaaaggtgt acactatggg ccctccaaga          1080
gaggaactgt cctctaggag cgtctccctg acctgtatga tcaacgggtt ttatccctcc          1140
gacatttctg tggagtggga aaagaacgga aaagccgagg ataattacaa gacaactcca          1200
gctgtgctgg acagtgatgg atcatatttc ctgtacagca aactgtccgt gcccactagt          1260
gaatggcaga gaggcgatgt ctttacctgt tcagtgatgc acgaggcact gcacaatcac          1320
tacactcaga agtccatctc aagaagccca gggaaatgat aa                          1362

<210> SEQ ID NO 205
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
atgagggctc ctgcacagat ttttggcttc ttgttgctct tgtttccagg tatcagatgt        60
gctgtgctca cccagaccgc cagccctgtg tccgccgctg tgggcggcac agtgaccatc       120
agctgtcagt ccagccagag cgtgtacaac aacaaggagc tgagctggtt ccagcagaaa       180
cctggccagc ctccaaagct gctgatcagc tacgcctcta ccctggccac cggcgtgccc       240
agcagattca agggctctgg cagcggcacc caatttaccc tgacaatctc tgatctggaa       300
tgcgacgacg ccgccacata ctactgcctg ggcggatatg ccagcacaat cgacatgtgg       360
gccttcggcg gaggaaccga ggtggtggtc aaggggatc ctgtggcacc aactgtcctg        420
atctttccac ccgctgcaga ccaggtggca actggcaccg tcacaattgt ctgcgtggcc       480
aataagtact ttccagacgt gactgtgacc tgggaggtgg atggcactac ccagacaact       540
gggattgaaa acagcaaaac tccccagaac tccgctgatt gtacctataa cctgtctagt       600
acactgactc tgaccagtac acagtacaat tcacacaagg aatatacctg taaggtgacc       660
cagggcacaa caagcgtcgt ccagtctttc aacaggggg attgctaata a               711

<210> SEQ ID NO 206
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Ser Thr His Asp
            20                  25                  30

Ile Ser Trp Val Arg Gln Ala Pro Gly Lys Gly Leu Glu Trp Ile Gly
        35                  40                  45

Val Ile Ala Arg Arg Gly Ser Thr Tyr Tyr Ala Ser Trp Ala Arg Gly
    50                  55                  60

Arg Phe Thr Ile Ser Lys Thr Ser Thr Thr Val Asp Leu Lys Ile Thr
65                  70                  75                  80

Ser Pro Thr Ile Glu Asp Thr Ala Thr Tyr Phe Cys Ala Arg Glu Glu
                85                  90                  95

Phe Asp Phe Trp Gly Gln Gly Thr Leu Val Thr Val Ser Ser
                100                 105                 110

<210> SEQ ID NO 207
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Ala Val Leu Thr Gln Thr Ala Ser Pro Val Ser Ala Ala Val Gly Gly
1               5                   10                  15

Thr Val Thr Ile Ser Cys Gln Gly Ser Gln Ser Val Tyr Asn Asn Lys
                20                  25                  30

Glu Leu Ser Trp Phe Gln Gln Lys Pro Gly Gln Pro Pro Lys Leu Leu
            35                  40                  45

Ile Ser Tyr Ala Ser Thr Leu Ala Ser Gly Val Pro Ser Arg Phe Lys
        50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 208
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Ala Val Leu Thr Gln Thr Ala Ser Pro Val Ser Ala Ala Val Gly Gly
1               5                   10                  15

Thr Val Thr Ile Ser Cys Gln Met Ser Gln Ser Val Tyr Asn Asn Lys
                20                  25                  30

Glu Leu Ser Trp Phe Gln Gln Lys Pro Gly Gln Pro Pro Lys Leu Leu
            35                  40                  45

Ile Ser Tyr Ala Ser Thr Leu Ala Ser Gly Val Pro Ser Arg Phe Lys
        50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 209
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Ala Val Leu Thr Gln Thr Ala Ser Pro Val Ser Ala Ala Val Gly Gly
1               5                   10                  15

Thr Val Thr Ile Ser Cys Gln Thr Ser Gln Ser Val Tyr Asn Asn Lys
                20                  25                  30

Glu Leu Ser Trp Phe Gln Gln Lys Pro Gly Gln Pro Pro Lys Leu Leu
            35                  40                  45

Ile Ser Tyr Ala Ser Thr Leu Ala Ser Gly Val Pro Ser Arg Phe Lys
        50                  55                  60

Gly Ser Gly Ser Gly Thr Gln Phe Thr Leu Thr Ile Ser Asp Leu Glu

-continued

```
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 210
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Ala Val Leu Thr Gln Thr Ala Ser Pro Val Ser Ala Ala Val Gly Gly
1               5                   10                  15

Thr Val Thr Ile Ser Cys Gln Ser Ala Gln Ser Val Tyr Asn Asn Lys
            20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 211
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Ala Val Leu Thr Gln Thr Ala Ser Pro Val Ser Ala Ala Val Gly Gly
1               5                   10                  15

Thr Val Thr Ile Ser Cys Gln Ser Arg Gln Ser Val Tyr Asn Asn Lys
            20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 212
<211> LENGTH: 111
<212> TYPE: PRT
<213> ORGANISM: Artificial Sequence
<220> FEATURE:
<223> OTHER INFORMATION: Description of Artificial Sequence: Synthetic
```

-continued

_____ polypeptide

<400> SEQUENCE: 212

Ala Val Leu Thr Gln Thr Ala Ser Pro Val Ser Ala Ala Val Gly Gly
1               5                   10                  15

Thr Val Thr Ile Ser Cys Gln Ser Leu Gln Ser Val Tyr Asn Asn Lys
            20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 213
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Ala Val Leu Thr Gln Thr Ala Ser Pro Val Ser Ala Ala Val Gly Gly
1               5                   10                  15

Thr Val Thr Ile Ser Cys Gln Ser Thr Gln Ser Val Tyr Asn Asn Lys
            20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 214
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Ala Val Leu Thr Gln Thr Ala Ser Pro Val Ser Ala Ala Val Gly Gly
1               5                   10                  15

Thr Val Thr Ile Ser Cys Gln Ser His Gln Ser Val Tyr Asn Asn Lys
            20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

```
Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
                100                 105                 110
```

```
<210> SEQ ID NO 215
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215
```

```
Ala Val Leu Thr Gln Thr Ala Ser Pro Val Ser Ala Ala Val Gly Gly
1                   5                   10                  15

Thr Val Thr Ile Ser Cys Gln Ser Lys Gln Ser Val Tyr Asn Asn Lys
                20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
                100                 105                 110
```

```
<210> SEQ ID NO 216
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216
```

```
Ala Val Leu Thr Gln Thr Ala Ser Pro Val Ser Ala Ala Val Gly Gly
1                   5                   10                  15

Thr Val Thr Ile Ser Cys Gln Ser Ser Gln Lys Val Tyr Asn Asn Lys
                20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
                100                 105                 110
```

```
<210> SEQ ID NO 217
<211> LENGTH: 111
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 217

Ala Val Leu Thr Gln Thr Ala Ser Pro Val Ser Ala Ala Val Gly Gly
1               5                   10                  15

Thr Val Thr Ile Ser Cys Gln Ser Ser Gln Tyr Val Tyr Asn Asn Lys
            20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 218
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Ala Val Leu Thr Gln Thr Ala Ser Pro Val Ser Ala Ala Val Gly Gly
1               5                   10                  15

Thr Val Thr Ile Ser Cys Gln Ser Ser Gln Met Val Tyr Asn Asn Lys
            20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 219
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Ala Val Leu Thr Gln Thr Ala Ser Pro Val Ser Ala Ala Val Gly Gly
1               5                   10                  15

Thr Val Thr Ile Ser Cys Gln Ser Ser Gln Thr Val Tyr Asn Asn Lys
            20                  25                  30

Glu Leu Ser Trp Phe Gln Gln Lys Pro Gly Gln Pro Pro Lys Leu Leu
        35                  40                  45

```
Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
                100                 105                 110
```

<210> SEQ ID NO 220
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

```
Ala Val Leu Thr Gln Thr Ala Ser Pro Val Ser Ala Ala Val Gly Gly
1               5                   10                  15

Thr Val Thr Ile Ser Cys Gln Ser Ser Gln Phe Val Tyr Asn Asn Lys
                20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
                100                 105                 110
```

<210> SEQ ID NO 221
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

```
Ala Val Leu Thr Gln Thr Ala Ser Pro Val Ser Ala Ala Val Gly Gly
1               5                   10                  15

Thr Val Thr Ile Ser Cys Gln Ser Ser Gln Val Val Tyr Asn Asn Lys
                20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
                100                 105                 110
```

<210> SEQ ID NO 222
<211> LENGTH: 111

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Ala Val Leu Thr Gln Thr Ala Ser Pro Val Ser Ala Ala Val Gly Gly
1               5                   10                  15

Thr Val Thr Ile Ser Cys Gln Ser Ser Gln Ser Val Tyr Lys Asn Lys
            20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 223
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Ala Val Leu Thr Gln Thr Ala Ser Pro Val Ser Ala Ala Val Gly Gly
1               5                   10                  15

Thr Val Thr Ile Ser Cys Gln Ser Ser Gln Ser Val Tyr Arg Asn Lys
            20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 224
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Ala Val Leu Thr Gln Thr Ala Ser Pro Val Ser Ala Ala Val Gly Gly
1               5                   10                  15

Thr Val Thr Ile Ser Cys Gln Ser Ser Gln Ser Val Tyr His Asn Lys
            20                  25                  30

Glu Leu Ser Trp Phe Gln Gln Lys Pro Gly Gln Pro Pro Lys Leu Leu
```

```
            35                  40                  45

Ile Ser Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
                100                 105                 110

<210> SEQ ID NO 225
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Ala Val Leu Thr Gln Thr Ala Ser Pro Val Ser Ala Ala Val Gly Gly
1               5                   10                  15

Thr Val Thr Ile Ser Cys Gln Ser Ser Gln Ser Val Tyr Asn Asn Lys
                20                  25                  30

Glu Leu Ser Trp Phe Gln Gln Lys Pro Gly Gln Pro Pro Lys Leu Leu
            35                  40                  45

Ile Ser Tyr Ala Ser Thr Ser Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
                100                 105                 110

<210> SEQ ID NO 226
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Ala Val Leu Thr Gln Thr Ala Ser Pro Val Ser Ala Ala Val Gly Gly
1               5                   10                  15

Thr Val Thr Ile Ser Cys Gln Ser Ser Gln Ser Val Tyr Asn Asn Lys
                20                  25                  30

Glu Leu Ser Trp Phe Gln Gln Lys Pro Gly Gln Pro Pro Lys Leu Leu
            35                  40                  45

Ile Ser Tyr Ala Ser Thr Asn Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
                100                 105                 110
```

-continued

```
<210> SEQ ID NO 227
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Ala Val Leu Thr Gln Thr Ala Ser Pro Val Ser Ala Ala Val Gly Gly
1               5                   10                  15

Thr Val Thr Ile Ser Cys Gln Ser Ser Gln Ser Val Tyr Asn Asn Lys
            20                  25                  30

Glu Leu Ser Trp Phe Gln Gln Lys Pro Gly Gln Pro Pro Lys Leu Leu
        35                  40                  45

Ile Ser Tyr Ala Ser Thr Leu Ala His Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ala Ser Thr
                85                  90                  95

Ile Asp Met Trp Ala Phe Gly Gly Gly Thr Glu Val Val Val Lys
            100                 105                 110

<210> SEQ ID NO 228
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228
cagagcctgg aggaaagcgg tggtcgtctg gtgaccccgg gtggtagcct gaccctgacc      60
tgcaccgtta gcggtttcag cctgagcacc cacgacatca gctgggtgcg tcaagcgccg     120
ggcaagggtc tggagtggat cggtgttatt gcgcgtcgtg gcagcaccta ctatgcgagc     180
tgggcgcggg gccgtttcac cattagcaaa accagcacca ccgtggacct gaaaatcacc     240
agcccgacca ttgaagatac cgcgacctac ttttgcgcgc gtgaggaatt cgatttttgg     300
ggtcagggca ccctggtgac cgttagcagc                                      330

<210> SEQ ID NO 229
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229
gcggtgctga cccagaccgc gagcccggtt agcgcggcgg tgggtggcac cgttaccatc      60
agctgccagg gtagccaaag cgtttacaac aacaaggagc tgagctggtt ccagcaaaag     120
ccgggtcagc cgccgaaact gctgattagc tatgcgagca ccctggcgag cggtgtgccg     180
agccgtttca aaggcagcgg tagcggcacc caatttaccc tgaccatcag cgacctggag     240
tgcgacgatg cggcgaccta ctattgcctg ggtggctacg cgagcaccat tgatatgtgg     300
gcgtttggtg cggtaccga agtggttgtg aag                                   333

<210> SEQ ID NO 230
```

```
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
gcggtgctga cccagaccgc gagcccggtt agcgcggcgg tgggtggcac cgttaccatc      60
agctgccaga tgagccaaag cgtttacaac aacaaggagc tgagctggtt ccagcaaaag     120
ccgggtcagc cgccgaaact gctgattagc tatgcgagca ccctggcgag cggtgtgccg     180
agccgtttca aaggcagcgg tagcggcacc caatttaccc tgaccatcag cgacctggag     240
tgcgacgatg cggcgaccta ctattgcctg ggtggctacg cgagcaccat tgatatgtgg     300
gcgtttggtg gcggtaccga agtggttgtg aag                                  333

<210> SEQ ID NO 231
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
gcggtgctga cccagaccgc gagcccggtt agcgcggcgg tgggtggcac cgttaccatc      60
agctgccaga ctagccaaag cgtttacaac aacaaggagc tgagctggtt ccagcaaaag     120
ccgggtcagc cgccgaaact gctgattagc tatgcgagca ccctggcgag cggtgtgccg     180
agccgtttca aaggcagcgg tagcggcacc caatttaccc tgaccatcag cgacctggag     240
tgcgacgatg cggcgaccta ctattgcctg ggtggctacg cgagcaccat tgatatgtgg     300
gcgtttggtg gcggtaccga agtggttgtg aag                                  333

<210> SEQ ID NO 232
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232
gcggtgctga cccagaccgc gagcccggtt agcgcggcgg tgggtggcac cgttaccatc      60
agctgccaga gcgcgcaaag cgtttacaac aacaaggagc tgagctggtt ccagcaaaag     120
ccgggtcagc cgccgaaact gctgattagc tatgcgagca ccctggcgag cggtgtgccg     180
agccgtttca aaggcagcgg tagcggcacc caatttaccc tgaccatcag cgacctggag     240
tgcgacgatg cggcgaccta ctattgcctg ggtggctacg cgagcaccat tgatatgtgg     300
gcgtttggtg gcggtaccga agtggttgtg aag                                  333

<210> SEQ ID NO 233
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
gcggtgctga cccagaccgc gagcccggtt agcgcggcgg tgggtggcac cgttaccatc      60
```

-continued

```
agctgccaga gcaggcaaag cgtttacaac aacaaggagc tgagctggtt ccagcaaaag    120
ccgggtcagc cgccgaaact gctgattagc tatgcgagca ccctggcgag cggtgtgccg    180
agccgtttca aaggcagcgg tagcggcacc caatttaccc tgaccatcag cgacctggag    240
tgcgacgatg cggcgaccta ctattgcctg ggtggctacg cgagcaccat tgatatgtgg    300
gcgtttggtg gcggtaccga agtggttgtg aag                                 333
```

```
<210> SEQ ID NO 234
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 234
```

```
gcggtgctga cccagaccgc gagcccggtt agcgcggcgg tgggtggcac cgttaccatc     60
agctgccaga gcctgcaaag cgtttacaac aacaaggagc tgagctggtt ccagcaaaag    120
ccgggtcagc cgccgaaact gctgattagc tatgcgagca ccctggcgag cggtgtgccg    180
agccgtttca aaggcagcgg tagcggcacc caatttaccc tgaccatcag cgacctggag    240
tgcgacgatg cggcgaccta ctattgcctg ggtggctacg cgagcaccat tgatatgtgg    300
gcgtttggtg gcggtaccga agtggttgtg aag                                 333
```

```
<210> SEQ ID NO 235
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 235
```

```
gcggtgctga cccagaccgc gagcccggtt agcgcggcgg tgggtggcac cgttaccatc     60
agctgccaga gcactcaaag cgtttacaac aacaaggagc tgagctggtt ccagcaaaag    120
ccgggtcagc cgccgaaact gctgattagc tatgcgagca ccctggcgag cggtgtgccg    180
agccgtttca aaggcagcgg tagcggcacc caatttaccc tgaccatcag cgacctggag    240
tgcgacgatg cggcgaccta ctattgcctg ggtggctacg cgagcaccat tgatatgtgg    300
gcgtttggtg gcggtaccga agtggttgtg aag                                 333
```

```
<210> SEQ ID NO 236
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 236
```

```
gcggtgctga cccagaccgc gagcccggtt agcgcggcgg tgggtggcac cgttaccatc     60
agctgccaga gccatcaaag cgtttacaac aacaaggagc tgagctggtt ccagcaaaag    120
ccgggtcagc cgccgaaact gctgattagc tatgcgagca ccctggcgag cggtgtgccg    180
agccgtttca aaggcagcgg tagcggcacc caatttaccc tgaccatcag cgacctggag    240
tgcgacgatg cggcgaccta ctattgcctg ggtggctacg cgagcaccat tgatatgtgg    300
gcgtttggtg gcggtaccga agtggttgtg aag                                 333
```

-continued

```
<210> SEQ ID NO 237
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 237
gcggtgctga cccagaccgc gagcccggtt agcgcggcgg tgggtggcac cgttaccatc      60
agctgccaga gcaagcaaag cgtttacaac aacaaggagc tgagctggtt ccagcaaaag     120
ccgggtcagc cgccgaaact gctgattagc tatgcgagca ccctggcgag cggtgtgccg     180
agccgtttca aaggcagcgg tagcggcacc caatttaccc tgaccatcag cgacctggag     240
tgcgacgatg cggcgaccta ctattgcctg ggtggctacg cgagcaccat tgatatgtgg     300
gcgtttggtg gcggtaccga agtggttgtg aag                                  333

<210> SEQ ID NO 238
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238
gcggtgctga cccagaccgc gagcccggtt agcgcggcgg tgggtggcac cgttaccatc      60
agctgccaga gcagccaaaa ggtttacaac aacaaggagc tgagctggtt ccagcaaaag     120
ccgggtcagc cgccgaaact gctgattagc tatgcgagca ccctggcgag cggtgtgccg     180
agccgtttca aaggcagcgg tagcggcacc caatttaccc tgaccatcag cgacctggag     240
tgcgacgatg cggcgaccta ctattgcctg ggtggctacg cgagcaccat tgatatgtgg     300
gcgtttggtg gcggtaccga agtggttgtg aag                                  333

<210> SEQ ID NO 239
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 239
gcggtgctga cccagaccgc gagcccggtt agcgcggcgg tgggtggcac cgttaccatc      60
agctgccaga gcagccaata tgtttacaac aacaaggagc tgagctggtt ccagcaaaag     120
ccgggtcagc cgccgaaact gctgattagc tatgcgagca ccctggcgag cggtgtgccg     180
agccgtttca aaggcagcgg tagcggcacc caatttaccc tgaccatcag cgacctggag     240
tgcgacgatg cggcgaccta ctattgcctg ggtggctacg cgagcaccat tgatatgtgg     300
gcgtttggtg gcggtaccga agtggttgtg aag                                  333

<210> SEQ ID NO 240
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<400> SEQUENCE: 240
gcggtgctga cccagaccgc gagcccggtt agcgcggcgg tgggtggcac cgttaccatc        60
agctgccaga gcagccaaat ggtttacaac aacaaggagc tgagctggtt ccagcaaaag       120
ccgggtcagc cgccgaaact gctgattagc tatgcgagca ccctggcgag cggtgtgccg       180
agccgtttca aaggcagcgg tagcggcacc caatttaccc tgaccatcag cgacctggag       240
tgcgacgatg cggcgaccta ctattgcctg ggtggctacg cgagcaccat tgatatgtgg       300
gcgtttggtg gcggtaccga agtggttgtg aag                                     333

<210> SEQ ID NO 241
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241
gcggtgctga cccagaccgc gagcccggtt agcgcggcgg tgggtggcac cgttaccatc        60
agctgccaga gcagccaaac ggtttacaac aacaaggagc tgagctggtt ccagcaaaag       120
ccgggtcagc cgccgaaact gctgattagc tatgcgagca ccctggcgag cggtgtgccg       180
agccgtttca aaggcagcgg tagcggcacc caatttaccc tgaccatcag cgacctggag       240
tgcgacgatg cggcgaccta ctattgcctg ggtggctacg cgagcaccat tgatatgtgg       300
gcgtttggtg gcggtaccga agtggttgtg aag                                     333

<210> SEQ ID NO 242
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 242
gcggtgctga cccagaccgc gagcccggtt agcgcggcgg tgggtggcac cgttaccatc        60
agctgccaga gcagccaatt tgtttacaac aacaaggagc tgagctggtt ccagcaaaag       120
ccgggtcagc cgccgaaact gctgattagc tatgcgagca ccctggcgag cggtgtgccg       180
agccgtttca aaggcagcgg tagcggcacc caatttaccc tgaccatcag cgacctggag       240
tgcgacgatg cggcgaccta ctattgcctg ggtggctacg cgagcaccat tgatatgtgg       300
gcgtttggtg gcggtaccga agtggttgtg aag                                     333

<210> SEQ ID NO 243
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 243
gcggtgctga cccagaccgc gagcccggtt agcgcggcgg tgggtggcac cgttaccatc        60
agctgccaga gcagccaagt ggtttacaac aacaaggagc tgagctggtt ccagcaaaag       120
ccgggtcagc cgccgaaact gctgattagc tatgcgagca ccctggcgag cggtgtgccg       180
agccgtttca aaggcagcgg tagcggcacc caatttaccc tgaccatcag cgacctggag       240
```

```
tgcgacgatg cggcgaccta ctattgcctg ggtggctacg cgagcaccat tgatatgtgg      300
gcgtttggtg gcggtaccga agtggttgtg aag                                    333

<210> SEQ ID NO 244
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 244
gcggtgctga cccagaccgc gagcccggtt agcgcggcgg tgggtggcac cgttaccatc       60
agctgccaga gcagccaaag cgtttacaag aacaaggagc tgagctggtt ccagcaaaag      120
ccgggtcagc cgccgaaact gctgattagc tatgcgagca ccctggcgag cggtgtgccg      180
agccgtttca aaggcagcgg tagcggcacc caatttaccc tgaccatcag cgacctggag      240
tgcgacgatg cggcgaccta ctattgcctg ggtggctacg cgagcaccat tgatatgtgg      300
gcgtttggtg gcggtaccga agtggttgtg aag                                    333

<210> SEQ ID NO 245
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 245
gcggtgctga cccagaccgc gagcccggtt agcgcggcgg tgggtggcac cgttaccatc       60
agctgccaga gcagccaaag cgtttaccgg aacaaggagc tgagctggtt ccagcaaaag      120
ccgggtcagc cgccgaaact gctgattagc tatgcgagca ccctggcgag cggtgtgccg      180
agccgtttca aaggcagcgg tagcggcacc caatttaccc tgaccatcag cgacctggag      240
tgcgacgatg cggcgaccta ctattgcctg ggtggctacg cgagcaccat tgatatgtgg      300
gcgtttggtg gcggtaccga agtggttgtg aag                                    333

<210> SEQ ID NO 246
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246
gcggtgctga cccagaccgc gagcccggtt agcgcggcgg tgggtggcac cgttaccatc       60
agctgccaga gcagccaaag cgtttaccat aacaaggagc tgagctggtt ccagcaaaag      120
ccgggtcagc cgccgaaact gctgattagc tatgcgagca ccctggcgag cggtgtgccg      180
agccgtttca aaggcagcgg tagcggcacc caatttaccc tgaccatcag cgacctggag      240
tgcgacgatg cggcgaccta ctattgcctg ggtggctacg cgagcaccat tgatatgtgg      300
gcgtttggtg gcggtaccga agtggttgtg aag                                    333

<210> SEQ ID NO 247
<211> LENGTH: 333
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 247
gcggtgctga cccagaccgc gagcccggtt agcgcggcgg tgggtggcac cgttaccatc      60
agctgccaga gcagccaaag cgtttacaac aacaaggagc tgagctggtt ccagcaaaag     120
ccgggtcagc cgccgaaact gctgattagc tatgcgagca ccagtgcgag cggtgtgccg     180
agccgtttca aaggcagcgg tagcggcacc caatttaccc tgaccatcag cgacctggag     240
tgcgacgatg cggcgaccta ctattgcctg ggtggctacg cgagcaccat tgatatgtgg     300
gcgtttggtg gcggtaccga agtggttgtg aag                                  333

<210> SEQ ID NO 248
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 248
gcggtgctga cccagaccgc gagcccggtt agcgcggcgg tgggtggcac cgttaccatc      60
agctgccaga gcagccaaag cgtttacaac aacaaggagc tgagctggtt ccagcaaaag     120
ccgggtcagc cgccgaaact gctgattagc tatgcgagca ccaatgcgag cggtgtgccg     180
agccgtttca aaggcagcgg tagcggcacc caatttaccc tgaccatcag cgacctggag     240
tgcgacgatg cggcgaccta ctattgcctg ggtggctacg cgagcaccat tgatatgtgg     300
gcgtttggtg gcggtaccga agtggttgtg aag                                  333

<210> SEQ ID NO 249
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249
gcggtgctga cccagaccgc gagcccggtt agcgcggcgg tgggtggcac cgttaccatc      60
agctgccaga gcagccaaag cgtttacaac aacaaggagc tgagctggtt ccagcaaaag     120
ccgggtcagc cgccgaaact gctgattagc tatgcgagca ccctggcgca tggtgtgccg     180
agccgtttca aaggcagcgg tagcggcacc caatttaccc tgaccatcag cgacctggag     240
tgcgacgatg cggcgaccta ctattgcctg ggtggctacg cgagcaccat tgatatgtgg     300
gcgtttggtg gcggtaccga agtggttgtg aag                                  333

<210> SEQ ID NO 250
<211> LENGTH: 100
<212> TYPE: PRT
<213> ORGANISM: Mycobacterium orygis

<400> SEQUENCE: 250

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

```
Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

<210> SEQ ID NO 251
<211> LENGTH: 100
<212> TYPE: PRT
<213> ORGANISM: Mycobacterium pinnipedii

<400> SEQUENCE: 251

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

<210> SEQ ID NO 252
<211> LENGTH: 100
<212> TYPE: PRT
<213> ORGANISM: Mycobacterium tuberculosis

<400> SEQUENCE: 252

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

<210> SEQ ID NO 253
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 253

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Gly Ser Leu Thr Leu Thr Cys Thr Val Ser Gly Phe Ser Leu Ser
        35                  40                  45

Thr His Asp Ile Ser Trp Val Arg Gln Ala Pro Gly Lys Gly Leu Glu
    50                  55                  60

Trp Ile Gly Val Ile Ala Arg Arg Gly Ser Thr Tyr Tyr Ala Ser Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Ile Glu Asp Thr Ala Thr Tyr Phe Cys Ala
            100                 105                 110

Arg Glu Glu Phe Asp Phe Trp Gly Gln Gly Thr Leu Val Thr Val Ser
        115                 120                 125

Ser

<210> SEQ ID NO 254
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Ala Ser Pro
            20                  25                  30

Val Ser Ala Ala Val Gly Gly Thr Val Thr Ile Ser Cys Gln Ser Ser
        35                  40                  45

Gln Ser Val Tyr Asn Asn Lys Glu Leu Ser Trp Phe Gln Gln Lys Pro
    50                  55                  60

Gly Gln Pro Pro Lys Leu Leu Ile Ser Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Leu Gly Gly Tyr Ala Ser Thr Ile Asp Met Trp Ala Phe Gly Gly Gly
        115                 120                 125

Thr Glu Val Val Val Lys
    130

<210> SEQ ID NO 255
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Met Asp Thr Arg Ala Pro Thr Gln Leu Leu Gly Leu Leu Leu Leu Trp

-continued

```
1               5                       10                      15

Leu Pro Gly Ala Thr Phe Ala Ala Val Leu Thr Gln Thr Pro Ser Pro
            20                      25                      30

Val Ser Ala Ala Val Gly Gly Thr Val Thr Ile Asn Cys Gln Ser Ser
            35                      40                      45

Lys Ser Val Tyr Asn Asn Asn Cys Leu Ser Trp Tyr Gln Gln Lys Gln
    50                      55                      60

Gly Gln Pro Pro Lys Leu Leu Ile Tyr Gln Ala Ser Thr Pro Ala Ser
65                      70                      75                      80

Gly Val Pro Ser Arg Phe Lys Gly Ser Gly Ser Gly Thr Gln Phe Thr
                85                      90                      95

Leu Thr Ile Asn Asp Val Gln Cys Asp Asp Ala Ala Thr Tyr Tyr Cys
                100                     105                     110

Ala Gly Cys Phe Ala Ser Thr Ser Asp Met Tyr Gly Phe Gly Gly Gly
                115                     120                     125

Thr Gly Val Val Val Lys
        130
```

```
<210> SEQ ID NO 256
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Met Glu Thr Gly Leu Arg Trp Leu Leu Leu Val Ala Val Leu Lys Gly
1               5                       10                      15

Val Gln Cys Gln Ser Val Glu Glu Ser Gly Gly Arg Leu Val Thr Pro
            20                      25                      30

Gly Thr Pro Leu Thr Leu Thr Cys Thr Val Ser Gly Ile Asp Leu Ser
            35                      40                      45

Ser Asn Ala Val Gly Trp Val Arg Gln Ala Pro Gly Glu Gly Leu Glu
    50                      55                      60

Trp Ile Gly Ser Ile Tyr Ser Ser Gly Asn Ser Tyr Tyr Ala Ser Trp
65                      70                      75                      80

Ala Lys Gly Arg Phe Ala Ile Ser Arg Thr Ser Thr Thr Val Asp Leu
                85                      90                      95

Lys Met Thr Arg Leu Thr Ala Ala Asp Thr Ala Thr Tyr Phe Cys Ala
                100                     105                     110

Arg Leu Phe Asn Ile Trp Gly Pro Gly Thr Leu Val Thr Val Ser Ser
                115                     120                     125
```

```
<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Cys Val Arg Glu Glu Phe Asp Phe Trp
1               5
```

```
<210> SEQ ID NO 258
<211> LENGTH: 14
<212> TYPE: PRT
```

-continued

<213> ORGANISM: Artificial Sequence
<220> FEATURE:
<223> OTHER INFORMATION: Description of Artificial Sequence: Synthetic
      peptide

<400> SEQUENCE: 258

Cys Leu Gly Gly Tyr Ala Ser Ile Ile Asp Met Trp Thr Phe
1               5                   10

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Cys Ala Arg Glu Glu Phe Asn Leu Trp
1               5

<210> SEQ ID NO 260
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Cys Ala Gly Tyr Lys Ser Ser Ser Asp Gly Pro Ala Phe
1               5                   10

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Cys Ala Gly Gly Ala Pro Gly Tyr Thr Pro Phe Asn Leu Trp
1               5                   10

<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Cys Ala Gly Gly Tyr Ser Ser Ser Leu Asp Ile Tyr Ala Phe
1               5                   10

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Cys Ala Arg Glu Glu Phe Asp Phe Trp
1               5

```
<210> SEQ ID NO 264
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Cys Leu Gly Gly Tyr Ala Ser Thr Ile Asp Met Trp Ala Phe
1               5                   10

<210> SEQ ID NO 265
<211> LENGTH: 100
<212> TYPE: PRT
<213> ORGANISM: Mycobacterium bovis

<400> SEQUENCE: 265

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
        50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

<210> SEQ ID NO 266
<211> LENGTH: 100
<212> TYPE: PRT
<213> ORGANISM: Mycobacterium canetti

<400> SEQUENCE: 266

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
        50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

<210> SEQ ID NO 267
<211> LENGTH: 100
<212> TYPE: PRT
<213> ORGANISM: Mycobacterium caprae
```

```
<400> SEQUENCE: 267

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100
```